(12) United States Patent
Diener et al.

(10) Patent No.: US 7,998,939 B2
(45) Date of Patent: Aug. 16, 2011

(54) APTAMERS THAT BIND THROMBIN WITH HIGH AFFINITY

(75) Inventors: John L. Diener, Cambridge, MA (US); Jess Wagner-Whyte, Lynn, MA (US); David Fontana, Clyde Hill, WA (US)

(73) Assignee: Archemix Corporation, Cambridge, MA (US)

( * ) Notice: Subject to any disclaimer, the term of this patent is extended or adjusted under 35 U.S.C. 154(b) by 194 days.

(21) Appl. No.: 11/990,998

(22) PCT Filed: Aug. 23, 2006

(86) PCT No.: PCT/US2006/033092
§ 371 (c)(1),
(2), (4) Date: Mar. 17, 2008

(87) PCT Pub. No.: WO2007/025049
PCT Pub. Date: Mar. 1, 2007

(65) Prior Publication Data
US 2009/0221680 A1 Sep. 3, 2009

Related U.S. Application Data

(60) Provisional application No. 60/711,768, filed on Aug. 26, 2005, provisional application No. 60/808,590, filed on May 26, 2006.

(51) Int. Cl.
*A61K 48/00* (2006.01)
*C07H 21/02* (2006.01)
*C07H 21/04* (2006.01)

(52) U.S. Cl. .................. 514/44; 536/23.1; 536/24.5

(58) Field of Classification Search .................. None
See application file for complete search history.

(56) References Cited

U.S. PATENT DOCUMENTS 5,756,291 A 5/1998 Griffin et al.
6,056,715 A * 5/2000 Demopulos et al. .......... 604/500
2003/0054360 A1 3/2003 Gold et al.
2004/0197804 A1 10/2004 Keefe et al.
2006/0057573 A1 * 3/2006 Gold et al. .................. 435/6

FOREIGN PATENT DOCUMENTS

| WO | WO 92/14842 A1 | 9/1992 |
| WO | WO 9214842 A1 * | 9/1992 |
| WO | WO 2003/070984 A1 | 8/2003 |
| WO | WO 2005/010150 | 2/2005 |
| WO | WO 2007/036016 A1 | 4/2007 |
| WO | WO 2007/044851 A2 | 4/2007 |

OTHER PUBLICATIONS

Fitter, et al., "Deconvolution of a Complex Target Using DNA Aptamers," *J Biol Chem* 280(40):34193-34201 (2005).
Bock et al., "Selection of single-stranded DNA molecules that bind and inhibit human thrombin," *Nature*, 355(6360):564-566, 1992.
Burmeister et al., "2'-deoxy purine, 2'-0-methyl pyrimidine (dRmY) aptamers as candidate therapeutics," *Oligonucleotides*, 16(4):337-351, 2006.
Di Giusto et al., "Construction, stability, and activity of multivalent circular anticoagulant aptamers," *Journal of Biological Chemistry*, 279(45):46483-46489, 2004.
Griffin et al., "The discovery and characterization of a novel nucleotide-based thrombin inhibitor," *Gene*, 137(1):25-31, 1993.
Office Communication, issued in European Patent Application No. 06813718.1, dated Sep. 28, 2010.
Smirnov et al., "Effect of loop sequence and size on DNA aptamer stability," *Biochemistry*, 39(1):1462-1468, 2000.
Tasset et al., "Oligonucleotide inhibitors of human thrombin that bind distinct epitopes," *Journal of Molecular Biology*, 272(5):688-698, 1997.

* cited by examiner

*Primary Examiner* — Amy Bowman
(74) *Attorney, Agent, or Firm* — Fulbright & Jaworski L.L.P.

(57) ABSTRACT

The invention provides aptamers capable of binding to thrombin useful as therapeutics for and diagnostics of coagulation related disorders and/or other diseases or disorders in which thrombin has been implicated. The invention further provides materials and methods for the administration of aptamers capable of binding to thrombin.

30 Claims, 20 Drawing Sheets

Figure 4
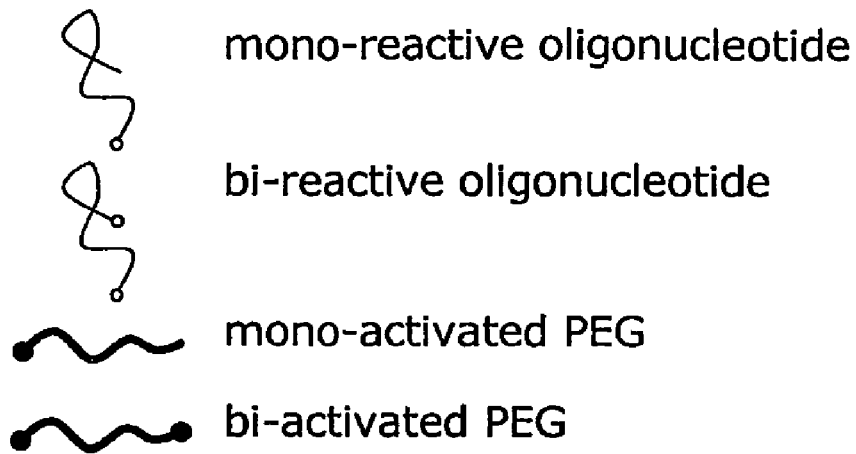
standard PEGylation
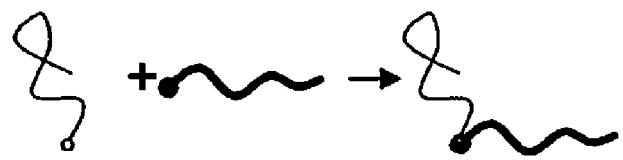
multiple PEGylation
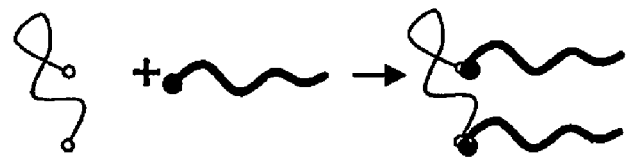
dimerization via PEGylation
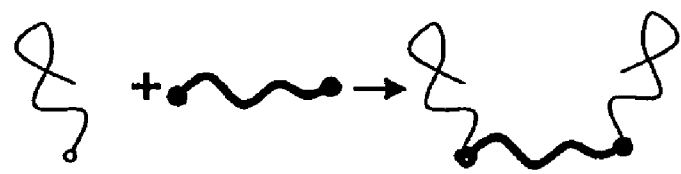

Derivatives of ARC2169 and ARC2172 were used for most studies including in vivo studies

Figure 12

| Aptamer | Type | No. of rats | Dose μmole/kg | Dose mg (oligonucleotide only)/kg | Maximum ACT (sec) | Time to Act of 170 sec (min) |
|---|---|---|---|---|---|---|
| ARC2949 | 24 nt 2 x 2'-OMe base pairs | 3 | 1.5 | 11.5 | 372.3 | 4.6 |
| ARC2172 | 26 nt | 7 | 1.5 | 12.2 | 469.5 | 9.7 |
| ARC2324 | 26 nt w/ 5' amine | 5 | 1.5 | 12.5 | 430.0 | 13.1 |
| ARC2327 | 26 nt w/ 5' amine + 2K PEG | 2 | 1.5 | 12.5 | 441.0 | 22.1 |
| ARC2338 | 26 nt w/ 5' amine + 5K PEG | 2 | 1.5 | 12.5 | 593.5 | 37.4 |
| ARC2329 | 26 nt w/ 5' amine + 10K PEG | 3 | 1.5 | 12.5 | 656.3 | 56.0 |
| ARC2840 | 26 nt AU-rich 2'-OMe stem | 3 | 1.5 | 12.2 | 175.7 | 1.1 |
| ARC2321 | 30 nt w/ 5' amine | 6 | 1.5 | 14.35 | 482.0 | 25.4 |
| ARC2323 | 30 nt w/ 5' amine + 10K PEG | 3 | 1.5 | 14.35 | 574.7 | 115.6 |
| ARC2828 | 30 nt AT-rich 2'-oMe stem | 3 | 1.5 | 14.5 | 518.0 | 30.3 |
| ARC183 | 15 nt | 3 | 6.35 | 30 | 313.7 | 3.6 |

| Test Article | Number of Rats | Bolus Dose (mg/kg) | Treatment Regimen | Sampling |
|---|---|---|---|---|
| ARC2172 | 4 | 12.2 | IV bolus | ACT |
| ARC183 | 6 | 30 | | |

| Test Article | Type | Bolus Dose (mg/kg) | Maximum ACT (sec) | Time to an ACT of 200 sec (min) | Time to an ACT of 170 sec (min) |
|---|---|---|---|---|---|
| ARC2172 | 26 nt | 12.2 | 419 | 9.5 | 12.2 |
| ARC183 | 15 nt | 30 | 328 | 2.7 | 4.1 |

| Group Number | No. of Animals | Test Article | Test Article | Aptamer Dose Volume | Dosing Conc. |
|---|---|---|---|---|---|
| | Males | | mg/kg | mL/kg | mg/mL |
| 1A (ligated) | 4 | ARC2172 | 12.2 | 0.5 mL/kg | 24 mg/mL |
| 1B (sham) | 4 | ARC2172 | 12.2 | 0.5 mL/kg | 24 mg/mL |
| 2A (ligated) | 6 | ARC183 | 30 | 1.5 mL/kg | 20 mg/mL |
| 2B (sham) | 6 | ARC183 | 30 | 1.5 mL/kg | 20 mg/mL |

| Aptamer | Type | No. of monkeys | Dose | | Maximum ACT (sec) | Time to Act of 170 sec (min) |
|---|---|---|---|---|---|---|
| | | | µmole/kg | mg (oligonucleotide only)/kg | | |
| ARC2949 | 24 nt 2 x 2'-OMe base pairs | 3 | 0.46 | 3.52 | 402.7 | 14.9 |
| ARC2840 | 26 nt AU-rich 2'-OMe stem | 3 | 0.46 | 3.75 | 223.3 | 2.2 |
| ARC2172 | 26 nt | 3 | 0.46 | 3.75 | 526.8 | 24.9 |
| ARC2169 | 30 nt | 3 | 0.46 | 4.32 | 541.7 | 54.6 |

Figure 22

| Test Article | Number of Monkeys | Bolus dose (mg/kg) | Infusion rate (mg/kg/min) | Target Plasma Concentration | Treatment regimen | Sampling |
|---|---|---|---|---|---|---|
| ARC2172 | 3 | 3.0 | 0.144 | 5 µM (40.8 µg/mL) | IV bolus plus one hour infusion | ACT, PK |
| ARC2172 | 3 | 3.25 | 0.233 | 7.5 µM (61.2 µg/mL) | | |
| ARC183 | 3 | 8.5 | 2.5 | 15 µM (71.3 µg/mL) | | |

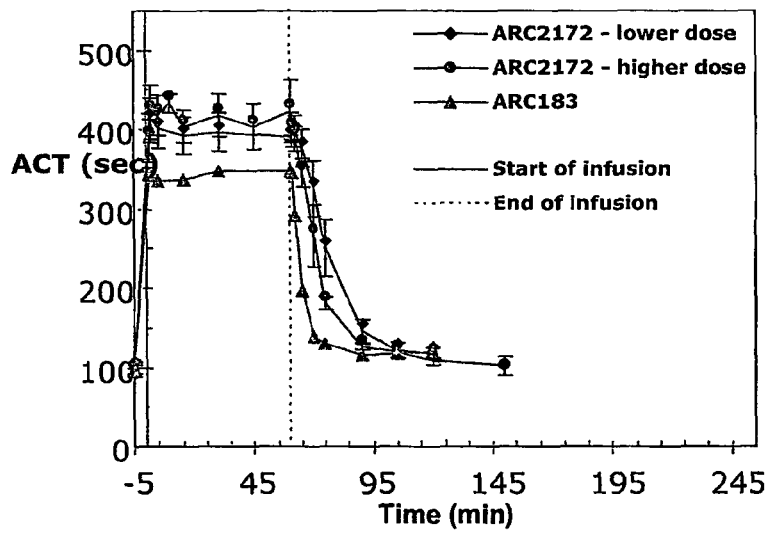

| Test Article | Target Plasma Conc. (µg/mL/µM) | Bolus Dose (mg/kg) | Infusion Dose (mg/kg/min) | Average ACT during infusion (sec) | Time to an ACT of 200 sec after end of infusion (min) | Time to an ACT of 170 sec after end of infusion (min) |
|---|---|---|---|---|---|---|
| ARC2172 | 5µM (40.8 µg/mL) | 3.0 | 0.144 | 397 | 22.2 | 26.5 |
| ARC2172 | 7.5µM (61.2 µg/mL) | 3.25 | 0.233 | 414 | 13.9 | 18.0 |
| ARC183 | 15µM (71.3 µg/mL) | 8.5 | 2.5 | 343 | 4.9 | 7.3 |

Figure 27

ARC2172 Porcine CPB Study Design

| Group Number | Animal number | Test Article | Crossclamp / Cardioplegia | Final Aptamer Bolus + Infusion Rate to Maintain ACT > 400 (mg/kg/min) |
|---|---|---|---|---|
| 2 | 26 | Heparin | No | NA |
| 2 | 27 | Heparin | No | NA |
| 2 | 28 | Heparin | No | NA |
| 2 | 29 | Heparin | No | NA |
| 2 | 30 | Heparin | No | NA |
| 1 | 36 | Control | No | NA |
| 1 | 37 | Control | No | NA |
| 3 | 38 | ARC2172 | No | Bolus -4.6mg/kg; Infusion – 0.233 mg/kg/min |
| 3 | 39 | ARC2172 | No | Bolus -4.6 mg/kg; Infusion – 0.2 mg/kg/min |
| 3 | 40 | ARC2172 | No | Bolus -2.7 mg/kg; Infusion – 0.139 mg/kg/min |
| 3 | 43 | ARC2172 | No | Bolus -2.7 mg/kg; Infusion – 0.139 mg/kg/min |
| 3 | 44 | ARC2172 | No | Bolus -2.7 mg/kg; Infusion – 0.139 mg/kg/min |
| 3 | 47 | ARC2172 | No | Bolus -2.7 mg/kg; Infusion – 0.139 mg/kg/min |
| 3 | 48 | ARC2172 | No | Bolus -2.7 mg/kg; Infusion – 0.139 mg/kg/min |

SEQUENCE LISTING

```
<160> NUMBER OF SEQ ID NOS: 446

<210> SEQ ID NO 1
<211> LENGTH: 93
<212> TYPE: DNA
<213> ORGANISM: Artificial Sequence
<220> FEATURE:
<223> OTHER INFORMATION: synthetic template
<220> FEATURE:
<221> NAME/KEY: misc_feature
<222> LOCATION: (25)..(54)
<223> OTHER INFORMATION: Wherein  n is a, t, c, or g.

<400> SEQUENCE: 1
catcgatgct agtcgtaacg atccnnnnnn nnnnnnnnnn nnnnnnnnnn nnncgagaa      60 cgttctctcc tctccctata gtgagtcgta tta                                 93

<210> SEQ ID NO 2
<211> LENGTH: 92
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (24)..(53)
<223> OTHER INFORMATION: Wherein n is a, t, c, or g.

<400> SEQUENCE: 2
catgcatcgc gactgactag ccgnnnnnnn nnnnnnnnnn nnnnnnnnnn nnngtagaac      60
gttctctcct ctccctatag tgagtcgtat ta                                  92

<210> SEQ ID NO 3
<211> LENGTH: 92
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (24)..(53)
<223> OTHER INFORMATION: Wherein n is a, t, c, or g.

<400> SEQUENCE: 3
catcgatcga tcgatcgaca gcgnnnnnnn nnnnnnnnnn nnnnnnnnnn nnngtagaac      60
gttctctcct ctccctatag tgagtcgtat ta                                  92

<210> SEQ ID NO 4
<211> LENGTH: 15
<212> TYPE: DNA
<213> ORGANISM: Artificial Sequence
<220> FEATURE:
<223> OTHER INFORMATION: synthetic aptamer
```

```
<400> SEQUENCE: 4
ggttggtgtg gttgg                                              15

<210> SEQ ID NO 5
<211> LENGTH: 70
<212> TYPE: DNA
<213> ORGANISM: Artificial Sequence
<220> FEATURE:
<223> OTHER INFORMATION: synthetic template
<220> FEATURE:
<221> NAME/KEY: misc_feature
<222> LOCATION: (18)..(46)
<223> OTHER INFORMATION: n is a, c, g, or t

<400> SEQUENCE: 5
gatcgatcct cagccacnnn nnnnnnnnnn nnnnnnnnnn nnnnnnggga tttagcttcc    60
tcttacacgc                                                    70

<210> SEQ ID NO 6
<211> LENGTH: 17
<212> TYPE: DNA
<213> ORGANISM: Artificial Sequence
<220> FEATURE:
<223> OTHER INFORMATION: synthetic primer

<400> SEQUENCE: 6
gatcgatcct cagccac                                            17

<210> SEQ ID NO 7
<211> LENGTH: 31
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (31)..(31)
<223> OTHER INFORMATION: Wherein adenosine at position 31 is ribo-
      adenosine.

<400> SEQUENCE: 7
tatacgactc agcgtgtaag aggaagctaa a                            31

<210> SEQ ID NO 8
<211> LENGTH: 50
<212> TYPE: DNA
<213> ORGANISM: Artificial Sequence
<220> FEATURE:
<223> OTHER INFORMATION: synthetic template
<220> FEATURE:
<221> NAME/KEY: misc_feature
<222> LOCATION: (5)..(33)
<223> OTHER INFORMATION: Wherein n is a, t, c, or g.

<400> SEQUENCE: 8
tcccnnnnnn nnnnnnnnnn nnnnnnnnnn nnngtggctg aggatcgatc        50

<210> SEQ ID NO 9
<211> LENGTH: 49
<212> TYPE: DNA
<213> ORGANISM: Artificial Sequence
<220> FEATURE:
<223> OTHER INFORMATION: synthetic aptamer

<400> SEQUENCE: 9
tcccatcgat ctggggtaat ttactgggtc gggtggctga ggatcgatc         49
```

```
<210> SEQ ID NO 10
<211> LENGTH: 50
<212> TYPE: DNA
<213> ORGANISM: Artificial Sequence
<220> FEATURE:
<223> OTHER INFORMATION: synthetic aptamer

<400> SEQUENCE: 10
atcccaatgt tgagacgagt aggtgtgggt agggtggctg aggatcgatc          50

<210> SEQ ID NO 11
<211> LENGTH: 50
<212> TYPE: DNA
<213> ORGANISM: Artificial Sequence
<220> FEATURE:
<223> OTHER INFORMATION: synthetic aptamer

<400> SEQUENCE: 11
tcccatcgag ctcagtctag gatgggtagg gtggtggctg aggatcgatc          50

<210> SEQ ID NO 12
<211> LENGTH: 49
<212> TYPE: DNA
<213> ORGANISM: Artificial Sequence
<220> FEATURE:
<223> OTHER INFORMATION: synthetic aptamer

<400> SEQUENCE: 12
tcccatcgag ccggggtatg attatgggtg gggtggctga ggatcgatc           49

<210> SEQ ID NO 13
<211> LENGTH: 50
<212> TYPE: DNA
<213> ORGANISM: Artificial Sequence
<220> FEATURE:
<223> OTHER INFORMATION: synthetic aptamer

<400> SEQUENCE: 13
tcccatcgat ctggggtagt tttattgggt cgggtggctg aggatcgatc          50

<210> SEQ ID NO 14
<211> LENGTH: 50
<212> TYPE: DNA
<213> ORGANISM: Artificial Sequence
<220> FEATURE:
<223> OTHER INFORMATION: synthetic aptamer

<400> SEQUENCE: 14
tcccgatcgg tctggggtgt gttcatggtt tgggtggctg aggatcgatc          50

<210> SEQ ID NO 15
<211> LENGTH: 50
<212> TYPE: DNA
<213> ORGANISM: Artificial Sequence
<220> FEATURE:
<223> OTHER INFORMATION: synthetic aptamer

<400> SEQUENCE: 15
tcctgattga tctgaggggt attgttggcg tgggtggctg aggatcgatc          50

<210> SEQ ID NO 16
<211> LENGTH: 50
<212> TYPE: DNA
<213> ORGANISM: Artificial Sequence
<220> FEATURE:
<223> OTHER INFORMATION: synthetic aptamer
```

```
<400> SEQUENCE: 16
tcccgattga tctgaggggt attgttggcg tgggtggctg aggatcgatc        50

<210> SEQ ID NO 17
<211> LENGTH: 49
<212> TYPE: DNA
<213> ORGANISM: Artificial Sequence
<220> FEATURE:
<223> OTHER INFORMATION: synthetic aptamer

<400> SEQUENCE: 17
tcccgtaatc gagtctggta ttgttggtct gggtggctga ggatcgatc         49

<210> SEQ ID NO 18
<211> LENGTH: 49
<212> TYPE: DNA
<213> ORGANISM: Artificial Sequence
<220> FEATURE:
<223> OTHER INFORMATION: synthetic aptamer

<400> SEQUENCE: 18
tcctatgatc gaatgactaa ggggtggggt gggtggctga ggatcgatc         49

<210> SEQ ID NO 19
<211> LENGTH: 49
<212> TYPE: DNA
<213> ORGANISM: Artificial Sequence
<220> FEATURE:
<223> OTHER INFORMATION: synthetic aptamer

<400> SEQUENCE: 19
tcccgggtcg tatccgtttg tgggtggtct gggtggctga ggatcgatc         49

<210> SEQ ID NO 20
<211> LENGTH: 49
<212> TYPE: DNA
<213> ORGANISM: Artificial Sequence
<220> FEATURE:
<223> OTHER INFORMATION: synthetic aptamer

<400> SEQUENCE: 20
tcccgtaatt gagcctggta ttgttggtct gggtggctga ggatcgatc         49

<210> SEQ ID NO 21
<211> LENGTH: 49
<212> TYPE: DNA
<213> ORGANISM: Artificial Sequence
<220> FEATURE:
<223> OTHER INFORMATION: synthetic aptamer

<400> SEQUENCE: 21
tcctgatcgg atgtggtggg ttattggttt gggtggctga ggatcgatc         49

<210> SEQ ID NO 22
<211> LENGTH: 50
<212> TYPE: DNA
<213> ORGANISM: Artificial Sequence
<220> FEATURE:
<223> OTHER INFORMATION: synthetic aptamer

<400> SEQUENCE: 22
tcccgagcga tactgtctag gttgggtagg gtggtggctg aggatcgatc        50
```

-continued

<210> SEQ ID NO 23
<211> LENGTH: 50
<212> TYPE: DNA
<213> ORGANISM: Artificial Sequence
<220> FEATURE:
<223> OTHER INFORMATION: synthetic aptamer

<400> SEQUENCE: 23
tcccgagcga tattgtctag gttgggtagg gtggtggctg aggatcgatc        50

<210> SEQ ID NO 24
<211> LENGTH: 49
<212> TYPE: DNA
<213> ORGANISM: Artificial Sequence
<220> FEATURE:
<223> OTHER INFORMATION: synthetic aptamer

<400> SEQUENCE: 24
tcccatgatc gttagattca gggatggtgt gggtggctga ggatcgatc         49

<210> SEQ ID NO 25
<211> LENGTH: 48
<212> TYPE: DNA
<213> ORGANISM: Artificial Sequence
<220> FEATURE:
<223> OTHER INFORMATION: synthetic aptamer

<400> SEQUENCE: 25
tcccgtatcg agcttggtat tgttggtctg ggtggctgag gatcgatc          48

<210> SEQ ID NO 26
<211> LENGTH: 49
<212> TYPE: DNA
<213> ORGANISM: Artificial Sequence
<220> FEATURE:
<223> OTHER INFORMATION: synthetic aptamer

<400> SEQUENCE: 26
tcccttttga cctgcaagaa cggttggtgt gggtggctga ggatcgatc         49

<210> SEQ ID NO 27
<211> LENGTH: 50
<212> TYPE: DNA
<213> ORGANISM: Artificial Sequence
<220> FEATURE:
<223> OTHER INFORMATION: synthetic aptamer

<400> SEQUENCE: 27
tcccggatcg ttttgcttca aaggttgggt tgggtggctg aggatcgatc        50

<210> SEQ ID NO 28
<211> LENGTH: 49
<212> TYPE: DNA
<213> ORGANISM: Artificial Sequence
<220> FEATURE:
<223> OTHER INFORMATION: synthetic aptamer

<400> SEQUENCE: 28
cccgactgat tcttacctta gggatggtgt gggtggctga ggatcgatc         49

<210> SEQ ID NO 29
<211> LENGTH: 49
<212> TYPE: DNA
<213> ORGANISM: Artificial Sequence
<220> FEATURE:
<223> OTHER INFORMATION: synthetic aptamer

```
<400> SEQUENCE: 29
tccctggttt cgatctgttt tggttggtct gggtggctga ggatcgatc        49

<210> SEQ ID NO 30
<211> LENGTH: 49
<212> TYPE: DNA
<213> ORGANISM: Artificial Sequence
<220> FEATURE:
<223> OTHER INFORMATION: synthetic aptamer

<400> SEQUENCE: 30
tcccatcgat tcggggtttt ttagtggtat gggtggctga ggatcgatc        49

<210> SEQ ID NO 31
<211> LENGTH: 50
<212> TYPE: DNA
<213> ORGANISM: Artificial Sequence
<220> FEATURE:
<223> OTHER INFORMATION: synthetic aptamer

<400> SEQUENCE: 31
tcccatcgat ttggggtagt tctattgggt tgggtggctg aggatcgatc       50

<210> SEQ ID NO 32
<211> LENGTH: 50
<212> TYPE: DNA
<213> ORGANISM: Artificial Sequence
<220> FEATURE:
<223> OTHER INFORMATION: synthetic aptamer

<400> SEQUENCE: 32
tccctgcttg tcgatatttt agggttggtg tgggtggctg aggatcgatc       50

<210> SEQ ID NO 33
<211> LENGTH: 49
<212> TYPE: DNA
<213> ORGANISM: Artificial Sequence
<220> FEATURE:
<223> OTHER INFORMATION: synthetic aptamer

<400> SEQUENCE: 33
tccctcgatc cggggtgtct ttcgtgggct gggtggctga ggatcgatc        49

<210> SEQ ID NO 34
<211> LENGTH: 50
<212> TYPE: DNA
<213> ORGANISM: Artificial Sequence
<220> FEATURE:
<223> OTHER INFORMATION: synthetic aptamer

<400> SEQUENCE: 34
tcccgagcga tattgcctag gttgggtagg gtggtggctg aggatcgatc       50

<210> SEQ ID NO 35
<211> LENGTH: 49
<212> TYPE: DNA
<213> ORGANISM: Artificial Sequence
<220> FEATURE:
<223> OTHER INFORMATION: synthetic aptamer

<400> SEQUENCE: 35
tccctcgatc taaggtgttt attatggtgt gggtggctga ggatcgatc        49
```

```
<210> SEQ ID NO 36
<211> LENGTH: 49
<212> TYPE: DNA
<213> ORGANISM: Artificial Sequence
<220> FEATURE:
<223> OTHER INFORMATION: synthetic aptamer

<400> SEQUENCE: 36
tccctgcatc gagcctctat gggatggttt gggtggctga ggatcgatc                49

<210> SEQ ID NO 37
<211> LENGTH: 50
<212> TYPE: DNA
<213> ORGANISM: Artificial Sequence
<220> FEATURE:
<223> OTHER INFORMATION: synthetic aptamer

<400> SEQUENCE: 37
tcccgatcgt tccgtggggt agtgttggtt ggggtggctg aggatcgatc               50

<210> SEQ ID NO 38
<211> LENGTH: 50
<212> TYPE: DNA
<213> ORGANISM: Artificial Sequence
<220> FEATURE:
<223> OTHER INFORMATION: synthetic aptamer

<400> SEQUENCE: 38
tccctatgga ttcggggtac gttagtggtc tgggtggctg aggatcgatc               50

<210> SEQ ID NO 39
<211> LENGTH: 50
<212> TYPE: DNA
<213> ORGANISM: Artificial Sequence
<220> FEATURE:
<223> OTHER INFORMATION: synthetic aptamer

<400> SEQUENCE: 39
tcccatcgat ctggggtagt tttattgggt tgggtggctg aggatcgatc               50

<210> SEQ ID NO 40
<211> LENGTH: 50
<212> TYPE: DNA
<213> ORGANISM: Artificial Sequence
<220> FEATURE:
<223> OTHER INFORMATION: synthetic aptamer

<400> SEQUENCE: 40
tccctgttgt tccggggtgg tttaatggtt tgggtggctg aggatcgatc               50

<210> SEQ ID NO 41
<211> LENGTH: 48
<212> TYPE: DNA
<213> ORGANISM: Artificial Sequence
<220> FEATURE:
<223> OTHER INFORMATION: synthetic aptamer

<400> SEQUENCE: 41
tcccattagg tccgtatact ggtgaggttg ggtggctgag gatcgatc                 48

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide - 3' fixed sequence
```

-continued

<400> SEQUENCE: 42
gtggctgagg atcgtatc                                                 18

<210> SEQ ID NO 43
<211> LENGTH: 49
<212> TYPE: DNA
<213> ORGANISM: Artificial Sequence
<220> FEATURE:
<223> OTHER INFORMATION: synthetic aptamer

<400> SEQUENCE: 43
tccctgcaat tcgatcagca ggggtggtgt gggtggctga ggatcgatc              49

<210> SEQ ID NO 44
<211> LENGTH: 51
<212> TYPE: DNA
<213> ORGANISM: Artificial Sequence
<220> FEATURE:
<223> OTHER INFORMATION: synthetic aptamer

<400> SEQUENCE: 44
tcccgggaga tcgcttcgaa aatggttggc gtgggtggct gaggatcgat c           51

<210> SEQ ID NO 45
<211> LENGTH: 50
<212> TYPE: DNA
<213> ORGANISM: Artificial Sequence
<220> FEATURE:
<223> OTHER INFORMATION: synthetic aptamer

<400> SEQUENCE: 45
tcccacgcat cgatcctata tgggtggcat ggggtggctg aggatcgatc             50

<210> SEQ ID NO 46
<211> LENGTH: 49
<212> TYPE: DNA
<213> ORGANISM: Artificial Sequence
<220> FEATURE:
<223> OTHER INFORMATION: synthetic aptamer

<400> SEQUENCE: 46
tcccgtaatc gagcctggta ttgttggcct gggtggctga ggatcgatc              49

<210> SEQ ID NO 47
<211> LENGTH: 49
<212> TYPE: DNA
<213> ORGANISM: Artificial Sequence
<220> FEATURE:
<223> OTHER INFORMATION: synthetic aptamer

<400> SEQUENCE: 47
tcccgcaatc ggtactcagg aggatggttg gggtggctga ggatcgatc              49

<210> SEQ ID NO 48
<211> LENGTH: 50
<212> TYPE: DNA
<213> ORGANISM: Artificial Sequence
<220> FEATURE:
<223> OTHER INFORMATION: synthetic aptamer

<400> SEQUENCE: 48
tcccgggatc gagtccgatt agggatggtg tgggtggctg aggatcgatc             50

```
<210> SEQ ID NO 49
<211> LENGTH: 50
<212> TYPE: DNA
<213> ORGANISM: Artificial Sequence
<220> FEATURE:
<223> OTHER INFORMATION: synthetic aptamer

<400> SEQUENCE: 49
tcccgggtgg ttatcttctc agggatggtg tgggtggctg aggatcgatc            50

<210> SEQ ID NO 50
<211> LENGTH: 49
<212> TYPE: DNA
<213> ORGANISM: Artificial Sequence
<220> FEATURE:
<223> OTHER INFORMATION: synthetic aptamer

<400> SEQUENCE: 50
tcccaagcga tctgtaaggg atggggttgc gggtggctga ggatcgatc             49

<210> SEQ ID NO 51
<211> LENGTH: 50
<212> TYPE: DNA
<213> ORGANISM: Artificial Sequence
<220> FEATURE:
<223> OTHER INFORMATION: synthetic aptamer

<400> SEQUENCE: 51
tcccgagtgt catatcatca gaggttggag tgggtggctg aggatcgatc            50

<210> SEQ ID NO 52
<211> LENGTH: 50
<212> TYPE: DNA
<213> ORGANISM: Artificial Sequence
<220> FEATURE:
<223> OTHER INFORMATION: synthetic aptamer

<400> SEQUENCE: 52
tcccaagatc ggtacataca gtgggtggtg agggtggctg aggatcgatc            50

<210> SEQ ID NO 53
<211> LENGTH: 50
<212> TYPE: DNA
<213> ORGANISM: Artificial Sequence
<220> FEATURE:
<223> OTHER INFORMATION: synthetic aptamer

<400> SEQUENCE: 53
tcctatcgat acggggtctt ctattgggtc ggggtggctg aggatcgatc            50

<210> SEQ ID NO 54
<211> LENGTH: 49
<212> TYPE: DNA
<213> ORGANISM: Artificial Sequence
<220> FEATURE:
<223> OTHER INFORMATION: synthetic aptamer

<400> SEQUENCE: 54
tcccgacttc gattactcag gggtggctgt gggtggctga ggatcgatc             49

<210> SEQ ID NO 55
<211> LENGTH: 49
<212> TYPE: DNA
<213> ORGANISM: Artificial Sequence
<220> FEATURE:
<223> OTHER INFORMATION: synthetic aptamer
```

-continued

```
<400> SEQUENCE: 55
tcccggtcga gtcctcacga agggttggga gggtggctga ggatcgatc            49

<210> SEQ ID NO 56
<211> LENGTH: 49
<212> TYPE: DNA
<213> ORGANISM: Artificial Sequence
<220> FEATURE:
<223> OTHER INFORMATION: synthetic aptamer

<400> SEQUENCE: 56
tcccatgatc gtcagattca gggatggtgt gggtggctga ggatcgatc            49

<210> SEQ ID NO 57
<211> LENGTH: 50
<212> TYPE: DNA
<213> ORGANISM: Artificial Sequence
<220> FEATURE:
<223> OTHER INFORMATION: synthetic aptamer

<400> SEQUENCE: 57
tcccggtcgt attagtgtgg gtggtgtagg gtggtggctg aggatcgatc           50

<210> SEQ ID NO 58
<211> LENGTH: 49
<212> TYPE: DNA
<213> ORGANISM: Artificial Sequence
<220> FEATURE:
<223> OTHER INFORMATION: synthetic aptamer

<400> SEQUENCE: 58
tcccatagta tcgagccgat tggatggtct gggtggctga ggatcgatc            49

<210> SEQ ID NO 59
<211> LENGTH: 49
<212> TYPE: DNA
<213> ORGANISM: Artificial Sequence
<220> FEATURE:
<223> OTHER INFORMATION: synthetic aptamer

<400> SEQUENCE: 59
tcccacggtc ctcacctagg atggttaggg tggtggctga ggatcgatc            49

<210> SEQ ID NO 60
<211> LENGTH: 49
<212> TYPE: DNA
<213> ORGANISM: Artificial Sequence
<220> FEATURE:
<223> OTHER INFORMATION: synthetic aptamer

<400> SEQUENCE: 60
tcccagagcg gaaatcctca ggggtggggt gggtggctga ggatcgatc            49

<210> SEQ ID NO 61
<211> LENGTH: 49
<212> TYPE: DNA
<213> ORGANISM: Artificial Sequence
<220> FEATURE:
<223> OTHER INFORMATION: synthetic aptamer

<400> SEQUENCE: 61
tcccggtagc gatccagaga gggatggggt gggtggctga ggatcgatc            49
```

```
<210> SEQ ID NO 62
<211> LENGTH: 49
<212> TYPE: DNA
<213> ORGANISM: Artificial Sequence
<220> FEATURE:
<223> OTHER INFORMATION: synthetic aptamer

<400> SEQUENCE: 62
tcccgcagta tcggtctggt tggttggatg gggtggctga ggatcgatc            49

<210> SEQ ID NO 63
<211> LENGTH: 47
<212> TYPE: DNA
<213> ORGANISM: Artificial Sequence
<220> FEATURE:
<223> OTHER INFORMATION: synthetic aptamer

<400> SEQUENCE: 63
tccgattgac gtggtgggtt actggtttgg gtggctgagg atcgatc              47

<210> SEQ ID NO 64
<211> LENGTH: 49
<212> TYPE: DNA
<213> ORGANISM: Artificial Sequence
<220> FEATURE:
<223> OTHER INFORMATION: synthetic aptamer

<400> SEQUENCE: 64
tcccattgat ctgtggtggt tttgtggttt gggtggctga ggatcgatc            49

<210> SEQ ID NO 65
<211> LENGTH: 49
<212> TYPE: DNA
<213> ORGANISM: Artificial Sequence
<220> FEATURE:
<223> OTHER INFORMATION: synthetic aptamer

<400> SEQUENCE: 65
tcccgtaatc gagcctggta ttgttggtct gggtggctga ggatcgatc            49

<210> SEQ ID NO 66
<211> LENGTH: 49
<212> TYPE: DNA
<213> ORGANISM: Artificial Sequence
<220> FEATURE:
<223> OTHER INFORMATION: synthetic aptamer

<400> SEQUENCE: 66
tcccatcgat ttggggtatg ttatgggctc gggtggctga ggatcgatc            49

<210> SEQ ID NO 67
<211> LENGTH: 50
<212> TYPE: DNA
<213> ORGANISM: Artificial Sequence
<220> FEATURE:
<223> OTHER INFORMATION: synthetic aptamer

<400> SEQUENCE: 67
tccctatcga gctgtggtag tattctggtt tgggtggctg aggatcgatc           50

<210> SEQ ID NO 68
<211> LENGTH: 49
<212> TYPE: DNA
<213> ORGANISM: Artificial Sequence
<220> FEATURE:
<223> OTHER INFORMATION: synthetic aptamer
```

<400> SEQUENCE: 68
tcccatcggt ccggggtaat ttactgggtc gggtggctga ggatcgatc     49

<210> SEQ ID NO 69
<211> LENGTH: 49
<212> TYPE: DNA
<213> ORGANISM: Artificial Sequence
<220> FEATURE:
<223> OTHER INFORMATION: synthetic aptamer

<400> SEQUENCE: 69
tcccgtcgag ccggggtatg attatgggtg gggtggctga ggatcgatc     49

<210> SEQ ID NO 70
<211> LENGTH: 50
<212> TYPE: DNA
<213> ORGANISM: Artificial Sequence
<220> FEATURE:
<223> OTHER INFORMATION: synthetic aptamer

<400> SEQUENCE: 70
tccctggaga tccggggtag tatactggtt tgggtggctg aggatcgatc     50

<210> SEQ ID NO 71
<211> LENGTH: 48
<212> TYPE: DNA
<213> ORGANISM: Artificial Sequence
<220> FEATURE:
<223> OTHER INFORMATION: synthetic aptamer

<400> SEQUENCE: 71
tcccaatcga gccggggttt gtttgttctg ggtggctgag gatcgatc     48

<210> SEQ ID NO 72
<211> LENGTH: 49
<212> TYPE: DNA
<213> ORGANISM: Artificial Sequence
<220> FEATURE:
<223> OTHER INFORMATION: synthetic aptamer

<400> SEQUENCE: 72
tcccgtaatc gagcctggta ttgttggtct gggtggctga ggatcgatc     49

<210> SEQ ID NO 73
<211> LENGTH: 50
<212> TYPE: DNA
<213> ORGANISM: Artificial Sequence
<220> FEATURE:
<223> OTHER INFORMATION: synthetic aptamer

<400> SEQUENCE: 73
tcccagatgt gatccgtatc ctggtttggt tgggtggctg aggatcgatc     50

<210> SEQ ID NO 74
<211> LENGTH: 49
<212> TYPE: DNA
<213> ORGANISM: Artificial Sequence
<220> FEATURE:
<223> OTHER INFORMATION: synthetic aptamer

<400> SEQUENCE: 74
tccctgatcc ttaggctagg ttgggtgggg tggtggctga ggatcgatc     49

```
<210> SEQ ID NO 75
<211> LENGTH: 49
<212> TYPE: DNA
<213> ORGANISM: Artificial Sequence
<220> FEATURE:
<223> OTHER INFORMATION: synthetic aptamer

<400> SEQUENCE: 75
tcccatcgag ccggggatgg tttgttggag gggtggctga ggatcgatc            49

<210> SEQ ID NO 76
<211> LENGTH: 49
<212> TYPE: DNA
<213> ORGANISM: Artificial Sequence
<220> FEATURE:
<223> OTHER INFORMATION: synthetic aptamer

<400> SEQUENCE: 76
tccctcgatc ttggggtact atagtggtgt gggtggctga ggatcgatc            49

<210> SEQ ID NO 77
<211> LENGTH: 49
<212> TYPE: DNA
<213> ORGANISM: Artificial Sequence
<220> FEATURE:
<223> OTHER INFORMATION: synthetic aptamer

<400> SEQUENCE: 77
tcccgctcga tttcgaagaa tggttggttt gggtggctga ggatcgatc            49

<210> SEQ ID NO 78
<211> LENGTH: 48
<212> TYPE: DNA
<213> ORGANISM: Artificial Sequence
<220> FEATURE:
<223> OTHER INFORMATION: synthetic aptamer

<400> SEQUENCE: 78
tcccgattat ccgttggtat tgttggtctg ggtggctgag gatcgatc             48

<210> SEQ ID NO 79
<211> LENGTH: 47
<212> TYPE: DNA
<213> ORGANISM: Artificial Sequence
<220> FEATURE:
<223> OTHER INFORMATION: synthetic aptamer

<400> SEQUENCE: 79
tcccaacgat ctgtggtttt tttgttctgg gtggctgagg atcgatc              47

<210> SEQ ID NO 80
<211> LENGTH: 48
<212> TYPE: DNA
<213> ORGANISM: Artificial Sequence
<220> FEATURE:
<223> OTHER INFORMATION: synthetic aptamer

<400> SEQUENCE: 80
tcccaaggat ccggggtagt tagtggctga ggtggctgag gatcgatc             48

<210> SEQ ID NO 81
<211> LENGTH: 49
<212> TYPE: DNA
<213> ORGANISM: Artificial Sequence
<220> FEATURE:
<223> OTHER INFORMATION: synthetic aptamer
```

```
<400> SEQUENCE: 81
tcccatgtgt tagatccgtg tggttggact gggtggctga ggatcgatc        49

<210> SEQ ID NO 82
<211> LENGTH: 50
<212> TYPE: DNA
<213> ORGANISM: Artificial Sequence
<220> FEATURE:
<223> OTHER INFORMATION: synthetic aptamer

<400> SEQUENCE: 82
tccccgatgt gtcagcctag ggtggttagg gtggtggctg aggatcgatc       50

<210> SEQ ID NO 83
<211> LENGTH: 50
<212> TYPE: DNA
<213> ORGANISM: Artificial Sequence
<220> FEATURE:
<223> OTHER INFORMATION: synthetic aptamer

<400> SEQUENCE: 83
tcccatgatt ggccggggtg tcttttgggt cgggtggctg aggatcgatc       50

<210> SEQ ID NO 84
<211> LENGTH: 49
<212> TYPE: DNA
<213> ORGANISM: Artificial Sequence
<220> FEATURE:
<223> OTHER INFORMATION: synthetic aptamer

<400> SEQUENCE: 84
tcctgaggga tcaggctagg ttgggtaggg tggtggctga ggatcgatc        49

<210> SEQ ID NO 85
<211> LENGTH: 50
<212> TYPE: DNA
<213> ORGANISM: Artificial Sequence
<220> FEATURE:
<223> OTHER INFORMATION: synthetic aptamer

<400> SEQUENCE: 85
tcccgatcgt ttcgtggggt agtgttggtt ggggtggctg aggatcgatc       50

<210> SEQ ID NO 86
<211> LENGTH: 50
<212> TYPE: DNA
<213> ORGANISM: Artificial Sequence
<220> FEATURE:
<223> OTHER INFORMATION: synthetic aptamer

<400> SEQUENCE: 86
tcccgagcga tactgcctag gctgggtagg gtggtggctg aggatcgatc       50

<210> SEQ ID NO 87
<211> LENGTH: 47
<212> TYPE: DNA
<213> ORGANISM: Artificial Sequence
<220> FEATURE:
<223> OTHER INFORMATION: synthetic aptamer

<400> SEQUENCE: 87
tcctgtcgat cggtacgttt tcgtttctgg gtggctgagg atcgatc          47
```

```
<210> SEQ ID NO 88
<211> LENGTH: 49
<212> TYPE: DNA
<213> ORGANISM: Artificial Sequence
<220> FEATURE:
<223> OTHER INFORMATION: synthetic aptamer

<400> SEQUENCE: 88
tccctgcaat cggtgctcga gaggttgggt gggtggctga ggatcgatc            49

<210> SEQ ID NO 89
<211> LENGTH: 50
<212> TYPE: DNA
<213> ORGANISM: Artificial Sequence
<220> FEATURE:
<223> OTHER INFORMATION: synthetic aptamer

<400> SEQUENCE: 89
tcccgatttg agtttagtag ggtgggtagg atggtggctg aggatcgatc            50

<210> SEQ ID NO 90
<211> LENGTH: 49
<212> TYPE: DNA
<213> ORGANISM: Artificial Sequence
<220> FEATURE:
<223> OTHER INFORMATION: synthetic aptamer

<400> SEQUENCE: 90
tcccatgatc gggtcggtat ttgttggtca gggtggctga ggatcgatc            49

<210> SEQ ID NO 91
<211> LENGTH: 50
<212> TYPE: DNA
<213> ORGANISM: Artificial Sequence
<220> FEATURE:
<223> OTHER INFORMATION: synthetic aptamer

<400> SEQUENCE: 91
tcccagcggt cctaatgggt agtgttggtt tgggtggctg aggatcgatc            50

<210> SEQ ID NO 92
<211> LENGTH: 50
<212> TYPE: DNA
<213> ORGANISM: Artificial Sequence
<220> FEATURE:
<223> OTHER INFORMATION: synthetic aptamer

<400> SEQUENCE: 92
tcccgagcga tactgcctag gttgggtagg gtggtggctg aggatcgatc            50

<210> SEQ ID NO 93
<211> LENGTH: 49
<212> TYPE: DNA
<213> ORGANISM: Artificial Sequence
<220> FEATURE:
<223> OTHER INFORMATION: synthetic aptamer

<400> SEQUENCE: 93
tcccttgtcg attctggtat gttttggtcc gggtggctga ggatcgatc            49

<210> SEQ ID NO 94
<211> LENGTH: 49
<212> TYPE: DNA
<213> ORGANISM: Artificial Sequence
<220> FEATURE:
<223> OTHER INFORMATION: synthetic aptamer
```

```
<400> SEQUENCE: 94
tcccatgaac tcagggtaat tttttggtgt gggtggctga ggatcgatc          49

<210> SEQ ID NO 95
<211> LENGTH: 48
<212> TYPE: DNA
<213> ORGANISM: Artificial Sequence
<220> FEATURE:
<223> OTHER INFORMATION: synthetic aptamer

<400> SEQUENCE: 95
tcccatcgat ccggggtatt cttatttctg ggtggctgag gatcgatc           48

<210> SEQ ID NO 96
<211> LENGTH: 49
<212> TYPE: DNA
<213> ORGANISM: Artificial Sequence
<220> FEATURE:
<223> OTHER INFORMATION: synthetic aptamer

<400> SEQUENCE: 96
tcccggtcga gactcggagt atggcagggt gggtggctga ggatcgatc          49

<210> SEQ ID NO 97
<211> LENGTH: 50
<212> TYPE: DNA
<213> ORGANISM: Artificial Sequence
<220> FEATURE:
<223> OTHER INFORMATION: synthetic aptamer

<400> SEQUENCE: 97
tcccgagtga tccggggtgt tttttgggt tgggtggctg aggatcgatc          50

<210> SEQ ID NO 98
<211> LENGTH: 47
<212> TYPE: DNA
<213> ORGANISM: Artificial Sequence
<220> FEATURE:
<223> OTHER INFORMATION: synthetic aptamer

<400> SEQUENCE: 98
tcccgatcgg acgtggtggg ttacttctgg gtggctgagg atcgatc            47

<210> SEQ ID NO 99
<211> LENGTH: 50
<212> TYPE: DNA
<213> ORGANISM: Artificial Sequence
<220> FEATURE:
<223> OTHER INFORMATION: synthetic aptamer

<400> SEQUENCE: 99
tcccatcgag acggggtgtc ttttgtggct tgggtggctg aggatcgatc         50

<210> SEQ ID NO 100
<211> LENGTH: 50
<212> TYPE: DNA
<213> ORGANISM: Artificial Sequence
<220> FEATURE:
<223> OTHER INFORMATION: synthetic aptamer

<400> SEQUENCE: 100 tccctttgatc tggggtgcgt tattgtggtt cgggtggctg aggatcgatc        50
```

<210> SEQ ID NO 101
<211> LENGTH: 49
<212> TYPE: DNA
<213> ORGANISM: Artificial Sequence
<220> FEATURE:
<223> OTHER INFORMATION: synthetic aptamer

<400> SEQUENCE: 101
tccctatcga ccggggttct ttcgtggttc gggtggctga ggatcgatc            49

<210> SEQ ID NO 102
<211> LENGTH: 50
<212> TYPE: DNA
<213> ORGANISM: Artificial Sequence
<220> FEATURE:
<223> OTHER INFORMATION: synthetic aptamer

<400> SEQUENCE: 102
tcccattggt ccggggattg gtggctgggt ggggtggctg aggatcgatc            50

<210> SEQ ID NO 103
<211> LENGTH: 48
<212> TYPE: DNA
<213> ORGANISM: Artificial Sequence
<220> FEATURE:
<223> OTHER INFORMATION: synthetic aptamer

<400> SEQUENCE: 103
tcccggatct gtggtaggtt tgttgggttg ggtggctgag gatcgatc              48

<210> SEQ ID NO 104
<211> LENGTH: 49
<212> TYPE: DNA
<213> ORGANISM: Artificial Sequence
<220> FEATURE:
<223> OTHER INFORMATION: synthetic aptamer

<400> SEQUENCE: 104
tcccatcgag tcgtggtgtt ttgttggcct gggtggctga ggatcgatc            49

<210> SEQ ID NO 105
<211> LENGTH: 47
<212> TYPE: DNA
<213> ORGANISM: Artificial Sequence
<220> FEATURE:
<223> OTHER INFORMATION: synthetic aptamer

<400> SEQUENCE: 105
tcccgatcga gagtggtatt tgttttctgg gtggctgagg atcgatc               47

<210> SEQ ID NO 106
<211> LENGTH: 50
<212> TYPE: DNA
<213> ORGANISM: Artificial Sequence
<220> FEATURE:
<223> OTHER INFORMATION: synthetic aptamer

<400> SEQUENCE: 106
tcccttgatc cggtggtagt tttattggtg cgggtggctg aggatcgatc            50

<210> SEQ ID NO 107
<211> LENGTH: 49
<212> TYPE: DNA
<213> ORGANISM: Artificial Sequence
<220> FEATURE:
<223> OTHER INFORMATION: synthetic aptamer -continued

<400> SEQUENCE: 107
tcccatcgat ccgtggtact tttgtggcta gggtggctga ggatcgatc        49

<210> SEQ ID NO 108
<211> LENGTH: 49
<212> TYPE: DNA
<213> ORGANISM: Artificial Sequence
<220> FEATURE:
<223> OTHER INFORMATION: synthetic aptamer

<400> SEQUENCE: 108
tcccgtcgat ctggggtgtc tatgtgggtg gggtggctga ggatcgatc        49

<210> SEQ ID NO 109
<211> LENGTH: 49
<212> TYPE: DNA
<213> ORGANISM: Artificial Sequence
<220> FEATURE:
<223> OTHER INFORMATION: synthetic aptamer

<400> SEQUENCE: 109
tcccgatcgt agtcctggta ttgttggtct gggtggctga ggatcgatc        49

<210> SEQ ID NO 110
<211> LENGTH: 48
<212> TYPE: DNA
<213> ORGANISM: Artificial Sequence
<220> FEATURE:
<223> OTHER INFORMATION: synthetic aptamer

<400> SEQUENCE: 110
tccctaacga tctgaggtgt tttttttctg ggtggctgag gatcgatc         48

<210> SEQ ID NO 111
<211> LENGTH: 50
<212> TYPE: DNA
<213> ORGANISM: Artificial Sequence
<220> FEATURE:
<223> OTHER INFORMATION: synthetic aptamer

<400> SEQUENCE: 111
tccctgtcgt tccgtggtgt ttttatgggc tgggtggctg aggatcgatc       50

<210> SEQ ID NO 112
<211> LENGTH: 49
<212> TYPE: DNA
<213> ORGANISM: Artificial Sequence
<220> FEATURE:
<223> OTHER INFORMATION: synthetic aptamer

<400> SEQUENCE: 112
tcccatcggt cggggtaatt ttattgggtg gggtggctga ggatcgatc        49

<210> SEQ ID NO 113
<211> LENGTH: 50
<212> TYPE: DNA
<213> ORGANISM: Artificial Sequence
<220> FEATURE:
<223> OTHER INFORMATION: synthetic aptamer

<400> SEQUENCE: 113
tcccttgttt gatccggggt gttaatggtt ggggtggctg aggatcgatc       50

```
<210> SEQ ID NO 114
<211> LENGTH: 51
<212> TYPE: DNA
<213> ORGANISM: Artificial Sequence
<220> FEATURE:
<223> OTHER INFORMATION: synthetic aptamer

<400> SEQUENCE: 114
tccctcgatg cttatgggta ttgtatgggt ttgggtggct gaggatcgat c          51

<210> SEQ ID NO 115
<211> LENGTH: 48
<212> TYPE: DNA
<213> ORGANISM: Artificial Sequence
<220> FEATURE:
<223> OTHER INFORMATION: synthetic aptamer

<400> SEQUENCE: 115
tcccatcggt ccaaggtatt tttgtttctg ggtggctgag gatcgatc              48

<210> SEQ ID NO 116
<211> LENGTH: 50
<212> TYPE: DNA
<213> ORGANISM: Artificial Sequence
<220> FEATURE:
<223> OTHER INFORMATION: synthetic aptamer

<400> SEQUENCE: 116
tcccatcttc tgtagcctag gttgggtagg gtggtggctg aggatcgatc            50

<210> SEQ ID NO 117
<211> LENGTH: 48
<212> TYPE: DNA
<213> ORGANISM: Artificial Sequence
<220> FEATURE:
<223> OTHER INFORMATION: synthetic aptamer

<400> SEQUENCE: 117
tccctatgga tccggggtac gttagttctg ggtggctgag gatcgatc              48

<210> SEQ ID NO 118
<211> LENGTH: 50
<212> TYPE: DNA
<213> ORGANISM: Artificial Sequence
<220> FEATURE:
<223> OTHER INFORMATION: synthetic aptamer

<400> SEQUENCE: 118
tccctcggtc ctcgtctttt ttggtctggg tgggtggctg aggatcgatc            50

<210> SEQ ID NO 119
<211> LENGTH: 47
<212> TYPE: DNA
<213> ORGANISM: Artificial Sequence
<220> FEATURE:
<223> OTHER INFORMATION: synthetic aptamer

<400> SEQUENCE: 119
tccctgcgtc gatcgtggta tcgtttctgg gtggctgagg atcgatc               47

<210> SEQ ID NO 120
<211> LENGTH: 50
<212> TYPE: DNA
<213> ORGANISM: Artificial Sequence
<220> FEATURE:
<223> OTHER INFORMATION: synthetic aptamer
```

<400> SEQUENCE: 120
tcctgagcga ttcggggtgt tttcatggtt cgggtggctg aggatcgatc        50

<210> SEQ ID NO 121
<211> LENGTH: 50
<212> TYPE: DNA
<213> ORGANISM: Artificial Sequence
<220> FEATURE:
<223> OTHER INFORMATION: synthetic aptamer

<400> SEQUENCE: 121
tccctatcga ttgctcctag gatgggtagg gtggtggctg aggatcgatc        50

<210> SEQ ID NO 122
<211> LENGTH: 49
<212> TYPE: DNA
<213> ORGANISM: Artificial Sequence
<220> FEATURE:
<223> OTHER INFORMATION: synthetic aptamer

<400> SEQUENCE: 122
tcccatggat ccgaggtgtt ttagtggtcc gggtggctga ggatcgatc         49

<210> SEQ ID NO 123
<211> LENGTH: 50
<212> TYPE: DNA
<213> ORGANISM: Artificial Sequence
<220> FEATURE:
<223> OTHER INFORMATION: synthetic aptamer

<400> SEQUENCE: 123
tctctgacga tccggggtgc aaattgtggt ggggtggctg aggatcgatc        50

<210> SEQ ID NO 124
<211> LENGTH: 49
<212> TYPE: DNA
<213> ORGANISM: Artificial Sequence
<220> FEATURE:
<223> OTHER INFORMATION: synthetic aptamer

<400> SEQUENCE: 124
tcccgtaatt gagcttggta ttgttggtct gggtggctga ggatcgatc         49

<210> SEQ ID NO 125
<211> LENGTH: 49
<212> TYPE: DNA
<213> ORGANISM: Artificial Sequence
<220> FEATURE:
<223> OTHER INFORMATION: synthetic aptamer

<400> SEQUENCE: 125
tcccaccgat ccggggtaaa tgaatggcgt gggtggctga ggatcgatc         49

<210> SEQ ID NO 126
<211> LENGTH: 48
<212> TYPE: DNA
<213> ORGANISM: Artificial Sequence
<220> FEATURE:
<223> OTHER INFORMATION: synthetic aptamer

<400> SEQUENCE: 126
tccctcgatc aaggtgttta ttatggtgtg ggtggctgag gatcgatc          48

```
<210> SEQ ID NO 127
<211> LENGTH: 50
<212> TYPE: DNA
<213> ORGANISM: Artificial Sequence
<220> FEATURE:
<223> OTHER INFORMATION: synthetic aptamer

<400> SEQUENCE: 127
tcccttctga tccgaggtgt tttattggtg tgggtggctg aggatcgatc          50

<210> SEQ ID NO 128
<211> LENGTH: 50
<212> TYPE: DNA
<213> ORGANISM: Artificial Sequence
<220> FEATURE:
<223> OTHER INFORMATION: synthetic aptamer

<400> SEQUENCE: 128
tcccatcgaa ccttgagggt attgttggtt tgggtggctg aggatcgatc          50

<210> SEQ ID NO 129
<211> LENGTH: 49
<212> TYPE: DNA
<213> ORGANISM: Artificial Sequence
<220> FEATURE:
<223> OTHER INFORMATION: synthetic aptamer

<400> SEQUENCE: 129
tcccatcgat tcgtggtctt tttatggtgt gggtggctga ggatcgatc           49

<210> SEQ ID NO 130
<211> LENGTH: 49
<212> TYPE: DNA
<213> ORGANISM: Artificial Sequence
<220> FEATURE:
<223> OTHER INFORMATION: synthetic aptamer

<400> SEQUENCE: 130
tcccgtaatc gagcttggta ttgttggtct gggtggctga ggatcgatc           49

<210> SEQ ID NO 131
<211> LENGTH: 50
<212> TYPE: DNA
<213> ORGANISM: Artificial Sequence
<220> FEATURE:
<223> OTHER INFORMATION: synthetic aptamer

<400> SEQUENCE: 131
tccctcgtat tccgggggat catattggtc ggggtggctg aggatcgatc          50

<210> SEQ ID NO 132
<211> LENGTH: 49
<212> TYPE: DNA
<213> ORGANISM: Artificial Sequence
<220> FEATURE:
<223> OTHER INFORMATION: synthetic aptamer

<400> SEQUENCE: 132
tcccaggacc gatcctggta ttgttggtgg gggtggctga ggatcgatc           49

<210> SEQ ID NO 133
<211> LENGTH: 50
<212> TYPE: DNA
<213> ORGANISM: Artificial Sequence
<220> FEATURE:
<223> OTHER INFORMATION: synthetic aptamer
```

```
<400> SEQUENCE: 133
tcctgtcgat ccctacgggt agtgttggtt tgggtggctg aggatcgatc            50

<210> SEQ ID NO 134
<211> LENGTH: 49
<212> TYPE: DNA
<213> ORGANISM: Artificial Sequence
<220> FEATURE:
<223> OTHER INFORMATION: synthetic aptamer

<400> SEQUENCE: 134
tcccattgat ccggggtggt tttctggttt gggtggctga ggatcgatc             49

<210> SEQ ID NO 135
<211> LENGTH: 48
<212> TYPE: DNA
<213> ORGANISM: Artificial Sequence
<220> FEATURE:
<223> OTHER INFORMATION: synthetic aptamer

<400> SEQUENCE: 135
tcccgtcgat tcggtatggt ttcgtttctg ggtggctgag gatcgatc              48

<210> SEQ ID NO 136
<211> LENGTH: 49
<212> TYPE: DNA
<213> ORGANISM: Artificial Sequence
<220> FEATURE:
<223> OTHER INFORMATION: synthetic aptamer

<400> SEQUENCE: 136
tcccatcgat ttgtcctcag aggttggcgt gggtggctga ggatcgatc             49

<210> SEQ ID NO 137
<211> LENGTH: 50
<212> TYPE: DNA
<213> ORGANISM: Artificial Sequence
<220> FEATURE:
<223> OTHER INFORMATION: synthetic aptamer

<400> SEQUENCE: 137
tcccgagcga tcggggtggt tttttgggag tgggtggctg aggatcgatc            50

<210> SEQ ID NO 138
<211> LENGTH: 50
<212> TYPE: DNA
<213> ORGANISM: Artificial Sequence
<220> FEATURE:
<223> OTHER INFORMATION: synthetic aptamer

<400> SEQUENCE: 138
tcccgtcgat caggggtaat ttgctggtgg tgggtggctg aggatcgatc            50

<210> SEQ ID NO 139
<211> LENGTH: 50
<212> TYPE: DNA
<213> ORGANISM: Artificial Sequence
<220> FEATURE:
<223> OTHER INFORMATION: synthetic aptamer

<400> SEQUENCE: 139
ttcctgtcga taaggggtat tatagtggtg tgggtggctg aggatcgatc            50
```

```
<210> SEQ ID NO 140
<211> LENGTH: 49
<212> TYPE: DNA
<213> ORGANISM: Artificial Sequence
<220> FEATURE:
<223> OTHER INFORMATION: synthetic aptamer

<400> SEQUENCE: 140
tctcattcgt tccggggtat ttagtgggtc gggtggctga ggatcgatc          49

<210> SEQ ID NO 141
<211> LENGTH: 50
<212> TYPE: DNA
<213> ORGANISM: Artificial Sequence
<220> FEATURE:
<223> OTHER INFORMATION: synthetic aptamer

<400> SEQUENCE: 141
tcccgaggga cgacgcctag gttgggtagg gtggtggctg aggatcgatc         50

<210> SEQ ID NO 142
<211> LENGTH: 50
<212> TYPE: DNA
<213> ORGANISM: Artificial Sequence
<220> FEATURE:
<223> OTHER INFORMATION: synthetic aptamer

<400> SEQUENCE: 142
tcccgatcta tccggggtac atttgtggtt tgggtggctg aggatcgatc         50

<210> SEQ ID NO 143
<211> LENGTH: 48
<212> TYPE: DNA
<213> ORGANISM: Artificial Sequence
<220> FEATURE:
<223> OTHER INFORMATION: synthetic aptamer

<400> SEQUENCE: 143
tcccgatcgc tgtcctagga tgggtagggt ggtggctgag gatcgatc           48

<210> SEQ ID NO 144
<211> LENGTH: 50
<212> TYPE: DNA
<213> ORGANISM: Artificial Sequence
<220> FEATURE:
<223> OTHER INFORMATION: synthetic aptamer

<400> SEQUENCE: 144
tcccgcgatc tctggggtaa cgttttggtg tgggtggctg aggatcgatc         50

<210> SEQ ID NO 145
<211> LENGTH: 48
<212> TYPE: DNA
<213> ORGANISM: Artificial Sequence
<220> FEATURE:
<223> OTHER INFORMATION: synthetic aptamer

<400> SEQUENCE: 145
tcccgattga ttctgggagg tttggttctg ggtggctgag gatcgatc           48

<210> SEQ ID NO 146
<211> LENGTH: 50
<212> TYPE: DNA
<213> ORGANISM: Artificial Sequence
<220> FEATURE:
<223> OTHER INFORMATION: synthetic aptamer
```

<400> SEQUENCE: 146
tcccgttcga gtcctggtgt tttattggcc tgggtggctg aggatcgatc      50

<210> SEQ ID NO 147
<211> LENGTH: 50
<212> TYPE: DNA
<213> ORGANISM: Artificial Sequence
<220> FEATURE:
<223> OTHER INFORMATION: synthetic aptamer

<400> SEQUENCE: 147
tcccgcattg aataggactc agggatggtg tgggtggctg aggatcgatc      50

<210> SEQ ID NO 148
<211> LENGTH: 49
<212> TYPE: DNA
<213> ORGANISM: Artificial Sequence
<220> FEATURE:
<223> OTHER INFORMATION: synthetic aptamer

<400> SEQUENCE: 148
tccctcgatc taaggtgctt ttagtggttt gggtggctga ggatcgatc       49

<210> SEQ ID NO 149
<211> LENGTH: 49
<212> TYPE: DNA
<213> ORGANISM: Artificial Sequence
<220> FEATURE:
<223> OTHER INFORMATION: synthetic aptamer

<400> SEQUENCE: 149
tctcgatcgg acgtggtggg ttactggctt gggtggctga ggatcgatc       49

<210> SEQ ID NO 150
<211> LENGTH: 49
<212> TYPE: DNA
<213> ORGANISM: Artificial Sequence
<220> FEATURE:
<223> OTHER INFORMATION: synthetic aptamer

<400> SEQUENCE: 150
tcccaggatc gattctggta ttgttggtgg gggtggctga ggatcgatc       49

<210> SEQ ID NO 151
<211> LENGTH: 49
<212> TYPE: DNA
<213> ORGANISM: Artificial Sequence
<220> FEATURE:
<223> OTHER INFORMATION: synthetic aptamer

<400> SEQUENCE: 151
tcccatcgat ctgtggtggt tttgtggttt gggtggctga ggatcgatc       49

<210> SEQ ID NO 152
<211> LENGTH: 49
<212> TYPE: DNA
<213> ORGANISM: Artificial Sequence
<220> FEATURE:
<223> OTHER INFORMATION: synthetic aptamer

<400> SEQUENCE: 152
tcccagagag ccggggtata attgtggtgt gggtggctga ggatcgatc       49

```
<210> SEQ ID NO 153
<211> LENGTH: 48
<212> TYPE: DNA
<213> ORGANISM: Artificial Sequence
<220> FEATURE:
<223> OTHER INFORMATION: synthetic aptamer

<400> SEQUENCE: 153
tcccatcgat ctgtggtctt ttttggtgtg ggtggctgag gatcgatc                  48

<210> SEQ ID NO 154
<211> LENGTH: 49
<212> TYPE: DNA
<213> ORGANISM: Artificial Sequence
<220> FEATURE:
<223> OTHER INFORMATION: synthetic aptamer

<400> SEQUENCE: 154
tcccacgatc cggggtgtct ttcgtgggct gggtggctga ggatcgatc                 49

<210> SEQ ID NO 155
<211> LENGTH: 48
<212> TYPE: DNA
<213> ORGANISM: Artificial Sequence
<220> FEATURE:
<223> OTHER INFORMATION: synthetic aptamer

<400> SEQUENCE: 155
tcccgatttc gattctggta gtgttttctg ggtggctgag gatcgatc                  48

<210> SEQ ID NO 156
<211> LENGTH: 50
<212> TYPE: DNA
<213> ORGANISM: Artificial Sequence
<220> FEATURE:
<223> OTHER INFORMATION: synthetic aptamer

<400> SEQUENCE: 156
tcccatcgaa ccgcgggtaa tcttatgggt cgggtggctg aggatcgatc                50

<210> SEQ ID NO 157
<211> LENGTH: 50
<212> TYPE: DNA
<213> ORGANISM: Artificial Sequence
<220> FEATURE:
<223> OTHER INFORMATION: synthetic aptamer

<400> SEQUENCE: 157
tcccatcgag ccgggtatgt ttcgttgggc tgggtggctg aggatcgatc                50

<210> SEQ ID NO 158
<211> LENGTH: 49
<212> TYPE: DNA
<213> ORGANISM: Artificial Sequence
<220> FEATURE:
<223> OTHER INFORMATION: synthetic aptamer

<400> SEQUENCE: 158
tcccatcgat ccgcggtact ttcgtggctt gggtggctga ggatcgatc                 49

<210> SEQ ID NO 159
<211> LENGTH: 49
<212> TYPE: DNA
<213> ORGANISM: Artificial Sequence
<220> FEATURE:
<223> OTHER INFORMATION: synthetic aptamer
```

```
<400> SEQUENCE: 159
tcccatcgat acggggtgga atcttgsggt gggtggctga ggatcgatc         49

<210> SEQ ID NO 160
<211> LENGTH: 50
<212> TYPE: DNA
<213> ORGANISM: Artificial Sequence
<220> FEATURE:
<223> OTHER INFORMATION: synthetic aptamer

<400> SEQUENCE: 160
tcccgattgt cataggtggt ttgtctgggt agggtggctg aggatcgatc        50

<210> SEQ ID NO 161
<211> LENGTH: 50
<212> TYPE: DNA
<213> ORGANISM: Artificial Sequence
<220> FEATURE:
<223> OTHER INFORMATION: synthetic aptamer

<400> SEQUENCE: 161
tcccgagatc tttatagggt attgttggtt ggggtggctg aggatcgatc        50

<210> SEQ ID NO 162
<211> LENGTH: 50
<212> TYPE: DNA
<213> ORGANISM: Artificial Sequence
<220> FEATURE:
<223> OTHER INFORMATION: synthetic aptamer

<400> SEQUENCE: 162
tcccgtgatc tctggggtaa cgtcttggtg tgggtggctg aggatcgatc        50

<210> SEQ ID NO 163
<211> LENGTH: 47
<212> TYPE: DNA
<213> ORGANISM: Artificial Sequence
<220> FEATURE:
<223> OTHER INFORMATION: synthetic aptamer

<400> SEQUENCE: 163
tcccttgatc ctggtacata tattttctgg gtggctgagg atcgatc           47

<210> SEQ ID NO 164
<211> LENGTH: 50
<212> TYPE: DNA
<213> ORGANISM: Artificial Sequence
<220> FEATURE:
<223> OTHER INFORMATION: synthetic aptamer

<400> SEQUENCE: 164
tccttgtcga gccttggggt agtgttggtt tgggtggctg aggatcgatc        50

<210> SEQ ID NO 165
<211> LENGTH: 49
<212> TYPE: DNA
<213> ORGANISM: Artificial Sequence
<220> FEATURE:
<223> OTHER INFORMATION: synthetic aptamer

<400> SEQUENCE: 165
tcccgttcgg tccgtatact ggtggtggtt gggtggctga ggatcgatc         49
```

<210> SEQ ID NO 166
<211> LENGTH: 48
<212> TYPE: DNA
<213> ORGANISM: Artificial Sequence
<220> FEATURE:
<223> OTHER INFORMATION: synthetic aptamer

<400> SEQUENCE: 166
tccctagatc gggtcctggt agtgtttctg ggtggctgag gatcgatc        48

<210> SEQ ID NO 167
<211> LENGTH: 48
<212> TYPE: DNA
<213> ORGANISM: Artificial Sequence
<220> FEATURE:
<223> OTHER INFORMATION: synthetic aptamer

<400> SEQUENCE: 167
tcccaagatc gatgctggta gtgttttctg ggtggctgag gatcgatc        48

<210> SEQ ID NO 168
<211> LENGTH: 50
<212> TYPE: DNA
<213> ORGANISM: Artificial Sequence
<220> FEATURE:
<223> OTHER INFORMATION: synthetic aptamer

<400> SEQUENCE: 168
tcccgatcgg tcccaagggt attgttggtt tgggtggctg aggatcgatc        50

<210> SEQ ID NO 169
<211> LENGTH: 50
<212> TYPE: DNA
<213> ORGANISM: Artificial Sequence
<220> FEATURE:
<223> OTHER INFORMATION: synthetic aptamer

<400> SEQUENCE: 169
tcccgctatt cgatcttcaa ttgggtggtc agggtggctg aggatcgatc        50

<210> SEQ ID NO 170
<211> LENGTH: 48
<212> TYPE: DNA
<213> ORGANISM: Artificial Sequence
<220> FEATURE:
<223> OTHER INFORMATION: synthetic aptamer

<400> SEQUENCE: 170
tcccgtcggt ccgttcggta tttttttctg ggtggctgag gatcgatc        48

<210> SEQ ID NO 171
<211> LENGTH: 48
<212> TYPE: DNA
<213> ORGANISM: Artificial Sequence
<220> FEATURE:
<223> OTHER INFORMATION: synthetic aptamer

<400> SEQUENCE: 171
tccctatgga ttcggggtac gttagttctg ggtggctgag gatcgatc        48

<210> SEQ ID NO 172
<211> LENGTH: 49
<212> TYPE: DNA
<213> ORGANISM: Artificial Sequence
<220> FEATURE:
<223> OTHER INFORMATION: synthetic aptamer

```
<400> SEQUENCE: 172
tcccgattgg aaagcctagg atgggtaggg tggtggctga ggatcgatc          49

<210> SEQ ID NO 173
<211> LENGTH: 49
<212> TYPE: DNA
<213> ORGANISM: Artificial Sequence
<220> FEATURE:
<223> OTHER INFORMATION: synthetic aptamer

<400> SEQUENCE: 173
tcccaggacc gatcttggta ttgttggtgg gggtggctga ggatcgatc          49

<210> SEQ ID NO 174
<211> LENGTH: 47
<212> TYPE: DNA
<213> ORGANISM: Artificial Sequence
<220> FEATURE:
<223> OTHER INFORMATION: synthetic aptamer

<400> SEQUENCE: 174
tcccatcgtc tgtggtatag gaacttctgg gtggctgagg atcgatc            47

<210> SEQ ID NO 175
<211> LENGTH: 50
<212> TYPE: DNA
<213> ORGANISM: Artificial Sequence
<220> FEATURE:
<223> OTHER INFORMATION: synthetic aptamer

<400> SEQUENCE: 175
tcccatcgaa cctcgagggt attgttggct tgggtggctg aggatcgatc         50

<210> SEQ ID NO 176
<211> LENGTH: 50
<212> TYPE: DNA
<213> ORGANISM: Artificial Sequence
<220> FEATURE:
<223> OTHER INFORMATION: synthetic aptamer

<400> SEQUENCE: 176
tcccggtatc gtcatgctgg tggaattggt tgggtggctg aggatcgatc         50

<210> SEQ ID NO 177
<211> LENGTH: 50
<212> TYPE: DNA
<213> ORGANISM: Artificial Sequence
<220> FEATURE:
<223> OTHER INFORMATION: synthetic aptamer

<400> SEQUENCE: 177
tcccatcgat cagtggtggc ttggctggtt tgggtggctg aggatcgatc         50

<210> SEQ ID NO 178
<211> LENGTH: 49
<212> TYPE: DNA
<213> ORGANISM: Artificial Sequence
<220> FEATURE:
<223> OTHER INFORMATION: synthetic aptamer

<400> SEQUENCE: 178
tcccatcgat ctgtggtggt tttgtggctt gggtggctga ggatcgatc          49
```

```
<210> SEQ ID NO 179
<211> LENGTH: 50
<212> TYPE: DNA
<213> ORGANISM: Artificial Sequence
<220> FEATURE:
<223> OTHER INFORMATION: synthetic aptamer

<400> SEQUENCE: 179
tcccgtgaga gctggggtgt ttatatgggt cgggtggctg aggatcgatc        50

<210> SEQ ID NO 180
<211> LENGTH: 48
<212> TYPE: DNA
<213> ORGANISM: Artificial Sequence
<220> FEATURE:
<223> OTHER INFORMATION: synthetic aptamer

<400> SEQUENCE: 180
tcccgatcgc tgtcctagga tgggtagggt ggtggctgag gatcgatc          48

<210> SEQ ID NO 181
<211> LENGTH: 48
<212> TYPE: DNA
<213> ORGANISM: Artificial Sequence
<220> FEATURE:
<223> OTHER INFORMATION: synthetic aptamer

<400> SEQUENCE: 181
tccccatcga tcctggtctc ttttgttctg ggtggctgag gatcgatc          48

<210> SEQ ID NO 182
<211> LENGTH: 48
<212> TYPE: DNA
<213> ORGANISM: Artificial Sequence
<220> FEATURE:
<223> OTHER INFORMATION: synthetic aptamer

<400> SEQUENCE: 182
tcccggatcc tcgtgggtat tgttgggttg ggtggctgag gatcgatc          48

<210> SEQ ID NO 183
<211> LENGTH: 50
<212> TYPE: DNA
<213> ORGANISM: Artificial Sequence
<220> FEATURE:
<223> OTHER INFORMATION: synthetic aptamer

<400> SEQUENCE: 183
tcccatcgaa cctcgagggt attgttggtt tgggtggctg aggatcgatc        50

<210> SEQ ID NO 184
<211> LENGTH: 49
<212> TYPE: DNA
<213> ORGANISM: Artificial Sequence
<220> FEATURE:
<223> OTHER INFORMATION: synthetic aptamer

<400> SEQUENCE: 184
tcccgacttt agatccgtgt tggatggcct gggtggctga ggatcgatc         49

<210> SEQ ID NO 185
<211> LENGTH: 49
<212> TYPE: DNA
<213> ORGANISM: Artificial Sequence
<220> FEATURE:
<223> OTHER INFORMATION: synthetic aptamer
```

```
<400> SEQUENCE: 185
tcccaatcgg tcctggtaat atattggtcg gggtggctga ggatcgatc              49

<210> SEQ ID NO 186
<211> LENGTH: 50
<212> TYPE: DNA
<213> ORGANISM: Artificial Sequence
<220> FEATURE:
<223> OTHER INFORMATION: synthetic aptamer

<400> SEQUENCE: 186
tcccgagaga ttcaaaaggg actgggcggt tgggtggctg aggatcgatc             50

<210> SEQ ID NO 187
<211> LENGTH: 49
<212> TYPE: DNA
<213> ORGANISM: Artificial Sequence
<220> FEATURE:
<223> OTHER INFORMATION: synthetic aptamer

<400> SEQUENCE: 187
tcccggagat ctgaggtgtt ttattggttt gggtggctga ggatcgatc              49

<210> SEQ ID NO 188
<211> LENGTH: 50
<212> TYPE: DNA
<213> ORGANISM: Artificial Sequence
<220> FEATURE:
<223> OTHER INFORMATION: synthetic aptamer

<400> SEQUENCE: 188
tcccggttgt cgattctggt attgttgggc tgggtggctg aggatcgatc             50

<210> SEQ ID NO 189
<211> LENGTH: 49
<212> TYPE: DNA
<213> ORGANISM: Artificial Sequence
<220> FEATURE:
<223> OTHER INFORMATION: synthetic aptamer

<400> SEQUENCE: 189
tccctggtat cgtatccaaa ggggtggtgt gggtggctga ggatcgatc              49

<210> SEQ ID NO 190
<211> LENGTH: 49
<212> TYPE: DNA
<213> ORGANISM: Artificial Sequence
<220> FEATURE:
<223> OTHER INFORMATION: synthetic aptamer

<400> SEQUENCE: 190
tcccggagat ccgaggtgtt ttattggttt gggtggctga ggatcgatc              49

<210> SEQ ID NO 191
<211> LENGTH: 27
<212> TYPE: DNA
<213> ORGANISM: Artificial Sequence
<220> FEATURE:
<223> OTHER INFORMATION: synthetic aptamer

<400> SEQUENCE: 191
cctcagggat ggtgtgggtg gctgagg                                      27
```

```
<210> SEQ ID NO 192
<211> LENGTH: 15
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (15)..(15)
<223> OTHER INFORMATION: thymidine at position 15 is an inverted deoxy
      thymidine (3'-3' linked).

<400> SEQUENCE: 192
gggatttagc ttcct                                                    15

<210> SEQ ID NO 193
<211> LENGTH: 33
<212> TYPE: DNA
<213> ORGANISM: Artificial Sequence
<220> FEATURE:
<223> OTHER INFORMATION: synthetic aptamer

<400> SEQUENCE: 193
cccttggtat tgttggtctg ggtggctgag cgg                                33

<210> SEQ ID NO 194
<211> LENGTH: 35
<212> TYPE: DNA
<213> ORGANISM: Artificial Sequence
<220> FEATURE:
<223> OTHER INFORMATION: synthetic aptamer

<400> SEQUENCE: 194
ccgcctggta ttgttggtct gggtggctga ggcgg                              35

<210> SEQ ID NO 195
<211> LENGTH: 15
<212> TYPE: DNA
<213> ORGANISM: Artificial Sequence
<220> FEATURE:
<223> OTHER INFORMATION: synthetic aptamer

<400> SEQUENCE: 195
ggttgggtag ggtgg                                                    15

<210> SEQ ID NO 196
<211> LENGTH: 13
<212> TYPE: DNA
<213> ORGANISM: Artificial Sequence
<220> FEATURE:
<223> OTHER INFORMATION: synthetic aptamer

<400> SEQUENCE: 196
ggtagggtgg tgg                                                      13

<210> SEQ ID NO 197
<211> LENGTH: 44
<212> TYPE: DNA
<213> ORGANISM: Artificial Sequence
<220> FEATURE:
<223> OTHER INFORMATION: synthetic aptamer

<400> SEQUENCE: 197
ggcgatactg cctaggttgg gtagggtggt ggctgaggat cgcc                    44
```

```
<210> SEQ ID NO 198
<211> LENGTH: 24
<212> TYPE: DNA
<213> ORGANISM: Artificial Sequence
<220> FEATURE:
<223> OTHER INFORMATION: synthetic aptamer

<400> SEQUENCE: 198
actgcctagg ttgggtaggg tggt                                          24

<210> SEQ ID NO 199
<211> LENGTH: 38
<212> TYPE: DNA
<213> ORGANISM: Artificial Sequence
<220> FEATURE:
<223> OTHER INFORMATION: synthetic aptamer

<400> SEQUENCE: 199
ggcgatactg cttcgcaggg tggtggctga ggatcgcc                           38

<210> SEQ ID NO 200
<211> LENGTH: 45
<212> TYPE: DNA
<213> ORGANISM: Artificial Sequence
<220> FEATURE:
<223> OTHER INFORMATION: synthetic aptamer

<400> SEQUENCE: 200
ggccgatcag gctaggttgg gtagggtggt ggctgaggat cggcc                   45

<210> SEQ ID NO 201
<211> LENGTH: 40
<212> TYPE: DNA
<213> ORGANISM: Artificial Sequence
<220> FEATURE:
<223> OTHER INFORMATION: synthetic aptamer

<400> SEQUENCE: 201
ggcgatactg cctttggtag ggtggtggct gaggatcgcc                         40

<210> SEQ ID NO 202
<211> LENGTH: 44
<212> TYPE: DNA
<213> ORGANISM: Artificial Sequence
<220> FEATURE:
<223> OTHER INFORMATION: synthetic aptamer

<400> SEQUENCE: 202
ggcgatactg cccaggttgg gcagggtggt ggctgaggat cgcc                    44

<210> SEQ ID NO 203
<211> LENGTH: 27
<212> TYPE: DNA
<213> ORGANISM: Artificial Sequence
<220> FEATURE:
<223> OTHER INFORMATION: synthetic aptamer

<400> SEQUENCE: 203
ggccgatcag gctgctgagg atcggcc                                       27

<210> SEQ ID NO 204
<211> LENGTH: 29
<212> TYPE: DNA
<213> ORGANISM: Artificial Sequence
<220> FEATURE:
<223> OTHER INFORMATION: synthetic aptamer
```

<400> SEQUENCE: 204
ccggctaggt tgggtagggt ggtggctgg                                              29

<210> SEQ ID NO 205
<211> LENGTH: 78
<212> TYPE: DNA
<213> ORGANISM: Artificial Sequence
<220> FEATURE:
<223> OTHER INFORMATION: synthetic template

<400> SEQUENCE: 205
atgcttttat accttcggcg atactgccta ggttgggtag ggtggtggct gaggatcgcc           60
gaatttcccg agagttcc                                                         78

<210> SEQ ID NO 206
<211> LENGTH: 19
<212> TYPE: DNA
<213> ORGANISM: Artificial Sequence
<220> FEATURE:
<223> OTHER INFORMATION: synthetic primer

<400> SEQUENCE: 206
atgcttttat accttcggc                                                        19

<210> SEQ ID NO 207
<211> LENGTH: 19
<212> TYPE: DNA
<213> ORGANISM: Artificial Sequence
<220> FEATURE:
<223> OTHER INFORMATION: synthetic primer

<400> SEQUENCE: 207
ggaactctcg ggaaattcg                                                        19

<210> SEQ ID NO 208
<211> LENGTH: 78
<212> TYPE: DNA
<213> ORGANISM: Artificial Sequence
<220> FEATURE:
<223> OTHER INFORMATION: synthetic aptamer

<400> SEQUENCE: 208
atgcttttat accttcggcc atactgcata ggttgggtag ggtggttgct gtggctggcc           60
gaatttcccg agagttcc                                                         78

<210> SEQ ID NO 209
<211> LENGTH: 77
<212> TYPE: DNA
<213> ORGANISM: Artificial Sequence
<220> FEATURE:
<223> OTHER INFORMATION: synthetic aptamer

<400> SEQUENCE: 209
atgcttttat accttcggcg atatccctag gttgggtagg gtggtggttg atgattgtcg           60
aatttcccga gagttcc                                                          77

<210> SEQ ID NO 210
<211> LENGTH: 78
<212> TYPE: DNA
<213> ORGANISM: Artificial Sequence
<220> FEATURE:
<223> OTHER INFORMATION: synthetic aptamer

```
<400> SEQUENCE: 210
atgcttttat accttcggcg atacagtcta ggatgggtag ggtggtggct gagcatcgcc    60
gaatttcccg agagttcc                                                  78

<210> SEQ ID NO 211
<211> LENGTH: 78
<212> TYPE: DNA
<213> ORGANISM: Artificial Sequence
<220> FEATURE:
<223> OTHER INFORMATION: synthetic aptamer

<400> SEQUENCE: 211
atgcttttat accttcggcg acattgtcta ggttgggtag ggtggtggct cagtattgcc    60
gaatttcccg agagttcc                                                  78

<210> SEQ ID NO 212
<211> LENGTH: 78
<212> TYPE: DNA
<213> ORGANISM: Artificial Sequence
<220> FEATURE:
<223> OTHER INFORMATION: synthetic aptamer

<400> SEQUENCE: 212
atgcttttat accttcggcc atactgctta ggttgggtag ggcggtagct gtagatagcc    60
gaatttcccg agagttcc                                                  78

<210> SEQ ID NO 213
<211> LENGTH: 78
<212> TYPE: DNA
<213> ORGANISM: Artificial Sequence
<220> FEATURE:
<223> OTHER INFORMATION: synthetic aptamer

<400> SEQUENCE: 213
atgcttttat accttcggcc atacatgtta ggttgtgtag tgtgggccct gaggattgcc    60
gaatttcccg agagttcc                                                  78

<210> SEQ ID NO 214
<211> LENGTH: 78
<212> TYPE: DNA
<213> ORGANISM: Artificial Sequence
<220> FEATURE:
<223> OTHER INFORMATION: synthetic aptamer

<400> SEQUENCE: 214
atgcttttat accttcggcg agactgccta ggttgggtag ggtggtggct gaggattgcc    60
gaatttcccg agagttcc                                                  78

<210> SEQ ID NO 215
<211> LENGTH: 79
<212> TYPE: DNA
<213> ORGANISM: Artificial Sequence
<220> FEATURE:
<223> OTHER INFORMATION: synthetic aptamer

<400> SEQUENCE: 215
atgcttttat accttcggcc aagactgcct aggatgggta gggtggtggt ttagggttgc    60
cgaatttccc gagagttcc                                                 79
```

```
<210> SEQ ID NO 216
<211> LENGTH: 78
<212> TYPE: DNA
<213> ORGANISM: Artificial Sequence
<220> FEATURE:
<223> OTHER INFORMATION: synthetic aptamer

<400> SEQUENCE: 216 atgctttat accttcggcg atagtgccta ggttgggtag ggtggtggta gtggatcgcc    60
gaatttcccg agagttcc                                                 78

<210> SEQ ID NO 217
<211> LENGTH: 78
<212> TYPE: DNA
<213> ORGANISM: Artificial Sequence
<220> FEATURE:
<223> OTHER INFORMATION: synthetic aptamer

<400> SEQUENCE: 217 atgctttat accttcggcg gtcgtgtcta gggtgggtag ggtggtgact caggtttgcc    60
gaatttcccg agagttcc                                                 78

<210> SEQ ID NO 218
<211> LENGTH: 78
<212> TYPE: DNA
<213> ORGANISM: Artificial Sequence
<220> FEATURE:
<223> OTHER INFORMATION: synthetic aptamer

<400> SEQUENCE: 218 atgctttat accttcggcc aaactgacta ggttgggtag ggtggtggct gtggtgggcc    60
gaatttcccg agagttcc                                                 78

<210> SEQ ID NO 219
<211> LENGTH: 78
<212> TYPE: DNA
<213> ORGANISM: Artificial Sequence
<220> FEATURE:
<223> OTHER INFORMATION: synthetic aptamer

<400> SEQUENCE: 219 atgctttat accttcggcg atagtgccta ggttgggtag ggtggtggct gaggcgtgcc    60
gaatttcccg agagttcc                                                 78

<210> SEQ ID NO 220
<211> LENGTH: 78
<212> TYPE: DNA
<213> ORGANISM: Artificial Sequence
<220> FEATURE:
<223> OTHER INFORMATION: synthetic aptamer

<400> SEQUENCE: 220 atgctttat accttcggcg acagtgccta ggttgggtag ggtggtggct taggcgcgcc    60
gaatttcccg agagttcc                                                 78

<210> SEQ ID NO 221
<211> LENGTH: 78
<212> TYPE: DNA
<213> ORGANISM: Artificial Sequence
<220> FEATURE:
<223> OTHER INFORMATION: synthetic aptamer
```

-continued

<400> SEQUENCE: 221
atgcttttat accttcggcg atgtagacta ggttgggtag ggtggtggct aagtattgcc    60
gaatttcccg agagttcc                                                 78

<210> SEQ ID NO 222
<211> LENGTH: 78
<212> TYPE: DNA
<213> ORGANISM: Artificial Sequence
<220> FEATURE:
<223> OTHER INFORMATION: synthetic aptamer

<400> SEQUENCE: 222
atgcttttat accttcggct atactgtcta ggttgggtag ggtggtgact tagtgttgcc    60
gaatttcccg agagttcc                                                 78

<210> SEQ ID NO 223
<211> LENGTH: 78
<212> TYPE: DNA
<213> ORGANISM: Artificial Sequence
<220> FEATURE:
<223> OTHER INFORMATION: synthetic aptamer

<400> SEQUENCE: 223
atgcttttat accttcggcg ggattgttta ggttgggtag ggtggtggca gaggatcgcc    60
gaatttcccg agagttcc                                                 78

<210> SEQ ID NO 224
<211> LENGTH: 78
<212> TYPE: DNA
<213> ORGANISM: Artificial Sequence
<220> FEATURE:
<223> OTHER INFORMATION: synthetic aptamer

<400> SEQUENCE: 224
atgcttttat accttcggcg ggatgtccta ggttgggtag ggtggtggct gaggtttgcc    60
gaatttcccg agagttcc                                                 78

<210> SEQ ID NO 225
<211> LENGTH: 78
<212> TYPE: DNA
<213> ORGANISM: Artificial Sequence
<220> FEATURE:
<223> OTHER INFORMATION: synthetic aptamer

<400> SEQUENCE: 225
atgcttttat accttcggct atactgcata ggttgggtag ggtggtggct gagtgttgcc    60
gaatttcccg agagttcc                                                 78

<210> SEQ ID NO 226
<211> LENGTH: 78
<212> TYPE: DNA
<213> ORGANISM: Artificial Sequence
<220> FEATURE:
<223> OTHER INFORMATION: synthetic aptamer

<400> SEQUENCE: 226
atgcttttat accttcggcg atactgacta ggttgggtag ggtggtggct gatcttcgcc    60
gaatttcccg agagttcc                                                 78

```
<210> SEQ ID NO 227
<211> LENGTH: 78
<212> TYPE: DNA
<213> ORGANISM: Artificial Sequence
<220> FEATURE:
<223> OTHER INFORMATION: synthetic aptamer

<400> SEQUENCE: 227
atgcttttat accttcggcg aaagtgctta ggatgggtag ggtggtggct gcggatcgcc      60
gaatttcccg agagttcc                                                   78

<210> SEQ ID NO 228
<211> LENGTH: 78
<212> TYPE: DNA
<213> ORGANISM: Artificial Sequence
<220> FEATURE:
<223> OTHER INFORMATION: synthetic aptamer

<400> SEQUENCE: 228
atgcttttat accttcggcg gtagtgccta ggttgggtag ggtggtggct ctggatcgcc      60
gaatttcccg agagttcc                                                   78

<210> SEQ ID NO 229
<211> LENGTH: 78
<212> TYPE: DNA
<213> ORGANISM: Artificial Sequence
<220> FEATURE:
<223> OTHER INFORMATION: synthetic aptamer

<400> SEQUENCE: 229
atgcttttat accttcggcg atattgccta ggttgggtag ggtggtggct gaactttgcc      60
gaatttcccg agagttcc                                                   78

<210> SEQ ID NO 230
<211> LENGTH: 78
<212> TYPE: DNA
<213> ORGANISM: Artificial Sequence
<220> FEATURE:
<223> OTHER INFORMATION: synthetic aptamer

<400> SEQUENCE: 230
atgcttttat accttcggcg acacagacta ggatgggtag ggtggtggct gaggctcgcc      60
gaatttcccg agagttcc                                                   78

<210> SEQ ID NO 231
<211> LENGTH: 79
<212> TYPE: DNA
<213> ORGANISM: Artificial Sequence
<220> FEATURE:
<223> OTHER INFORMATION: synthetic aptamer

<400> SEQUENCE: 231
atgcttttat accttcggcg gacattggct aggttgggta gggtggtggc tgcggattgc      60
cgaatttccc gagagttcc                                                  79

<210> SEQ ID NO 232
<211> LENGTH: 78
<212> TYPE: DNA
<213> ORGANISM: Artificial Sequence
<220> FEATURE:
<223> OTHER INFORMATION: synthetic aptamer
```

-continued

<400> SEQUENCE: 232 atgctttat accttcggcg atactgtgta ggttgggtag ggtggtcgta gaggattgcc    60
gaatttcccg agagttcc                                                  78

<210> SEQ ID NO 233
<211> LENGTH: 78
<212> TYPE: DNA
<213> ORGANISM: Artificial Sequence
<220> FEATURE:
<223> OTHER INFORMATION: synthetic aptamer

<400> SEQUENCE: 233 atgctttat accttcggcg ataatgtcta ggttgggtag ggtggtggct gtgaattgcc    60
gaatttcccg agagttcc                                                  78

<210> SEQ ID NO 234
<211> LENGTH: 78
<212> TYPE: DNA
<213> ORGANISM: Artificial Sequence
<220> FEATURE:
<223> OTHER INFORMATION: synthetic aptamer

<400> SEQUENCE: 234 atgctttat accttcggcg gtcctgccta ggatgggtag ggtggtggcc gaggattgcc    60
gaatttcccg agagttcc                                                  78

<210> SEQ ID NO 235
<211> LENGTH: 79
<212> TYPE: DNA
<213> ORGANISM: Artificial Sequence
<220> FEATURE:
<223> OTHER INFORMATION: synthetic aptamer

<400> SEQUENCE: 235 atgctttat accttcggcg aagattgact aggttgggta gggtggtgtt ttaggattgc    60
cgaatttccc gagagttcc                                                 79

<210> SEQ ID NO 236
<211> LENGTH: 78
<212> TYPE: DNA
<213> ORGANISM: Artificial Sequence
<220> FEATURE:
<223> OTHER INFORMATION: synthetic aptamer

<400> SEQUENCE: 236 atgctttat accttcggcc atattgctta ggttgggtag ggtggtagct gagtattgcc    60
gaatttcccg agagttcc                                                  78

<210> SEQ ID NO 237
<211> LENGTH: 78
<212> TYPE: DNA
<213> ORGANISM: Artificial Sequence
<220> FEATURE:
<223> OTHER INFORMATION: synthetic aptamer

<400> SEQUENCE: 237 atgctttat accttcggcg agagtgcata ggttgggtag ggtggttgct gttgatcgcc    60
gaatttcccg agagttcc                                                  78

```
<210> SEQ ID NO 238
<211> LENGTH: 79
<212> TYPE: DNA
<213> ORGANISM: Artificial Sequence
<220> FEATURE:
<223> OTHER INFORMATION: synthetic aptamer

<400> SEQUENCE: 238
atgcttttat accttcggcg gatacaggct aggttgggta gggtggtggc tgttaatcgc    60
cgaatttccc gagagttcc                                                 79

<210> SEQ ID NO 239
<211> LENGTH: 78
<212> TYPE: DNA
<213> ORGANISM: Artificial Sequence
<220> FEATURE:
<223> OTHER INFORMATION: synthetic aptamer

<400> SEQUENCE: 239
atgcttttat accttcggcg atattgccta ggttgggtag ggtggtggct ggggattgcc    60
gaatttcccg agagttcc                                                  78

<210> SEQ ID NO 240
<211> LENGTH: 78
<212> TYPE: DNA
<213> ORGANISM: Artificial Sequence
<220> FEATURE:
<223> OTHER INFORMATION: synthetic aptamer

<400> SEQUENCE: 240
atgcttttat accttcggcc ataataacta ggttgggtag ggtggtggct gattatcgcc    60
gaatttcccg agagttcc                                                  78

<210> SEQ ID NO 241
<211> LENGTH: 78
<212> TYPE: DNA
<213> ORGANISM: Artificial Sequence
<220> FEATURE:
<223> OTHER INFORMATION: synthetic aptamer

<400> SEQUENCE: 241
atgcttttat accttcggcg atattgccta ggatgggtag ggtggtggct aaggtttgcc    60
gaatttcccg agagttcc                                                  78

<210> SEQ ID NO 242
<211> LENGTH: 78
<212> TYPE: DNA
<213> ORGANISM: Artificial Sequence
<220> FEATURE:
<223> OTHER INFORMATION: synthetic aptamer

<400> SEQUENCE: 242
atgcttttat accttcggcg acacagagta ggttgggtag ggtggtatct gtcgaatgcc    60
gaatttcccg agagttcc                                                  78

<210> SEQ ID NO 243
<211> LENGTH: 78
<212> TYPE: DNA
<213> ORGANISM: Artificial Sequence
<220> FEATURE:
<223> OTHER INFORMATION: synthetic aptamer
```

-continued

<400> SEQUENCE: 243
atgcttttat accttcggcg atactgccta ggttgggtag ggtggtggct agggatcgcc    60
gaatttcccg agagttcc    78

<210> SEQ ID NO 244
<211> LENGTH: 78
<212> TYPE: DNA
<213> ORGANISM: Artificial Sequence
<220> FEATURE:
<223> OTHER INFORMATION: synthetic aptamer

<400> SEQUENCE: 244
atgcttttat accttcggcg acattaccta ggttgggtag ggtggtggct aagggttgcc    60
gaatttcccg agagttcc    78

<210> SEQ ID NO 245
<211> LENGTH: 78
<212> TYPE: DNA
<213> ORGANISM: Artificial Sequence
<220> FEATURE:
<223> OTHER INFORMATION: synthetic aptamer

<400> SEQUENCE: 245
atgcttttat accttcggcg gttcagccta ggatgggtag ggtggtgggt gaggattgcc    60
gaatttcccg agagttcc    78

<210> SEQ ID NO 246
<211> LENGTH: 78
<212> TYPE: DNA
<213> ORGANISM: Artificial Sequence
<220> FEATURE:
<223> OTHER INFORMATION: synthetic aptamer

<400> SEQUENCE: 246
atgcttttat accttcggcg acatagggta ggttgggtag ggtggtgcct gaggattgcc    60
gaatttcccg agagttcc    78

<210> SEQ ID NO 247
<211> LENGTH: 78
<212> TYPE: DNA
<213> ORGANISM: Artificial Sequence
<220> FEATURE:
<223> OTHER INFORMATION: synthetic aptamer

<400> SEQUENCE: 247
atgcttttat accttcggcg gtactgcata ggttgggtag ggtggtggct gaacattgcc    60
gaatttcccg agagttcc    78

<210> SEQ ID NO 248
<211> LENGTH: 78
<212> TYPE: DNA
<213> ORGANISM: Artificial Sequence
<220> FEATURE:
<223> OTHER INFORMATION: synthetic aptamer

<400> SEQUENCE: 248
atgcttttat accttcggcg gtagggttta ggttgggtag ggtggtgtct gaggattgcc    60
gaatttcccg agagttcc    78

<210> SEQ ID NO 249
<211> LENGTH: 78
<212> TYPE: DNA
<213> ORGANISM: Artificial Sequence
<220> FEATURE:
<223> OTHER INFORMATION: synthetic aptamer

<400> SEQUENCE: 249
atgcttttat accttcggcc atacagacta ggttgggtag ggtggtgtct gaggatcgcc    60
gaatttcccg agagttcc                                                 78

<210> SEQ ID NO 250
<211> LENGTH: 78
<212> TYPE: DNA
<213> ORGANISM: Artificial Sequence
<220> FEATURE:
<223> OTHER INFORMATION: synthetic aptamer

<400> SEQUENCE: 250
atgcttttat accttcggcg atagtgctta ggttgggtag ggtggtagct gatcattgcc    60
gaatttcccg agagttcc                                                 78

<210> SEQ ID NO 251
<211> LENGTH: 78
<212> TYPE: DNA
<213> ORGANISM: Artificial Sequence
<220> FEATURE:
<223> OTHER INFORMATION: synthetic aptamer

<400> SEQUENCE: 251
atgcttttat accttcggcg gtactgcata ggttgggtag ggtggtggct gagaatcgcc    60
gaatttcccg agagttcc                                                 78

<210> SEQ ID NO 252
<211> LENGTH: 78
<212> TYPE: DNA
<213> ORGANISM: Artificial Sequence
<220> FEATURE:
<223> OTHER INFORMATION: synthetic aptamer

<400> SEQUENCE: 252
atgcttttat accttcggcg gcactggcta ggatgggtag ggtggtggct gagcattgcc    60
gaatttcccg agagttcc                                                 78

<210> SEQ ID NO 253
<211> LENGTH: 79
<212> TYPE: DNA
<213> ORGANISM: Artificial Sequence
<220> FEATURE:
<223> OTHER INFORMATION: synthetic aptamer

<400> SEQUENCE: 253
atgcttttat accttcggcg ataactgcct aggttgggta gggtggtggc tcacgatcgt    60
cgaatttccc gagagttcc                                                79

<210> SEQ ID NO 254
<211> LENGTH: 78
<212> TYPE: DNA
<213> ORGANISM: Artificial Sequence
<220> FEATURE:
<223> OTHER INFORMATION: synthetic aptamer -continued

<400> SEQUENCE: 254
atgcttttat accttcggcg atactgcata ggatgggtag ggtggttgct gatgtgtgcc    60
gaatttcccg agagttcc                                                  78

<210> SEQ ID NO 255
<211> LENGTH: 78
<212> TYPE: DNA
<213> ORGANISM: Artificial Sequence
<220> FEATURE:
<223> OTHER INFORMATION: synthetic aptamer

<400> SEQUENCE: 255
atgcttttat accttcggcg atgttgccta ggttgggtag ggtggtggtt gtgagttgcc    60
gaatttcccg agagttcc                                                  78

<210> SEQ ID NO 256
<211> LENGTH: 78
<212> TYPE: DNA
<213> ORGANISM: Artificial Sequence
<220> FEATURE:
<223> OTHER INFORMATION: synthetic aptamer

<400> SEQUENCE: 256
atgcttttat accttcggcg acactgtata ggttgggtag ggtggtggct gatgattgcc    60
gaatttcccg agagttcc                                                  78

<210> SEQ ID NO 257
<211> LENGTH: 78
<212> TYPE: DNA
<213> ORGANISM: Artificial Sequence
<220> FEATURE:
<223> OTHER INFORMATION: synthetic aptamer

<400> SEQUENCE: 257
atgcttttat accttcggcc acattgcata ggttgggtag ggtggtggca aagtactgcc    60
gaatttcccg agagttcc                                                  78

<210> SEQ ID NO 258
<211> LENGTH: 78
<212> TYPE: DNA
<213> ORGANISM: Artificial Sequence
<220> FEATURE:
<223> OTHER INFORMATION: synthetic aptamer

<400> SEQUENCE: 258
atgcttttat accttcggcg atacaggtta ggatgggtag ggtggtggct gagtactgcc    60
gaatttcccg agagttcc                                                  78

<210> SEQ ID NO 259
<211> LENGTH: 78
<212> TYPE: DNA
<213> ORGANISM: Artificial Sequence
<220> FEATURE:
<223> OTHER INFORMATION: synthetic aptamer

<400> SEQUENCE: 259
atgcttttat accttcggcg ataagggcta ggatgggtag ggtggtgact aaaactcgcc    60
gaatttcccg agagttcc                                                  78

```
<210> SEQ ID NO 260
<211> LENGTH: 78
<212> TYPE: DNA
<213> ORGANISM: Artificial Sequence
<220> FEATURE:
<223> OTHER INFORMATION: synthetic aptamer

<400> SEQUENCE: 260
atgcttttat accttcggcg agattggcta gggtgggtag ggtggtgcta gatgattgcc    60
gaatttcccg agagttcc                                                  78

<210> SEQ ID NO 261
<211> LENGTH: 78
<212> TYPE: DNA
<213> ORGANISM: Artificial Sequence
<220> FEATURE:
<223> OTHER INFORMATION: synthetic aptamer

<400> SEQUENCE: 261
atgcttttat accttcggcg acaatgacta ggttgggtag ggtggtgtct taggatggcc    60
gaatttcccg agagttcc                                                  78

<210> SEQ ID NO 262
<211> LENGTH: 78
<212> TYPE: DNA
<213> ORGANISM: Artificial Sequence
<220> FEATURE:
<223> OTHER INFORMATION: synthetic aptamer

<400> SEQUENCE: 262
atgcttttat accttcggcg gtactgtcta ggttgggtag ggtggtgtca gttgatcgcc    60
gaatttcccg agagttcc                                                  78

<210> SEQ ID NO 263
<211> LENGTH: 78
<212> TYPE: DNA
<213> ORGANISM: Artificial Sequence
<220> FEATURE:
<223> OTHER INFORMATION: synthetic aptamer

<400> SEQUENCE: 263
atgcttttat accttcggcc atacaaacta ggttgggtag ggtggtgttt gctgattgcc    60
gaatttcccg agagttcc                                                  78

<210> SEQ ID NO 264
<211> LENGTH: 78
<212> TYPE: DNA
<213> ORGANISM: Artificial Sequence
<220> FEATURE:
<223> OTHER INFORMATION: synthetic aptamer

<400> SEQUENCE: 264
atgcttttat accttcggcg aaacagtata ggttgggtag ggtggttgct gattatcgcc    60
gaatttcccg agagttcc                                                  78

<210> SEQ ID NO 265
<211> LENGTH: 78
<212> TYPE: DNA
<213> ORGANISM: Artificial Sequence
<220> FEATURE:
<223> OTHER INFORMATION: synthetic aptamer
```

```
<400> SEQUENCE: 265
atgcttttat accttcggcg atattgccta ggttgggtag ggtggtggtt gaaaatcgcc    60
gaatttcccg agagttcc                                                 78

<210> SEQ ID NO 266
<211> LENGTH: 78
<212> TYPE: DNA
<213> ORGANISM: Artificial Sequence
<220> FEATURE:
<223> OTHER INFORMATION: synthetic aptamer

<400> SEQUENCE: 266
atgcttttat accttcggcg gtacggtcta ggttgggtag ggtggtgttt gggtgtcgcc    60
gaatttcccg agagttcc                                                 78

<210> SEQ ID NO 267
<211> LENGTH: 78
<212> TYPE: DNA
<213> ORGANISM: Artificial Sequence
<220> FEATURE:
<223> OTHER INFORMATION: synthetic aptamer

<400> SEQUENCE: 267
atgcttttat accttcggcg atactgtcta ggttgggtag ggtggtggct taggattgcc    60
gaatttcccg agagttcc                                                 78

<210> SEQ ID NO 268
<211> LENGTH: 78
<212> TYPE: DNA
<213> ORGANISM: Artificial Sequence
<220> FEATURE:
<223> OTHER INFORMATION: synthetic aptamer

<400> SEQUENCE: 268
atgcttttat accttcggcg gtactgtata ggttgggtag ggtggttgct gtggattgtc    60
gaatttcccg agagttcc                                                 78

<210> SEQ ID NO 269
<211> LENGTH: 78
<212> TYPE: DNA
<213> ORGANISM: Artificial Sequence
<220> FEATURE:
<223> OTHER INFORMATION: synthetic aptamer

<400> SEQUENCE: 269
atgcttttat accttcggcg atagggccta ggttgggtag gatggtggtc ataaatcgcc    60
gaatttcccg agagttcc                                                 78

<210> SEQ ID NO 270
<211> LENGTH: 78
<212> TYPE: DNA
<213> ORGANISM: Artificial Sequence
<220> FEATURE:
<223> OTHER INFORMATION: synthetic aptamer

<400> SEQUENCE: 270
atgcttttat accttcggcg ctacaggcta ggttgggtag ggtggtggtt gggaatcgcc    60
gaatttcccg agagttcc                                                 78
```

```
<210> SEQ ID NO 271
<211> LENGTH: 78
<212> TYPE: DNA
<213> ORGANISM: Artificial Sequence
<220> FEATURE:
<223> OTHER INFORMATION: synthetic aptamer

<400> SEQUENCE: 271
atgcttttat accttcggcc atactgtcta ggttgggtag ggtggtggtt gagtattgcc      60
gaatttcccg agagttcc                                                   78

<210> SEQ ID NO 272
<211> LENGTH: 79
<212> TYPE: DNA
<213> ORGANISM: Artificial Sequence
<220> FEATURE:
<223> OTHER INFORMATION: synthetic aptamer

<400> SEQUENCE: 272
atgcttttat accttcggcg gatactgtct aggttgggta gggtggtgac tgaggatggt      60
cgaatttccc gagagttcc                                                  79

<210> SEQ ID NO 273
<211> LENGTH: 78
<212> TYPE: DNA
<213> ORGANISM: Artificial Sequence
<220> FEATURE:
<223> OTHER INFORMATION: synthetic aptamer

<400> SEQUENCE: 273
atgcttttat accttcggcg gtggtctgta ggttgggtag ggtggttgct tggaatcgcc      60
gaatttcccg agagttcc                                                   78

<210> SEQ ID NO 274
<211> LENGTH: 78
<212> TYPE: DNA
<213> ORGANISM: Artificial Sequence
<220> FEATURE:
<223> OTHER INFORMATION: synthetic aptamer

<400> SEQUENCE: 274
atgcttttat accttcggcg cgattgccta ggttgggtag ggtggtggct tagtattgcc      60
gaatttcccg agagttcc                                                   78

<210> SEQ ID NO 275
<211> LENGTH: 78
<212> TYPE: DNA
<213> ORGANISM: Artificial Sequence
<220> FEATURE:
<223> OTHER INFORMATION: synthetic aptamer

<400> SEQUENCE: 275
atgcttttat accttcggcg atagggacta ggttgggtag ggtggtggct gagtattgcc      60
gaatttcccg agagttcc                                                   78

<210> SEQ ID NO 276
<211> LENGTH: 78
<212> TYPE: DNA
<213> ORGANISM: Artificial Sequence
<220> FEATURE:
<223> OTHER INFORMATION: synthetic aptamer
```

<400> SEQUENCE: 276
atgcttttat accttcggcg acaatggcta gggtgggtag ggtggtggct taggattgcc    60
gaatttcccg agagttcc                                                  78

<210> SEQ ID NO 277
<211> LENGTH: 78
<212> TYPE: DNA
<213> ORGANISM: Artificial Sequence
<220> FEATURE:
<223> OTHER INFORMATION: synthetic aptamer

<400> SEQUENCE: 277
atgcttttat accttcggcg gtagtgtgta gggtgggtag ggtggtagct gaggatcgcc    60
gaatttcccg agagttcc                                                  78

<210> SEQ ID NO 278
<211> LENGTH: 78
<212> TYPE: DNA
<213> ORGANISM: Artificial Sequence
<220> FEATURE:
<223> OTHER INFORMATION: synthetic aptamer

<400> SEQUENCE: 278
atgcttttat accttcggcg acactggtta gggtgggtag ggtggtggtt gtggattgcc    60
gaatttcccg agagttcc                                                  78

<210> SEQ ID NO 279
<211> LENGTH: 78
<212> TYPE: DNA
<213> ORGANISM: Artificial Sequence
<220> FEATURE:
<223> OTHER INFORMATION: synthetic aptamer

<400> SEQUENCE: 279
atgcttttat accttcggcg atactgtcta ggttgggtag ggtggtgttt taggattgcc    60
gaatttcccg agagttcc                                                  78

<210> SEQ ID NO 280
<211> LENGTH: 78
<212> TYPE: DNA
<213> ORGANISM: Artificial Sequence
<220> FEATURE:
<223> OTHER INFORMATION: synthetic aptamer

<400> SEQUENCE: 280
atgcttttat accttcggcg gtacagtcta ggttgggtag ggtggtggct gttgatggcc    60
gaatttcccg agagttcc                                                  78

<210> SEQ ID NO 281
<211> LENGTH: 79
<212> TYPE: DNA
<213> ORGANISM: Artificial Sequence
<220> FEATURE:
<223> OTHER INFORMATION: synthetic aptamer

<400> SEQUENCE: 281
atgcttttat accttcggcg ggtattgcct aggttgggta gggtggtggc tcagtcttgc    60
cgaatttccc gagagttcc                                                 79

```
<210> SEQ ID NO 282
<211> LENGTH: 78
<212> TYPE: DNA
<213> ORGANISM: Artificial Sequence
<220> FEATURE:
<223> OTHER INFORMATION: synthetic aptamer

<400> SEQUENCE: 282
atgcttttat accttcggcg gcacggtcta ggatgggtag ggtggttgct gataatcgcc      60
gaatttcccg agagttcc                                                   78

<210> SEQ ID NO 283
<211> LENGTH: 30
<212> TYPE: DNA
<213> ORGANISM: Artificial Sequence
<220> FEATURE:
<223> OTHER INFORMATION: synthetic aptamer

<400> SEQUENCE: 283
actgcctagg ttgggtaggg tggtggcagt                                      30

<210> SEQ ID NO 284
<211> LENGTH: 30
<212> TYPE: DNA
<213> ORGANISM: Artificial Sequence
<220> FEATURE:
<223> OTHER INFORMATION: synthetic aptamer

<400> SEQUENCE: 284
actgcctagg atgggtaggg tggtggcagt                                      30

<210> SEQ ID NO 285
<211> LENGTH: 30
<212> TYPE: DNA
<213> ORGANISM: Artificial Sequence
<220> FEATURE:
<223> OTHER INFORMATION: synthetic aptamer

<400> SEQUENCE: 285
actgcctagg gtgggtaggg tggtggcagt                                      30

<210> SEQ ID NO 286
<211> LENGTH: 30
<212> TYPE: DNA
<213> ORGANISM: Artificial Sequence
<220> FEATURE:
<223> OTHER INFORMATION: synthetic aptamer

<400> SEQUENCE: 286
actgcctagg ttgggtagtg tggtggcagt                                      30

<210> SEQ ID NO 287
<211> LENGTH: 30
<212> TYPE: DNA
<213> ORGANISM: Artificial Sequence
<220> FEATURE:
<223> OTHER INFORMATION: synthetic aptamer

<400> SEQUENCE: 287
actgcctagg ttgggtagga tggtggcagt                                      30

<210> SEQ ID NO 288
<211> LENGTH: 30
<212> TYPE: DNA
<213> ORGANISM: Artificial Sequence
<220> FEATURE:
<223> OTHER INFORMATION: synthetic aptamer
```

```
<400> SEQUENCE: 288
actgcctagg ttgggtaggg cggtggcagt                                    30

<210> SEQ ID NO 289
<211> LENGTH: 30
<212> TYPE: DNA
<213> ORGANISM: Artificial Sequence
<220> FEATURE:
<223> OTHER INFORMATION: synthetic aptamer

<400> SEQUENCE: 289
actgcatagg ttgggtaggg tggttgcagt                                    30

<210> SEQ ID NO 290
<211> LENGTH: 30
<212> TYPE: DNA
<213> ORGANISM: Artificial Sequence
<220> FEATURE:
<223> OTHER INFORMATION: synthetic aptamer

<400> SEQUENCE: 290
actgcatagg ttgggtaggg tggtggcagt                                    30

<210> SEQ ID NO 291
<211> LENGTH: 29
<212> TYPE: DNA
<213> ORGANISM: Artificial Sequence
<220> FEATURE:
<223> OTHER INFORMATION: synthetic aptamer

<400> SEQUENCE: 291
actgcatagg ttgggtaggg tggtgcagt                                     29

<210> SEQ ID NO 292
<211> LENGTH: 30
<212> TYPE: DNA
<213> ORGANISM: Artificial Sequence
<220> FEATURE:
<223> OTHER INFORMATION: synthetic aptamer

<400> SEQUENCE: 292
gctgcctagg ttgggtaggg tggtggcagc                                    30

<210> SEQ ID NO 293
<211> LENGTH: 28
<212> TYPE: DNA
<213> ORGANISM: Artificial Sequence
<220> FEATURE:
<223> OTHER INFORMATION: synthetic aptamer

<400> SEQUENCE: 293
ctgcctaggt tgggtagggt ggtggcag                                      28

<210> SEQ ID NO 294
<211> LENGTH: 26
<212> TYPE: DNA
<213> ORGANISM: Artificial Sequence
<220> FEATURE:
<223> OTHER INFORMATION: synthetic aptamer

<400> SEQUENCE: 294
cgcctaggtt gggtagggtg gtggcg                                        26
```

```
<210> SEQ ID NO 295
<211> LENGTH: 29
<212> TYPE: DNA
<213> ORGANISM: Artificial Sequence
<220> FEATURE:
<223> OTHER INFORMATION: synthetic aptamer

<400> SEQUENCE: 295
acctcaggga tggtgtgggt ggctgaggt                                   29

<210> SEQ ID NO 296
<211> LENGTH: 31
<212> TYPE: DNA
<213> ORGANISM: Artificial Sequence
<220> FEATURE:
<223> OTHER INFORMATION: synthetic aptamer

<400> SEQUENCE: 296
tacctcaggg atggtgtggg tggctgaggt a                                31

<210> SEQ ID NO 297
<211> LENGTH: 33
<212> TYPE: DNA
<213> ORGANISM: Artificial Sequence
<220> FEATURE:
<223> OTHER INFORMATION: synthetic aptamer

<400> SEQUENCE: 297
ctacctcagg gatggtgtgg gtggctgagg tag                              33

<210> SEQ ID NO 298
<211> LENGTH: 35
<212> TYPE: DNA
<213> ORGANISM: Artificial Sequence
<220> FEATURE:
<223> OTHER INFORMATION: synthetic aptamer

<400> SEQUENCE: 298
actacctcag ggatggtgtg ggtggctgag gtagt                            35

<210> SEQ ID NO 299
<211> LENGTH: 37
<212> TYPE: DNA
<213> ORGANISM: Artificial Sequence
<220> FEATURE:
<223> OTHER INFORMATION: synthetic aptamer

<400> SEQUENCE: 299
gactacctca gggatggtgt gggtggctga ggtagtc                          37

<210> SEQ ID NO 300
<211> LENGTH: 32
<212> TYPE: DNA
<213> ORGANISM: Artificial Sequence
<220> FEATURE:
<223> OTHER INFORMATION: synthetic aptamer

<400> SEQUENCE: 300
aactgcctag gttgggtagg gtggtggcag tt                               32

<210> SEQ ID NO 301
<211> LENGTH: 34
<212> TYPE: DNA
<213> ORGANISM: Artificial Sequence
<220> FEATURE:
<223> OTHER INFORMATION: synthetic aptamer
```

-continued

<400> SEQUENCE: 301
taactgccta ggttgggtag ggtggtggca gtta                              34

<210> SEQ ID NO 302
<211> LENGTH: 36
<212> TYPE: DNA
<213> ORGANISM: Artificial Sequence
<220> FEATURE:
<223> OTHER INFORMATION: synthetic aptamer

<400> SEQUENCE: 302
ctaactgcct aggttgggta gggtggtggc agttag                            36

<210> SEQ ID NO 303
<211> LENGTH: 38
<212> TYPE: DNA
<213> ORGANISM: Artificial Sequence
<220> FEATURE:
<223> OTHER INFORMATION: synthetic aptamer

<400> SEQUENCE: 303
actaactgcc taggttgggt agggtggtgg cagttagt                          38

<210> SEQ ID NO 304
<211> LENGTH: 40
<212> TYPE: DNA
<213> ORGANISM: Artificial Sequence
<220> FEATURE:
<223> OTHER INFORMATION: synthetic aptamer

<400> SEQUENCE: 304
gactaactgc ctaggttggg tagggtggtg gcagttagtc                        40

<210> SEQ ID NO 305
<211> LENGTH: 27
<212> TYPE: DNA
<213> ORGANISM: Artificial Sequence
<220> FEATURE:
<223> OTHER INFORMATION: synthetic aptamer

<400> SEQUENCE: 305
cctcagggtt ggtgtggttg gctgagg                                      27

<210> SEQ ID NO 306
<211> LENGTH: 30
<212> TYPE: DNA
<213> ORGANISM: Artificial Sequence
<220> FEATURE:
<223> OTHER INFORMATION: synthetic aptamer

<400> SEQUENCE: 306
actgcctagg ttggtgtggt tggtggcagt                                   30

<210> SEQ ID NO 307
<211> LENGTH: 30
<212> TYPE: DNA
<213> ORGANISM: Artificial Sequence
<220> FEATURE:
<223> OTHER INFORMATION: synthetic aptamer

<400> SEQUENCE: 307
cctcagggat ggtgtgggtg gctgaggttt                                   30

```
<210> SEQ ID NO 308
<211> LENGTH: 33
<212> TYPE: DNA
<213> ORGANISM: Artificial Sequence
<220> FEATURE:
<223> OTHER INFORMATION: synthetic aptamer

<400> SEQUENCE: 308
cctcagggat ggtgtgggtg gctgaggttt ttt                              33

<210> SEQ ID NO 309
<211> LENGTH: 30
<212> TYPE: DNA
<213> ORGANISM: Artificial Sequence
<220> FEATURE:
<223> OTHER INFORMATION: synthetic aptamer

<400> SEQUENCE: 309
tttcctcagg gatggtgtgg gtggctgagg                                  30

<210> SEQ ID NO 310
<211> LENGTH: 33
<212> TYPE: DNA
<213> ORGANISM: Artificial Sequence
<220> FEATURE:
<223> OTHER INFORMATION: synthetic aptamer

<400> SEQUENCE: 310 tttttcctc agggatggtg tgggtggctg agg                               33

<210> SEQ ID NO 311
<211> LENGTH: 33
<212> TYPE: DNA
<213> ORGANISM: Artificial Sequence
<220> FEATURE:
<223> OTHER INFORMATION: synthetic aptamer

<400> SEQUENCE: 311
tttcctcagg gatggtgtgg gtggctgagg ttt                              33

<210> SEQ ID NO 312
<211> LENGTH: 39
<212> TYPE: DNA
<213> ORGANISM: Artificial Sequence
<220> FEATURE:
<223> OTHER INFORMATION: synthetic aptamer

<400> SEQUENCE: 312 tttttcctc agggatggtg tgggtggctg aggtttttt                         39

<210> SEQ ID NO 313
<211> LENGTH: 31
<212> TYPE: DNA
<213> ORGANISM: Artificial Sequence
<220> FEATURE:
<223> OTHER INFORMATION: synthetic aptamer

<400> SEQUENCE: 313
ctgcctaggt tgggtagggt ggtggcagtt t                                31

<210> SEQ ID NO 314
<211> LENGTH: 34
<212> TYPE: DNA
<213> ORGANISM: Artificial Sequence
<220> FEATURE:
<223> OTHER INFORMATION: synthetic aptamer
```

```
<400> SEQUENCE: 314
ctgcctaggt tgggtagggt ggtggcagtt tttt                                 34

<210> SEQ ID NO 315
<211> LENGTH: 31
<212> TYPE: DNA
<213> ORGANISM: Artificial Sequence
<220> FEATURE:
<223> OTHER INFORMATION: synthetic aptamer

<400> SEQUENCE: 315
tttctgccta ggttgggtag ggtggtggca g                                    31

<210> SEQ ID NO 316
<211> LENGTH: 34
<212> TYPE: DNA
<213> ORGANISM: Artificial Sequence
<220> FEATURE:
<223> OTHER INFORMATION: synthetic aptamer

<400> SEQUENCE: 316 tttttctgc ctaggttggg tagggtggtg gcag                                  34

<210> SEQ ID NO 317
<211> LENGTH: 34
<212> TYPE: DNA
<213> ORGANISM: Artificial Sequence
<220> FEATURE:
<223> OTHER INFORMATION: synthetic aptamer

<400> SEQUENCE: 317
tttctgccta ggttgggtag ggtggtggca gttt                                 34

<210> SEQ ID NO 318
<211> LENGTH: 40
<212> TYPE: DNA
<213> ORGANISM: Artificial Sequence
<220> FEATURE:
<223> OTHER INFORMATION: synthetic aptamer

<400> SEQUENCE: 318 tttttctgc ctaggttggg tagggtggtg gcagttttt                             40

<210> SEQ ID NO 319
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (1)..(1)
<223> OTHER INFORMATION: wherein adenosine at position 1 is 2'-O-methyl
      adenosine

<400> SEQUENCE: 319
actgcctagg ttgggtaggg tggtggcagt                                      30

<210> SEQ ID NO 320
<211> LENGTH: 30
<212> TYPE: DNA
<213> ORGANISM: Artificial Sequence
<220> FEATURE:
<223> OTHER INFORMATION: synthetic aptamer
```

```
<220> FEATURE:
<221> NAME/KEY: modified_base
<222> LOCATION: (2)..(2)
<223> OTHER INFORMATION: Wherein cytidine at position 2 is 2'-O-methyl
      cytidine.

<400> SEQUENCE: 320
actgcctagg ttgggtaggg tggtggcagt                                           30

<210> SEQ ID NO 321
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (3)..(3)
<223> OTHER INFORMATION: Wherein uridine at position 3 is 2'-O-methyl
      uridine.

<400> SEQUENCE: 321
acugcctagg ttgggtaggg tggtggcagt                                           30

<210> SEQ ID NO 322
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (4)..(4)
<223> OTHER INFORMATION: Wherein guanosine at position 4 is 2'-O-methyl.

<400> SEQUENCE: 322
actgcctagg ttgggtaggg tggtggcagt                                           30

<210> SEQ ID NO 323
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (5)..(5)
<223> OTHER INFORMATION: Wherein cytidine at position 5 is 2'-O-methyl.

<400> SEQUENCE: 323
actgcctagg ttgggtaggg tggtggcagt                                           30

<210> SEQ ID NO 324
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (6)..(6)
<223> OTHER INFORMATION: Wherein cytidine at position 6 is 2'-O-methyl.

<400> SEQUENCE: 324
actgcctagg ttgggtaggg tggtggcagt                                           30

<210> SEQ ID NO 325
<211> LENGTH: 30
<212> TYPE: DNA
<213> ORGANISM: Artificial Sequence
```

```
<220> FEATURE:
<223> OTHER INFORMATION: synthetic aptamer
<220> FEATURE:
<221> NAME/KEY: modified_base
<222> LOCATION: (7)..(7)
<223> OTHER INFORMATION: Wherein uridine at position 7 is 2'-O-methyl.

<400> SEQUENCE: 325
actgccuagg ttgggtaggg tggtggcagt                                              30

<210> SEQ ID NO 326
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (8)..(8)
<223> OTHER INFORMATION: Wherein adenosine at position 8 is 2'-O-methyl.

<400> SEQUENCE: 326
actgcctagg ttgggtaggg tggtggcagt                                              30

<210> SEQ ID NO 327
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (9)..(9)
<223> OTHER INFORMATION: Wherein guanosine at position 9 is 2'-O-methyl.

<400> SEQUENCE: 327
actgcctagg ttgggtaggg tggtggcagt                                              30

<210> SEQ ID NO 328
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (10)..(10)
<223> OTHER INFORMATION: Wherein guanosine at position 10 is 2'-O-
      methyl.

<400> SEQUENCE: 328
actgcctagg ttgggtaggg tggtggcagt                                              30

<210> SEQ ID NO 329
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (11)..(11)
<223> OTHER INFORMATION: Wherein uridine at position 11 is 2'-O-methyl.

<400> SEQUENCE: 329
actgcctagg utgggtaggg tggtggcagt                                              30
```

```
<210> SEQ ID NO 330
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (12)..(12)
<223> OTHER INFORMATION: Wherein uridine at position 12 is 2'-O-methyl.

<400> SEQUENCE: 330
actgcctagg tugggtaggg tggtggcagt                                           30

<210> SEQ ID NO 331
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (13)..(13)
<223> OTHER INFORMATION: Wherein guanosine at position 13 is 2'-O-
      methyl.

<400> SEQUENCE: 331
actgcctagg ttgggtaggg tggtggcagt                                           30

<210> SEQ ID NO 332
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (14)..(14)
<223> OTHER INFORMATION: Wherein guanosine at position 14 is 2'-O-
      methyl.

<400> SEQUENCE: 332
actgcctagg ttgggtaggg tggtggcagt                                           30

<210> SEQ ID NO 333
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (15)..(15)
<223> OTHER INFORMATION: Wherein guanosine at position 15 is 2'-O-
      methyl.

<400> SEQUENCE: 333
actgcctagg ttgggtaggg tggtggcagt                                           30

<210> SEQ ID NO 334
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (16)..(16)
<223> OTHER INFORMATION: Wherein uridine at position 16 is 2'-O-methyl.
```

```
<400> SEQUENCE: 334
actgcctagg ttgggguaggg tggtggcagt                                              30

<210> SEQ ID NO 335
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (17)..(17)
<223> OTHER INFORMATION: Wherein adenosine at position 17 is 2'-O-
      methyl.

<400> SEQUENCE: 335
actgcctagg ttgggtaggg tggtggcagt                                              30

<210> SEQ ID NO 336
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (18)..(18)
<223> OTHER INFORMATION: Wherein guanosine at position 18 is 2'-O-
      methyl.

<400> SEQUENCE: 336
actgcctagg ttgggtaggg tggtggcagt                                              30

<210> SEQ ID NO 337
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (19)..(19)
<223> OTHER INFORMATION: Wherein guanosine at position 19 is 2'-O-
      methyl.

<400> SEQUENCE: 337
actgcctagg ttgggtaggg tggtggcagt                                              30

<210> SEQ ID NO 338
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (20)..(20)
<223> OTHER INFORMATION: Wherein guanosine at position 20 is 2'-O-
      methyl.

<400> SEQUENCE: 338
actgcctagg ttgggtaggg tggtggcagt                                              30

<210> SEQ ID NO 339
<211> LENGTH: 30
<212> TYPE: DNA
<213> ORGANISM: Artificial Sequence
<220> FEATURE:
<223> OTHER INFORMATION: synthetic aptamer
```

-continued

```
<220> FEATURE:
<221> NAME/KEY: modified_base
<222> LOCATION: (21)..(21)
<223> OTHER INFORMATION: Wherein uridine at position 21 is 2'-O-methyl.

<400> SEQUENCE: 339
actgcctagg ttgggtaggg uggtggcagt                                   30

<210> SEQ ID NO 340
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (22)..(22)
<223> OTHER INFORMATION: Wherein guanosine at position 22 is 2'-O-
      methyl.

<400> SEQUENCE: 340
actgcctagg ttgggtaggg tggtggcagt                                   30

<210> SEQ ID NO 341
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (23)..(23)
<223> OTHER INFORMATION: Wherein guanosine at position 23 is 2'-O-
      methyl.

<400> SEQUENCE: 341
actgcctagg ttgggtaggg tggtggcagt                                   30

<210> SEQ ID NO 342
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (24)..(24)
<223> OTHER INFORMATION: Wherein uridine at position 24 is 2'-O-methyl.

<400> SEQUENCE: 342
actgcctagg ttgggtaggg tgguggcagt                                   30

<210> SEQ ID NO 343
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (25)..(25)
<223> OTHER INFORMATION: Wherein guanosine at position 25 is 2'-O-
      methyl.

<400> SEQUENCE: 343
actgcctagg ttgggtaggg tggtggcagt                                   30
```

```
<210> SEQ ID NO 344
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (26)..(26)
<223> OTHER INFORMATION: Wherein guanosine at position 26 is 2'-O-
      methyl.

<400> SEQUENCE: 344
actgcctagg ttgggtaggg tggtggcagt                                      30

<210> SEQ ID NO 345
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (27)..(27)
<223> OTHER INFORMATION: Wherein cytidine at position 27 is 2'-O-methyl.

<400> SEQUENCE: 345
actgcctagg ttgggtaggg tggtggcagt                                      30

<210> SEQ ID NO 346
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (28)..(28)
<223> OTHER INFORMATION: Wherein adenosine at position 28 is 2'-O-
      methyl.

<400> SEQUENCE: 346
actgcctagg ttgggtaggg tggtggcagt                                      30

<210> SEQ ID NO 347
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (29)..(29)
<223> OTHER INFORMATION: Wherein guanosine at position 29 is 2'-O-
      methyl.

<400> SEQUENCE: 347
actgcctagg ttgggtaggg tggtggcagt                                      30

<210> SEQ ID NO 348
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: modified_base
<222> LOCATION: (30)..(30)
<223> OTHER INFORMATION: Wherein uridine at position 30 is 2'-O-methyl.
```

```
<400> SEQUENCE: 348
actgcctagg ttgggtaggg tggtggcagu                                              30

<210> SEQ ID NO 349
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(2)
<223> OTHER INFORMATION: Wherein adenosine at position 1 is linked to
      cytidine at position 2 via a phosphorothioate linkage.

<400> SEQUENCE: 349
actgcctagg ttgggtaggg tggtggcagt                                              30

<210> SEQ ID NO 350
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (2)..(3)
<223> OTHER INFORMATION: Wherein cytidine at position 2 is linked to
      thymidine at position 3 via a phosphorothioate linkage.

<400> SEQUENCE: 350
actgcctagg ttgggtaggg tggtggcagt                                              30

<210> SEQ ID NO 351
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (3)..(4)
<223> OTHER INFORMATION: Wherein thymidine at position 3 is linked to
      guanosine at position 4 via a phosphorothioate linkage.

<400> SEQUENCE: 351
actgcctagg ttgggtaggg tggtggcagt                                              30

<210> SEQ ID NO 352
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (4)..(5)
<223> OTHER INFORMATION: Wherein guanosine at position 4 is linked to
      cytidine at position 5 via a phosphorothioate linkage.

<400> SEQUENCE: 352
actgcctagg ttgggtaggg tggtggcagt                                              30

<210> SEQ ID NO 353
<211> LENGTH: 30
<212> TYPE: DNA
<213> ORGANISM: Artificial Sequence
<220> FEATURE:
<223> OTHER INFORMATION: synthetic aptamer
```

```
<220> FEATURE:
<221> NAME/KEY: misc_feature
<222> LOCATION: (5)..(6)
<223> OTHER INFORMATION: Wherein cytidine at position 5 is linked to
      cytidine at position 6 via a phosphorothioate linkage.

<400> SEQUENCE: 353
actgcctagg ttgggtaggg tggtggcagt                                        30

<210> SEQ ID NO 354
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (6)..(7)
<223> OTHER INFORMATION: Wherein cytidine at position 6 is linked to
      thymidine at position 7 via a phosphorothioate linkage.

<400> SEQUENCE: 354
actgcctagg ttgggtaggg tggtggcagt                                        30

<210> SEQ ID NO 355
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (7)..(8)
<223> OTHER INFORMATION: Wherein thymidine at position 7 is linked to
      adenosine at position 8 via a phosphorothioate linkage.

<400> SEQUENCE: 355
actgcctagg ttgggtaggg tggtggcagt                                        30

<210> SEQ ID NO 356
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (8)..(9)
<223> OTHER INFORMATION: Wherein adenosine at position 8 is linked to
      guanosine at position 9 via a phosphorothioate linkage.

<400> SEQUENCE: 356
actgcctagg ttgggtaggg tggtggcagt                                        30

<210> SEQ ID NO 357
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (9)..(10)
<223> OTHER INFORMATION: Wherein guansine at position 9 is linked to
      guanosine at position 10 via a phosphorothioate linkage.

<400> SEQUENCE: 357
actgcctagg ttgggtaggg tggtggcagt                                        30
```

```
<210> SEQ ID NO 358
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (10)..(11)
<223> OTHER INFORMATION: Wherein guanosine at position 10 is linked to
      thymidine at position 11 via a phopshorothioate linkage.

<400> SEQUENCE: 358
actgcctagg ttgggtaggg tggtggcagt                                      30

<210> SEQ ID NO 359
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (11)..(12)
<223> OTHER INFORMATION: Wherein thymidine at position 11 is linked to
      thymidine at position 12 via a phosphorothioate linkage.

<400> SEQUENCE: 359
actgcctagg ttgggtaggg tggtggcagt                                      30

<210> SEQ ID NO 360
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (12)..(13)
<223> OTHER INFORMATION: Wherein thymidine at position 12 is linked to
      guanosine at position 13 via a phosphorothioate linkage.

<400> SEQUENCE: 360
actgcctagg ttgggtaggg tggtggcagt                                      30

<210> SEQ ID NO 361
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (13)..(14)
<223> OTHER INFORMATION: Wherein guanosine at position 13 is linked to
      guanosine at position 14 via a phosphorothioate linkage.

<400> SEQUENCE: 361
actgcctagg ttgggtaggg tggtggcagt                                      30

<210> SEQ ID NO 362
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (14)..(15)
<223> OTHER INFORMATION: Wherein guanosine at position 14 is linked to
      guanosine at position 15 via a phosphorothioate linkage.
```

```
<400> SEQUENCE: 362
actgcctagg ttgggtaggg tggtggcagt                                        30

<210> SEQ ID NO 363
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (15)..(16)
<223> OTHER INFORMATION: Wherein guanosine at position 15 is linked to
      thymidine at position 16 via a phosphorothioate linkage.

<400> SEQUENCE: 363
actgcctagg ttgggtaggg tggtggcagt                                        30

<210> SEQ ID NO 364
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (16)..(17)
<223> OTHER INFORMATION: Wherein thymidine at position 16 is linked to
      adenosine at position 17 via a phosphorothioate linkage.

<400> SEQUENCE: 364
actgcctagg ttgggtaggg tggtggcagt                                        30

<210> SEQ ID NO 365
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (17)..(18)
<223> OTHER INFORMATION: Wherein adenosine at position 17 is linked to
      guanosine at position 18 via a phosphorothioate linkage.

<400> SEQUENCE: 365
actgcctagg ttgggtaggg tggtggcagt                                        30

<210> SEQ ID NO 366
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (18)..(19)
<223> OTHER INFORMATION: Wherein guanosine at position 18 is linked to
      guanosine at position 19 via a phosphorothioate linkage.

<400> SEQUENCE: 366
actgcctagg ttgggtaggg tggtggcagt                                        30

<210> SEQ ID NO 367
<211> LENGTH: 30
<212> TYPE: DNA
<213> ORGANISM: Artificial Sequence
<220> FEATURE:
<223> OTHER INFORMATION: synthetic aptamer
```

```
<220> FEATURE:
<221> NAME/KEY: misc_feature
<222> LOCATION: (19)..(20)
<223> OTHER INFORMATION: Wherein guanosine at position 19 is linked to
      guanosine at position 20 via a phosphorothioate linkage.

<400> SEQUENCE: 367
actgcctagg ttgggtaggg tggtggcagt                                            30

<210> SEQ ID NO 368
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (20)..(21)
<223> OTHER INFORMATION: Wherein guanosine at position 20 is linked to
      thymidine at position 21 via a phosphorothioate linkage.

<400> SEQUENCE: 368
actgcctagg ttgggtaggg tggtggcagt                                            30

<210> SEQ ID NO 369
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (21)..(22)
<223> OTHER INFORMATION: Wherein thymidine at position 21 is linked to
      guanosine at position 22 via a phosphorothioate linkage.

<400> SEQUENCE: 369
actgcctagg ttgggtaggg tggtggcagt                                            30

<210> SEQ ID NO 370
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (22)..(23)
<223> OTHER INFORMATION: Wherein guanosine at position 22 is linked to
      guanosine at position 23 via a phosphorothioate linkage.

<400> SEQUENCE: 370
actgcctagg ttgggtaggg tggtggcagt                                            30

<210> SEQ ID NO 371
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (23)..(24)
<223> OTHER INFORMATION: Wherein guanosine at position 23 is linked to
      thymidine at position 24 via a phosphorothioate linkage.

<400> SEQUENCE: 371
actgcctagg ttgggtaggg tggtggcagt                                            30
```

```
<210> SEQ ID NO 372
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (24)..(25)
<223> OTHER INFORMATION: Wherein thymidine at position 24 is linked to
      guanosine at position 25 via a phosphorothioate linkage.

<400> SEQUENCE: 372
actgcctagg ttgggtaggg tggtggcagt                                    30

<210> SEQ ID NO 373
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (25)..(26)
<223> OTHER INFORMATION: Wherein guanosine at position 25 is linked to
      guanosine at position 26 via a phosphorothioate linkage.

<400> SEQUENCE: 373
actgcctagg ttgggtaggg tggtggcagt                                    30

<210> SEQ ID NO 374
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (26)..(27)
<223> OTHER INFORMATION: Wherein guanosine at position 26 is linked to
      cytidine at position 27 via a phosphorothioate linkage.

<400> SEQUENCE: 374
actgcctagg ttgggtaggg tggtggcagt                                    30

<210> SEQ ID NO 375
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (27)..(28)
<223> OTHER INFORMATION: Wherein cytidine at position 27 is linked to
      adenosine at position 28 via a phosphorothioate linkage.

<400> SEQUENCE: 375
actgcctagg ttgggtaggg tggtggcagt                                    30

<210> SEQ ID NO 376
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (28)..(29)
<223> OTHER INFORMATION: Wherein adenosine at position 28 is linked to
      guanosine at position 29 via a phosphorothioate linkage.
```

```
<400> SEQUENCE: 376
actgcctagg ttgggtaggg tggtggcagt                                    30

<210> SEQ ID NO 377
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (29)..(30)
<223> OTHER INFORMATION: Wherein guanosine at position 29 is linked to
      thymidine at position 30 via a phosphorothioate linkage.

<400> SEQUENCE: 377
actgcctagg ttgggtaggg tggtggcagt                                    30

<210> SEQ ID NO 378
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (4)..(4)
<223> OTHER INFORMATION: Wherein n at position 4 is deoxy inosine.

<400> SEQUENCE: 378
actncctagg ttgggtaggg tggtggcagt                                    30

<210> SEQ ID NO 379
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (9)..(9)
<223> OTHER INFORMATION: Wherein n at position 9 is deoxy inosine.

<400> SEQUENCE: 379
actgcctang ttgggtaggg tggtggcagt                                    30

<210> SEQ ID NO 380
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (10)..(10)
<223> OTHER INFORMATION: Wherein n at position 10 is deoxy inosine.

<400> SEQUENCE: 380
actgcctagn ttgggtaggg tggtggcagt                                    30

<210> SEQ ID NO 381
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (13)..(13)
<223> OTHER INFORMATION: Wherein n at position 13 is deoxy inosine.
```

-continued

```
<400> SEQUENCE: 381
actgcctagg ttnggtaggg tggtggcagt                                          30

<210> SEQ ID NO 382
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (14)..(14)
<223> OTHER INFORMATION: Wherein n at position 14 is deoxy inosine.

<400> SEQUENCE: 382
actgcctagg ttgngtaggg tggtggcagt                                          30

<210> SEQ ID NO 383
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (15)..(15)
<223> OTHER INFORMATION: Wherein n at position 15 is deoxy inosine.

<400> SEQUENCE: 383
actgcctagg ttggntaggg tggtggcagt                                          30

<210> SEQ ID NO 384
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (18)..(18)
<223> OTHER INFORMATION: Wherein n at position 18 is deoxy inosine.

<400> SEQUENCE: 384
actgcctagg ttgggtangg tggtggcagt                                          30

<210> SEQ ID NO 385
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (19)..(19)
<223> OTHER INFORMATION: Wherein n at position 19 is deoxy inosine.

<400> SEQUENCE: 385
actgcctagg ttgggtagng tggtggcagt                                          30

<210> SEQ ID NO 386
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (20)..(20)
<223> OTHER INFORMATION: Wherein n at position 20 is deoxy inosine.
```

```
<400> SEQUENCE: 386
actgcctagg ttgggtaggn tggtggcagt                                              30

<210> SEQ ID NO 387
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (22)..(22)
<223> OTHER INFORMATION: Wherein n at position 22 is deoxy inosine.

<400> SEQUENCE: 387
actgcctagg ttgggtaggg tngtggcagt                                              30

<210> SEQ ID NO 388
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (23)..(23)
<223> OTHER INFORMATION: Wherein n at position 23 is deoxy inosine.

<400> SEQUENCE: 388
actgcctagg ttgggtaggg tgntggcagt                                              30

<210> SEQ ID NO 389
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (25)..(25)
<223> OTHER INFORMATION: Wherein n at position 25 is deoxy inosine.

<400> SEQUENCE: 389
actgcctagg ttgggtaggg tggtngcagt                                              30

<210> SEQ ID NO 390
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (26)..(26)
<223> OTHER INFORMATION: Wherein n at position 26 is deoxy inosine.

<400> SEQUENCE: 390
actgcctagg ttgggtaggg tggtgncagt                                              30

<210> SEQ ID NO 391
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (29)..(29)
<223> OTHER INFORMATION: Wherein n at position 29 is deoxy inosine.
```

```
<400> SEQUENCE: 391
actgcctagg ttgggtaggg tggtggcant                                              30

<210> SEQ ID NO 392
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (4)..(4)
<223> OTHER INFORMATION: Wherein n at position 4 is 2'-O-methyl inosine.

<400> SEQUENCE: 392
actncctagg ttgggtaggg tggtggcagt                                              30

<210> SEQ ID NO 393
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (9)..(9)
<223> OTHER INFORMATION: Wherein n at position 9 is 2'-O-methyl inosine.

<400> SEQUENCE: 393
actgcctang ttgggtaggg tggtggcagt                                              30

<210> SEQ ID NO 394
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (10)..(10)
<223> OTHER INFORMATION: Wherein n at position 10 is 2'-O-methyl
      inosine.

<400> SEQUENCE: 394
actgcctagn ttgggtaggg tggtggcagt                                              30

<210> SEQ ID NO 395
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (13)..(13)
<223> OTHER INFORMATION: Wherein n at position 13 is 2'-O-methyl
      inosine.

<400> SEQUENCE: 395
actgcctagg ttnggtaggg tggtggcagt                                              30

<210> SEQ ID NO 396
<211> LENGTH: 30
<212> TYPE: DNA
<213> ORGANISM: Artificial Sequence
<220> FEATURE:
<223> OTHER INFORMATION: synthetic aptamer
```

-continued

```
<220> FEATURE:
<221> NAME/KEY: misc_feature
<222> LOCATION: (14)..(14)
<223> OTHER INFORMATION: Wherein n at position 14 is 2'-O-methyl
      inosine.

<400> SEQUENCE: 396
actgcctagg ttgngtaggg tggtggcagt                                          30

<210> SEQ ID NO 397
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (15)..(15)
<223> OTHER INFORMATION: Wherein n at position 15 is 2'-O-methyl
      inosine.

<400> SEQUENCE: 397
actgcctagg ttggntaggg tggtggcagt                                          30

<210> SEQ ID NO 398
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (18)..(18)
<223> OTHER INFORMATION: Wherein n at position 18 is 2'-O-methyl
      inosine.

<400> SEQUENCE: 398
actgcctagg ttgggtangg tggtggcagt                                          30

<210> SEQ ID NO 399
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (19)..(19)
<223> OTHER INFORMATION: Wherein n at position 19 is 2'-O-methyl
      inosine.

<400> SEQUENCE: 399
actgcctagg ttgggtagng tggtggcagt                                          30

<210> SEQ ID NO 400
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (20)..(20)
<223> OTHER INFORMATION: Wherein n at position 20 is 2'-O-methyl
      inosine.

<400> SEQUENCE: 400
actgcctagg ttgggtaggn tggtggcagt                                          30
```

```
<210> SEQ ID NO 401
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (22)..(22)
<223> OTHER INFORMATION: Wherein n at position 22 is 2'-O-methyl
      inosine.

<400> SEQUENCE: 401
actgcctagg ttgggtaggg tngtggcagt                                       30

<210> SEQ ID NO 402
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (23)..(23)
<223> OTHER INFORMATION: Wherein n at position 23 is 2'-O-methyl
      inosine.

<400> SEQUENCE: 402
actgcctagg ttgggtaggg tgntggcagt                                       30

<210> SEQ ID NO 403
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (25)..(25)
<223> OTHER INFORMATION: Wherein n at position 25 is 2'-O-methyl
      inosine.

<400> SEQUENCE: 403
actgcctagg ttgggtaggg tggtngcagt                                       30

<210> SEQ ID NO 404
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (26)..(26)
<223> OTHER INFORMATION: Wherein n at position 26 is 2'-O-methyl
      inosine.

<400> SEQUENCE: 404
actgcctagg ttgggtaggg tggtgncagt                                       30

<210> SEQ ID NO 405
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (29)..(29)
<223> OTHER INFORMATION: Wherein n at position 29 is 2'-O-methyl
      inosine.
```

-continued

```
<400> SEQUENCE: 405
actgcctagg ttgggtaggg tggtggcant                                   30

<210> SEQ ID NO 406
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(7)
<223> OTHER INFORMATION: Wherein nucleotides from positions 1-7 are 2'-
      O-methyl modified nucleotides.
<220> FEATURE:
<221> NAME/KEY: misc_feature
<222> LOCATION: (8)..(23)
<223> OTHER INFORMATION: Wherein nucleotides from positions 8-23 are
      deoxy nucleotides.
<220> FEATURE:
<221> NAME/KEY: misc_feature
<222> LOCATION: (24)..(30)
<223> OTHER INFORMATION: Wherein nucleotides from positions 24-30 are
      2'-O-methyl modified nucleotides.

<400> SEQUENCE: 406
acugccuagg ttgggtaggg tgguggcagu                                   30

<210> SEQ ID NO 407
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(6)
<223> OTHER INFORMATION: Wherein nucleotides from positions 1-6 are 2-O-
      methyl modified nucleotides.
<220> FEATURE:
<221> NAME/KEY: misc_feature
<222> LOCATION: (7)..(24)
<223> OTHER INFORMATION: Wherein nucleotides from positions 7-24 are
      deoxy nucleotides.
<220> FEATURE:
<221> NAME/KEY: misc_feature
<222> LOCATION: (25)..(30)
<223> OTHER INFORMATION: Wherein nucleotides from positions 25-30 are 2-
      O-methyl modified nucleotides.

<400> SEQUENCE: 407
acugcctagg ttgggtaggg tggtggcagu                                   30

<210> SEQ ID NO 408
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(5)
<223> OTHER INFORMATION: Wherein nucleotides from positions 1-5 are 2'-
      O-methyl modified nucleotides.
<220> FEATURE:
<221> NAME/KEY: misc_feature
<222> LOCATION: (6)..(26)
<223> OTHER INFORMATION: Wherein nucleotides from positions 6-26 are
      deoxy nucleotides.
<220> FEATURE:
<221> NAME/KEY: misc_feature
<222> LOCATION: (27)..(30)
<223> OTHER INFORMATION: Wherein nucleotides from positions 27-30 are
      2'-O-methyl modified nucleotides.
```

-continued

```
<400> SEQUENCE: 408
acugcctagg ttgggtaggg tggtggcagu                                              30

<210> SEQ ID NO 409
<211> LENGTH: 30
<212> TYPE: DNA
<213> ORGANISM: Artificial Sequence
<220> FEATURE:
<223> OTHER INFORMATION: synthetic aptamer

<400> SEQUENCE: 409
aatgattagg ttgggtaggg tggtatcatt                                              30

<210> SEQ ID NO 410
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(7)
<223> OTHER INFORMATION: Wherein nucleotides from positions 1-7 are 2'-
      O-methyl modified nucleotides.
<220> FEATURE:
<221> NAME/KEY: misc_feature
<222> LOCATION: (8)..(23)
<223> OTHER INFORMATION: Wherein nucleotides 8-23 are deoxy nucleotides.
<220> FEATURE:
<221> NAME/KEY: misc_feature
<222> LOCATION: (24)..(30)
<223> OTHER INFORMATION: Wherein nucleotides 24-30 are 2'-O-methyl
      modified nucleotides.

<400> SEQUENCE: 410
aaugauuagg ttgggtaggg tgguaucauu                                              30

<210> SEQ ID NO 411
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(6)
<223> OTHER INFORMATION: Wherein nucleotides from positions 1-6 are 2'-
      O-methyl modified nucleotides.
<220> FEATURE:
<221> NAME/KEY: misc_feature
<222> LOCATION: (7)..(24)
<223> OTHER INFORMATION: Wherein nucleotides from positions 7-24 are
      deoxy nucleotides.
<220> FEATURE:
<221> NAME/KEY: misc_feature
<222> LOCATION: (25)..(30)
<223> OTHER INFORMATION: Wherein nucleotides from positions 25-30 are
      2'-O-methyl modified nucleotides.

<400> SEQUENCE: 411
aaugautagg ttgggtaggg tggtaucauu                                              30

<210> SEQ ID NO 412
<211> LENGTH: 30
<212> TYPE: DNA
<213> ORGANISM: Artificial Sequence
<220> FEATURE:
<223> OTHER INFORMATION: synthetic aptamer
```

```
<220> FEATURE:
<221> NAME/KEY: misc_feature
<222> LOCATION: (1)..(5)
<223> OTHER INFORMATION: Wherein nucleotides from positions 1-5 are
      2'-O-methyl modified nucleotides.
<220> FEATURE:
<221> NAME/KEY: misc_feature
<222> LOCATION: (6)..(25)
<223> OTHER INFORMATION: Wherein nucleotides from positions 6-25 are
      deoxy nucleotides.
<220> FEATURE:
<221> NAME/KEY: misc_feature
<222> LOCATION: (26)..(30)
<223> OTHER INFORMATION: Wherein nucleotides from positions 26-30 are
      2'-O-methyl modified nucleotides.

<400> SEQUENCE: 412
aaugattagg ttgggtaggg tggtaucauu                                           30

<210> SEQ ID NO 413
<211> LENGTH: 28
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(6)
<223> OTHER INFORMATION: Wherein nucleotides from positions 1-6 are 2'-
      O-methyl modified nucleotides.
<220> FEATURE:
<221> NAME/KEY: misc_feature
<222> LOCATION: (7)..(22)
<223> OTHER INFORMATION: Wherein nucleotides from positions 7-22 are
      deoxy nucleotides.
<220> FEATURE:
<221> NAME/KEY: misc_feature
<222> LOCATION: (23)..(28)
<223> OTHER INFORMATION: Wherein nucleotides from positions 23-28 are
      2'-O-methyl modified nucleotides.

<400> SEQUENCE: 413
cugccuaggt tgggtagggt gguggcag                                             28

<210> SEQ ID NO 414
<211> LENGTH: 28
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(5)
<223> OTHER INFORMATION: Wherein nucleotides from positions 1-5 are 2'-
      O-methyl modified nucleotides.
<220> FEATURE:
<221> NAME/KEY: misc_feature
<222> LOCATION: (6)..(23)
<223> OTHER INFORMATION: Wherein nucleotides from positions 6-23 are
      deoxy nucleotides.
<220> FEATURE:
<221> NAME/KEY: misc_feature
<222> LOCATION: (24)..(28)
<223> OTHER INFORMATION: Wherein nucleotides from positions 24-28 are
      2'-O-methyl modified nucleotides.

<400> SEQUENCE: 414
cugcctaggt tgggtagggt ggtggcag                                             28

<210> SEQ ID NO 415
<211> LENGTH: 28
<212> TYPE: DNA
<213> ORGANISM: Artificial Sequence
```

```
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
<220> FEATURE:
<221> NAME/KEY: misc_feature
<222> LOCATION: (5)..(25)
<223> OTHER INFORMATION: Wherein nucleotides from positions 5-25 are
      deoxy nucleotides.
<220> FEATURE:
<221> NAME/KEY: misc_feature
<222> LOCATION: (26)..(28)
<223> OTHER INFORMATION: Wherein nucleotides from positions 26-28 are
      2'-O-methyl modified nucleotides.

<400> SEQUENCE: 415
cugcctaggt tgggtagggt ggtggcag                                     28

<210> SEQ ID NO 416
<211> LENGTH: 28
<212> TYPE: DNA
<213> ORGANISM: Artificial Sequence
<220> FEATURE:
<223> OTHER INFORMATION: synthetic aptamer

<400> SEQUENCE: 416
atgattaggt tgggtagggt ggtatcat                                     28

<210> SEQ ID NO 417
<211> LENGTH: 28
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(6)
<223> OTHER INFORMATION: Wherein nucleotides from positions 1-6 are 2'-
      O-methyl modified nucleotides.
<220> FEATURE:
<221> NAME/KEY: misc_feature
<222> LOCATION: (7)..(22)
<223> OTHER INFORMATION: Wherein nucleotides from positions 7-22 are
      deoxy nucleotides.
<220> FEATURE:
<221> NAME/KEY: misc_feature
<222> LOCATION: (23)..(28)
<223> OTHER INFORMATION: Wherein nucleotides from positions 23-28 are
      2'-O-methyl modified nucleotides.

<400> SEQUENCE: 417
augauuaggt tgggtagggt gguaucau                                     28

<210> SEQ ID NO 418
<211> LENGTH: 28
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(5)
<223> OTHER INFORMATION: Wherein nucleotides from positions 1-5 are 2'-
      O-methyl modified nucleotides.
<220> FEATURE:
<221> NAME/KEY: misc_feature
<222> LOCATION: (6)..(23)
<223> OTHER INFORMATION: Wherein nucleotides from positions 6-23 are
      deoxy nucleotides.
```

```
<220> FEATURE:
<221> NAME/KEY: misc_feature
<222> LOCATION: (24)..(28)
<223> OTHER INFORMATION: Wherein nucleotides from positions 24-28 are
      2'-O-methyl modified nucleotides.

<400> SEQUENCE: 418
augautaggt tgggtagggt ggtaucau                                         28

<210> SEQ ID NO 419
<211> LENGTH: 28
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
<220> FEATURE:
<221> NAME/KEY: misc_feature
<222> LOCATION: (5)..(24)
<223> OTHER INFORMATION: Wherein nucleotides from positions 5-24 are
      deoxy nucleotides.
<220> FEATURE:
<221> NAME/KEY: misc_feature
<222> LOCATION: (25)..(28)
<223> OTHER INFORMATION: Wherein nucleotides from positions 25-28 are
      2-O-methyl modified nucleotides.

<400> SEQUENCE: 419
augattaggt tgggtagggt ggtaucau                                         28

<210> SEQ ID NO 420
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(5)
<223> OTHER INFORMATION: Wherein nucleotides from positions 1-5 are 2'-
      O-methyl modified nucleotides.
<220> FEATURE:
<221> NAME/KEY: misc_feature
<222> LOCATION: (6)..(21)
<223> OTHER INFORMATION: Wherein nucleotides from positions 6-21 are
      deoxy nucleotides.
<220> FEATURE:
<221> NAME/KEY: misc_feature
<222> LOCATION: (22)..(26)
<223> OTHER INFORMATION: Wherein nucleotides from positions 22-26 are
      2'-O-methyl modified nucleotides.

<400> SEQUENCE: 420
ugccuaggtt gggtagggtg guggca                                           26

<210> SEQ ID NO 421
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
```

```
<220> FEATURE:
<221> NAME/KEY: misc_feature
<222> LOCATION: (5)..(22)
<223> OTHER INFORMATION: Wherein nucleotides from positions 5-22 are
      deoxy nucleotides.
<220> FEATURE:
<221> NAME/KEY: misc_feature
<222> LOCATION: (23)..(26)
<223> OTHER INFORMATION: Wherein nucleotides from positions 23-26 are
      2'-O-methyl modified nucleotides.

<400> SEQUENCE: 421
ugcctaggtt gggtagggtg gtggca                                              26

<210> SEQ ID NO 422
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(3)
<223> OTHER INFORMATION: Wherein nucleotides from positions 1-3 are 2'-
      O-methyl modified nucleotides.
<220> FEATURE:
<221> NAME/KEY: misc_feature
<222> LOCATION: (4)..(24)
<223> OTHER INFORMATION: Wherein nucleotides from positions 4-24 are
      deoxy nucleotides.
<220> FEATURE:
<221> NAME/KEY: misc_feature
<222> LOCATION: (25)..(26)
<223> OTHER INFORMATION: Wherein nucleotides from positions 25-26 are
      2'-O-methyl modified nucleotides.

<400> SEQUENCE: 422
ugcctaggtt gggtagggtg gtggca                                              26

<210> SEQ ID NO 423
<211> LENGTH: 26
<212> TYPE: DNA
<213> ORGANISM: Artificial Sequence
<220> FEATURE:
<223> OTHER INFORMATION: synthetic aptamer

<400> SEQUENCE: 423
tgattaggtt gggtagggtg gtatca                                              26

<210> SEQ ID NO 424
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(5)
<223> OTHER INFORMATION: Wherein nucleotides from positions 1-5 are 2'-
      O-methyl modified nucleotides.
<220> FEATURE:
<221> NAME/KEY: misc_feature
<222> LOCATION: (6)..(21)
<223> OTHER INFORMATION: Wherein nucleotides from positions 6-21 are
      deoxy nucleotides.
<220> FEATURE:
<221> NAME/KEY: misc_feature
<222> LOCATION: (22)..(26)
<223> OTHER INFORMATION: Wherein nucleotides from positions 22-26 are
      2'-O-methyl modified nucleotides.

<400> SEQUENCE: 424
ugauuaggtt gggtagggtg guauca                                              26
```

```
<210> SEQ ID NO 425
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
<220> FEATURE:
<221> NAME/KEY: misc_feature
<222> LOCATION: (5)..(22)
<223> OTHER INFORMATION: Wherein nucleotides from positions 5-22 are
      deoxy nucleotides.
<220> FEATURE:
<221> NAME/KEY: misc_feature
<222> LOCATION: (23)..(26)
<223> OTHER INFORMATION: Wherein nucleotides from positions 23-26 are
      2'-O-methyl modified nucleotides.

<400> SEQUENCE: 425
ugautaggtt gggtagggtg gtauca                                          26

<210> SEQ ID NO 426
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(3)
<223> OTHER INFORMATION: Wherein nucleotides from positions 1-3 are 2'-
      O-methyl modified nucleotides.
<220> FEATURE:
<221> NAME/KEY: misc_feature
<222> LOCATION: (4)..(23)
<223> OTHER INFORMATION: Wherein nucleotides from positions 4-23 are
      deoxy nucleotides.
<220> FEATURE:
<221> NAME/KEY: misc_feature
<222> LOCATION: (24)..(26)
<223> OTHER INFORMATION: Wherein nucleotides from positions 24-26 are
      2'-O-methyl modified ucleotides.

<400> SEQUENCE: 426
ugattaggtt gggtagggtg gtauca                                          26

<210> SEQ ID NO 427
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
<220> FEATURE:
<221> NAME/KEY: misc_feature
<222> LOCATION: (5)..(20)
<223> OTHER INFORMATION: Wherein nucleotides from positions 5-20 are
      deoxy nucleotides.
<220> FEATURE:
<221> NAME/KEY: misc_feature
<222> LOCATION: (21)..(24)
<223> OTHER INFORMATION: Wherein nucleotides from positions 21-24 are
      2'-O-methyl modified nucleotides.

<400> SEQUENCE: 427
gccuaggttg ggtagggtgg uggc                                            24
```

```
<210> SEQ ID NO 428
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(3)
<223> OTHER INFORMATION: Wherein nucleotides from positions 1-3 are 2'-
      O-methyl modified nucleotides.
<220> FEATURE:
<221> NAME/KEY: misc_feature
<222> LOCATION: (4)..(21)
<223> OTHER INFORMATION: Wherein nucleotides from positions 4-21 are
      deoxy nucleotides.
<220> FEATURE:
<221> NAME/KEY: misc_feature
<222> LOCATION: (22)..(24)
<223> OTHER INFORMATION: Wherein nucleotides from positions 22-24 are
      2'-O-methyl modified nucleotides.

<400> SEQUENCE: 428
gcctaggttg ggtagggtgg tggc                                            24

<210> SEQ ID NO 429
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(2)
<223> OTHER INFORMATION: Wherein nucleotides from positions 1-2 are 2'-
      O-methyl modified nucleotides.
<220> FEATURE:
<221> NAME/KEY: misc_feature
<222> LOCATION: (3)..(24)
<223> OTHER INFORMATION: Wherein nucleotides from positions 3-24 are
      deoxy nucleotides.

<400> SEQUENCE: 429
gcctaggttg ggtagggtgg tggc

<210> SEQ ID NO 430
<211> LENGTH: 24
<212> TYPE: DNA
<213> ORGANISM: Artificial Sequence
<220> FEATURE:
<223> OTHER INFORMATION: synthetic aptamer

<400> SEQUENCE: 430
gattaggttg ggtagggtgg tatc                                            24

<210> SEQ ID NO 431
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(4)
<223> OTHER INFORMATION: Wherein nucleotides from positions 1-4 are 2'-
      O-methyl modified nucleotides.
<220> FEATURE:
<221> NAME/KEY: misc_feature
<222> LOCATION: (5)..(20)
<223> OTHER INFORMATION: Wherein nucleotides from positions 5-20 are
      deoxy nucleotides.
```

```
<220> FEATURE:
<221> NAME/KEY: misc_feature
<222> LOCATION: (21)..(24)
<223> OTHER INFORMATION: Wherein nucleotides from positions 21-24 are
      2'-O-methyl modified nucleotides.

<400> SEQUENCE: 431
gauuaggttg ggtagggtgg uauc                                              24

<210> SEQ ID NO 432
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(3)
<223> OTHER INFORMATION: Wherein nucleotides from positions 1-3 are 2'-
      O-methyl modified nucleotides.
<220> FEATURE:
<221> NAME/KEY: misc_feature
<222> LOCATION: (4)..(21)
<223> OTHER INFORMATION: Wherein nucleotides from positions 4-21 are
      deoxy nucleotides.
<220> FEATURE:
<221> NAME/KEY: misc_feature
<222> LOCATION: (22)..(24)
<223> OTHER INFORMATION: Wherein nucleotides from positions 22-24 are
      2'-O-methyl modified nucleotides.

<400> SEQUENCE: 432
gautaggttg ggtagggtgg tauc                                              24

<210> SEQ ID NO 433
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(2)
<223> OTHER INFORMATION: Wherein nucleotides from positions 1-2 are 2'-
      O-methyl modified nucleotides.
<220> FEATURE:
<221> NAME/KEY: misc_feature
<222> LOCATION: (3)..(22)
<223> OTHER INFORMATION: Wherein nucleotides from positions 3-22 are
      deoxy nucleotides.
<220> FEATURE:
<221> NAME/KEY: misc_feature
<222> LOCATION: (23)..(24)
<223> OTHER INFORMATION: Wherein nucleotides from positions 23-24 are
      2'-O-methyl modified nucleotides.

<400> SEQUENCE: 433
gattaggttg ggtagggtgg tauc                                              24

<210> SEQ ID NO 434
<211> LENGTH: 24
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(2)
<223> OTHER INFORMATION: Wherein nucleotides from positions 1-2 are 2'-
      O-methyl modified nucleotides.
```

```
<220> FEATURE:
<221> NAME/KEY: misc_feature
<222> LOCATION: (3)..(22)
<223> OTHER INFORMATION: Wherein nucleotides from positions 3-22 are
      deoxy nucleotides.
<220> FEATURE:
<221> NAME/KEY: misc_feature
<222> LOCATION: (23)..(24)
<223> OTHER INFORMATION: Wherein nucleotides from positions 23-24 are
      2'-O-methyl modified nucleotides.

<400> SEQUENCE: 434
cgctaggttg ggtagggtgg tgcg                                            24

<210> SEQ ID NO 435
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein adenosine at position 1 has an amine
      linker attached to the 5' end.

<400> SEQUENCE: 435
actgcctagg ttgggtaggg tggtggcagt                                      30

<210> SEQ ID NO 436
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein cytidine at position 1 has an amine
      linker attached to the 5' end.

<400> SEQUENCE: 436
cgcctaggtt gggtagggtg gtggcg                                          26

<210> SEQ ID NO 437
<211> LENGTH: 30
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein adenosine at position 1 has a 10 kDa
      PEG group attached to the 5' end via an amine linker.

<400> SEQUENCE: 437
actgcctagg ttgggtaggg tggtggcagt                                      30

<210> SEQ ID NO 438
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein cytidine at position 1 has a 2 kDa PEG
      group attached to the 5' end via an amine linker.
```

```
<400> SEQUENCE: 438
cgcctaggtt gggtagggtg gtggcg                                          26

<210> SEQ ID NO 439
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein cytidine at position 1 has a 5 kDa PEG
      group attached to the 5' end via an amine linker.

<400> SEQUENCE: 439
cgcctaggtt gggtagggtg gtggcg                                          26

<210> SEQ ID NO 440
<211> LENGTH: 26
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: Wherein cytidine at position 1 has a 10 kDa PEG
      group attached to the 5' end via an amine linker.

<400> SEQUENCE: 440
cgcctaggtt gggtagggtg gtggcg                                          26

<210> SEQ ID NO 441
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 441
cctaggttgg gtagggtggt gg                                              22

<210> SEQ ID NO 442
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is any nucleotide that forms a base pair with
      n at position 24
<220> FEATURE:
<221> NAME/KEY: misc_feature
<222> LOCATION: (2)..(2)
<223> OTHER INFORMATION: n is any nucleotide that forms a base pair with
      n at position 23
<220> FEATURE:
<221> NAME/KEY: misc_feature
<222> LOCATION: (3)..(3)
<223> OTHER INFORMATION: n is any nucleotide that forms a base pair with
      n at position 22
<220> FEATURE:
<221> NAME/KEY: misc_feature
<222> LOCATION: (22)..(22)
<223> OTHER INFORMATION: n is any nucleotide that forms a base pair with
      n at position 3
```

```
<220> FEATURE:
<221> NAME/KEY: misc_feature
<222> LOCATION: (23)..(23)
<223> OTHER INFORMATION: n is any nucleotide that forms a base pair with
      n at position 2
<220> FEATURE:
<221> NAME/KEY: misc_feature
<222> LOCATION: (24)..(24)
<223> OTHER INFORMATION: n is any nucleotide that forms a base pair with
      n at position 1

<400> SEQUENCE: 442
nnntaggttg ggtagggtgg tnnn                                              24

<210> SEQ ID NO 443
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is any nucleotide that forms a base pair with
      n at position 26
<220> FEATURE:
<221> NAME/KEY: misc_feature
<222> LOCATION: (2)..(2)
<223> OTHER INFORMATION: n is any nucleotide that forms a base pair with
      n at position 25
<220> FEATURE:
<221> NAME/KEY: misc_feature
<222> LOCATION: (3)..(3)
<223> OTHER INFORMATION: n is any nucleotide that forms a base pair with
      n at position 24
<220> FEATURE:
<221> NAME/KEY: misc_feature
<222> LOCATION: (4)..(4)
<223> OTHER INFORMATION: n is any nucleotide that forms a base pair with
      n at position 23
<220> FEATURE:
<221> NAME/KEY: misc_feature
<222> LOCATION: (23)..(23)
<223> OTHER INFORMATION: n is any nucleotide that forms a base pair with
      n at position 4
<220> FEATURE:
<221> NAME/KEY: misc_feature
<222> LOCATION: (24)..(24)
<223> OTHER INFORMATION: n is any nucleotide that forms a base pair with
      n at position 3
<220> FEATURE:
<221> NAME/KEY: misc_feature
<222> LOCATION: (25)..(25)
<223> OTHER INFORMATION: n is any nucleotide that forms a base pair with
      n at position 2
<220> FEATURE:
<221> NAME/KEY: misc_feature
<222> LOCATION: (26)..(26)
<223> OTHER INFORMATION: n is any nucleotide that forms a base pair with
      n at position 1

<400> SEQUENCE: 443
nnnntaggtt gggtagggtg gtnnnn                                            26

<210> SEQ ID NO 444
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is any nucleotide that forms a base pair with
      n at position 28
```

```
<220> FEATURE:
<221> NAME/KEY: misc_feature
<222> LOCATION: (2)..(2)
<223> OTHER INFORMATION: n is any nucleotide that forms a base pair with
      n at position 27
<220> FEATURE:
<221> NAME/KEY: misc_feature
<222> LOCATION: (3)..(3)
<223> OTHER INFORMATION: n is any nucleotide that forms a base pair with
      n at position 26
<220> FEATURE:
<221> NAME/KEY: misc_feature
<222> LOCATION: (4)..(4)
<223> OTHER INFORMATION: n is any nucleotide that forms a base pair with
      n at position 25
<220> FEATURE:
<221> NAME/KEY: misc_feature
<222> LOCATION: (5)..(5)
<223> OTHER INFORMATION: n is any nucleotide that forms a base pair with
      n at position 24
<220> FEATURE:
<221> NAME/KEY: misc_feature
<222> LOCATION: (24)..(24)
<223> OTHER INFORMATION: n is any nucleotide that forms a base pair with
      n at position 5
<220> FEATURE:
<221> NAME/KEY: misc_feature
<222> LOCATION: (25)..(25)
<223> OTHER INFORMATION: n is any nucleotide that forms a base pair with
      n at position 4
<220> FEATURE:
<221> NAME/KEY: misc_feature
<222> LOCATION: (26)..(26)
<223> OTHER INFORMATION: n is any nucleotide that forms a base pair with
      n at position 3
<220> FEATURE:
<221> NAME/KEY: misc_feature
<222> LOCATION: (27)..(27)
<223> OTHER INFORMATION: n is any nucleotide that forms a base pair with
      n at position 2
<220> FEATURE:
<221> NAME/KEY: misc_feature
<222> LOCATION: (28)..(28)
<223> OTHER INFORMATION: n is any nucleotide that forms a base pair with
      n at position 1

<400> SEQUENCE: 444
nnnnntaggt tgggtagggt ggtnnnnn                                              28

<210> SEQ ID NO 445
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is any nucleotide that forms a base pair with
      n at position 30
<220> FEATURE:
<221> NAME/KEY: misc_feature
<222> LOCATION: (2)..(2)
<223> OTHER INFORMATION: n is any nucleotide that forms a base pair with
      n at position 29
<220> FEATURE:
<221> NAME/KEY: misc_feature
<222> LOCATION: (3)..(3)
<223> OTHER INFORMATION: n is any nucleotide that forms a base pair with
      n at position 28
<220> FEATURE:
<221> NAME/KEY: misc_feature
<222> LOCATION: (4)..(4)
<223> OTHER INFORMATION: n is any nucleotide that forms a base pair with
      n at position 27
```

```
<220> FEATURE:
<221> NAME/KEY: misc_feature
<222> LOCATION: (5)..(5)
<223> OTHER INFORMATION: n is any nucleotide that forms a base pair with
      n at position 26
<220> FEATURE:
<221> NAME/KEY: misc_feature
<222> LOCATION: (6)..(6)
<223> OTHER INFORMATION: n is any nucleotide that forms a base pair with
      n at position 25
<220> FEATURE:
<221> NAME/KEY: misc_feature
<222> LOCATION: (25)..(25)
<223> OTHER INFORMATION: n is any nucleotide that forms a base pair with
      n at position 6
<220> FEATURE:
<221> NAME/KEY: misc_feature
<222> LOCATION: (26)..(26)
<223> OTHER INFORMATION: n is any nucleotide that forms a base pair with
      n at position 5
<220> FEATURE:
<221> NAME/KEY: misc_feature
<222> LOCATION: (27)..(27)
<223> OTHER INFORMATION: n is any nucleotide that forms a base pair with
      n at position 4
<220> FEATURE:
<221> NAME/KEY: misc_feature
<222> LOCATION: (28)..(28)
<223> OTHER INFORMATION: n is any nucleotide that forms a base pair with
      n at position 3
<220> FEATURE:
<221> NAME/KEY: misc_feature
<222> LOCATION: (29)..(29)
<223> OTHER INFORMATION: n is any nucleotide that forms a base pair with
      n at position 2
<220> FEATURE:
<221> NAME/KEY: misc_feature
<222> LOCATION: (30)..(30)
<223> OTHER INFORMATION: n is any nucleotide that forms a base pair with
      n at position 1

<400> SEQUENCE: 445
nnnnnntagg ttgggtaggg tggtnnnnnn                                     30

<210> SEQ ID NO 446
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 446
taggttgggt agggtggt                                                  18
```

APTAMERS THAT BIND THROMBIN WITH HIGH AFFINITY

This application is a 35 U.S.C. §371 filing of PCT/US2006/033092, filed Aug. 23, 2006, from which priority is claimed under 35 U.S.C. §120, which in turn claims the benefit under 35 USC §119(e)(1) of provisional application Ser. No. 60/711,768, filed Aug. 26, 2005 and provisional application Ser. No. 60/808,590, filed May 26, 2006, which applications are hereby incorporated by reference in their entireties.

FIELD OF INVENTION

The invention relates generally to the field of nucleic acids and more particularly to aptamers capable of binding to thrombin useful as therapeutics for and diagnostics of coagulation related disorders and/or other diseases or disorders in which thrombin has been implicated. The invention further relates to materials and methods for the administration of aptamers capable of binding to thrombin.

BACKGROUND OF THE INVENTION

Aptamers are nucleic acid molecules having highly specific binding affinity to molecules through interactions other than classic Watson-Crick base pairing.

Aptamers, like peptides generated by phage display or monoclonal antibodies ("mAbs"), are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and high selective binding in antibody-antigen complexes.

Aptamers have a number of desirable characteristics for use as therapeutics and diagnostics including high selectivity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the selectivity and affinity of the aptamer to be tightly controlled and allows the generation of leads, including leads against both toxic and non-immunogenic targets.

2) Toxicity and Immunogenicity. Aptamers as a class have demonstrated therapeutically acceptable toxicity and lack of immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 24 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment.

5) Stability. Therapeutic aptamers are chemically robust. They are intrinsically adapted to regain activity following exposure to factors such as heat and denaturants and can be stored for extended periods (>1 yr) at room temperature as lyophilized powders.

Thrombin

Thrombin is a multifunctional serine protease that has procoagulant and anticoagulant activities. As a procoagulant enzyme, thrombin clots fibrinogen, activates clotting factors V, VIII, and XIII, and activates platelets. The specific cleavage of fibrinogen by thrombin initiates the polymerization of fibrin monomers, a primary event in blood clot formation. The central event in the formation of platelet thrombi is the activation of platelets from the "nonbinding" to the "binding" mode. Thrombin is a physiologic activator of platelet aggregation. Thus, as a procoagulant, thrombin plays a key role in the arrest of bleeding (physiologic hemostasis) and formation of vaso-occlusive thrombi (pathologic thrombosis).

As an anticoagulant thrombin binds to thrombomodulin (TM), a glycoprotein expressed on the surface of vascular endothelial cells. TM alters substrate specificity from fibrinogen and platelets to protein C through a combination of an allosteric change in the active site conformation and an overlap of the TM and fibrinogen binding sites on thrombin. Activated protein C, in the presence of a phospholipid surface, $Ca^{2+}$, and a second vitamin K-dependent protein cofactor, protein S, inhibits coagulation by proteolytically degrading factors Va and VIIIa. Thus, the formation of the thrombin-TM complex converts thrombin from a procoagulant to an anticoagulant enzyme, and the normal balance between these opposing activities is critical to the regulation of hemostasis.

Coagulation Disorders

Vascular injury and thrombus formation represent the key events in the pathogenesis of various vascular diseases, including atherosclerosis. The pathogenic processes of the activation of platelets and/or the clotting system, leading to thrombosis in various disease states and in various sites, such as the coronary arteries, cardiac chambers, and prosthetic heart valves, appear to be different. Therefore, the use of a platelet inhibitor, an anticoagulant, or a combination of both may be required in conjunction with thrombolytics to open closed vessels and prevent reocclusion.

Controlled proteolysis by compounds of the coagulation cascade is critical for hemostasis. As a result, a variety of complex regulatory systems exist that are based, in part, on a series of highly specific protease inhibitors. In a pathological situation functional inhibitory activity can be interrupted by excessive production of active protease or inactivation of inhibitory activity. Perpetuation of inflammation in response to multiple trauma (tissue damage) or infection (sepsis) depends on proteolytic enzymes, both of plasma cascade systems, including thrombin, and of lysosomal origin. Multiple organ failure (MOF) in these cases is enhanced by the concurrently arising imbalance between proteases and their inhibitory regulators. Furthermore, an imbalance of thrombin activity in the brain may lead to neurodegenerative diseases.

Coronary Artery Bypass Graft (CABG) Surgery

In 2001, the American Heart Association reported that an estimated 12.4M patients in the U.S. were diagnosed with some form of coronary artery disease. Given thrombin's importance in the coagulation process, an anti-thrombin agent or an agent that decreases or inhibits thrombin activity is the anticoagulant used, e.g., during coronary artery bypass graft (hereinafter "CABG") surgery, percutaneous coronary intervention (hereinafter "PCI") and acute coronary syndrome. As of 2001, more than 570,000 CABG procedures were performed annually in the U.S. and it is estimated that over 700,000 procedures are performed worldwide. Currently, the most commonly used anticoagulant is heparin which must be used with the antidote protamine. However, heparin-protamine treatment is associated with a number of serious side-effects including bleeding and thrombocytopenia (platelet count reduction) which is often asymptomatic but may be associated with life-threatening arterial or venous thrombosis. In addition, heparin-protamine treatment has a number of other disadvantages including: non-specific binding to plasma proteins which results in resistance in some patients; heparin cannot inhibit clot-bound thrombin; heparin has non-linear kinetics making dosing difficult to control; and heparin is manufactured from beef or pork tissues which have an inherent safety risk arising from the possibility for transmission of viruses and/or prions. Consequently, a number of newer, higher-cost anticoagulants, such as low molecular weight heparins and Angiomax®, have gained significant penetration into this market. However, these compounds have similar side-effects and their anticoagulation activity cannot be reversed rapidly.

Thus, there is a significant unmet medical need for a safe, moderate-cost anticoagulant that does not require a separate reversing agent and which is not associated with the side effects and disadvantages listed above. Accordingly, it would be beneficial to have agents that decrease or inhibit the activity of thrombin for use as therapeutics in the treatment of coagulation-related disorders.

SUMMARY OF THE INVENTION

The present invention provides materials and methods for the treatment of thrombin mediated disorders, e.g. acute and chronic coagulation-related disorders. The present invention further provides therapeutic compositions and methods for thrombin modulation, particularly for decreasing or inhibiting thrombin mediated coagulation, for anticoagulation in a subject or patient.

In a particular embodiment, an aptamer that binds to a thrombin target, wherein the aptamer decreases or inhibits thrombin mediated coagulation and the aptamer is ARC2172 (SEQ ID NO 294) or an aptamer that has substantially the same ability as ARC2172 (SEQ ID NO 294) to decrease or inhibit thrombin mediated coagulation, wherein the aptamer binds to human thrombin with a $K_D$ of less than 1 nM, preferably less than 300 pM, more preferably less than 250 pM, and still more preferably less than 200 pM, and wherein the aptamer is 56 nucleotides or less, 55 nucleotides or less, 50 nucleotides or less, 45 nucleotides or less, 40 nucleotides or less, 35 nucleotides or less, 30 nucleotides or less, 28 nucleotides or less, 26 nucleotides or less in length is provided. In some embodiments, the aptamer is at least 22 nucleotides in length. In another embodiment, an aptamer that binds to a thrombin target, wherein the aptamer decreases or inhibits thrombin mediated coagulation and the aptamer is ARC2172 (SEQ ID NO 294) or an aptamer that has substantially the same ability as ARC2172 (SEQ ID NO 294) to decrease or inhibit thrombin mediated coagulation, and wherein the aptamer does not comprise a 5-bromodeoxyuridine modification the majority of its thymidine or uridine residues, is provided. In some embodiments the aptamer binds to human thrombin with a $K_D$ of less than 1 nM, preferably less than 300 pM, more preferably less than 250 pM, and still more preferably less than 200 pM. In some embodiments, the aptamer is 56 nucleotides or less, 55 nucleotides or less, 50 nucleotides or less, 45 nucleotides or less, 40 nucleotides or less, 35 nucleotides or less, 30 nucleotides or less, 28 nucleotides or less, 26 nucleotides or less in length is provided. In some embodiments, the aptamer is at least 22 nucleotides in length. In some embodiments, the dissociation constant may be determined by dot blot titration as described in Example 1 below.

In some embodiments, the ability of the aptamer of the invention to decrease or inhibit thrombin mediated coagulation is assessed by measuring the aptamer's ability to decrease or inhibit activated clotting time (ACT), prothrombin time (PT) and/or activated partial thromboplastin time (aPTT). Preferably, thrombin mediated coagulation is assessed by measuring the aptamer's ability to decrease ACT. In a preferred embodiment, the ability of the aptamer of the invention to decrease or inhibit coagulation is assessed by measuring ACT using a Hemochron Jr. instrument, (ITC Med, Edison N.J.) as described in Example 3B below. In some embodiments, the aptamer of the invention decreases or inhibits thrombin mediated coagulation in vivo particularly in a human subject. In some embodiments, the aptamer of the invention decreases or inhibits thrombin mediated coagulation in vitro.

In a particular embodiment, an aptamer that binds to thrombin wherein the aptamer is selected from the group consisting of: SEQ ID NOs 9-41, 43-191, 193-204, 208-304, 307-329, 331-332, 334, 336-337, 340-392, 396-397, 400, and 402-440, is provided. In one embodiment, an aptamer that binds to thrombin and comprises the following nucleic acid sequence: CCTAGGTTGGGTAGGGTGGTGG (SEQ ID NO: 441 is provided. In particular embodiments, an aptamer comprising a sequence selected from the group consisting of:

```
ACTGCCTAGGTTGGGTAGGGTGGT    (ARC2169 (SEQ ID NO 283))
GGCAGT

GCTGCCTAGGTTGGGTAGGGTGGT    (ARC2170 (SEQ ID NO 292))
GGCAGC

CTGCCTAGGTTGGGTAGGGTGGTG    (ARC2171 (SEQ ID NO 293))
GCAG,
and

CGCCTAGGTTGGGTAGGGTGGTGG    (ARC2172 (SEQ ID NO 294))
CG,
``` is provided.

In another embodiment, an aptamer comprising the following nucleic acid sequence $N_1N_2N_3$TAGGTTGGGTAGG-GTGGT$N'_3N'_2N'_1$ (SEQ ID NO: 442) wherein $N_1$, $N_2$, or $N_3$ is any nucleotide that forms a base pairs with $N'_1$, $N'_2$ or $N'_3$ respectively, wherein $N_1$, $N_2$, and $N_3$ may each be the same nucleotide or different nucleotides and the aptamer decreases or inhibits thrombin mediated coagulation is provided. In some embodiments, $N_1$, $N_2$, or $N_3$ are deoxy nucleotides. In other embodiments, at least two of $N_1$, $N_2$, or $N_3$ comprise a 2'OMe modification.

In another embodiment, an aptamer comprising the following nucleic acid sequence $N_1N_2N_3N_4$TAGGTTGGGTA-GGGTGGT (SEQ ID NO: 443) wherein $N_1$, $N_2$, $N_3$ or. $N_4$ is any nucleotide that forms a base pair with $N'_1$,$N'_2$,$N'_3$ or $N'_4$ respectively, wherein $N_1$, $N_2$, $N_3$ and $N_4$ may each be the same nucleotide or different nucleotides and the aptamer decreases or inhibits thrombin mediated coagulation is provided. In some embodiments, $N_1$, $N_2$, $N_3$ or $N_4$ are deoxy nucleotides. In other embodiments, at leak two of $N_1$, $N_2$, $N_3$ or $N_4$ comprise a 2'OMe modification.

In another embodiment, an aptamer comprising the following nucleic acid sequence $N_1N_2N_3N_4$ $N_5$TAGGTTGGGTA-GGGTGGTN'$_5$N'$_4$N'$_3$N'$_2$N'$_1$ (SEQ ID NO: 444) wherein $N_1$, $N_2$, $N_3$, $N_4$ or $N_5$ is any nucleotide that forms a base pairs with $N'_1$, $N'_2$, $N'_3$,$N'_4$ or $N'_5$ respectively, wherein $N_1$, $N_2$, $N_3$, $N_4$ and $N_5$ may each be the same nucleotide or different nucleotides and the aptamer decreases or inhibits thrombin mediated coagulation is provided. In some embodiments, $N_1$, $N_2$, $N_3$, $N_4$ or $N_5$ are deoxy nucleotides. In other embodiments, at least two of $N_1$, $N_2$, $N_3$, $N_4$ or $N_5$ comprise a 2'OMe modification.

In another embodiment, an aptamer comprising the sequence $N_1N_2N_3N_4N_5N_6$TAGGTTGGGTAGGGTGGT-N'$_6$N'$_5$N'$_4$N'$_3$N'$_2$N'$_1$ (SEQ ID NO: 445) Wherein $N_1$, $N_2$, $N_3$, $N_4$, $N_5$, or $N_6$ is any nucleotide that forms a base pairs with $N'_1$, $N'_2$, $N'_3$, $N'_4$, $N'_5$, or $N'_6$ respectively, wherein $N_1$, $N_2$, $N_3$, $N_4$, $N_5$, or $N_6$ may each be the same nucleotide or different nucleotides and the aptamer decreases or inhibits thrombin mediated coagulation is provided.

In some embodiments, N in the above described aptamers is a guanosine or cytidine nucleotide residue. In another embodiment of this aspect of the invention, the aptamer binds to thrombin with a $K_D$ of less than 1 nM. In another embodiment of this aspect of the invention, the aptamer has at least substantially the same ability as ARC2172 (SEQ ID NO 294) to decrease or inhibit thrombin mediated coagulation. In some embodiments, of this aspect the thrombin target is human thrombin.

In some embodiments the aptamers of the invention the majority of the nucleotides are deoxyribonucleic acid. In some embodiments, the aptamer of the invention are deoxyribonucleic acid particularly single stranded deoxyribonucleic acid. In some embodiments of the invention, at least 14, preferably at least 16, more preferably at least 18 nucleotides are deoxy nucleotides. In a particular embodiment, the aptamer comprises the deoxy nucleic acid sequence TAGGT-TGGGTAGGGTGGT (SEQ ID NO: 446). In some embodiments the aptamers of the invention comprise at least one chemical modification, particularly a chemical modification selected from the group consisting: of a chemical substitution at a sugar position; a chemical substitution at a phosphate position, and a chemical substitution at a base position, of the nucleic acid. In some embodiments, the chemical modification does not result in a 5-bromodeoxyuridine modification at the majority of the aptamer's thymidine or uridine residues In some embodiments, the modification is selected from the group consisting of: incorporation of a modified nucleotide, 3' capping, and conjugation to a high molecular weight, non-immunogenic compound, conjugation to a lipophilic compound, particularly wherein the high molecular weight, non-immunogenic compound is polyalkylene glycol, particularly a polyethylene glycol.

In some embodiments, the above described anti-thrombin aptamers of the invention, e.g. ARC2172, decrease or inhibit coagulation in stagnant blood, particularly for at least about 30 minutes at room temperature, more particularly for at least about 30 minutes at room temperature at a concentration of 5 µM.

In some embodiments, a method comprising administering an anti-thrombin aptamer of the invention to a subject, particularly a human subject, or an extracorporeal circuit in an amount effective to decrease or inhibit thrombin mediated coagulation in the subject is provided.

In some embodiments a composition comprising an anti-thrombin aptamer of the invention or a salt thereof in an amount effective to decrease or inhibit thrombin mediated coagulation in a subject and a pharmaceutically acceptable carrier or diluent is provided. In some embodiments, the anti-thrombin aptamer comprised in the composition of the invention is ARC2172 (SEQ ID NO 294). A method comprising administering the composition of the invention to a subject, particularly a human subject, in need thereof is provided. In some embodiments the human subject is renally impaired and the anti-thrombin aptamer of the invention administered in the method of the invention is not conjugated to a PEG. In some embodiments, the human subject to whom the aptamer is administered in the methods of the invention has heparin induced thrombocytopenia, is heparin resistant and/or has impaired hepatic function.

In some embodiments of the method of the invention, the anti-thrombin aptamer of the invention is administered to the subject, particularly a human subject, before, during, after or any combination thereof, a surgical procedure on the subject. In some embodiments the surgical procedure is a cardiac surgery. In some embodiments the surgical procedure is selected from the group consisting of cardiopulmonary by-pass surgery, coronary artery bypass graft surgery, percutaneous coronary intervention, angioplasty, cardiovascular and peripheral vascular open and endovascular surgery, stent placement surgery, heart valve replacement surgery, surgery to treat coronary disease and/or vascular disease in veins or arteries, and surgery to treat peripheral arterial occlusive disease. In some embodiments of the methods of the invention, the anti-thrombin aptamer is ARC2172 (SEQ ID NO 294). In a particular embodiment of the methods of the invention the aptamer is ARC2172 (SEQ ID NO 294) and the surgical procedure is coronary artery bypass graft surgery. In another particular embodiment of the methods of the invention the aptamer of the invention is ARC2172, the surgical procedure is cardiopulmonary by-pass surgery and an open, non-heparin bonded circuit is used during the surgery. In another particular embodiment of the methods of the invention, the aptamer is ARC2172 (SEQ ID NO 294) and the surgical procedure is percutaneous coronary intervention.

BRIEF DESCRIPTION OF THE DRAWINGS

FIG. 4 is an illustration depicting various PEGylation strategies representing standard mono-PEGylation, multiple PEGylation, and dimerization via PEGylation

FIG. 12 is a table showing the experimental study design for rat IV Bolus Studies of anti-thrombin aptamers, described in Example 4A.

FIG. 22 is a table showing the experimental study design for a monkey IV bolus plus infusion study of anti-thrombin aptamers, described in Example 4E.

FIG. 23 is a graph showing a comparison of the effects of ARC2172 (SEQ ID NO 294) (at two doses) and ARC183 on activated clot time (ACT) in cynomolgus monkeys when administered via a single IV bolus followed by a continuous 1 hour infusion.

FIG. 24 is a table summarizing the effects of ARC2172 (SEQ ID NO 294) (at two doses) and ARC183 on activated clot time (ACT) in cynomolgus monkeys when administered via a single IV bolus followed by a continuous 1 hour infusion.

FIG. 27 is a table showing the experimental design of the study of ARC2172 (SEQ ID NO 294) and heparin in a porcine cardiopulmonary bypass model, described in Example 5A.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

Figure 1:
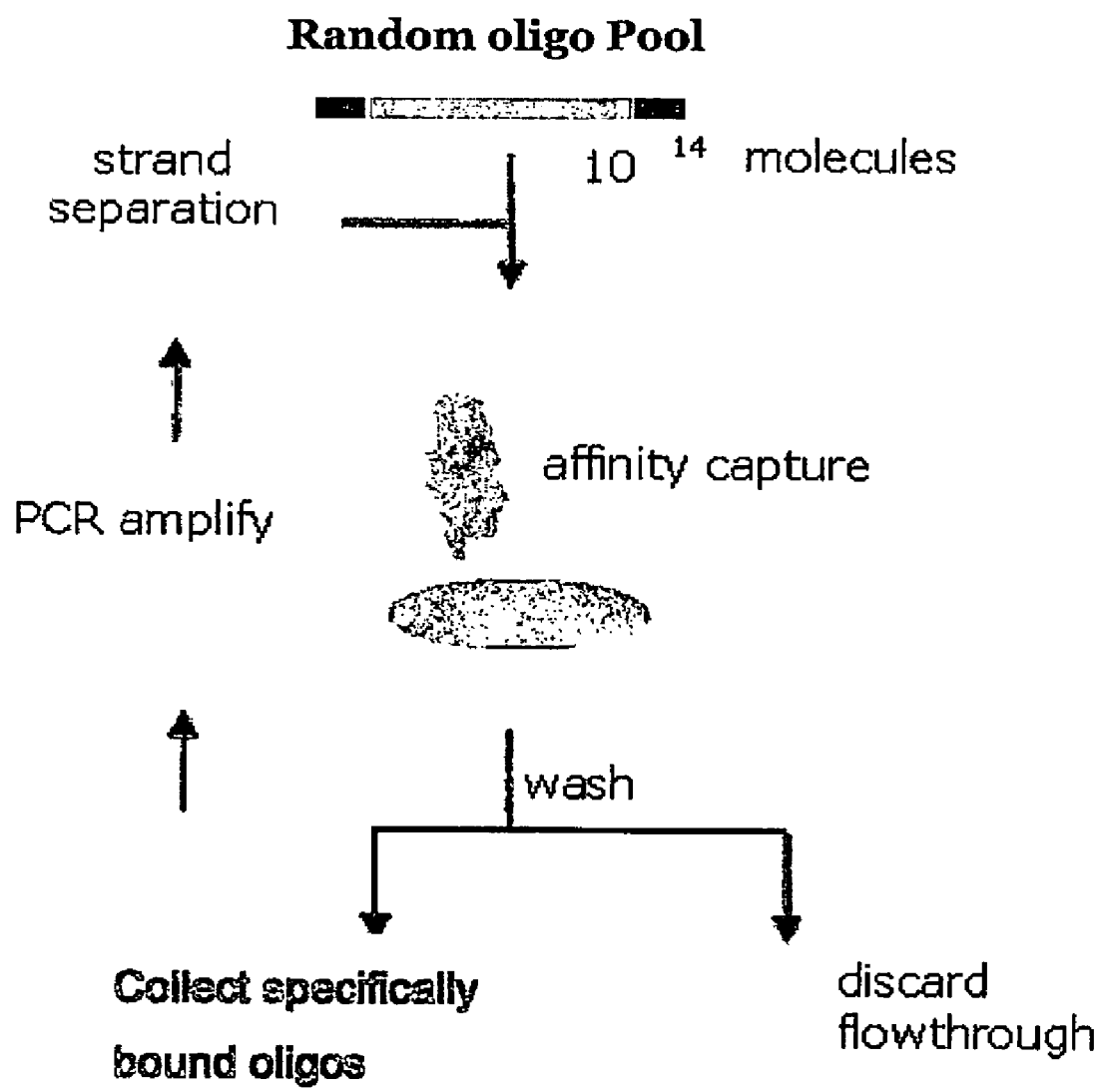
FIG. 1 is a schematic representation of the in vitro aptamer selection (SELEX™) process from pools of random sequence oligonucleotides.

A suitable method for generating an aptamer is with the process entitled "Systematic Evolution of Ligands by Exponential Enrichment" ("SELEX™") generally depicted in FIG. 1. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Aptamers are considered to have highly specific binding to target molecules, for example, because an aptamer comprises a binding affinity for the target orders of magnitude greater than the binding affinity of the starting nucleic acid library or pool that has not been previously exposed to the target. Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs described further below, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Random oligonucleotides can be synthesized from phosphodiester-linked nucleotides using solid phase oligonucleotide synthesis techniques well known in the art See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large-regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding, (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The highly target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photo reactive groups capable of binding and/or photo-crosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with highly specific affinity for the non-target molecule(s) are removed; and (f) amplifying the nucleic acids with highly specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'—$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping.

In one embodiment, oligonucleotides are provided in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical. As used herein, the term phosphorothioate encompasses one or more non-bridging oxygen atoms in a phosphodiester bond replaced by one or more sulfur atom.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both high specificity for their SELEX™ target and improved stability, e.g., in vivo stability. Post-SELEX™ process modifications made to nucleic acid ligands may result in improved stability, e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication. No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified. The aptamers with high specificity and binding affinity to the target(s) of the present invention are typically selected by the SELEX™ process as described herein. As part of the SELEX™ process, the sequences selected to bind to the target are then optionally minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

2' Modified SELEX™

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

Fluoro and amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX™ method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517, 039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl Substituted Nucleic Acids", each of which is herein incorporated by reference in its entirety.

The present invention includes aptamers that bind to and decrease or inhibit the function of thrombin which contain modified nucleotides (e.g. nucleotides which have a modification at the 2' position) to make the oligonucleotide more stable than the unmodified oligonucleotide to enzymatic and chemical degradation as well as thermal and physical degradation. Although there are several examples of 2'-OMe containing aptamers in the literature (see, e.g., Green et al., Current Biology 2,683-695, 1995) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by SELEX™ (and/or any of its variations and improvements, including those described herein), the methods of the present invention eliminate the need for stabilizing the selected aptamer oligonucleotides (e.g., by resynthesizing the aptamer oligonucleotides with modified nucleotides).

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-NH$_2$, and 2'-methoxyethyl modifications of the ATP, GTP, CTP, TTP, and UTP nucleotides. In another embodiment, the present invention provides aptamers comprising 56 combinations of 2'-OH, 2'-F, 2'-deoxy, 2'-OMe, 2'-NH$_2$, and 2'-methoxyethyl modifications of the ATP, GTP, CTP, TTP, and UTP nucleotides.

2' modified aptamers of the invention are created using modified polymerases, e.g., a modified T7 polymerase, having a rate of incorporation of modified nucleotides having bulky substituents at the furanose 2' position that is higher than that of wild-type polymerases. For example, a single mutant T7 polymerase (Y639F) in which the tyrosine residue at position 639 has been changed to phenylalanine readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a double T7 polymerase mutant (Y639F/H784A) having the histidine at position 784 changed to an alanine residue in addition to the Y639F mutation has been described and has been used in limited circumstances to incorporate modified pyrimidine NTPs. See Padilla, R. and Sousa, R., Nucleic Acids Res., 2002, 30(24): 138. A single mutant T7 polymerase (H784A) having the histidine at position 784 changed to an alanine residue has also been described. Padilla et al., Nucleic Acids Research, 2002, 30: 138. In both the Y639F/H784A double mutant and H784A single mutant T7 polymerases, the change to a smaller amino acid residue such as alanine allows for the incorporation of bulkier nucleotide substrates, e.g. 2'-OMe substituted nucleotides.

Generally, it has been found that under the conditions disclosed herein, the Y693F single mutant can be used for the incorporation of all 2'-OMe substituted NTPs except GTP and the Y639F/H784A double mutant can be used for the incorporation of all 2'-OMe substituted NTPs including GTP. It is expected that the H784A single mutant possesses properties similar to the Y639F and the Y639F/H784A mutants when used under the conditions disclosed herein.

2'-modified oligonucleotides may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts are generated using any combination of modifications, including for example, ribonucleotides (2'-OH), deoxyribonucleotides (2'-deoxy), 2'-F, and 2'-OMe nucleotides. A transcription mixture containing 2'-OMe C and U and 2'-OH A and G is referred to as an "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "rGmH" aptamers. A transcription mixture alternately containing 2'-OMe A, C, U and G and 2'-OMe A, U and C and 2'-F. G is referred to as an "alternating mixture" and aptamers selected therefrom are referred to as "alternating mixture" aptamers. A transcription mixture containing 2'-OMe A, U, C, and G, where up to 10% of the G's are ribonucleotides is referred to as a "r/mGmH" mixture and aptamers selected therefrom are referred to as "r/mGmH" aptamers. A transcription mixture containing 2'-OMe A, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "dGmH" aptamers. A transcription mixture containing deoxy A, and 2'-OMe C, G and U is referred to as a "dAmB" mixture and aptamers selected therefrom are referred to as "dAmB" aptamers, and a transcription mixture containing all 2'-OH nucleotides is referred to as a "rN" mixture and aptamers selected therefrom are referred to as "rN" or "rRrY" aptamers. A "mRmY" aptamer is one containing all 2'-O-methyl nucleotides and is usually derived from a r/mGmH oligonucleotide by post-SELEX™ replacement, when possible, of any 2'-OH Gs with 2'-OMe Gs.

A preferred embodiment includes any combination of 2'-OH, 2'-deoxy and 2'-OMe nucleotides. A more preferred embodiment includes any combination of 2'-deoxy and 2'-OMe nucleotides. An even more preferred embodiment is with any combination of 2'-deoxy and 2'-OMe nucleotides in which the pyrimidines are 2'-OMe (such as dRmY, mRmY or dGmH).

Incorporation of modified nucleotides into the aptamers of the invention is accomplished before (pre-) the selection process (e.g., a pre-SELEX™ process modification). Optionally, aptamers of the invention in which modified nucleotides have been incorporated by pre-SELEX™ process modification can be further modified by post-SELEX™ process modification (i.e., a post-SELEX™ process modification after a pre-SELEX™ modification). Pre-SELEX™ process modifications yield modified nucleic acid ligands with high affinity for the SELEX™ target and also improved in vivo stability. Post-SELEX™ process modifications, i.e., modification (e.g., truncation, deletion, substitution or additional nucleotide modifications of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

To generate pools of 2'-modified (e.g., 2'-OMe) RNA transcripts in conditions under which a polymerase accepts 2'-modified NTPs the preferred polymerase is the Y693F/H784A double mutant or the Y693F single mutant. Other polymerases, particularly those that exhibit a high tolerance for bulky 2'-substituents, may also be used in the present invention. Such polymerases can be screened for this capability by assaying their ability to incorporate modified nucleotides under the transcription conditions disclosed herein.

A number of factors have been determined to be important for the transcription conditions useful in the methods disclosed herein. For example, increases in the yields of modified transcript are observed when a leader sequence is incorporated into the 5' end of a fixed sequence at the 5' end of the DNA transcription template, such that at least about the first 6 residues of the resultant transcript are all purines.

Another important factor in obtaining transcripts incorporating modified nucleotides is the presence or concentration of 2'-OH GTP. Transcription can be divided into two phases: the first phase is initiation, during which an NTP is added to the 3'-hydroxyl end of GTP (or another substituted guanosine) to yield a dinucleotide which is then extended by about 10-12 nucleotides; the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe substituted nucleotides into transcripts is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTP's which complex divalent metal ions. To obtain the greatest yields of maximally 2' substituted O-methylated transcripts (i.e., all A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.6 mM magnesium chloride and 2.9 mM manganese chloride are preferred. In any case, departures from these concentrations of up to two-fold still give significant amounts of modified transcripts.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (6.5 mM where the concentration of each 2'-OMe NTP is 1.0 mM), MnCl$_2$ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 15 units/ml, inorganic pyrophosphatase 5 units/ml, and an all-purine leader sequence of at least 8 nucleotides long. As used herein, one unit of the Y639F/H784A mutant T7 RNA polymerase (or any other mutant T7 RNA polymerase specified herein) is defined as the amount of enzyme required to incorporate 1 mmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F T7 RNA Polymerase 15 units/ml, inorganic pyrophosphatase 5-units/ml, and an all-purine leader sequence of at least 8 nucleotides long.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.6 mM where the concentration of each 2'-OMe NTP is 2.0 mM), MnCl$_2$ 1.5 mM (2.9 mM where the concentration of each 2'-OMe NTP is 2.0 mM), 2'-OMe NTP (each) 500 µM (more preferably, 2.0 mM), pH 7.5, Y639F/H784A T7 RNA Polymerase 15 units/ml, inorganic pyrophosphatase 5 units/ml, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine 2 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.6 mM, MnCl$_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For each of the above (a) transcription is preferably performed at a temperature of from about 20° C. to about 50° C., preferably from about 30° C. to 45° C., and more preferably at about 37° C. for a period of at least two hours and (b) 50-300 nM of a double stranded DNA transcription template is used (200 nM template is used in round 1 to increase diversity (300 nM template is used in dRmY transcriptions)), and for subsequent rounds approximately 50 nM, a 1/10 dilution of an optimized PCR reaction, using conditions described herein, is used). The preferred DNA transcription templates are described below (where ARC254 and ARC256 transcribe under all 2'-OMe conditions and ARC255 transcribes under rRmY conditions).

```
                                                       SEQ ID NO 1
5'-CATCGATGCTAGTCGTAACGATCCNNNNNNNNNNNNNNNNNNNNNNN
NNNNNNNNCGAGAACGTTCTCTCCTCTCCCTATAGTGAGTCGTATTA-3'

SEQ ID NO 2
5'-CATGCATCGCGACTGACTAGCCGNNNNNNNNNNNNNNNNNNNNNNNN
NNNNNNNGTAGAACGTTCTCTCCTCTCCCTATAGTGAGTCGTATTA-3'

SEQ ID NO 3
5'-CATCGATCGATCGATCGACAGCGNNNNNNNNNNNNNNNNNNNNNNNN
NNNNNNNGTAGAACGTTCTCTCCTCTCCCTATAGTGAGTCGTATTA-3'
```

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise a sequence where 100% of all adenosine nucleotides are 2'-OH adenosine, 100% of all guanosine nucleotides are 2'-OH guanosine, 100% of all cytidine nucleotides are 2'-OH cytidine, and 100% of all uridine nucleotides are 2'-OH uridine.

Under rRmY transcription conditions of the present invention, the transcription reaction mixture comprises 2'-OH adenosine triphosphates, 2'-OH guanosine triphosphates, 2'-O-methyl cytidine triphosphates, and 2'-O-methyl uridine triphosphates. The modified oligonucleotides produced using the rRmY transcription mixtures of the present invention comprise substantially all 2'-OH adeno sine, 2'-OH guanosine, 2'-O-methyl cytidine and 2'-O-methyl uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-O-methyl cytidine and at least 80% of all uridine nucleotides are 2'-O-methyl uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-O-methyl cytidine and at least 90% of all uridine nucleotides are 2'-O-methyl uridine in a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-O-methyl cytidine and 100% of all uridine nucleotides are 2'-O-methyl uridine.

Under dRmY transcription conditions of the present invention, the transcription reaction mixture comprises 2'-deoxy adenosine triphosphates, 2'-deoxy guanosine triphosphates, 2'-O-methyl cytidine triphosphates, and 2'-O-methyl uridine triphosphates. The modified oligonucleotides produced using the dRmY transcription conditions of the present invention comprise substantially all 2'-deoxy adenosine, 2'-deoxy guanosine, 2'-O-methyl cytidine, and 2'-O-methyl uridine. In a preferred embodiment, the resulting modified oligonucleotides of the present invention comprise a sequence where at least 80% of all adenosine nucleotides are 2'-deoxy adenosine, at least 80% of all guanosine nucleotides are 2'-deoxy guanosine, at least 80% of all cytidine nucleotides are 2'-O-methyl cytidine, and at least 80% of all uridine nucleotides are 2'-O-methyl uridine. In a more preferred embodiment, the resulting modified oligonucleotides of the present invention comprise a sequence where at least 90% of all adenosine nucleotides are 2'-deoxy adenosine, at least 90% of all guanosine nucleotides are 2'-deoxy guanosine, at least 90% of all cytidine nucleotides are 2'-O-methyl cytidine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all guanosine nucleotides are 2'-deoxy guanosine, 100% of all cytidine nucleotides are 2'-O-methyl cytidine, and 100% of all uridine nucleotides are 2'-O-methyl uridine.

Under rGmH transcription conditions of the present invention, the transcription reaction mixture comprises 2'-OH guanosine triphosphates, 2'-O-methyl cytidine triphosphates, 2'-O-methyl uridine triphosphates, and 2'-O-methyl adenosine triphosphates. The modified oligonucleotides produced using the rGmH transcription mixtures of the present invention comprise substantially all 2'-OH guanosine, 2'-O-methyl cytidine, 2'-O-methyl uridine, and 2'-O-methyl adenosine. In a preferred embodiment, the resulting modified oligonucleotides comprise a sequence where at least 80% of all guanosine nucleotides are 2'-OH guanosine, at least 80% of all cytidine nucleotides are 2'-O-methyl cytidine, at least 80% of all uridine nucleotides are 2'-O-methyl uridine, and at least 80% of all adenosine nucleotides are 2'-O-methyl adenosine. In a more preferred embodiment, the resulting modified oligonucleotides comprise a sequence where at least 90% of all guanosine nucleotides are 2'-OH guanosine, at least 90% of all cytidine nucleotides are 2'-O-methyl cytidine, at least 90% of all uridine nucleotides are 2'-O-methyl uridine, and at least 90% of all adenosine nucleotides are 2'-methyl adenosine. In a most preferred embodiment, the resulting modified oligonucleotides comprise a sequence where 100% of all guanosine nucleotide's are 2'-OH guanosine, 100% of all cytidine nucleotides are 2'-O-methyl cytidine, 100% of all uridine nucleotides are 2'-O-methyl uridine, and 100% of all adenosine nucleotides are 2'-O-methyl adenosine.

Under r/mGmH transcription conditions of the present invention, the transcription reaction mixture comprises 2'-O-methyl adenosine triphosphate, 2'-O-methyl cytidine triphosphate, 2'-O-methyl guanosine triphosphate, 2'-O-methyl uridine triphosphate and 2'-OH guanosine triphosphate. The resulting modified oligonucleotides produced using the r/mGmH transcription mixtures of the present invention comprise substantially all 2'-O-methyl adenosine, 2'-O-methyl cytidine, 2'-O-methyl guanosine, and 2'-O-methyl uridine, wherein the population of guanosine nucleotides has a maximum of about 10% 2'-OH guanosine. In a preferred embodiment, the resulting r/mGmH modified oligonucleotides of the present invention comprise a sequence where at least 80% of all adenosine nucleotides are 2'-O-methyl adenosine, at least 80% of all cytidine nucleotides are 2'-O-methyl cytidine, at least 80% of all guanosine nucleotides are 2'-O-methyl guanosine, at least 80% of all uridine nucleotides are 2'-O-methyl uridine, and no more than about 10% of all guanosine nucleotides are 2'-OH guanosine. In a more preferred embodiment, the resulting modified oligonucleotides comprise a sequence where at least 90% of all adenosine nucleotides are 2'-O-methyl adenosine, at least 90% of all cytidine nucleotides are 2'-O-methyl cytidine, at least 90% of all guanosine nucleotides are 2'-O-methyl guanosine, at least 90% of all uridine nucleotides are 2'-O-methyl uridine, and no more than about 10% of all guanosine nucleotides are 2'-OH guanosine. In a most preferred embodiment, the resulting modified oligonucleotides comprise a sequence where 100% of all adenosine nucleotides are 2'-O-methyl adenosine, 100% of all cytidine-nucleotides are 2'-O-methyl cytidine, 90% of all guanosine nucleotides are 2'-O-methyl guanosine, and 100% of all uridine nucleotides are 2'-O-methyl uridine, and no more than about 10% of all guanosine nucleotides are 2'-OH guanosine.

Under fGmH transcription conditions of the present invention, the transcription reaction mixture comprises 2'-O-methyl adenosine triphosphates, 2'-O-methyl uridine triphosphates, 2'-O-methyl cytidine triphosphates, and 2'-F guanosine triphosphates. The modified oligonucleotides produced using the fGmH transcription conditions of the present invention comprise substantially all 2'-O-methyl adenosine, 2'-O-methyl uridine, 2'-O-methyl cytidine, and 2'-F guanosine. In a preferred embodiment, the resulting modified oligonucleotides comprise a sequence where at least 80% of all adenosine nucleotides are 2'-O-methyl adenosine, at least 80% of all uridine nucleotides are 2'-O-methyl uridine, at least 80% of all cytidine nucleotides are 2'-O-methyl cytidine, and at least 80% of all guanosine nucleotides are 2'-F guanosine. In a more preferred embodiment, the resulting modified oligonucleotides comprise a sequence where at least 90% of all adenosine nucleotides are 2'-O-methyl adenosine, at least 90% of all uridine nucleotides are 2'-O-methyl uridine, at least 90% of all cytidine nucleotides are 2'-O-methyl cytidine, and at least 90% of all guanosine nucleotides are 2'-F guanosine. In a most preferred embodiment, the resulting modified oligonucleotides comprise a sequence where 100% of all adenosine nucleotides are 2'-O-methyl adenosine, 100% of all uridine nucleotides are 2'-O-methyl uridine, 100% of all cytidine nucleotides are 2'-O-methyl cytidine, and 100% of all guanosine nucleotides are 2'-F guanosine.

Under dAmB transcription conditions of the present invention, the transcription reaction mixture comprises 2'-deoxy adenosine triphosphates, 2'-O-methyl cytidine triphosphates, 2'-O-methyl guanosine triphosphates, and 2'-O-methyl uridine triphosphates. The modified oligonucleotides produced using the dAmB transcription mixtures of the present invention comprise substantially all 2'-deoxy adenosine, 2'-O-methyl cytidine, 2'-O-methyl guanosine, and 2'-O-methyl uridine. In a preferred embodiment, the resulting modified oligonucleotides comprise a sequence where at least 80% of all adenosine nucleotides are 2'-deoxy adenosine, at least 80% of all cytidine nucleotides are 2'-O-methyl cytidine, at least 80% of all guanosine nucleotides are 2'-O-methyl guanosine, and at least 80% of all uridine nucleotides are 2'-O-methyl uridine. In a more preferred embodiment, the resulting modified oligonucleotides comprise a sequence where at least 90% of all adenosine nucleotide's are 2'-deoxy adenosine, at least 90% of all cytidine nucleotides are 2'-O-methyl cytidine, at least 90% of all guanosine nucleotides are 2'-O-methyl guanosine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

In each case, the transcription products can then be used as the library in the SELEX™ process to identify aptamers and/or to determine a conserved motif of sequences that have high binding specificity to a given target. The resulting sequences are already partially stabilized, eliminating this step from the process to arrive at an optimized aptamer sequence and giving a more highly stabilized aptamer as a result. Another advantage of the 2'-OMe SELEX™ process is that the resulting sequences are likely to have fewer 2'-OH nucleotides required in the sequence, possibly none. To the extent 2' OH nucleotides remain they can be removed by performing post-SELEX™ modifications.

As described below, lower but still useful yields of transcripts fully incorporating 2' substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5:1, more preferably, the ratio is about 3-4:1.

The 2'-OMe NTP concentration (each NTP) can range from 5 µM to 5 mM.

The 2'-OH GTP concentration can range from 0 µM to 300 µM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition including, for example, EDTA, EGTA, and DTT.

Aptamer Medicinal Chemistry

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry may be used, particularly, as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some As (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:
(1) Substituents already present in the body, e.g., 2'-deoxy, 2'-ribo, 2'-O-methyl purines or pyrimidines or 5-methyl cytosine.
(2) Substituents already part of an approved therapeutic, e.g., phosphorothioate-linked oligonucleotides.
(3) Substituents that hydrolyze or degrade to one of the above two categories, e.g., methylphosphonate-linked oligonucleotides.

The thrombin aptamers of the invention include aptamers developed through aptamer medicinal chemistry as described herein.

Thrombin Binding Aptamers

The materials of the present invention comprise a series of nucleic acid aptamers of 13-51 nucleotides in length that bind to thrombin and which, in some embodiments, decrease or inhibit, the activity of thrombin in in vivo and/or cell-based assays. Preferably, the aptamers of the present invention bind thrombin with high affinity, having a $K_D$ of less than about 300 pM, preferably less than 250 pM, and more preferably less than about 200 pM.

The aptamers of the present invention provide a low-toxicity, safe, and effective modality for treating and/or preventing certain coagulation related disorders which are known to be caused by or otherwise associated with thrombin. Aptamers of the invention also provide a safe, and effective modality for modulating coagulation, particularly for anticoagulation, in relation to surgical procedures such as percutaneous coronary intervention, including placement of stents, surgery related to peripheral arterial occlusion disease (PAOD), and cardiopulmonary bypass (CPB) procedures including coronary artery bypass graft (CABG)-surgery. The aptamers of the invention have effects on anticoagulation that can be measured by activated clotting time (ACT) and other routine measures of coagulation, and lack undesirable secondary effects such as platelet activation (as occurs, e.g., with heparin administration). In addition, in some embodiments the anti-thrombin aptamers possess a short pharmacokinetic (PK) and pharmacodynamic (PD) half-life, which results in rapid, reversible anti-thrombin effects.

Examples of thrombin binding aptamers for use as therapeutics and/or diagnostics in the present invention include the following sequences: SEQ ID NOs 9-41, 43-191, 193-204, 208-304, 307-329, 331-332, 334, 336-337, 340-392, 396-397, 400, and 402-440.

Other aptamers that bind thrombin are described below in Examples 1 and 2.

These aptamers may include modifications as described herein including, e.g., conjugation to lipophilic or high molecular weight compounds such as PEG, incorporation of a capping moiety, incorporation of modified nucleotides, substitutions in the phosphate backbone, and phosphorothioate internucleotide linkages.

In one embodiment of the invention an isolated, non-naturally occurring aptamer that binds to thrombin is provided. In some embodiments, the isolated, non-naturally occurring aptamer has a dissociation constant ("$K_D$") for thrombin of less than 100 µM, less than 1 µM, less than 500 nM, less than 100 nM, less than 50 nM, less than 1 nM, less than 500 pM, less than about 300 pM, preferably less than 250 pM, and more preferably less than about 200 pM. The dissociation constant may be determined by dot blot titration as described in Example 1 below.

In another embodiment, the aptamer of the invention decreases or inhibits a function of thrombin. In another embodiment of the invention, the aptamer binds to and decreases or inhibits a function of a variant of thrombin. A thrombin variant as used herein encompasses variants that perform essentially the same function as a thrombin function, preferably comprises substantially the same structure and in some embodiments comprises 70% sequence identity, preferably 80% sequence identity, more preferably 90% sequence identity, and more preferably 95% sequence identity to the amino acid sequence of thrombin. In some embodiments of the invention, the sequence identity of target variants is determined using BLAST as described below.

The terms "sequence identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004).

In another embodiment of the invention, the aptamer has substantially the same ability to bind thrombin as that of an aptamer comprising any one of SEQ ID NOS: 43-44, 48-49, 52, 63, 72, 82, 84, 92, 97, 116, 130, 141, 143, 146, 166, 172, 185, 283, 292-294, 319-329, 331-332, 334, 336-337, 340-392, 396-397, 400, 402-433. In other embodiment of the invention, the aptamer has substantially the same structure and ability to bind thrombin as that of an aptamer comprising any one of SEQ ID NOS: 43-44, 48-49, 52, 63, 72, 82, 84, 92, 97, 116, 130, 141, 143, 146, 166, 172, 185, 283, 292-294, 319-329, 331-332, 334, 336-337, 340-392, 396-397, 400, 402-433

In another embodiment of the invention, the aptamer has substantially the same ability to decrease or inhibit coagulation as any one of SEQ ID NOs.: 11, 15, 21, 23, 32, 34, 84, 86, 92, 94, 116, 191, 197, 200, 283-285, 287, 289-290, 292-304, 307-318, 411, 434-438, and 440. In another embodiment of the invention, the aptamer has substantially the same ability to decrease or inhibit coagulation and substantially the same structure as any one of SEQ ID NOs.: 11, 15, 21, 23, 32, 34, 84, 86, 92, 94, 116, 191, 197, 200, 283-285, 287, 289-290, 292-304, 307-318, 411, 434-438, and 440. In another embodiment, the aptamers of the invention have a sequence according to any one of SEQ ID NOS 191, 197, 283, 292-294, 411, and 434-440. In another embodiment, the aptamers of the invention are used as an active ingredient in pharmaceutical compositions. In another embodiment, the aptamers of the invention or compositions comprising the aptamers of the invention are used to treat coagulation related disorders, e.g. acute and chronic thrombin mediated coagulation disorders. In another embodiment, the aptamers of the invention or compositions comprising aptamers of the invention are used as an anticoagulant agent, before, during, after or any combination thereof, a surgical procedure such as coronary artery bypass graft (CABG) procedures or percutaneous coronary intervention.

In some embodiments aptamer therapeutics of the present invention have great affinity for and high specificity to their targets while reducing the deleterious side effects from non-naturally occurring nucleotide substitutions if the aptamer therapeutics break down in the body of patients or subjects. In some embodiments, the therapeutic compositions containing the aptamer therapeutics of the present invention are free of or have a reduced amount of fluorinated nucleotides.

The aptamers of the present invention can be synthesized using any oligonucleotide synthesis techniques known in the art including solid phase oligonucleotide synthesis techniques well known in the art (see, e.g., Froehler et al., Nucl. Acid Res. 14:5399-5467 (1986) and Froehler et al., Tet. Lett. 27:5575-5578 (1986)) and solution phase methods such as triester synthesis methods (see, e.g., Sood et al., Nucl. Acid Res. 4:2557 (1977) and Hirose et al., Tet. Lett., 28:2449 (1978)).

ARC2172 (SEQ ID NO 294) is synthetically manufactured and has a molecular formula of $C_{256}H_{319}N_{104}O_{158}P_{25}$ (free acid form) with a molecular weight (MW) of 8,155.24 Daltons. The sodium salt of ARC2172 (SEQ ID NO 294) has the molecular formula of $C_{256}H_{294}Na_{25}N_{104}O_{158}P_{25}$ and corresponding MW of 8704.77 Daltons. The chemical name for the sodium salt of ARC2172 (SEQ ID NO 294) is 2'-Deoxycytidylyl-(3'→5' O,O-phosphoryl)-2'-deoxyguanosylyl-(3'→5' O,O-phosphoryl)-2'-deoxycytidylyl-(3'→5' O,O-phosphoryl)-2'-deoxycytidylyl-(3'→5' O,O-phosphoryl)-2'-deoxythymidylyl-(3'→5' O,O-phosphoryl)-2'-deoxyadenosylyl-(3→5' O,O-phosphoryl)-2'-deoxyguanosylyl-(3'→5' O,O-phosphoryl)-2'-deoxyguanosylyl-(3'→5' O,O-phosphoryl)-2'-deoxythymidylyl-(3'→5' O,O-phosphoryl)-2'-deoxythymidylyl-(3'→5' O,O-phosphoryl)-2'-deoxyguanosylyl-(3'→5' O,O-phosphoryl)-2'-Deoxyguanosylyl-(3'→5' O,O-phosphoryl)-2'-deoxyguanosylyl-(3'→5' O,O-phosphoryl)-2'-deoxythymidylyl-(3'→5' O,O-phosphoryl)-2'-deoxyadenosylyl-(3'→5' O,O-phosphoryl)-2'-deoxyguanosylyl-(3'→5' O,O-phosphoryl)-2'-deoxyguanosylyl-(3'→5' O,O-phosphoryl)-2'-deoxyguanosylyl-(3'→5' O,O-phosphoryl)-2-deoxythymidylyl-(3'→5' O,O-phosphoryl)-2'-deoxyguanosylyl-(3'→5' O,O-phosphoryl)-2'-deoxyguanosylyl-(3'→5' O,O-phosphoryl)-2'-deoxythymidylyl-(3'→5' O,O-phosphoryl)-2'-deoxyguanosylyl-(3'→5' O,O-phosphoryl)-2'-deoxyguanosylyl-(3'→5' O,O-phosphoryl)-2'-deoxycytidylyl-(3'→5' O,O-phosphoryl)-2'-deoxyguanosine, 25-sodium salt Pharmaceutical Compositions The invention also includes pharmaceutical compositions containing aptamer molecules that bind to thrombin. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat or prevent a pathology, such as a disease or disorder, or alleviate the symptoms of such disease or disorder in a patient. For example, compositions of the present invention can be used to treat or prevent a pathology associated with coagulation, and in particular, those pathologies associated with thrombin related coagulation. Compositions of the invention are useful for administration to a subject suffering from, or predisposed to, a disease or disorder which is related to or derived from a target to which the aptamers of the invention bind with high affinity.

Compositions of the invention are useful for administration to a subject suffering from, or predisposed to, a disease or disorder which is related to or derived from a target to which the aptamers of the invention bind with high affinity. Compositions of the invention can be used in a method for treating a patient or subject having a pathology. The method involves administering to the patient or subject an aptamer or a composition comprising aptamers that bind a target protein (e.g. thrombin) involved with the pathology, so that binding of the aptamer to the target protein alters the biological function of the target, e.g. thrombin, thereby treating the pathology.

The patient or subject having a pathology and/or in need of anticoagulation, i.e., the patient or subject treated by the methods of this invention can be a vertebrate, more particularly a mammal, e.g., a dog, cat, monkey, and/or ungulate such as a horse, or more particularly, a human.

In some embodiments, the aptamer of the invention, e.g. ARC2172 (SEQ ID NO 294), is administered before, during, after or any combination thereof, surgical intervention, such as CABG, PCI, angioplasty, cardiovascular and peripheral vascular open and endovascular surgery, surgery to place stents in peripheral/coronary arteries or veins, artificial organs, heart valves, to treat coronary disease and/or vascular disease in veins or arteries, e.g. in the renal artery, the abdominal aorta, in the carotid artery, in peripheral arterial occlusive disease ("PAOD"). In some embodiments of the method, the aptamer of the invention is administered to prevent post-operative thrombosis, e.g. following lip replacement, knee replacement, etc. In some embodiments of the method, the aptamer is administered before, during, after or any combination thereof, minimally invasive procedures such as laproscopy, gynecological procedures, etc.

The aptamers of the invention, e.g. ARC2172 (SEQ ID NO 294), are used in the anticoagulant treatment of patients with heparin induced thrombocytopenia ("HIT"), heparin resistance, impaired renal function and/or impaired hepatic function. In a further embodiment the invention relates to treatment, in a human or other mammal, of conditions where decreasing or inhibiting thrombin is desired. The aptamers of the invention may be used in mammals, including man, in treatment and/or prophylaxis of thrombosis and/or hypercoagulability in blood and tissues, including acute coronary syndrome, congestive heart failure, atrial fibrillation, venous thrombosis, e.g. deep vein thrombosis, pulmonary embolism, arterial thrombosis, such as in myocardial ischemia, myocardial infarction, unstable angina, thrombosis-based stroke and peripheral arterial thrombosis. Further, the aptamers may be used in the treatment and/or prophylaxis of atherosclerotic disorders (diseases) such as coronary arterial disease, cerebral arterial disease and peripheral arterial disease. In some embodiments, the aptamers of the invention, e.g. ARC2172 (SEQ ID NO 294), may be used in anticoagulant treatment in hemodialysis and disseminated intravascular coagulation. In some embodiments, the aptamers of the invention may be used in methods of rinsing and/or coating of catheters, stents and mechanical devices used in patients in vivo, and as an anticoagulant for preservation of blood, plasma and other blood products in vitro.

Still further, the aptamers may be used in other diseases where blood coagulation could be a fundamental contributing process or a source of secondary pathology, such as cancer, including metastasis, inflammatory diseases, including arthritis, and diabetes.

Compositions of the invention can be used in a method for treating a patient or subject in need of anticoagulation, e.g. prior to, during and/or after surgery, such as cardiac surgery. In the methods of modulating coagulation in some embodiments of the present invention, e.g. prior to, during and/or after CABG surgery, an anti-thrombin aptamer can be administered by constant intravenous infusion or by intravenous bolus administration. In these embodiments, an aptamer may be provided in a composition of the invention, as its sodium salt, in an isotonic, pH neutral, aqueous, saline solution.

In practice, the aptamers or their pharmaceutically acceptable salts, are administered in amounts which will be sufficient to exert their desired biological activity, e.g., decreasing or inhibiting the binding of the aptamer target, thrombin to fibrinogen and PAR-1.

One aspect of the invention comprises an aptamer composition of the invention in combination with other treatments for coagulation related disorders. The aptamer composition of the invention may contain, for example, more than one aptamer. In some examples, an aptamer composition of the invention, containing one or more compounds of the invention, is administered in combination with another useful composition such as an anti-inflammatory agent, an immunosuppressant, an antiviral agent, or the like. Furthermore, the compounds of the invention may be administered in combination with a cytotoxic, cytostatic, or chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmaco kinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component can be combined with an oral, non-toxic, pharmaceutically acceptable inert carrier such as ethanol glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The compounds of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, and all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

The molecular weights given in the following dosages relate to aptamer oligo weight only and do not include any mass conferred by conjugation such as to a PEG moiety. Oral dosages of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 7500 mg/day. Subcutaneous, intravenous and intraperitoneal dosages will range between 0.05 to 12,000 mg/day.

Effective plasma levels of the compounds of the present invention range from 0.002 mg/mL to 50 mg/mL.

Compounds of the present invention may be administered in a single daily dose, or the total daily dosage may be administered in divided doses of two, three or four times daily.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. Thrombin binding aptamer-PEG conjugates of the invention with a longer half life ($t_{1/2}$) may be used in the treatment of a variety of disorders, such as, for example, heparin-induced thrombocytopenia (HIT), acute coronary syndrome (ACS) and deep vein thrombosis (DVT). The longer $t_{1/2}$ exhibited by these aptamer conjugates affects, e.g., lowers, the dosage necessary to produce the desired effect. Aptamer conjugates with a longer half life can also be used for chronic disorders. An aptamer of the invention with a longer half life ($t_{1/2}$), including an aptamer conjugate and/or stabilized aptamer of the invention, can also be used as an anticoagulant in a blood collection, blood circulation, or blood storage device where the device includes an effective amount of an anti-thrombin aptamer of the invention or of a mixture of anti-thrombin aptamers of the invention. Examples of such devices include but are not limited to blood collection bags, blood collection tubes and blood collection syringes. In a particular embodiment an effective amount of the aptamer of the invention is used in a blood storage device, e.g. blood bag, where the blood is stored at about 4° for several days and preferably for about two weeks.

The tunability of (i.e., the ability to decrease or inhibit) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in the provisional application U.S. Ser. No. 60/550,790, filed on Mar. 5, 2004, and entitled "Controlled Modulation of the Pharmacokinetics and Biodistribution of Aptamer Therapeutics", and in the non-provisional application U.S. Ser. No. 11/075,648, filed on Mar. 7, 2005, and entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (C1), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (C1) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions in vivo by conjugating an aptamer to a modulating moiety such as a small molecule, peptide; or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272(25): 16010-7)), Ant (a 16-amino acid sequence derived from the third helix of the Drosophila antennapedia homeotic protein (Pietersz, et al. (2001), Vaccine 19(11-12): 1397-405)) and $Arg_7$ (a short, positively charged cell-permeating peptides composed of polyarginine ($Arg_7$) Rothbard, et al. (2000), Nat. Med. 6(11): 1253-7; Rothbard, J et al. (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2° F. and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers.

While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

Peg-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used in the invention include polyethylene glycol ("PEG"), also known as polyethylene oxide ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: HO—$CH_2CH_2O$—($CH_2CH_2O)_n$—$CH_2CH_2$—OH. This polymer, alpha-, omega-dihydroxylpolyethylene glycol, can also be represented as HO-PEG-OH, where it is understood that the -PEG- symbol represents the following structural unit: —$CH_2CH_2O$—($CH_2CH_2O)_n$—$CH_2CH_2$— where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively non-reactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PBGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, —OCH$_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Figure 2:
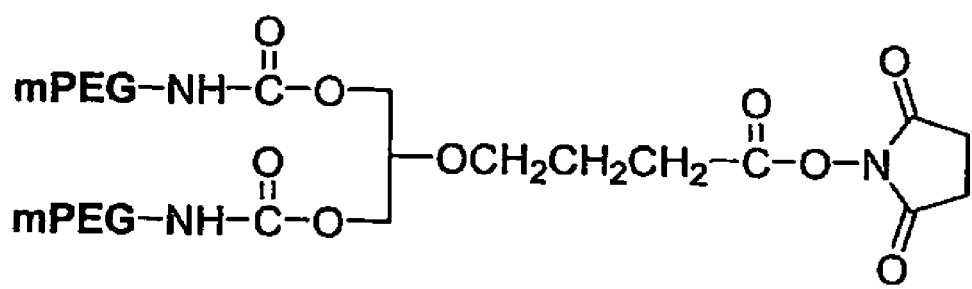
FIG. 2 is an illustration of a 40 kDa branched PEG.
Figure 3:
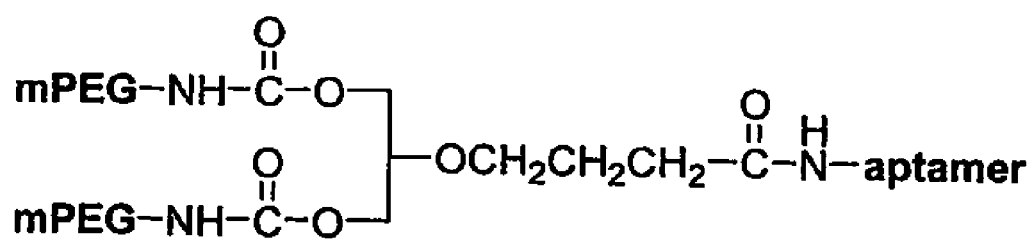
FIG. 3 is an illustration of a 40 kDa branched PEG attached to the 5' end of an aptamer.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched. In some embodiments the polymers are PEG. In some embodiment the polymers are branched PEG. In still other embodiments the polymers are 40 kDa branched PEG as depicted in FIG. 2. In some embodiments the 40 kDa branched PEG is attached to the 5' end of the aptamer as depicted in FIG. 3.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g. one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular-weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid), where n is greater than or equal to 1.

High molecular weight compositions of the invention include those having a molecular weight of at least 10 kDa. Compositions typically have a molecular weight between 10 and 80 KDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

PAG-Derivatization of a Reactive Nucleic Acid

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 4. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully, partially, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with thrombin will preclude the formation of complex between the aptamer and thrombin. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Aptamer Selection and Sequences

The overall goal of this program was to discover an aptamer that acts as a potent anti-coagulant by decreasing or inhibiting thrombin activity. Specifically, a potent aptamer anti-coagulant will bind to the fibrinogen binding exosite 1 of thrombin and thus compete with substrate (fibrinogen) for binding to the enzyme.

Aptamer selections were performed using a simple DNA composition in order to preserve the rapid-off pharmacodynamic properties associated with a previously identified thrombin binding DNA aptamer with the following sequence 5'GGTTGGTGTGGTTGG3' (SEQ ID NO 4) (ARC183). The discovery of high affinity exosite 1 binders was accomplished using nitrocellulose filter capture of complexes accompanied by addition of 10-100 fold molar excess of heparin, to effectively block the non-neutralizing exosite 2 from the aptamer pool. Additionally, other strategies went into our SELEX scheme including: capture and discarding of prothrombin aptamer complexes in an initial step designed to remove prothrombin binding aptamers, and contacting a mixture of prothrombin and the hirudin/thrombin complex with the aptamer pool, then capturing and discarding prothrombin/aptamer and thrombin/hirudin/aptamer complexes. Inclusion of the thrombin/hirudin complex was intended to effectively present exosite 2 for capture and removal from the pool of undesired non-inhibitory binders in the event that heparin competition was ineffective alone. Ultimately, these selection strategies lead to the generation of a series of aptamers having high affinity for thrombin that also decreased or inhibited the activity of thrombin in vitro and in vivo.

Example 1A

Thrombin DNA Selection #1

Nitrocellulose filter column based selections were performed to identify aptamers that bind to human thrombin using a nucleotide pool consisting of deoxy-nucleotides (DNA), which yielded high affinity aptamers for human thrombin.

Pool Preparation

A DNA template with the sequence 5'-GATCGATCCT-CAGCCANNNNNNNNNNNNNNNNNNNNNNNNNN-NNGGGATTTAGCTTCCTCTTACACGC-3' (ARC1488, SEQ ID NO 5) was synthesized using an ABI EXPEDITE™

DNA synthesizer, and deprotected by standard methods. The series of N's in the DNA template can be any combination of nucleotides and gives rise to the unique sequence region of the resulting aptamers. The template was PCR amplified with the primers 5'-GATCGATCCTCAGCCAC-3' (ARC1489, SEQ ID NO 6) and 5'-TATACGACTCAGCGTGTAAGAG-GAAGCTAArA-3' (ARC1490, SEQ ID NO 7) under standard conditions. After amplification, the PCR product was ethanol precipitated then subjected to alkaline hydrolysis (333 mM NaOH, 90° C., 15 min) followed by neutralization with HCL and addition of and formamide loading buffer before purification. The strands were separated on a 10% denaturing polyacrylamide gel and the single stranded DNA pool, which migrates with a higher mobility, was excised from the gel, passively eluted, and precipitated with isopropanol. The resulting pool sequence is the cleaved reverse compliment of ARC1488, is 50 nt in length, having the following sequence: 5'-TCCCNNNNNNNNNNNNNNNN-NNNNNNNNNNNNNNGTGGCTGAGGATCGATC-3' (ARC1538, SEQ ID NO. 8).

Selection

A total of 12 Rounds of selection were performed against human thrombin. In Round 1, a binding reaction consisting of 3 mL of 1×DPBS (w/Ca$^{2+}$ and Mg$^{2+}$) (Gibco, Catalog #14040, Invitrogen, Carlsbad, Calif.), 2×10$^{14}$ molecules of ARC1538 DNA pool, and 900 pmoles of Thrombin (300 nM final concentration) (Enzyme Research Labs, South Bend, Ind.) was prepared. The binding reaction was incubated for 2 hours at room temperature. During incubation, Centrex Nitrocellulose Filter columns (Schleicher & Schuell, Keene, N.H.) were prepared for selection. Each column was treated for 15 minutes with 1 mL of 0.5M KOH. After treatment, the KOH was removed by centrifugation (2000 rpm for 1 minute), and the column was treated with 1 mL of ddH$_2$O for an additional 15 minutes. The ddH$_2$O was then removed by centrifugation (2000 rpm for 1 minute). The selection binding reaction was added to the prepared filter column and spun through by centrifugation (2000 rpm for 1 minute). The column was then washed with 1 mL of 1×DPBS (w/Ca$^{2+}$ and Mg$^{2+}$) (Gibco, Catalog #14040, Invitrogen, Carlsbad, Calif.) and spun through. After washing, the column was eluted for 3 minutes with 1 mL of elution buffer (7M urea, 300 mM NaOAc, 5 mM EDTA) pre-heated to 90° C., then spun through by centrifugation (2000 rpm for 1 minute) and collected in a 1.5 mL Eppendorf tube. The eluent was then precipitated using one volume of isopropanol and 1 µl of glycogen.

For all subsequent rounds of selection after Round 1, a negative selection column was introduced prior to the positive selection to remove non-specific filter binders from the pool. The negative selection column was prepared as outlined above. A mixture of 200 µl of 1×DPBS (w/Ca$^{2+}$ and Mg$^{2+}$) (Gibco, Catalog #14040, Invitrogen, Carlsbad, Calif.) and 60 pmoles of pool from the previous round of selection was passed through the negative selection column and collected before proceeding to the binding reaction step previously described. Competitor tRNA was also added in subsequent Rounds to increase selective pressure, and heparin was added to the positive selection step in later rounds to bind to exosite 2 and prevent aptamers from binding to exosite 2 of thrombin. The selection conditions used are outlined in Table 1 below.

Amplification of the ARC1538 DNA pool requires phosphorylation at the 5'-end followed by specific ligation of the constant region to the 5'-end of the sequence (i.e. the 3'-primer used for amplification of the original ARC1488 synthetic DNA sequence), followed by standard. PCR amplification. Thus, after precipitation, the selected pool was re-suspended in 9 µl of ddH$_2$O, and 10 µA of 2× kinase compatible buffer (8 ul 1M DTT plus 1 mL 2× Quick Ligase buffer (New England Biolabs, Beverly, Mass.)) 1 µl of T4 PNK (New England Biolabs, Beverly, Mass.) was added to the reaction and incubated at 37° C. for 20 minutes. Post incubation, 100 pmoles of the 3' primer 5'-TATACGACTCAGCGTGTAAGAG-GAAGCTAArA-3' (ARC 1490) (SEQ ID NO 7) and 100 pmoles of a 3' ligation primer 5'-GGGATTTAGCTTCC[3T]-3' (ARC1491) (SEQ ID NO 192) were added with 1 µl of T4 ligase (New England Biolabs, Beverly, Mass.) and incubated at room temperature for 10 minutes. The reaction was brought up to 200 µl in PCR mix containing both the 5' primer 5'-GATCGATCCTCAGCCAC-3' (ARC 1489) (SEQ ID NO: 6) and 3' primer (ARC 1490). The PCR reaction was cycled using the following conditions: denaturing at 94° C. for 1 minute, cycling at 94° C. for 30 seconds, 54° C. for 30 seconds, and 72° C. for 1 minute. The PCR was cycled until the final product was approximately 10 ng/µl, estimated using a 4% E-Gel (Invitrogen, Carlsbad, Calif.) (referred to as "PCR Threshold" in the far right column of Table 1 below). The product was then seeded into a larger PCR reaction for further DNA amplification (20 µl into 400 µl total PCR volume).

After amplification, the PCR product was ethanol then subjected to alkaline hydrolysis (333 mM NaOH, 90° C., 15 min) followed by neutralization with HCL and addition of formamide loading buffer before purification on a 10% PAGE gel. The purified product was passively eluted, precipitated and quantified before going into the next round of selection.

The selection proceeded as a single selection until Round 7, in which the selection was split into two branches (See Table 1). One branch of the selection continued to increase in stringency, as measured by decreasing thrombin protein concentration.

TABLE 1

SELEX Conditions for DNA Selection #1 against human Thrombin:

| Round | Target (h Thrombin) | | Competitor | | PCR Threshold (# Cycles) | |
|---|---|---|---|---|---|---|
| 1 | 300 nM | | None | | 15 | |
| 2 | 300 nM | | .1 mg/mL tRNA | | 18 | |
| 3 | 300 nM | | .1 mg/mL tRNA | | 15 | |
| 4 | 300 nM | | .1 mg/mL tRNA | | 10 | |
| 5 | 300 nM | | .1 mg/mL tRNA and .1 mg · mL heparin | | 15 | |
| 6 | 100 nM | | .1 mg/mL tRNA and .1 mg/mL heparin | | 10 | |
| 7 | 100 nM | 30 nM | .1 mg/mL tRNA and 1 mg/mL | .1 mg/mL tRNA and 1 mg/mL | 10 | 10 |

Biosciences, Piscataway, N.J.) and GB002 gel blot paper (Schleicher & Schuell, Keene, N.H.). RNA that is bound to protein is captured on the nitrocellulose filter, whereas the non-protein bound RNA is captured on the nylon filter. The gel blot paper was included simply as a supporting medium for the other filters. Following filtration, the filter layers were separated, dried and exposed on a phosphor screen (Amersham Biosciences, Piscataway, N.J.) and quantified using a Storm 860 Phosphorimager®blot imaging system (Amhersham Biosciences, Piscataway, N.J.). When a significant positive ratio of binding of RNA in the presence of human thrombin versus in the absence of thrombin was seen, the pools were cloned using a TOPO TA cloning kit (Invitrogen, Carlsbad, Calif.) according to the manufacturer's instructions.

Rounds 9 and 12 Cloning and Sequencing

Based on pool binding, Round 9 and Round 12 pools were selected and for cloning and sequencing. For the purposes of screening by sequence family, Round 9 and Round 12 pools from both branches of the selection were combined. All unique DNA clone sequences were synthesized at 25 μmole synthesis scale. Clones from Round 9 were screened for the ability to decrease or inhibit thrombin activity using a prothrombin time (PT assay) described in Example 3A below. The PT assay results are reported in Table 17 in Example 3 below. The Round 12 pool was shown to have no new unique sequence leads to pursue.

Sequences of the clones resulting from Round 9 pools combined are listed in Table 2 below. The random region for each clone begins after the sequence 5'-TCCC, and ends before the GTGGCTGAGGATCGTATC 3' (SEQ ID NO 42). However since the 5'-TCCC sequence is not part of the PCR primer, some mutation may be observed during the SELEX and sequencing processes. Therefore point mutants in this region may be observed in the sequences below. Unless noted otherwise, individual sequences listed below are represented in the 5' to 3', orientation and were selected under DNA SELEX™ conditions wherein all of the nucleotides are deoxy.

TABLE 2

Clones from Round 9 DNA SELEX #1
Against Human Thrombin

AMX(453)_A6
(SEQ ID NO 9)
TCCCATCGATCTGGGGTAATTTACTGGGTCGGGTGGCTGAGGATCGATC

AMX(453)_A9
(SEQ ID NO 10)
ATCCCAATGTTGAGACGAGTAGGTGTGGGTAGGGTGGCTGAGGATCGATC

AMX(453)_B6
(SEQ ID NO 11)
TCCCATCGAGCTCAGTCTAGGATGGGTAGGGTGGTGGCTGAGGATCGATC

AMX(453)_B8
(SEQ ID NO 12)
TCCCATCGAGCCGGGGTATGATTATGGGTGGGGTGGCTGAGGATCGATC

AMX(453)_B10
(SEQ ID NO 13)
TCCCATCGATCTGGGGTAGTTTTATTGGGTCGGGTGGCTGAGGATCGATC

AMX(453)_B12
(SEQ ID NO 14)
TCCCGATCGGTCTGGGGTGTGTTCATGGTTTGGGTGGCTGAGGATCGATC

AMX(453)_C10
(SEQ ID NO 15)
TCCTGATTGATCTGAGGGGTATTGTTGGCGTGGGTGGCTGAGGATCGATC

AMX(453)_D12
(SEQ ID NO 16)
TCCCGATTGATCTGAGGGGTATTGTTGGCGTGGGTGGCTGAGGATCGATC

AMX(453)_E4
(SEQ ID NO 17)
TCCCGTAATCGAGTCTGGTATTGTTGGTCTGGGTGGCTGAGGATCGATC

AMX(453)_E8
(SEQ ID NO 18)
TCCTATGATCGAATGACTAAGGGGTGGGGTGGGTGGCTGAGGATCGATC

AMX(453)_E10
(SEQ ID NO 19)
TCCCGGGTCGTATCCGTTTGTGGGTGGTCTGGGTGGCTGAGGATCGATC

TABLE 2-continued

Clones from Round 9 DNA SELEX #1
Against Human Thrombin

AMX(453)_E12
(SEQ ID NO 20)
TCCCGTAATTGAGCCTGGTATTGTTGGTCTGGGTGGCTGAGGATCGATC

AMX(453)_F6
(SEQ ID NO 21)
TCCTGATCGGATGTGGTGGGTTATTGGTTTGGGTGGCTGAGGATCGATC

AMX(453)_F7
(SEQ ID NO 22)
TCCCGAGCGATACTGTCTAGGTTGGGTAGGGTGGTGGCTGAGGATCGATC

AMX(453)_F11
(SEQ ID NO 23)
TCCCGAGCGATATTGTCTAGGTTGGGTAGGGTGGTGGCTGAGGATCGATC

AMX(453)_G5
(SEQ ID NO 24)
TCCCATGATCGTTAGATTCAGGGATGGTGTGGGTGGCTGAGGATCGATC

AMX(453)_G11
(SEQ ID NO 25)
TCCCGTATCGAGCTTGGTATTGTTGGTCTGGGTGGCTGAGGATCGATC

AMX(453)_H11
(SEQ ID NO 26)
TCCCTTTTGACCTGCAAGAACGGTTGGTGTGGGTGGCTGAGGATCGATC

Example 1B

Thrombin DNA Selection #2 and #3

Two additional nitrocellulose filter column based DNA selections were performed to 1) identify aptamers having a high affinity for human thrombin over prothrombin by incorporating prothrombin in a negative SELEX step; and 2) to identify thrombin aptamers biased against exosite 2 binding by adding the thrombin/hirudin complex into the negative selection step. The thrombin/hirudin complex should effectively occlude exosite 1 and the active site of thrombin thereby allowing potential exosite 2 binders to be captured and removed from the pool. Additionally, as in selection 1, heparin was added to the positive selection step in later rounds to bind to exosite 2 and prevent aptamers from binding to exosite 2 of thrombin.

Pool Preparation and Selection

The DNA pool used for the new selections was prepared as described in Example 1A above. A total of 9 Rounds of selection were performed against human Thrombin (Enzyme Research Labs, South Bend, Ind.). In Round 1, the binding reaction consisted of 3 mL of 1×DPBS (w/$Ca^{2+}$ and $Mg^{2+}$) (Gibco Catalog #14040, Invitrogen, Carlsbad, Calif.), $2\times10^{14}$ molecules of ARC1538 DNA pool, and 900 pmoles of Thrombin (300 nM final concentration). The binding reaction was incubated for 2 hours at room temperature. During incubation, Centrex Filter columns (Schleicher & Schuell, Keene, N.H.) were prepared for selection. Each column was treated for 15 minutes with 1 mL of 0.5M KOH. After treatment, the KOH was removed by centrifugation (2000 rpm for 1 minute), and the column was treated with 1 mL of dd$H_2O$ for an additional 15 minutes. The dd$H_2O$ was then removed by centrifugation. The selection binding reaction was added to the prepared Centrex and spun through (2000 rpm for 1 minute). The column was then washed with 1 mL of 1×DPBS (w/$Ca^{2+}$ and $Mg^{2+}$) (Gibco, Catalog #14040, Invitrogen, Carlsbad, Calif.) and spun through by centrifugation (2000 rpm for 1 minute). After washing, the column was eluted with 1 mL of elution buffer (7M urea, 300 mM NaOAc, 5 mM EDTA) heated to 90° C. by allowing the elution buffer to sit on the column for 3 minutes before centrifugation at 2000 rpm for 1 minute and collected in an eppendorf tube. The eluent was precipitated using one volume of isopropanol and 1 µl of glycogen.

For all subsequent rounds after Round 1, a negative selection column was added before the positive selection to remove non-specific filter binders from the pool. This column was prepared as outlined above, and mixture of 200 µl of DPBS (w/Ca$^{2+}$ and Mg$^{2+}$) (Gibco, Catalog #14040, Invitrogen, Carlsbad, Calif.) and 60 pmoles of pool from the previous round were filtered and collected before proceeding to the binding reaction. Competitor tRNA was also added in subsequent rounds to increase selective pressure, and heparin was added to the positive selection step in later rounds to bind to exosite 2 and prevent aptamers from binding to exosite 2 of thrombin. The selection conditions used are outlined in Table 3 below. Selected pools were amplified and purified as described for SELEX 1 in Example 1A above.

The selection proceeded as a single selection until Round 3, in which the selection was split into two branches (See Table 3). One branch (Selection 2) continued as before, using 300 nM of human prothrombin in the negative selection step of each round. The other branch (Selection 3) was continued using 150 nM of prothrombin (Athens Research, Athens, Ga.) in the negative selection step and 150 nM of a Thrombin and Hirudin (American Diagnostica, Stamford, Conn.) complex.

Trace $^{32}$P-labeled RNA was combined with a dilution series of human Thrombin (1 nM-1000 nM) and incubated at room temperature for 30 minutes in 1×DPBS (w/Ca$^{2+}$ and Mg$^{2+}$) (Gibco, Catalog #14040, Invitrogen, Carlsbad, Calif.) plus 0.1 mg/ml BSA in a final volume of 30 µl. The binding reactions were analyzed by nitrocellulose filtration using a Minifold I dot-blot, 96-well vacuum filtration manifold (Schleicher & Schuell, Keene, N.H.). A three-layer filtration medium was used, consisting (from top to bottom) of Protran nitrocellulose (Schleicher & Schuell, Keene, N.H.), Hybond-P nylon (Amersham Biosciences, Piscataway, N.J.) and GB002 gel blot paper (Schleicher & Schuell, Keene, N.H.). RNA that is bound to protein is captured on the nitrocellulose filter, whereas the non-protein bound RNA is captured on the nylon filter. The gel blot paper was included simply as a supporting medium for the other filters. Following filtration, the filter layers were separated, dried and exposed on a phosphor screen (Amersham Biosciences, Piscataway, N.J.) and quantified using a Storm 860 Phosphorimager® blot imaging system (Amersham Biosciences, Piscataway, N.J.).

When a significant positive ratio of binding of RNA in the presence of human thrombin versus in the absence of thrombin was seen, the pools were cloned using a TOPO TA cloning kit (Invitrogen, Carlsbad, Calif.) according to the manufacturer's instructions.

Round 7 from DNA Selections #2 and #3: Sequencing and Clone Screening

Based on pool binding monitored throughout the selections as described above, Round 7 pools from both Selection #2 and #3 were cloned, sequenced and screened for the ability to bind thrombin using a sandwich filter binding assay. DNA clones were ordered synthesized by IDT at 25 µmole synthesis scale.

TABLE 3

Selection conditions for Thrombin DNA Selection #2 and #3

| Round | Negative Target | Positive Target | Competitor | PCR Threshold (# Cycles) | |
|---|---|---|---|---|---|
| 1 | None | 300 nM Thr | None | 15 | |
| 2 | 300 nM Prothr | 300 nM Thr | .1 mg/mL tRNA | 25 | |
| 3 | 300 nM Prothr | 150 nM Prothr and 150 nM Thr/Hirudin | 300 nM Thr | .1 mg/mL tRNA | 15 | 15 |
| 4 | 300 nM Prothr | 150 nM Prothr and 150 nM Thr/Hirudin | 300 nM Thr | .1 mg/mL tRNA | 15 | 15 |
| 5 | 300 nM Prothr | 150 nM Prothr and 150 nM Thr/Hirudin | 300 nM Thr | .1 mg/mL tRNA .1 mg/ml and heparin | 15 | 15 |
| 6 | 500 nM Prothr | 150 nM Prothr and 150 nM Thr/Hirudin | 100 nM Thr | .1 mg/mL tRNA .1 mg/ml and heparin | 15 | 15 |
| 7 | 500 nM Prothr | 150 nM Prothr and 150 nM Thr/Hirudin | 100 nM Thr | .1 mg/mL tRNA .1 mg/ml and heparin | 13 | 13 |
| 8 | 500 nM Prothr | 500 nM Prothr and 150 nM Thr/Hirudin | 30 nM Thr | .1 mg/mL tRNA and 1 mg/ml heparin | 15 | 15 |
| 9 | 500 nM Prothr | 500 nM Prothr and 150 nM Thr/Hirudin | 30 nM Thr | .1 mg/mL tRNA and 1 mg/ml heparin | 13 | 13 |

Monitoring the Progress of Selection:

Dot blot binding assays were performed throughout the selections to monitor the protein binding affinity of the pools.

Of the 66 combined sequences obtained from the Round 7 pools from both selections, 20 unique sequences were selected for assaying in a 1-point dot blot screen. Clone transcripts were 5' end labeled with $\bar{\gamma}^{32}$P ATP and spin purified with Centrisep columns (Princeton Separations, Adelphia, N.J.) to remove excess label. Trace amounts of labeled clone were incubated with +/−10 nM Thrombin and 0.1 mg/ml BSA in a total volume of 30 μl 1×DPBS (w/Ca$^{2+}$ and Mg$^{21}$) (Gibco, Catalog #14040, Invitrogen, Carlsbad, Calif.) for 30 minutes. Post incubation, the binding reaction applied the dot-blot binding assay apparatus previously described in Example 1A. For K$_D$ determination on select clones, the clone transcripts were 5' end labeled with $\bar{\gamma}^{32}$P ATP. K$_D$ values were determined using a dilution series of human Thrombin (ranging between 1 pM and 1000 nM depending the affinity of a specific clone for thrombin) in the dot blot binding assay and fitting an equation describing a 1:1 RNAT:protein complex to the resulting data (fraction aptamer bound=amplitude*([Thrombin]/(K$_D$+[Thrombin]))) (KaleidaGraph v. 3.51, Synergy Software, Reading, Pa.).

The sequences resulting from Round 7 are listed in Table 4 below. The corresponding binding characterization for each clone is tabulated in Table 5 below. For each of the sequences listed below in Table 4, the random region for each clone begins after the sequence 5'TCCC, and ends before the GTGGCTGAGGATCGTATC 3' (SEQ ID NO 42). Unless noted otherwise, individual sequences listed below are represented in the 5' to 3' orientation and were selected under DNA SELEX™ conditions wherein all of the nucleotides are deoxy.

TABLE 4

Sequences of Clones Obtained from Round 7, Thrombin DNA Selection #2 and #3

AMX(395)_A1
(SEQ ID NO 43)
TCCCTGCAATTCGATCAGCAGGGGTGGTGTGGGTGGCTGAGGATCGATC

AMX(395)_A4
(SEQ ID NO 44)
TCCCGGGAGATCGCTTCGAAAATGGTTGGCGTGGGTGGCTGAGGATCGATC

AMX(395)_A5
(SEQ ID NO 45)
TCCCACGCATCGATCCTATATGGGTGGCATGGGGTGGCTGAGGATCGATC

AMX(395)_A11
(SEQ ID NO 46)
TCCCGTAATCGAGCCTGGTATTGTTGGCCTGGGTGGCTGAGGATCGATC

AMX(395)_B5
(SEQ ID NO 47)
TCCCGCAATCGGTACTCAGGAGGATGGTTGGGGTGGCTGAGGATCGATC

AMX(395)_B7
(SEQ ID NO 48)
TCCCGGGATCGAGTCCGATTAGGGATGGTGTGGGTGGCTGAGGATCGATC

AMX(395)_C1
(SEQ ID NO 49)
TCCCGGGTGGTTATCTTCTCAGGGATGGTGTGGGTGGCTGAGGATCGATC

AMX(395)_C3
(SEQ ID NO 50)
TCCCAAGCGATCTGTAAGGGATGGGGTTGCGGGTGGCTGAGGATCGATC

AMX(395)_D5
(SEQ ID NO 51)
TCCCGAGTGTCATATCATCAGAGGTTGGAGTGGGTGGCTGAGGATCGATC

TABLE 4-continued

Sequences of Clones Obtained from Round 7, Thrombin DNA Selection #2 and #3

AMX(395)_D11
(SEQ ID NO 52)
TCCCAAGATCGGTACATACAGTGGGTGGTGAGGGTGGCTGAGGATCGATC

AMX(395)_E2
(SEQ ID NO 53)
TCCTATCGATACGGGGTCTTCTATTGGGTCGGGGTGGCTGAGGATCGATC

AMX(395)_E4
(SEQ ID NO 54)
TCCCGACTTCGATTACTCAGGGGTGGCTGTGGGTGGCTGAGGATCGATC

AMX(395)_E7
(SEQ ID NO 55)
TCCCGGTCGAGTCCTCACGAAGGGTTGGGAGGGTGGCTGAGGATCGATC

AMX(395)_E8
(SEQ ID NO 56)
TCCCATGATCGTCAGATTCAGGGATGGTGTGGGTGGCTGAGGATCGATC

AMX(395)_E11
(SEQ ID NO 57)
TCCCGGTCGTATTAGTGTGGGTGGTGTAGGGTGGTGGCTGAGGATCGATC

AMX(395)_F3
(SEQ ID NO 58)
TCCCATAGTATCGAGCCGATTGGATGGTCTGGGTGGCTGAGGATCGATC

AMX(395)_G2
(SEQ ID NO 59)
TCCCACGGTCCTCACCTAGGATGGTTAGGGTGGTGGCTGAGGATCGATC

AMX(395)_G11
(SEQ ID NO 60)
TCCCAGAGCGGAAATCCTCAGGGGTGGGGTGGGTGGCTGAGGATCGATC

AMX(395)_H9
(SEQ ID NO 61)
TCCCGGTAGCGATCCAGAGAGGGATGGGGTGGGTGGCTGAGGATCGATC

AMX(395)_H10
(SEQ ID NO 62)
TCCCGCAGTATCGGTCTGGTTGGTTGGATGGGGTGGCTGAGGATCGATC

TABLE 5

Binding Characterization of clones from Round 7 DNA Selections #2 and #3

| SEQ ID NO | Clone | % Bound at 10 nM Thrombin (screen) | Kd (nM) |
|---|---|---|---|
| 43 | AMX(395)_A1 | 40.77 | 6.40 |
| 44 | AMX(395)_A4 | 19.64 | 29.38 |
| 45 | AMX(395)_A5 | 3.29 | N/A |
| 46 | AMX(395)_A11 | 35.80 | N/A |
| 47 | AMX(395)_B5 | 17.10 | N/A |
| 48 | AMX(395)_B7 | 32.82 | 14.48 |
| 49 | AMX(395)_C1 | 40.23 | 7.48 |
| 50 | AMX(395)_C3 | 3.57 | N/A |
| 51 | AMX(395)_D5 | 13.39 | N/A |
| 52 | AMX(395)_D11 | 31.92 | 5.55 |
| 53 | AMX(395)_E2 | 6.51 | N/A |
| 54 | AMX(395)_E4 | 24.02 | N/A |
| 55 | AMX(395)_E7 | 9.12 | N/A |
| 56 | AMX(395)_E8 | 21.31 | N/A |
| 57 | AMX(395)_E11 | 33.70 | N/A |
| 58 | AMX(395)_F3 | 6.29 | N/A |
| 59 | AMX(395)_G2 | 33.10 | N/A |
| 60 | AMX(395)_G11 | 21.89 | N/A |

TABLE 5-continued

Binding Characterization of clones from Round 7 DNA Selections #2 and #3

| SEQ ID NO | Clone | % Bound at 10 nM Thrombin (screen) | Kd (nM) |
|---|---|---|---|
| 61 | AMX(395)_H9 | 9.61 | N/A |
| 62 | AMX(395)_H10 | 2.80 | N/A |

**N/A indicates $K_D$ was not measured

Round 9 from DNA Selections #2 and #3: Sequencing and Clone Screening

Based on pool binding monitored throughout the selections as described above, Round 9 Pools from both Selection #2 and #3 were also cloned using a TOPO TA Cloning kit (Invitrogen, Carlsbad, Calif.) according to manufacturer's instructions, and sequenced. Of the 136 sequences obtained from Round 9 of both selections, 130 unique sequences were selected for assaying in a single-point dot blot screen against thrombin and prothrombin to test for selective binding to thrombin. Clones were ordered from IDT (Coralville, Iowa) at 25 μmole synthesis scale. Clone transcripts were 5' end labeled with $\bar{\gamma}^{32}$P ATP and spin purified with Centrisep columns (Princeton Separations, Adelphia, N.J.) to remove excess label. Trace amounts of labeled clone were incubated with +/−10 nM Thrombin (or +/−50 nM prothrombin) and 0.1 mg/ml BSA in a total volume of 30 μl 1×DPBS (w/Ca$^{2+}$ and Mg$^{2+}$) (Gibco, Catalog #14040, Invitrogen, Carlsbad, Calif.) for 30 minutes. Post incubation, the binding reaction applied the dot-blot binding assay apparatus previously described. For $K_D$ determination on select clones, the clone transcripts were 5' end labeled with $\bar{\gamma}^{32}$P ATP. $K_D$ values were determined using a dilution series of human Thrombin (ranging between 1 pM and 1000 nM depending the affinity of a specific clone for thrombin) in the dot blot binding assay and fitting an equation describing a 1:1 RNA:protein complex to the resulting data (fraction aptamer bound=amplitude*([Thrombin]/($K_D$+[Thrombin]))) (KaleidaGraph v. 3.51, Synergy Software, Reading, Pa.).

The resulting sequences from Round 9 of DNA selections #2 and #3 are listed in Table 6 below. The corresponding binding characterization for each clone is tabulated in Table 7 below. For each of the sequences listed below in Table 6, the random region for each clone begins after the sequence 5'TCCC, and ends before the GTGGCTGAGGATCGTATC 3' (SEQ ID NO 42). Unless noted otherwise, individual sequences listed below are represented in the 5' to 3' orientation and were selected under DNA SELEX™ conditions wherein all of the nucleotides are deoxy.

TABLE 6

Sequences of Clones Obtained from Round 9, Thrombin DNA Selection #2 and #3

| SEQ ID NO | Clone Name | Sequence |
|---|---|---|
| 63 | AMX(398)_A1 | TCCGATTGACGTGGTGGGTTACTGGTT TGGGTGGCTGAGGATCGATC |
| 64 | AMX(398)_A2 | TCCCATTGATCTGTGGTGGTTTTGTGG TTTGGGTGGCTGAGGATCGATC |
| 65 | AMX(398)_A4 | TCCCGTAATCGAGCCTGGTATTGTTGG TCTGGGTGGCTGAGGATCGATC |
| 66 | AMX(398)_A6 | TCCCATCGATTTGGGGTATGTTATGGG CTCGGGTGGCTGAGGATCGATC |
| 67 | AMX(398)_A7 | TCCCTATCGAGCTGTGGTAGTATTCTG GTTTGGGTGGCTGAGGATCGATC |
| 68 | AMX(398)_A8 | TCCCATCGGTCCGGGGTAATTTACTGG GTCGGGTGGCTGAGGATCGATC |
| 69 | AMX(398)_A9 | TCCCGTCGAGCCGGGGTATGATTATGG GTGGGGTGGCTGAGGATCGATC |
| 70 | AMX(398)_A12 | TCCCTGGAGATCCGGGGTAGTATACTG GTTTGGGTGGCTGAGGATCGATC |
| 71 | AMX(398)_B1 | TCCCAATCGAGCCGGGGTTTGTTTGTT CTGGGTGGCTGAGGATCGATC |
| 72 | AMX(398)_B2 | TCCCGTAATCGAGCCTGGTATTGTTGG TCTGGGTGGCTGAGGATCGATC |
| 73 | AMX(398)_B3 | TCCCAGATGTGATCCGTATCCTGGTTT GGTTGGGTGGCTGAGGATCGATC |
| 74 | AMX(398)_B5 | TCCCTGATCCTTAGGCTAGGTTGGGTG GGGTGGTGGCTGAGGATCGATC |
| 75 | AMX(398)_B9 | TCCCATCGAGCCGGGGATGGTTTGTTG GAGGGGTGGCTGAGGATCGATC |
| 76 | AMX(398)_B10 | TCCCTCGATCTTGGGGTACTATAGTGG TGTGGGTGGCTGAGGATCGATC |
| 77 | AMX(398)_B11 | TCCCGCTCGATTTCGAAGAATGGTTGG TTTGGGTGGCTGAGGATCGATC |
| 78 | AMX(398)_B12 | TCCCGATTATCCGTTGGTATTGTTGGT CTGGGTGGCTGAGGATCGATC |
| 79 | AMX(398)_C1 | TCCCAACGATCTGTGGTTTTTTTGTTC TGGGTGGCTGAGGATCGATC |
| 80 | AMX(398)_C2 | TCCCAAGGATCCGGGGTAGTTAGTGGC TGAGGTGGCTGAGGATCGATC |
| 81 | AMX(398)_C3 | TCCCATGTGTTAGATCCGTGTGGTTGG ACTGGGTGGCTGAGGATCGATC |
| 82 | AMX(398)_C5 | TCCCCGATGTGTCAGCCTAGGGTGGTT AGGGTGGTGGCTGAGGATCGATC |
| 83 | AMX(398)_C6 | TCCCATGATTGGCCGGGGTGTCTTTTG GGTCGGGTGGCTGAGGATCGATC |
| 84 | AMX(398)_C8 | TCCTGAGGGATCAGGCTAGGTTGGGTA GGGTGGTGGCTGAGGATCGATC |
| 85 | AMX(398)_C9 | TCCCGATCGTTTCGTGGGTAGTGTTG GTTGGGGTGGCTGAGGATCGATC |
| 86 | AMX(398)_C10 | TCCCGAGCGATACTGCCTAGGCTGGGT AGGGTGGTGGCTGAGGATCGATC |
| 87 | AMX(398)_C11 | TCCTGTCGATCGGTACGTTTTCGTTTC TGGGTGGCTGAGGATCGATC |
| 88 | AMX(398)_C12 | TCCCTGCAATCGGTGCTCGAGAGGTTG GGTGGGTGGCTGAGGATCGATC |
| 89 | AMX(398)_D1 | TCCCGATTTGAGTTTAGTAGGGTGGGT AGGATGGTGGCTGAGGATCGATC |
| 90 | AMX(398)_D3 | TCCCATGATCGGGTCGGTATTTGTTGG TCAGGGTGGCTGAGGATCGATC |

TABLE 6-continued

Sequences of Clones Obtained from Round 9, Thrombin DNA Selection #2 and #3

| SEQ ID NO | Clone Name | Sequence |
|---|---|---|
| 91 | AMX(398)_D5 | TCCCAGCGGTCCTAATGGGTAGTGTTGGTTTGGGTGGCTGAGGATCGATC |
| 92 | AMX(398)_D6 (ARC2026) | TCCCGAGCGATACTGCCTAGGTTGGGTAGGGTGGTGGCTGAGGATCGATC |
| 93 | AMX(398)_D7 | TCCCTTGTCGATTCTGGTATGTTTTGGTCCGGGTGGCTGAGGATCGATC |
| 94 | AMX(398)_D9 | TCCCATGAACTCAGGGTAATTTTTTGGTGTGGGTGGCTGAGGATCGATC |
| 95 | AMX(398)_E1 | TCCCATCGATCCGGGGTATTCTTATTTCTGGGTGGCTGAGGATCGATC |
| 96 | AMX(398)_E2 | TCCCGGTCGAGACTCGGAGTATGGCAGGGTGGGTGGCTGAGGATCGATC |
| 97 | AMX(398)_E3 | TCCCGAGTGATCCGGGGTGTTTTTTTGGGTTGGGTGGCTGAGGATCGATC |
| 98 | AMX(398)_E5 | TCCCGATCGGACGTGGTGGGTTACTTCTGGGTGGCTGAGGATCGATC |
| 99 | AMX(398)_E6 | TCCCATCGAGACGGGGTGTCTTTTGTGGCTTGGGTGGCTGAGGATCGATC |
| 100 | AMX(398)_E7 | TCCCTTGATCTGGGGTGCGTTATTGTGGTTCGGGTGGCTGAGGATCGATC |
| 101 | AMX(398)_E8 | TCCCTATCGACCGGGGTTCTTTCGTGGTTCGGGTGGCTGAGGATCGATC |
| 102 | AMX(398)_E11 | TCCCATTGGTCGGGGATTGGTGGCTGGGTGGGGTGGCTGAGGATCGATC |
| 103 | AMX(398)_E12 | TCCCGGATCTGTGGTAGGTTTGTTGGGTTGGGTGGCTGAGGATCGATC |
| 104 | AMX(398)_F2 | TCCCATCGAGTCGTGGTGTTTTGTTGGCCTGGGTGGCTGAGGATCGATC |
| 105 | AMX(398)_F5 | TCCCGATCGAGAGTGGTATTTGTTTTCTGGGTGGCTGAGGATCGATC |
| 106 | AMX(398)_F6 | TCCCTTGATCCGGTGGTAGTTTTATTGGTGCGGGTGGCTGAGGATCGATC |
| 107 | AMX(398)_F8 | TCCCATCGATCCGTGGTACTTTTGTGGCTAGGGTGGCTGAGGATCGATC |
| 108 | AMX(398)_F9 | TCCCGTCGATCTGGGGTGTCTATGTGGGTGGGGTGGCTGAGGATCGATC |
| 109 | AMX(398)_F12 | TCCCGATCGTAGTCCTGGTATTGTTGGTCTGGGTGGCTGAGGATCGATC |
| 110 | AMX(398)_G2 | TCCCTAACGATCTGAGGTGTTTTTTTTCTGGGTGGCTGAGGATCGATC |
| 111 | AMX(398)_G6 | TCCCTGTCGTTCCGTGGTGTTTTTATGGGCTGGGTGGCTGAGGATCGATC |
| 112 | AMX(398)_G7 | TCCCATCGGTCGGGGTAATTTTATTGGGTGGGGTGGCTGAGGATCGATC |
| 113 | AMX(398)_G8 | TCCCTTGTTTGATCCGGGGTGTTAATGGTTGGGGTGGCTGAGGATCGATC |
| 114 | AMX(398)_G11 | TCCCTCGATGCTTATGGGTATTGTATGGGTTTGGGTGGCTGAGGATCGATC |
| 115 | AMX(398)_H1 | TCCCATCGGTCCAAGGTATTTTTGTTTCTGGGTGGCTGAGGATCGATC |
| 116 | AMX(398)_H5 | TCCCATCTTCTGTAGCCTAGGTTGGGTAGGGTGGTGGCTGAGGATCGATC |
| 117 | AMX(398)_H6 | TCCCTATGGATCCGGGGTACGTTAGTTCTGGGTGGCTGAGGATCGATC |
| 118 | AMX(398)_H7 | TCCCTCGGTCCTCGTCTTTTTTGGTCTGGGTGGGTGGCTGAGGATCGATC |
| 119 | AMX(398)_H8 | TCCCTGCGTCGATCGTGGTATCGTTTCTGGGTGGCTGAGGATCGATC |
| 120 | AMX(398)_H10 | TCCTGAGCGATTCGGGGTGTTTTCATGGTTCGGGTGGCTGAGGATCGATC |
| 121 | AMX(399)_A2 | TCCCTATCGATTGCTCCTAGGATGGGTAGGGTGGTGGCTGAGGATCGATC |
| 122 | AMX(399)_A3 | TCCCATGGATCCGAGGTGTTTTAGTGGTCCGGGTGGCTGAGGATCGATC |
| 123 | AMX(399)_A5 | TCTCTGACGATCCGGGGTGCAAATTGTGGTGGGGTGGCTGAGGATCGATC |
| 124 | AMX(399)_A6 | TCCCGTAATTGAGCTTGGTATTGTTGGTCTGGGTGGCTGAGGATCGATC |
| 125 | AMX(399)_A7 | TCCCACCGATCCGGGGTAAATGAATGGCGTGGGTGGCTGAGGATCGATC |
| 126 | AMX(399)_A10 | TCCCTCGATCAAGGTGTTTATTATGGTGTGGGTGGCTGAGGATCGATC |
| 127 | AMX(399)_A11 | TCCCTTCTGATCCGAGGTGTTTTATTGGTGTGGGTGGCTGAGGATCGATC |
| 128 | AMX(399)_A12 | TCCCATCGAACCTTGAGGGTATTGTTGGTTTGGGTGGCTGAGGATCGATC |
| 129 | AMX(399)_B2 | TCCCATCGATTCGTGGTCTTTTTATGGTGTGGGTGGCTGAGGATCGATC |
| 130 | AMX(399)_B3 | TCCCGTAATCGAGCTTGGTATTGTTGGTCTGGGTGGCTGAGGATCGATC |
| 131 | AMX(399)_B6 | TCCCTCGTATTCCGGGGATCATATTGGTCGGGGTGGCTGAGGATCGATC |
| 132 | AMX(399)_B8 | TCCCAGGACCGATCCTGGTATTGTTGGTGGGGGTGGCTGAGGATCGATC |
| 133 | AMX(399)_B9 | TCCTGTCGATCCCTACGGGTAGTGTTGGTTTGGGTGGCTGAGGATCGATC |
| 134 | AMX(399)_B10 | TCCCATTGATCCGGGGTGGTTTTCTGGTTTGGGTGGCTGAGGATCGATC |
| 135 | AMX(399)_B11 | TCCCGTCGATTCGGTATGGTTTCGTTTCTGGGTGGCTGAGGATCGATC |
| 136 | AMX(399)_B12 | TCCCATCGATTTGTCCTCAGAGGTTGGCGTGGGTGGCTGAGGATCGATC |
| 137 | AMX(399)_C7 | TCCCGAGCGATCGGGGTGGTTTTTTGGGAGTGGGTGGCTGAGGATCGATC |
| 138 | AMX(399)_C8 | TCCCGTCGATCAGGGGTAATTTGCTGGTGGTGGGTGGCTGAGGATCGATC |
| 139 | AMX(399)_C9 | TTCCTGTCGATAAGGGGTATTATAGTGGTGTGGGTGGCTGAGGATCGATC |
| 140 | AMX(399)_C10 | TCTCATTCGTTCCGGGGTATTTAGTGGGTCGGGTGGCTGAGGATCGATC |

TABLE 6-continued

Sequences of Clones Obtained from Round 9,
Thrombin DNA Selection #2 and #3

| SEQ ID NO | Clone Name | Sequence |
|---|---|---|
| 141 | AMX(399)_C11 | TCCCGAGGGACGACGCCTAGGTTGGGTAGGGTGGTGGCTGAGGATCGATC |
| 142 | AMX(399)_C12 | TCCCGATCTATCCGGGGTACATTTGTGGTTTGGGTGGCTGAGGATCGATC |
| 143 | AMX(399)_D2 | TCCCGATCGCTGTCCTAGGATGGGTAGGGTGGTGGCTGAGGATCGATC |
| 144 | AMX(399)_D3 | TCCCGCGATCTCTGGGGTAACGTTTTGGTGTGGGTGGCTGAGGATCGATC |
| 145 | AMX(399)_D4 | TCCCGATTGATTCTGGGAGGTTTGGTTCTGGGTGGCTGAGGATCGATC |
| 146 | AMX(399)_D5 | TCCCGTTCGAGTCCTGGTGTTTTATTGGCCTGGGTGGCTGAGGATCGATC |
| 147 | AMX(399)_D6 | TCCCGCATTGAATAGGACTCAGGGATGGTGTGGGTGGCTGAGGATCGATC |
| 148 | AMX(399)_D7 | TCCCTCGATCTAAGGTGCTTTTAGTGGTTTGGGTGGCTGAGGATCGATC |
| 149 | AMX(399)_D8 | TCTCGATCGGACGTGGTGGGTTACTGGCTTGGGTGGCTGAGGATCGATC |
| 150 | AMX(399)_D9 | TCCCAGGATCGATTCTGGTATTGTTGGTGGGGGTGGCTGAGGATCGATC |
| 151 | AMX(399)_D10 | TCCCATCGATCTGTGGTGGTTTTGTGGTTTGGGTGGCTGAGGATCGATC |
| 152 | AMX(399)_D11 | TCCCAGAGAGCCGGGGTATAATTGTGGTGTGGGTGGCTGAGGATCGATC |
| 153 | AMX(399)_D12 | TCCCATCGATCTGTGGTCTTTTTTGGTGTGGGTGGCTGAGGATCGATC |
| 154 | AMX(399)_E1 | TCCCACGATCCGGGGTGTCTTTCGTGGGCTGGGTGGCTGAGGATCGATC |
| 155 | AMX(399)_E3 | TCCCGATTTCGATTCTGGTAGTGTTTTCTGGGTGGCTGAGGATCGATC |
| 156 | AMX(399)_E4 | TCCCATCGAACCGCGGGTAATCTTATGGGTCGGGTGGCTGAGGATCGATC |
| 157 | AMX(399)_E5 | TCCCATCGAGCCGGGTATGTTTCGTTGGGCTGGGTGGCTGAGGATCGATC |
| 158 | AMX(399)_E8 | TCCCATCGATCCGGGTACTTTCGTGGCTTGGGTGGCTGAGGATCGATC |
| 159 | AMX(399)_E9 | TCCCATCGATACGGGGTGGAATCTTGGGGTGGGTGGCTGAGGATCGATC |
| 160 | AMX(399)_E10 | TCCCGATTGTCATAGGTGGTTTGTCTGGGTAGGGTGGCTGAGGATCGATC |
| 161 | AMX(399)_E12 | TCCCGAGATCTTTATAGGGTATTGTTGGTTGGGGTGGCTGAGGATCGATC |
| 162 | AMX(399)_F1 | TCCCGTGATCTCTGGGGTAACGTCTTGGTGTGGGTGGCTGAGGATCGATC |
| 163 | AMX(399)_F2 | TCCCTTGATCCTGGTACATATATTTTCTGGGTGGCTGAGGATCGATC |
| 164 | AMX(399)_F3 | TCCTTGTCGAGCCTTGGGGTAGTGTTGGTTTGGGTGGCTGAGGATCGATC |
| 165 | AMX(399)_F4 | TCCCGTTCGGTCCGTATACTGGTGGTGGTTGGGTGGCTGAGGATCGATC |
| 166 | AMX(399)_F5 | TCCCTAGATCGGGTCCTGGTAGTGTTTCTGGGTGGCTGAGGATCGATC |
| 167 | AMX(399)_F6 | TCCCAAGATCGATGCTGGTAGTGTTTTCTGGGTGGCTGAGGATCGATC |
| 168 | AMX(399)_F7 | TCCCGATCGGTCCCAAGGGTATTGTTGGTTTGGGTGGCTGAGGATCGATC |
| 169 | AMX(399)_F9 | TCCCGCTATTCGATCTTCAATTGGGTGGTCAGGGTGGCTGAGGATCGATC |
| 170 | AMX(399)_F10 | TCCCGTCGGTCCGTTCGGTATTTTTTTCTGGGTGGCTGAGGATCGATC |
| 171 | AMX(399)_F11 | TCCCTATGGATTCGGGGTACGTTAGTTCTGGGTGGCTGAGGATCGATC |
| 172 | AMX(399)_F12 | TCCCGATTGGAAAGCCTAGGATGGGTAGGGTGGTGGCTGAGGATCGATC |
| 173 | AMX(399)_G1 | TCCCAGGACCGATCTTGGTATTGTTGGTGGGGGTGGCTGAGGATCGATC |
| 174 | AMX(399)_G2 | TCCCATCGTCTGTGGTATAGGAACTTCTGGGTGGCTGAGGATCGATC |
| 175 | AMX(399)_G3 | TCCCATCGAACCTCGAGGGTATTGTTGGCTTGGGTGGCTGAGGATCGATC |
| 176 | AMX(399)_G5 | TCCCGGTATCGTCATGCTGGTGGAATTGGTTGGGTGGCTGAGGATCGATC |
| 177 | AMX(399)_G6 | TCCCATCGATCAGTGGTGGCTTGGCTGGTTTGGGTGGCTGAGGATCGATC |
| 178 | AMX(399)_G8 | TCCCATCGATCTGTGGTGGTTTTGTGGCTTGGGTGGCTGAGGATCGATC |
| 179 | AMX(399)_G9 | TCCCGTGAGAGCTGGGGTGTTTATATGGGTCGGGTGGCTGAGGATCGATC |
| 180 | AMX(399)_G10 | TCCCGATCGCTGTCCTAGGATGGGTAGGGTGGTGGCTGAGGATCGATC |
| 181 | AMX(399)_G11 | TCCCCATCGATCCTGGTCTCTTTTGTTCTGGGTGGCTGAGGATCGATC |
| 182 | AMX(399)_G12 | TCCCGGATCCTCGTGGGTATTGTTGGGTTGGGTGGCTGAGGATCGATC |
| 183 | AMX(399)_H1 | TCCCATCGAACCTCGAGGGTATTGTTGGTTTGGGTGGCTGAGGATCGATC |
| 184 | AMX(399)_H2 | TCCCGACTTTAGATCCGTGTTGGATGGCCTGGGTGGCTGAGGATCGATC |
| 185 | AMX(399)_H3 | TCCCAATCGGTCCTGGTAATATATTGGTCGGGTGGCTGAGGATCGATC |
| 186 | AMX(399)_H4 | TCCCGAGAGATTCAAAAGGGACTGGGCGGTTGGGTGGCTGAGGATCGATC |
| 187 | AMX(399)_H6 | TCCCGGAGATCTGAGGTGTTTTATTGGTTTGGGTGGCTGAGGATCGATC |
| 188 | AMX(399)_H7 | TCCCGGTTGTCGATTCTGGTATTGTTGGGCTGGGTGGCTGAGGATCGATC |
| 189 | AMX(399)_H8 | TCCCTGGTATCGTATCCAAAGGGGTGGTGTGGGTGGCTGAGGATCGATC |
| 190 | AMX(399)_H9 | TCCCGGAGATCCGAGGTGTTTTATTGGTTTGGGTGGCTGAGGATCGATC |

TABLE 7

Binding Characterization of Clones Obtained from Thrombin DNA Selections #2 and #3, Round 9:

| SEQ ID NO | Clone | % Bound at 10 nM Thrombin (screen) | % Bound at 50 nM Prothrombin (screen) | Kd for Thrombin (nM) |
|---|---|---|---|---|
| 63 | AMX(398)_A1 | 15.85 | 18.00 | 0.30 |
| 64 | AMX(398)_A2 | 26.67 | 28.45 | N/A |
| 65 | AMX(398)_A4 | 45.67 | 47.70 | 1.27 |
| 66 | AMX(398)_A6 | 31.15 | 31.27 | N/A |
| 67 | AMX(398)_A7 | 26.50 | 25.45 | N/A |
| 68 | AMX(398)_A8 | 40.02 | 43.87 | N/A |
| 69 | AMX(398)_A9 | 28.26 | 29.71 | N/A |
| 70 | AMX(398)_A12 | 35.36 | 37.47 | N/A |
| 71 | AMX(398)_B1 | 31.33 | 32.66 | N/A |
| 72 | AMX(398)_B2 | 47.76 | 51.75 | 0.39 |
| 73 | AMX(398)_B3 | 17.54 | 16.54 | N/A |
| 74 | AMX(398)_B5 | 12.48 | 8.27 | N/A |
| 75 | AMX(398)_B9 | 3.03 | 2.16 | N/A |
| 76 | AMX(398)_B10 | 26.81 | 25.66 | N/A |
| 77 | AMX(398)_B11 | 9.76 | 2.08 | N/A |
| 78 | AMX(398)_B12 | 20.11 | 20.21 | N/A |
| 79 | AMX(398)_C1 | 35.80 | 37.04 | N/A |
| 80 | AMX(398)_C2 | 0.20 | 0.66 | N/A |
| 81 | AMX(398)_C3 | 10.77 | 3.04 | N/A |
| 82 | AMX(398)_C5 | 40.83 | 19.23 | 2.20 |
| 83 | AMX(398)_C6 | 28.01 | 11.60 | N/A |
| 84 | AMX(398)_C8 (ARC2027) SEQ ID NO 84 | 49.27 | 48.47 | 0.42 |
| 85 | AMX(398)_C9 | 20.68 | 20.69 | N/A |
| 86 | AMX(398)_C10 | 41.00 | 40.92 | 3.27 |
| 87 | AMX(398)_C11 | 35.08 | 36.66 | N/A |
| 88 | AMX(398)_C12 | 22.80 | 15.47 | N/A |
| 89 | AMX(398)_D1 | 20.66 | 11.77 | N/A |
| 90 | AMX(398)_D3 | 20.02 | 20.84 | N/A |
| 91 | AMX(398)_D5 | 12.04 | 12.93 | N/A |
| 92 | AMX(398)_D6 (ARC2026) | 45.70 | 45.54 | 0.29 |
| 93 | AMX(398)_D7 | 34.98 | 34.65 | N/A |
| 94 | AMX(398)_D9 | 40.42 | 41.75 | 5.64 |
| 95 | AMX(398)_E1 | 23.36 | 20.89 | N/A |
| 96 | AMX(398)_E2 | 3.84 | 2.62 | N/A |
| 97 | AMX(398)_E3 | 45.41 | 47.52 | 0.89 |
| 98 | AMX(398)_E5 | 25.59 | 25.39 | N/A |
| 99 | AMX(398)_E6 | 29.52 | 30.31 | N/A |
| 100 | AMX(398)_E7 | 27.90 | 20.31 | N/A |
| 101 | AMX(398)_E8 | 26.38 | 26.67 | N/A |
| 102 | AMX(398)_E11 | 13.68 | 16.53 | N/A |
| 103 | AMX(398)_E12 | 40.43 | 39.87 | N/A |
| 104 | AMX(398)_F2 | 8.76 | 8.81 | N/A |
| 105 | AMX(398)_F5 | 21.33 | 19.40 | N/A |
| 106 | AMX(398)_F6 | 23.90 | 24.63 | N/A |
| 133 | AMX(399)_B9 | 14.68 | 14.26 | N/A |
| 134 | AMX(399)_B10 | 24.43 | 23.59 | N/A |
| 135 | AMX(399)_B11 | 18.72 | 18.18 | N/A |
| 136 | AMX(399)_B12 | 24.16 | 15.28 | N/A |
| 137 | AMX(399)_C7 | 6.80 | 6.94 | N/A |
| 138 | AMX(399)_C8 | 36.78 | 33.81 | N/A |
| 139 | AMX(399)_C9 | 11.20 | 10.88 | N/A |
| 140 | AMX(399)_C10 | 35.36 | 34.26 | N/A |
| 141 | AMX(399)_C11 | 42.77 | 41.62 | 1.74 |
| 142 | AMX(399)_C12 | 18.69 | 17.17 | N/A |
| 143 | AMX(399)_D2 | 46.04 | 44.08 | 1.33 |
| 144 | AMX(399)_D3 | 21.69 | 25.26 | N/A |
| 145 | AMX(399)_D4 | 10.38 | 9.02 | N/A |
| 146 | AMX(399)_D5 | 46.01 | 23.76 | 2.26 |
| 147 | AMX(399)_D6 | 22.67 | 22.04 | N/A |
| 148 | AMX(399)_D7 | 7.59 | 24.88 | N/A |
| 149 | AMX(399)_D8 | 22.16 | 19.57 | N/A |
| 150 | AMX(399)_D9 | 20.31 | 19.74 | N/A |
| 151 | AMX(399)_D10 | 38.78 | 40.76 | N/A |
| 152 | AMX(399)_D11 | 41.33 | 39.55 | N/A |
| 153 | AMX(399)_D12 | 32.62 | 32.21 | N/A |
| 154 | AMX(399)_E1 | 37.65 | 39.11 | N/A |
| 155 | AMX(399)_E3 | 13.00 | 13.29 | N/A |
| 156 | AMX(399)_E4 | 7.50 | 7.29 | N/A |
| 157 | AMX(399)_E5 | 15.03 | 12.53 | N/A |
| 158 | AMX(399)_E8 | 4.31 | 4.37 | N/A |
| 159 | AMX(399)_E9 | 14.83 | 13.77 | N/A |
| 160 | AMX(399)_E10 | 29.76 | 28.92 | N/A |
| 161 | AMX(399)_E12 | 20.31 | 25.11 | N/A |
| 162 | AMX(399)_F1 | 16.73 | 19.39 | N/A |
| 163 | AMX(399)_F2 | 7.37 | 7.92 | N/A |
| 164 | AMX(399)_F3 | 9.80 | 8.70 | N/A |
| 165 | AMX(399)_F4 | 28.11 | 25.03 | N/A |
| 166 | AMX(399)_F5 | 49.21 | 49.31 | 2.35 |
| 167 | AMX(399)_F6 | 10.04 | 11.90 | N/A |
| 168 | AMX(399)_F7 | 29.62 | 34.20 | N/A |
| 169 | AMX(399)_F9 | 25.18 | 25.97 | N/A |
| 170 | AMX(399)_F10 | 21.33 | 22.09 | N/A |
| 171 | AMX(399)_F11 | 35.13 | 35.73 | N/A |
| 172 | AMX(399)_F12 | 46.68 | 48.25 | 0.66 |
| 173 | AMX(399)_G1 | 4.89 | 2.44 | N/A |
| 174 | AMX(399)_G2 | 18.77 | 7.28 | N/A |
| 175 | AMX(399)_G3 | 20.79 | 22.58 | N/A |
| 176 | AMX(399)_G5 | 23.20 | 18.93 | N/A |
| 177 | AMX(399)_G6 | 39.69 | 38.60 | N/A |
| 178 | AMX(399)_G8 | 27.64 | 25.94 | N/A |
| 179 | AMX(399)_G9 | 21.30 | 22.51 | N/A |
| 180 | AMX(399)_G10 | 38.44 | 36.28 | N/A |
| 181 | AMX(399)_G11 | 12.75 | 11.79 | N/A |
| 182 | AMX(399)_G12 | 40.56 | 41.10 | N/A |
| 183 | AMX(399)_H1 | 21.23 | 20.45 | N/A |
| 184 | AMX(399)_H2 | 5.49 | 2.73 | N/A |
| 185 | AMX(399)_H3 | 44.82 | 45.52 | 1.93 |
| 186 | AMX(399)_H4 | 7.70 | 3.66 | N/A |
| 187 | AMX(399)_H6 | 8.48 | 6.32 | N/A |
| 188 | AMX(399)_H7 | 38.10 | 36.07 | N/A |
| 189 | AMX(399)_H8 | 23.34 | 14.34 | N/A |
| 190 | AMX(399)_H9 | 3.86 | 3.16 | N/A |

Example 2

Composition and Sequence Optimization and Sequences

Example 2A

Minimization of DNA Selection #2 and #3 Thrombin Aptamers

Minimization of Clones from Round 7 DNA Selection #2 and #3

An RNA folding program (RNAstructure©(1996-2004) David H. Mathews, Michael Zuker & Douglas H. Turner) was used to determine the putative secondary folds for the Round 7 clones for which the $K_D$'S were determined as described above in Example 1B. The high affinity clones were from related sequences and based on the folding of clone AMX (395)_C1 (SEQ ID NO 49), minimized aptamer sequences were designed and synthesized. $K_D$ values for each minimized construct were determined using a dilution series of human Thrombin (ranging between 1 pM and 1000 nM depending the affinity of a specific clone for thrombin) in the dot blot binding assay previously described in Example 1A and fitting an equation describing a 1:1 RNA:protein complex to the resulting data (fraction aptamer bound=amplitude* ([Thrombin]/($K_D$+[Thrombin]))) (KaleidaGraph v. 3.51, Synergy Software, Reading, Pa.). The sequence of the minimized construct based on parent aptamer AMX(395)_C1 (SEQ ID NO 49), and corresponding $K_D$ is listed in Table 8 below. As shown, ARC 1985, the resulting 27-mer identified during minimization, displayed the highest binding affinity for thrombin out of all clones identified and minimized from Round 7 of DNA Selection #2 and #3.

For the minimized DNA aptamers described in Table 8 below, all the nucleotides (A, T, C and G) are deoxy. Unless noted otherwise, the individual sequences are represented in the 5' to 3' orientation.

TABLE 8

Sequences and binding characterization of the AMX(395)_C1 (SEQ ID NO 49) truncated construct.

| SEQ ID NO | ARC# | Sequence | $K_D$ (nM) |
|---|---|---|---|
| 191 | ARC1985 | CCTCAGGGATGGTGTGGGTGGCTGAGG | 5.7 |

Minimization of clones from Round 9 DNA Selection #2 and #3

Minimized constructs were designed as described above from the clones identified in Round 9 of DNA Selections #2 and #3 that showed the highest binding affinity in the dot blot binding assay described above in Example 1B, as well as most anti-clotting ability in the PT assay described below in Example 3A. The sequences of the minimized constructs, and the relative parent aptamer for each construct are described in Table 9 below. The functional activity of each minimized construct was compared to the relative parent aptamer in the PT assay described below in Example 3A. Of the truncated constructs designed, ARC2091 (SEQ ID NO 197) showed comparable potency to the parent clone in the PT assay (See Example 3A below). ARC2091 (SEQ ID NO 197) displayed the best functional activity out of all clones identified and minimized from Round 9 of DNA Selections # 2 and #3, and was the basis for a doped re-selection described in Example 2B below.

For the minimized DNA aptamers described in Table 9 below, all the nucleotides (A, T, C and G) are deoxy. Unless noted otherwise, the individual sequences are represented in the 5' to 3' orientation.

TABLE 9

Sequences of Truncated Constructs designed from Clones identified in Round 9 of DNA Selection #2 and #3 Against Human Thrombin

| SEQ ID NO of Minimized Aptamer | Minimized Aptamer Name | Parent Aptamer (SEQ ID NO) | Sequence of Minimized Aptamer |
|---|---|---|---|
| 193 | Minimer 1 | AMX(399)_B3 (SEQ ID NO 130) | CCCTTGGTATTGTTGGTCTGGGTGGCTGAGCGG |
| 194 | Minimer 2 | AMX(398)_A4 (SEQ ID NO 65) | CCGCCTGGTATTGTTGGTCTGGGTGGCTGAGGCGG |
| 195 | Minimer 3 | AMX(398)_D6 (SEQ ID NO 92) | GGTTGGGTAGGGTGG |
| 196 | Minimer 4 | AMX(398)_D6 (SEQ ID NO 92) | GGTAGGGTGGTGG |
| 197 | Minimer 5 (ARC2091) | AMX(398)_D6 (SEQ ID NO 92) | GGCGATACTGCCTAGGTTGGGTAGGGTGGTGGCTGAGGATCGCC |
| 198 | Minimer 6 | AMX(398)_D6 (SEQ ID NO 92) | ACTGCCTAGGTTGGGTAGGGTGGT |
| 199 | Minimer 12 | AMX(398)_D6 (SEQ ID NO 92) | GGCGATACTGCTTCGCAGGGTGGTGGCTGAGGATCGCC |
| 200 | Minimer 7 | AMX(398)_C8 (SEQ ID NO 84) | GGCCGATCAGGCTAGGTTGGGTAGGGTGGTGGCTGAGGATCGGCC |
| 201 | Minimer 8 | AMX(398)_C8 (SEQ ID NO 84) | GGCGATACTGCCTTTGGTAGGGTGGTGGCTGAGGATCGCC |
| 202 | Minimer 9 | AMX(398)_C8 (SEQ ID NO 84) | GGCGATACTGCCCAGGTTGGGCAGGGTGGTGGCTGAGGATCGCC |
| 203 | Minimer 10 | AMX(398)_C8 (SEQ ID NO 84) | GGCCGATCAGGCTGCTGAGGATCGGCC |
| 204 | Minimer 11 | AMX(398)_C8 (SEQ ID NO 84) | CCGGCTAGGTTGGGTAGGGTGGTGGCTGG |

Example 2B

ARC2091 Doped Reselection

A selection using a doped pool based on the minimized human thrombin binding sequence ARC2091 (SEQ ID NO 197) (described in Example 2A) was performed in order to identify higher affinity binders to Thrombin. Doped reselections are used to explore the sequence requirements within an active clone or minimer. Selections are carried out with a synthetic, degenerate pool that has been designed based on a single sequence. The level of degeneracy usually varies from 70% to 85% wild type nucleotide. In general, neutral mutations are observed but in some cases sequence changes can result in improvements in affinity. The composite sequence information can then be used to identify the minimal binding motif and aid in optimization efforts.

Pool Preparation:

A DNA template with the sequence 5' ATGCTTTTATA-CCTTCGGCGATACTGCCTAGGTTGGGTAGGGTGGT-GGCTGAGGATCGCCGAATTTCCCGAGAGTTCC 3' (ARC2082, SEQ ID NO 205) was synthesized using an ABI EXPEDITE™ DNA synthesizer, and deprotected by standard methods. The nucleotides in bold had an 85% chance of being the indicated residue and a 5% chance of being one of the other 3 nucleotides. The templates were amplified with 5' primer 5' ATGCTTTTATACCTTCGGC 3' (ARC2083, SEQ ID NO 206) and 3' primer 5' GGAACTCTCGGGAAATTCG 3' (ARC2084, SEQ ID NO 207). After amplification, the PCR product was ethanol precipitated then subjected to alkaline hydrolysis (333 mM NaOH, 90° C., 15 min) followed by neutralization with HCL and addition of and formamide loading buffer before purification on a 10% PAGE gel.

Selection

A total of 3 Rounds of nitrocellulose column based doped reselection were performed against Thrombin (Enzyme Research Labs, South Bend, Ind.). Centrex columns (Schleicher & Schuell, Keen, N.H.) were prepared as previously described in Example 1A. A negative selection step was included starting at Round 1 to remove non-specific filter binders from the pool as follows. For each round, the negative filter was prepared as previously described in Example 1, and 100 pmoles of ARC2082 in 200 µl of 1×DPBS (500 nM pool concentration) was spun through and collected. After the negative selection step, 20 pmoles of thrombin (100 nM final concentration), 0.1 mg/ml of competitor tRNA and 0.1 mg/ml Heparin were added to the filtered pool and incubated at room temperature for 1 hour. The competitor tRNA was included to increase selective pressure and heparin was added to the positive selection step to bind to exosite 2 and prevent aptamers from binding to exosite 2 of thrombin. The selection conditions for each round are outlined in Table 10 below. For each round, the selection binding reaction was added to a prepared Centrex and spun through (2000 rpm for 1 minute). The column was then washed with 1 mL of 1× DPBS (w/Ca$^{2+}$ and Mg$^{2+}$) (Gibco, Catalog #14040, Invitrogen, Carlsbad, Calif.) and spun through by centrifugation (2000 rpm for 1 minute). After washing, the column was eluted with 1 mL of elution buffer (7M urea, 300 mM NaOAc, 5 mM EDTA) heated to 90° C. by allowing the elution buffer to sit on the column for 3 minutes before centrifugation at 2000 rpm for 1 minute and collected in an eppendorf tube. The eluent was precipitated using one volume of isopropanol and 1 µl of glycogen. The reaction was brought up to 200 µl in PCR mix containing the 5' Primer 5' ATGCTTTTATACCTTCGGC 3' (ARC2083) (SEQ ID NO 206) and 3' Primer 5' GGAACTCTCGGGAAATTCG 3' (ARC2084) (SEQ ID NO 2084 207). The PCR reaction was cycled using the following conditions: denaturing at 94° C. for 1 minute, cycling at 94° C. for 30 seconds, 54° C. for 30 seconds, and 72° C. for 1 minute; until the final product was approximately 10 ng/µl as measured by a 4% E-Gel (Invitrogen, Carlsbad, Calif.) (denoted as "PCR Threshold" in the far right column of Table 10). The product was then seeded into a larger PCR reaction for more amplification (20 µl into 400 ul total PCR volume).). After amplification, the PCR product was ethanol precipitated then subjected to alkaline hydrolysis (333 mM NaOH, 90° C., 15 min) followed by neutralization with HCL and addition of and formamide loading buffer before purification on a 10% PAGE gel. The purified product was eluted, concentrated and quantified before going into the next round of selection. Subsequent precipitation and gel purification occurred as stated previously.

TABLE 10

ARC2091 (SEQ ID NO 197) Doped Reselection Conditions

| Round | Negative | Thrombin (nM) | Competitor | PCR Threshold ((#Cycles) |
|---|---|---|---|---|
| 1 | Filter | 100 nM | .1 mg/ml tRNA and .1 mg/ml heparin | 20 |
| 2 | Filter | 30 nM | .1 mg/ml tRNA and 1 mg/ml heparin | 20 |
| 3 | Filter | 30 nM | .1 mg/ml tRNA and 1 mg/ml heparin | 20 |

Sequencing and Screening

After three rounds of selection, the doped pool was cloned using a TOPO TA Cloning (Invitrogen, Carlsbad, Calif.) kit according to the manufacturer's recommendations and sequenced. A total of 75 unique sequences identified, as shown below in Table 11. Prior to completion of the doped-reselection, a 30 mer derivative of ARC2091 (SEQ ID NO 197) referred to as ARC2169 (SEQ ID NO 283) that retained all of the thrombin binding affinity of ARC2091 (SEQ ID NO 197) was designed and synthesized. The sequences from the doped-reselection included mutations both within and without the core functional motif for the aptamer defined by the sequence of ARC2169 (SEQ ID NO 283). Mutations outside this core were discarded and mutations within the core were tested in the context of the ARC2169 (SEQ ID NO 283) sequence. Thus, from the sequences shown in Table 11 below, a panel of clones based on ARC2169 (SEQ ID NO 283) were designed using the data obtained from the doped reselection (see Table 12) to test the effect of further minimization and the effect of the most prevalent mutations resulting from the doped reselections on aptamer function. The effect of the mutations on aptamer function was measured using the PT assay and is described in Example 3 below.

For the DNA aptamers described in Table 11 and Table 12 below, all the nucleotides (A, T, C and G) are deoxy. Unless noted otherwise, the individual sequences are represented in the 5' to 3' orientation.

TABLE 11

Clones from ARC2091 (SEQ ID NO 197) Doped Reselection, Round 3

| SEQ ID NO | Clone Name | Sequence |
|---|---|---|
| 208 | AMX(449)_A1 | ATGCTTTTATACCTTCGGCCATACTGCATAGGTTGGGTAGGGTGGTTGCTGTGGCTGGCCGAATTTCCCGAGAGTTCC |
| 209 | AMX(449)_A4 | ATGCTTTTATACCTTCGGCGATATCCCTAGGTTGGGTAGGGTGGTGGTTGATGATTGTCGAATTTCCCGAGAGTTCC |
| 210 | AMX(449)_A6 | ATGCTTTTATACCTTCGGCGATACAGTCTAGGATGGGTAGGGTGGTGGCTGAGCATCGCCGAATTTCCCGAGAGTTCC |
| 211 | AMX(449)_A7 | ATGCTTTTATACCTTCGGCGACATTGTCTAGGTTGGGTAGGGTGGTGGCTCAGTATTGCCGAATTTCCCGAGAGTTCC |
| 212 | AMX(449)_A8 | ATGCTTTTATACCTTCGGCCATACTGCTTAGGTTGGGTAGGGCGGTAGCTGTAGATAGCCGAATTTCCCGAGAGTTCC |
| 213 | AMX(449)_A9 | ATGCTTTTATACCTTCGGCCATACATGTTAGGTTGTGTAGTGTGGGCCCTGAGGATGCCGAATTTCCCGAGAGTTCC |
| 214 | AMX(449)_A11 | ATGCTTTTATACCTTCGGCGAGACTGCCTAGGTTGGGTAGGGTGGTGGCTGAGGATTGCCGAATTTCCCGAGAGTTCC |
| 215 | AMX(449)_A12 | ATGCTTTTATACCTTCGGCCAAGACTGCCTAGGATGGGTAGGGTGGTGGTTTAGGGTTGCCGAATTTCCCGAGAGTTCC |
| 216 | AMX(449)_B1 | ATGCTTTTATACCTTCGGCGATAGTGCCTAGGTTGGGTAGGGTGGTGGTAGTGGATCGCCGAATTTCCCGAGAGTTCC |
| 217 | AMX(449)_B2 | ATGCTTTTATACCTTCGGCGGTCGTGTCTAGGGTGGGTAGGGTGGTGACTCAGGTTTGCCGAATTTCCCGAGAGTTCC |
| 218 | AMX(449)_B3 | ATGCTTTTATACCTTCGGCCAAACTGACTAGGTTGGGTAGGGTGGTGGCTGTGGTGGGCCGAATTTCCCGAGAGTTCC |
| 219 | AMX(449)_B4 | ATGCTTTTATACCTTCGGCGATAGTGCCTAGGTTGGGTAGGGTGGTGGCTGAGGCGTGCCGAATTTCCCGAGAGTTCC |
| 220 | AMX(449)_B5 | ATGCTTTTATACCTTCGGCGACAGTGCCTAGGTTGGGTAGGGTGGTGGCTTAGGCGCGCCGAATTTCCCGAGAGTTCC |
| 221 | AMX(449)_B6 | ATGCTTTTATACCTTCGGCGATGTAGACTAGGTTGGGTAGGGTGGTGGCTAAGTATTGCCGAATTTCCCGAGAGTTCC |
| 222 | AMX(449)_B8 | ATGCTTTTATACCTTCGGCTATACTGTCTAGGTTGGGTAGGGTGGTGACTTAGTGTTGCCGAATTTCCCGAGAGTTCC |
| 223 | AMX(449)_B9 | ATGCTTTTATACCTTCGGCGGGATTGTTTAGGTTGGGTAGGGTGGTGGCAGAGGATCGCCGAATTTCCCGAGAGTTCC |
| 224 | AMX(449)_B10 | ATGCTTTTATACCTTCGGCGGGATGTCCTAGGTTGGGTAGGGTGGTGGCTGAGGTTTGCCGAATTTCCCGAGAGTTCC |
| 225 | AMX(449)_B11 | ATGCTTTTATACCTTCGGCTATACTGCATAGGTTGGGTAGGGTGGTGGCTGAGTGTTGCCGAATTTCCCGAGAGTTCC |
| 226 | AMX(449)_C2 | ATGCTTTTATACCTTCGGCGATACTGACTAGGTTGGGTAGGGTGGTGGCTGATCTTCGCCGAATTTCCCGAGAGTTCC |
| 227 | AMX(449)_C4 | ATGCTTTTATACCTTCGGCGAAAGTGCTTAGGATGGGTAGGGTGGTGGCTGCGGATCGCCGAATTTCCCGAGAGTTCC |
| 228 | AMX(449)_C5 | ATGCTTTTATACCTTCGGCGGTAGTGCCTAGGTTGGGTAGGGTGGTGGCTCTGGATCGCCGAATTTCCCGAGAGTTCC |
| 229 | AMX(449)_C6 | ATGCTTTTATACCTTCGGCGATATTGCCTAGGTTGGGTAGGGTGGTGGCTGAACTTTGCCGAATTTCCCGAGAGTTCC |
| 230 | AMX(449)_C10 | ATGCTTTTATACCTTCGGCGACACAGACTAGGATGGGTAGGGTGGTGGCTGAGGCTCGCCGAATTTCCCGAGAGTTCC |
| 231 | AMX(449)_C11 | ATGCTTTTATACCTTCGGCGGACATTGGCTAGGTTGGGTAGGGTGGTGGCTGCGGATTGCCGAATTTCCCGAGAGTTCC |
| 232 | AMX(449)_C12 | ATGCTTTTATACCTTCGGCGATACTGTGTAGGTTGGGTAGGGTGGTCGTAGAGGATTGCCGAATTTCCCGAGAGTTCC |
| 233 | AMX(449)_D1 | ATGCTTTTATACCTTCGGCGATAATGTCTAGGTTGGGTAGGGTGGTGGCTGTGAATTGCCGAATTTCCCGAGAGTTCC |
| 234 | AMX(449)_D2 | ATGCTTTTATACCTTCGGCGGTCCTGCCTAGGATGGGTAGGGTGGTGGCCGAGGATTGCCGAATTTCCCGAGAGTTCC |
| 235 | AMX(449)_D3 | ATGCTTTTATACCTTCGGCGAAGATTGACTAGGTTGGGTAGGGTGGTGTTTTAGGATTGCCGAATTTCCCGAGAGTTCC |
| 236 | AMX(449)_D5 | ATGCTTTTATACCTTCGGCCATATTGCTTAGGTTGGGTAGGGTGGTAGCTGAGTATTGCCGAATTTCCCGAGAGTTCC |
| 237 | AMX(449)_D6 | ATGCTTTTATACCTTCGGCGAGAGTGCATAGGTTGGGTAGGGTGGTTGCTGTTGATCGCCGAATTTCCCGAGAGTTCC |
| 238 | AMX(449)_D7 | ATGCTTTTATACCTTCGGCGGATACAGGCTAGGTTGGGTAGGGTGGTGGCTGTTTAATCGCCGAATTTCCCGAGAGTTCC |
| 239 | AMX(449)_D8 | ATGCTTTTATACCTTCGGCGATATTGCCTAGGTTGGGTAGGGTGGTGGCTGGGGATTGCCGAATTTCCCGAGAGTTCC |
| 240 | AMX(449)_D9 | ATGCTTTTATACCTTCGGCCATAATAACTAGGTTGGGTAGGGTGGTGGCTGATTATCGCCGAATTTCCCGAGAGTTCC |
| 241 | AMX(449)_D10 | ATGCTTTTATACCTTCGGCGATATTGCCTAGGATGGGTAGGGTGGTGGCTAAGGTTTGCCGAATTTCCCGAGAGTTCC |
| 242 | AMX(449)_D11 | ATGCTTTTATACCTTCGGCGACACAGAGTAGGTTGGGTAGGGTGGTATCTGTCGAATGCCGAATTTCCCGAGAGTTCC |
| 243 | AMX(449)_D12 | ATGCTTTTATACCTTCGGCGATACTGCCTAGGTTGGGTAGGGTGGTGGCTAGGGATCGCCGAATTTCCCGAGAGTTCC |
| 244 | AMX(449)_E1 | ATGCTTTTATACCTTCGGCGACATTACCTAGGTTGGGTAGGGTGGTGGCTAAGGGTTGCCGAATTTCCCGAGAGTTCC |
| 245 | AMX(449)_E2 | ATGCTTTTATACCTTCGGCGGTTCAGCCTAGGATGGGTAGGGTGGTGGGTGAGGATTGCCGAATTTCCCGAGAGTTCC |

TABLE 11-continued

Clones from ARC2091 (SEQ ID NO 197)
Doped Reselection, Round 3

| SEQ ID NO | Clone Name | Sequence |
|---|---|---|
| 246 | AMX(449)_E4 | ATGCTTTTATACCTTCGGCGACATAGG GTAGGTTGGGTAGGGTGGTGCCTGAGG ATTGCCGAATTTCCCGAGAGTTCC |
| 247 | AMX(449)_E5 | ATGCTTTTATACCTTCGGCGGTACTGC ATAGGTTGGGTAGGGTGGTGGCTGAAC ATTGCCGAATTTCCCGAGAGTTCC |
| 248 | AMX(449)_E7 | ATGCTTTTATACCTTCGGCGGTAGGGT TTAGGTTGGGTAGGGTGGTGTCTGAGG ATTGCCGAATTTCCCGAGAGTTCC |
| 249 | AMX(449)_E9 | ATGCTTTTATACCTTCGGCCATACAGA CTAGGTTGGGTAGGGTGGTGTCTGAGG ATCGCCGAATTTCCCGAGAGTTCC |
| 250 | AMX(449)_E10 | ATGCTTTTATACCTTCGGCGATAGTGC TTAGGTTGGGTAGGGTGGTAGCTGATC ATTGCCGAATTTCCCGAGAGTTCC |
| 251 | AMX(449)_E11 | ATGCTTTTATACCTTCGGCGGTACTGC ATAGGTTGGGTAGGGTGGTGGCTGAGA ATCGCCGAATTTCCCGAGAGTTCC |
| 252 | AMX(449)_E12 | ATGCTTTTATACCTTCGGCGGCACTGG CTAGGATGGGTAGGGTGGTGGCTGAGC ATTGCCGAATTTCCCGAGAGTTCC |
| 253 | AMX(449)_F1 | ATGCTTTTATACCTTCGGCGATAACTG CCTAGGTTGGGTAGGGTGGTGGCTCAC GATCGTCGAATTTCCCGAGAGTTCC |
| 254 | AMX(449)_F3 | ATGCTTTTATACCTTCGGCGATACTGC ATAGGATGGGTAGGGTGGTTGCTGATG TGTGCCGAATTTCCCGAGAGTTCC |
| 255 | AMX(449)_F4 | ATGCTTTTATACCTTCGGCGATGTTGC CTAGGTTGGGTAGGGTGGTGGTTGTGA GTTGCCGAATTTCCCGAGAGTTCC |
| 256 | AMX(449)_F5 | ATGCTTTTATACCTTCGGCGACACTGT ATAGGTTGGGTAGGGTGGTGGCTGATG ATTGCCGAATTTCCCGAGAGTTCC |
| 257 | AMX(449)_F6 | ATGCTTTTATACCTTCGGCCACATTGC ATAGGTTGGGTAGGGTGGTGGCAAAGT ACTGCCGAATTTCCCGAGAGTTCC |
| 258 | AMX(449)_F7 | ATGCTTTTATACCTTCGGCGATACAGG TTAGGATGGGTAGGGTGGTGGCTGAGT ACTGCCGAATTTCCCGAGAGTTCC |
| 259 | AMX(449)_F9 | ATGCTTTTATACCTTCGGCGATAAGGG CTAGGATGGGTAGGGTGGTGACTAAAA CTCGCCGAATTTCCCGAGAGTTCC |
| 260 | AMX(449)_F10 | ATGCTTTTATACCTTCGGCGAGATTGG CTAGGGTGGGTAGGGTGGTGCTAGATG ATTGCCGAATTTCCCGAGAGTTCC |
| 261 | AMX(449)_F11 | ATGCTTTTATACCTTCGGCGACAATGA CTAGGTTGGGTAGGGTGGTGTCTTAGG ATGGCCGAATTTCCCGAGAGTTCC |
| 262 | AMX(449)_F12 | ATGCTTTTATACCTTCGGCGGTACTGT CTAGGTTGGGTAGGGTGGTGTCAGTTG ATCGCCGAATTTCCCGAGAGTTCC |
| 263 | AMX(449)_G1 | ATGCTTTTATACCTTCGGCCATACAAA CTAGGTTGGGTAGGGTGGTGTTTGCTG ATTGCCGAATTTCCCGAGAGTTCC |
| 264 | AMX(449)_G2 | ATGCTTTTATACCTTCGGCGAAACAGT ATAGGTTGGGTAGGGTGGTTGCTGATT ATCGCCGAATTTCCCGAGAGTTCC |

TABLE 11-continued

Clones from ARC2091 (SEQ ID NO 197)
Doped Reselection, Round 3

| SEQ ID NO | Clone Name | Sequence |
|---|---|---|
| 265 | AMX(449)_G3 | ATGCTTTTATACCTTCGGCGATATTGC CTAGGTTGGGTAGGGTGGTGGTTGAAA ATCGCCGAATTTCCCGAGAGTTCC |
| 266 | AMX(449)_G4 | ATGCTTTTATACCTTCGGCGGTACGGT CTAGGTTGGGTAGGGTGGTGTTTGGGT GTCGCCGAATTTCCCGAGAGTTCC |
| 267 | AMX(449)_G6 | ATGCTTTTATACCTTCGGCGATACTGT CTAGGTTGGGTAGGGTGGTGGCTTAGG ATTGCCGAATTTCCCGAGAGTTCC |
| 268 | AMX(449)_G8 | ATGCTTTTATACCTTCGGCGGTACTGT ATAGGTTGGGTAGGGTGGTTGCTGTGG ATTGTCGAATTTCCCGAGAGTTCC |
| 269 | AMX(449)_G9 | ATGCTTTTATACCTTCGGCGATAGGGC CTAGGTTGGGTAGGATGGTGGTCATAA ATCGCCGAATTTCCCGAGAGTTCC |
| 270 | AMX(449)_G10 | ATGCTTTTATACCTTCGGCGCTACAGG CTAGGTTGGGTAGGGTGGTGGTTGGGA ATCGCCGAATTTCCCGAGAGTTCC |
| 271 | AMX(449)_G11 | ATGCTTTTATACCTTCGGCCATACTGT CTAGGTTGGGTAGGGTGGTGGTTGAGT ATTGCCGAATTTCCCGAGAGTTCC |
| 272 | AMX(449)_G12 | ATGCTTTTATACCTTCGGCGGATACTG TCTAGGTTGGGTAGGGTGGTGACTGAG GATGGTCGAATTTCCCGAGAGTTCC |
| 273 | AMX(449)_H2 | ATGCTTTTATACCTTCGGCGGTGGTCT GTAGGTTGGGTAGGGTGGTTGCTTGGA ATCGCCGAATTTCCCGAGAGTTCC |
| 274 | AMX(449)_H3 | ATGCTTTTATACCTTCGGCGCGATTGC CTAGGTTGGGTAGGGTGGTGGCTTAGT ATTGCCGAATTTCCCGAGAGTTCC |
| 275 | AMX(449)_H4 | ATGCTTTTATACCTTCGGCGATAGGGA CTAGGTTGGGTAGGGTGGTGGCTGAGT ATTGCCGAATTTCCCGAGAGTTCC |
| 276 | AMX(449)_H5 | ATGCTTTTATACCTTCGGCGACAATGG CTAGGGTGGGTAGGGTGGTGGCTTAGG ATTGCCGAATTTCCCGAGAGTTCC |
| 277 | AMX(449)_H6 | ATGCTTTTATACCTTCGGCGGTAGTGT GTAGGGTGGGTAGGGTGGTAGCTGAGG ATCGCCGAATTTCCCGAGAGTTCC |
| 278 | AMX(449)_H7 | ATGCTTTTATACCTTCGGCGACACTGG TTAGGGTGGGTAGGGTGGTGGTTGTGG ATTGCCGAATTTCCCAGAGAGTTCC |
| 279 | AMX(449)_H8 | ATGCTTTTATACCTTCGGCGATACTGT CTAGGTTGGGTAGGGTGGTGTTTTAGG ATTGCCGAATTTCCCGAGAGTTCC |
| 280 | AMX(449)_H9 | ATGCTTTTATACCTTCGGCGGTACAGT CTAGGTTGGGTAGGGTGGTGGCTGTTG ATGGCCGAATTTCCCGAGAGTTCC |
| 281 | AMX(449)_H10 | ATGCTTTTATACCTTCGGCGGGTATTG CCTAGGTTGGGTAGGGTGGTGGCTCAG TCTTGCCGAATTTCCCGAGAGTTCC |
| 282 | AMX(449)_H11 | ATGCTTTTATACCTTCGGCGGCACGGT CTAGGATGGGTAGGGTGGTTGCTGATA ATCGCCGAATTTCCCGAGAGTTCC |

TABLE 12

Panel of minimized constructs designed with mutations resulting from the ARC2091 (SEQ ID NO 197) Doped Reselection

| SEQ ID NO | Clone Name | Sequence |
|---|---|---|
| 283 | ARC2169 | ACTGCCTAGGTTGGGTAGGGTGGTGGCAGT |
| 284 | ARC2169.1 | ACTGCCTAGGATGGGTAGGGTGGTGGCAGT |
| 285 | ARC2169.2 | ACTGCCTAGGGTGGGTAGGGTGGTGGCAGT |
| 286 | ARC2169.3 | ACTGCCTAGGTTGGGTAGTGTGGTGGCAGT |
| 287 | ARC2169.4 | ACTGCCTAGGTTGGGTAGGATGGTGGCAGT |
| 288 | ARC2169.5 | ACTGCCTAGGTTGGGTAGGGCGGTGGCAGT |
| 289 | ARC2169.6 | ACTGCATAGGTTGGGTAGGGTGGTTGCAGT |
| 290 | ARC2169.7 | ACTGCATAGGTTGGGTAGGGTGGTGGCAGT |
| 291 | ARC2169.8 | ACTGCATAGGTTGGGTAGGGTGGTGCAGT |

Figure 5:
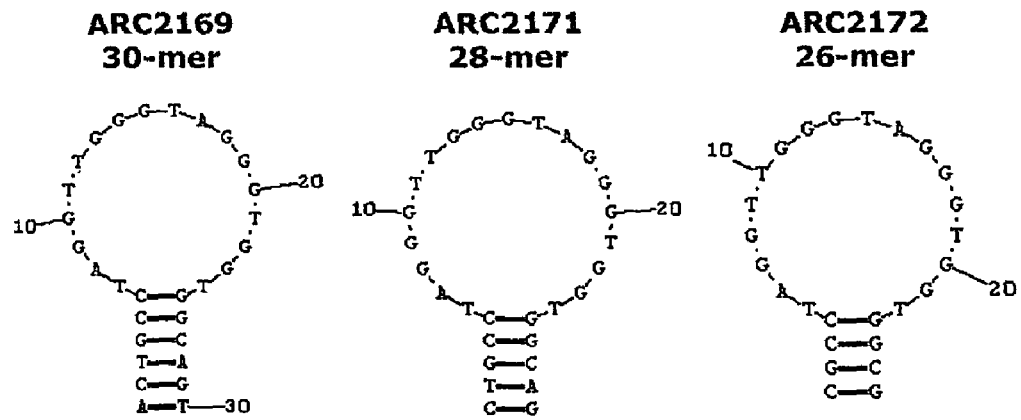
FIG. 5 depicts the predictive secondary structures for thrombin aptamers ARC2169 (SEQ ID NO 283), ARC2171 (SEQ ID NO 293) and ARC2172 (SEQ ID NO 294).

Using ARC2091 (SEQ ID NO 197) and the doped reselection data, further minimization of ARC2169 (SEQ ID NO 283) to a 26 nucleotide aptamer referred to as ARC2172 (SEQ ID NO 294)) was achieved without compromising binding affinity for Thrombin, as shown in Table 13 below. For the DNA aptamers described in Table 13 below, all the nucleotides (A, T, C and G) are deoxy. Putative secondary structures (using RNAstructure© (1996-2004) David H. Mathews, Michael Zuker & Douglas H. Turner) for ARC2169 (SEQ ID NO 283), ARC2171 (SEQ ID NO 293) and ARC2172 (SEQ ID NO 294) are shown in FIG. 5. Unless noted otherwise, the individual sequences are represented in the 5' to 3' orientation.

TABLE 13

Sequences and binding characterization of minimized constructs based on parent aptamer ARC2169 (SEQ ID NO 283)

| SEQ ID NO | Clone Name | Sequence | $K_D$ for Thrombin (nM) |
|---|---|---|---|
| 283 | ARC2169 | ACTGCCTAGGTTGGGTAGGGTGGTGGCAGT | 0.135 |
| 292 | ARC2170 | GCTGCCTAGGTTGGGTAGGGTGGTGGCAGC | 0.190 |
| 293 | ARC2171 | CTGCCTAGGTTGGGTAGGGTGGTGCAG | 0.221 |
| 294 | ARC2172 | CGCCTAGGTTGGGTAGGGTGGTGGCG | 0.140 |

Figure 6:
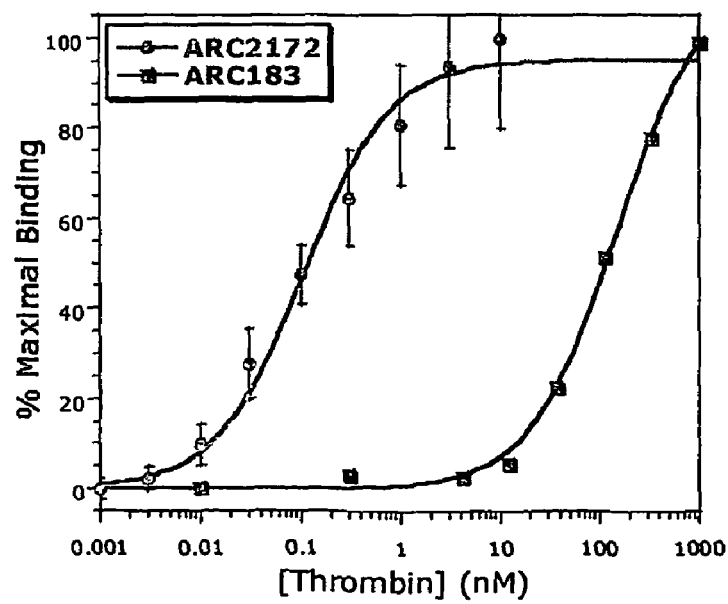
FIG. 6 is a graph depicting the binding curves for ARC2172 (SEQ ID NO 294) and ARC183 to human thrombin, as measured using a nitrocellulose filter binding assay.

The binding affinity of ARC2172 (SEQ ID NO 294) was compared to the previously identified thrombin binding DNA aptamer, ARC183, using the nitrocellulose filter binding assay previously described in Example 1A. As can be seen in FIG. 6, ARC2172 (SEQ ID NO 294) shows significantly improved affinity for thrombin relative to ARC183.

Figure 7:
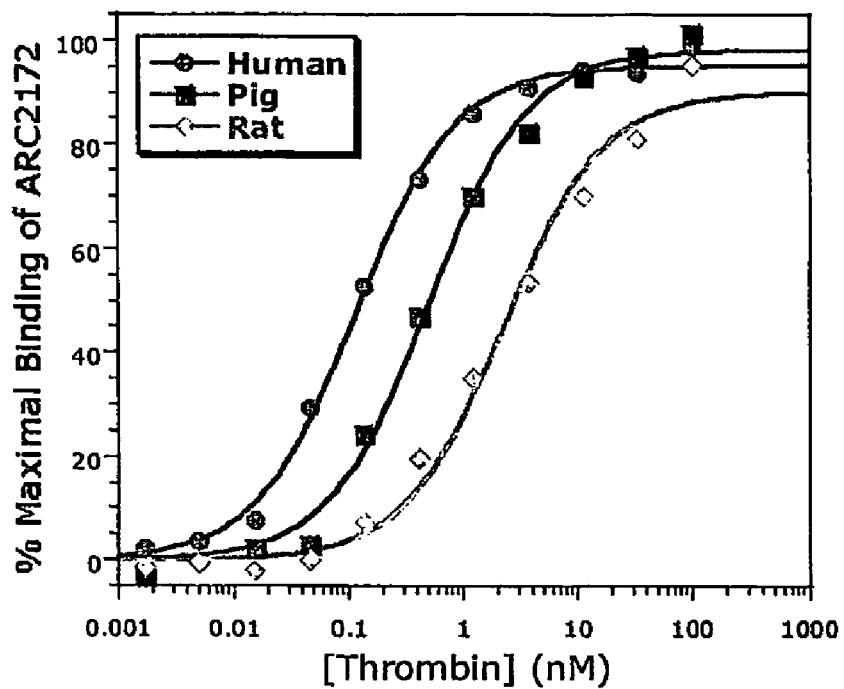
FIG. 7 is a graph depicting the binding curves for ARC2172 (SEQ ID NO 294) to human, pig and rat thrombin, as measured using a nitrocellulose filter binding assay.

ARC2172 (SEQ ID NO 294) was also tested for species cross-reactivity against human, pig, and rat thrombin (each from Enzyme Research Labs, South Bend, Ind.), using the nitrocellulose filter binding assay. As shown in FIG. 7, ARC2172 (SEQ ID NO 294) binds to pig and rat thrombin, in addition to human thrombin.

Example 2C

Optimization of Minimized Clones ARC1985 and ARC2169

A slight general downward trend was seen where aptamer function as measured by an ACT assay (see Example 3B) decreased as aptamers decreased in size upon minimization efforts. Thus, initial optimization efforts involved lengthening molecules by adding additional base pairs or poly-T tails to the putative stem structure. The following molecules whose sequences are listed below in Table 14 were based on either ARC1985 (SEQ ID NO 191) and ARC2169 (SEQ ID NO 283): ARC2173-ARC2184 were designed having additions of one to five additional base pairs; ARC2185-ARC2196 were designed having additions of either three or six "T" additions to either the 5' or 3' terminus; ARC2183 and ARC2184 are aptamers based on a previously selected anti-thrombin aptamers (ARC183) (SEQ ID NO 4) incorporating the stem elements of ARC1985 (for ARC2183) or ARC2169 (for ARC2184) onto ARC183 in an effort to determine any similarities between the previously selected thrombin aptamer, ARC183, and the present set of molecules. These optimized aptamers were tested for functionality using a single point screen (10 µM aptamer concentration) in the ACT assay described below in Example 3B.

For the DNA aptamers described in Table 14 below, all the nucleotides (A, T, C and G) are deoxy. Unless noted otherwise, the individual sequences are represented in the 5' to 3' orientation

TABLE 14

Sequences of Aptamers Generated During Phase 1 Optimization of ARC1985 and ARC2169 (SEQ ID NO 283)

| SEQ ID NO | Clone Name | Sequence |
|---|---|---|
| 295 | ARC2173 | ACCTCAGGGATGGTGTGGGTGGCTGAGGT |
| 296 | ARC2174 | TACCTCAGGGATGGTGTGGGTGGCTGAGGTA |
| 297 | ARC2175 | CTACCTCAGGGATGGTGTGGGTGGCTGAGGTAG |
| 298 | ARC2176 | ACTACCTCAGGGATGGTGTGGGTGGCTGAGGTAGT |
| 299 | ARC2177 | GACTACCTCAGGGATGGTGTGGGTGGCTGAGGTAGTC |
| 300 | ARC2178 | AACTGCCTAGGTTGGGTAGGGTGGTGGCAGTT |
| 301 | ARC2179 | TAACTGCCTAGGTTGGGTAGGGTGGTGGCAGTTA |
| 302 | ARC2180 | CTAACTGCCTAGGTTGGGTAGGGTGGTGGCAGTTAG |
| 303 | ARC2181 | ACTAACTGCCTAGGTTGGGTAGGGTGGTGGCAGTTAGT |
| 304 | ARC2182 | GACTAACTGCCTAGGTTGGGTAGGGTGGTGGCAGTTAGTC |
| 305 | ARC2183 | CCTCAGGGTTGGTGTGGTTGGCTGAGG |
| 306 | ARC2184 | ACTGCCTAGGTTGGTGTGGTTGGTGGCAGT |
| 307 | ARC2185 | CCTCAGGGATGGTGTGGGTGGCTGAGGTTT |
| 308 | ARC2186 | CCTCAGGGATGGTGTGGGTGGCTGAGGTTTTTT |
| 309 | ARC2187 | TTTCCTCAGGGATGGTGTGGGTGGCTGAGG |
| 310 | ARC2188 | TTTTTTCCTCAGGGATGGTGTGGGTGGCTGAGG |

TABLE 14-continued

Sequences of Aptamers Generated During Phase 1 Optimization of ARC1985 and ARC2169 (SEQ ID NO 283)

| SEQ ID NO | Clone Name | Sequence |
|---|---|---|
| 311 | ARC2189 | TTTCCTCAGGGATGGTGTGGGTGGCTGAGGTTT |
| 312 | ARC2190 | TTTTTTCCTCAGGGATGGTGTGGGTGGCTGAGGTTTTTT |
| 313 | ARC2191 | CTGCCTAGGTTGGGTAGGGTGGTGGCAGTTT |
| 314 | ARC2192 | CTGCCTAGGTTGGGTAGGGTGGTGGCAGTTTTTT |
| 315 | ARC2193 | TTTCTGCCTAGGTTGGGTAGGGTGGTGGCAG |
| 316 | ARC2194 | TTTTTTCTGCCTAGGTTGGGTAGGGTGGTGGCAG |
| 317 | ARC2195 | TTTCTGCCTAGGTTGGGTAGGGTGGTGGCAGTTT |
| 318 | ARC2196 | TTTTTTCTGCCTAGGTTGGGTAGGGTGGTGGCAGTTTTTT |

Further optimization employed ARC2169 (SEQ ID NO 283) as a base molecule, and a series of derivatives were synthesized at 1 µmole to replace every base individually with either a 2'-OMe or phosphorothioate base. All dG (deoxy guanosine) bases were individually substituted with a dI (deoxy inosine) or ml (2'-OMe) base. Each molecule was purified by PAGE gel and assayed for binding to Thrombin using the dot blot binding assay under the conditions previously described in Example 1. The sequences and binding characterization of these ARC2169 (SEQ ID NO 283) derivatives are listed in Table 15 below. Based on the binding data shown in Table 15, it was determined that no single substitution greatly increased binding to Thrombin.

For the aptamers described in Table 15 below, d denotes a deoxy nucleotide, "m" denotes 2'-OMe nucleotide, "I" denotes inosine, and "s" denotes a phosphorothioate internucleotide linkage. Unless noted otherwise, the individual sequences are represented in the 5' to 3' orientation.

TABLE 15

Sequences of Aptamers Generated During Further Optimization of ARC2169 (SEQ ID NO 283)

| SEQ ID NO | Clone Name | Sequence | $K_D$ (pM) |
|---|---|---|---|
| 319 | ARC2613 | mAdCTdGdCdCTdAdGdGTTdGdGdGTdAdGdGdGTdGdGTdGdGdCdAdGT | 173 |
| 320 | ARC2614 | dAmCTdGdCdCTdAdGdGTTdGdGdGTdAdGdGdGTdGdGTdGdGdCdAdGT | 52 |
| 321 | ARC2615 | dAdCmUdGdCdCTdAdGdGTTdGdGdGTdAdGdGdGTdGdGTdGdGdCdAdGT | 94 |
| 322 | ARC2616 | dAdCTmGdCdCTdAdGdGTTdGdGdGTdAdGdGdGTdGdGTdGdGdCdAdGT | 91 |
| 323 | ARC2617 | CAdCTdCmCdCTdAdGdGTTdGdGdGTdAdGdGdGTdGdGTdGdGdCdAdGT | 80 |
| 324 | ARC2618 | dAdCTdGdCmCTdAdGdGTTdGdGdGTdAdGdGdGTdGdGTdGdGdCdAdGT | 121 |
| 325 | ARC2619 | dAdCTdGdCdCmUdAdGdGTTdGdGdGTdAdGdGdGTdGdGTdGdGdCdAdGT | 215 |
| 326 | ARC2620 | dAdCTdGdCdCTmAdGdGTTdGdGdGTdAdGdGdGTdGdGTdGdGdCdAdGT | 7100 |
| 327 | ARC2621 | dAdCTdGdCdCTdAmGdGTTdGdGdGTdAdGdGdGTdGdGTdGdGdCdAdGT | 1519 |
| 328 | ARC2622 | dAdCTdGdCdCTdAdGmGTTdGdGdGTdAdGdGdGTdGdGTdGdGdCdAdGT | 38 |
| 329 | ARC2623 | dAdCTdGdCdCTdAdGdGmUTdGdGdGTdAdGdGdGTdGdGTdGdGdCdAdGT | 746 |
| 330 | ARC2624 | dAdCTdGdCdCTdAdGdGTmUdGdGdGTdAdGdGdGTdGdGTdGdGdCdAdGT | NB |
| 331 | ARC2625 | dAdCTdGdCdCTdAdGdGTTmGdGdGTdAdGdGdGTdGdGTdGdGdCdAdGT | 568 |
| 332 | ARC2626 | dAdCTdGdCdCTdAdGdGTTdGmGdGTdAdGdGdGTdGdGTdGdGdCdAdGT | 1587 |
| 333 | ARC2627 | dAdCTdGdCdCTdAdGdGTTdGdGmGTdAdGdGdGTdGdGTdGdGdCdAdGT | NB |
| 334 | ARC2628 | dAdCTdGdCdCTdAdGdGTTdGdGdGmUdAdGdGdGTdGdGTdGdGdCdAdGT | 207 |
| 335 | ARC2629 | dAdCTdGdCdCTdAdGdGTTdGdGdGTmAdGdGdGTdGdGTdGdGdCdAdGT | NB |
| 336 | ARC2630 | dAdCTdGdCdCTdAdGdGTTdGdGdGTdAmGdGdGTdGdGTdGdGdCdAdGT | 5244 |
| 337 | ARC2631 | dAdCTdGdCdCTdAdGdGTTdGdGdGTdAdGmGdGTdGdGTdGdGdCdAdGT | 4957 |
| 338 | ARC2632 | dAdCTdGdCdCTdAdGdGTTdGdGdGTdAdGdGmGTdGdGTdGdGdCdAdGT | NB |
| 339 | ARC2633 | dAdCTdGdCdCTdAdGdGTTdGdGdGTdAdGdGdGmUdGdGTdGdGdCdAdGT | NB |
| 340 | ARC2634 | dAdCTdGdCdCTdAdGdGTTdGdGdGTdAdGdGdGTmGdGTdGdGdCdAdGT | 549 |
| 341 | ARC2635 | dAdCTdGdCdCTdAdGdGTTdGdGdGTdAdGdGdGTdGmGTdGdGdCdAdGT | 248 |
| 342 | ARC2636 | dAdCTdGdCdCTdAdGdGTTdGdGdGTdAdGdGdGTdGdGmUdGdGdCdAdGT | 102 |
| 343 | ARC2637 | dAdCTdGdCdCTdAdGdGTTdGdGdGTdAdGdGdGTdGdGTmGdGdCdAdGT | 118 |
| 344 | ARC2638 | dAdCTdGdCdCTdAdGdGTTdGdGdGTdAdGdGdGTdGdGTdGmGdCdAdGT | 192 |
| 345 | ARC2639 | dAdCTdGdCdCTdAdGdGTTdGdGdGTdAdGdGdGTdGdGTdGdGmCdAdGT | 80 |
| 346 | ARC2640 | dAdCTdGdCdCTdAdGdGTTdGdGdGTdAdGdGdGTdGdGTdGdGdCmAdGT | 174 |
| 347 | ARC2641 | dAdCTdGdCdCTdAdGdGTTdGdGdGTdAdGdGdGTdGdGTdGdGdCdAmGT | 171 |
| 348 | ARC2642 | dAdCTdGdCdCTdAdGdGTTdGdGdGTdAdGdGdGTdGdGTdGdGdCdAdGmU | 94 |
| 349 | ARC2644 | dA-s-dCTdGdCdCTdAdGdGTTdGdGdGTdAdGdGdGTdGdGTdGdGdCdAdGT | 183 |
| 350 | ARC2645 | dAdC-s-TdGdCdCTdAdGdGTTdGdGdGTdAdGdGdGTdGdGTdGdGdCdAdGT | 167 |

TABLE 15-continued

Sequences of Aptamers Generated During Further Optimization of ARC2169 (SEQ ID NO 283)

| SEQ ID NO | Clone Name | Sequence | $K_D$ (pM) |
|---|---|---|---|
| 351 | ARC2646 | dAdCT-s-dGdCdCTdAdGdGTTdGdGdGdTdAdGdGdGTdGdGdTdGdGdGdCdAdGT | 169 |
| 352 | ARC2647 | dAdCTdG-s-dCdCTdAdGdGTTdGdGdGdTdAdGdGdGdTdGdGdTdGdGdGdCdAdGT | 161 |
| 353 | ARC2648 | dAdCTdGdC-s-dCTdAdGdGTTdGdGdGdTdAdGdGdGdTdGdGdTdGdGdGdCdAdGT | 128 |
| 354 | ARC2649 | dAdCTdGdCdC-s-TdAdGdGTTdGdGdGdTdAdGdGdGdTdGdGdTdGdGdGdCdAdGT | 264 |
| 355 | ARC2650 | dAdCTdGdCdCT-s-dAdGdGTTdGdGdGdTdAdGdGdGdTdGdGdTdGdGdGdCdAdGT | 230 |
| 356 | ARC2651 | dAdCTdGdCdCTdA-s-dGdGTTdGdGdGdTdAdGdGdGdTdGdGdTdGdGdGdCdAdGT | 111 |
| 357 | ARC2652 | dAdCTdGdCdCTdAdG-s-dGTTdGdGdGdTdAdGdGdGdTdGdGdTdGdGdGdCdAdGT | 192 |
| 358 | ARC2653 | dAdCTdGdCdCTdAdGdG-s-TTdGdGdGdTdAdGdGdGdTdGdGdTdGdGdGdCdAdGT | 66 |
| 359 | ARC2654 | dAdCTdGdCdCTdAdGdGT-s-TdGdGdGdTdAdGdGdGdTdGdGdTdGdGdGdCdAdGT | 95 |
| 360 | ARC2655 | dAdCTdGdCdCTdAdGdGTT-s-dGdGdGdTdAdGdGdGdTdGdGdTdGdGdGdCdAdGT | 79 |
| 361 | ARC2656 | dAdCTdGdCdCTdAdGdGTTdG-s-dGdGTdAdGdGdGdTdGdGdTdGdGdGdCdAdGT | 151 |
| 362 | ARC2657 | dAdCTdGdCdCTdAdGdGTTdGdG-s-dGTdAdGdGdGdTdGdGdTdGdGdGdCdAdGT | 219 |
| 363 | ARC2658 | dAdCTdGdCdCTdAdGdGTTdGdGdG-s-TdAdGdGdGdTdGdGdTdGdGdGdCdAdGT | 253 |
| 364 | ARC2659 | dAdCTdGdCdCTdAdGdGTTdGdGdGT-s-dAdGdGdGdTdGdGdTdGdGdGdCdAdGT | 452 |
| 365 | ARC2660 | dAdCTdGdCdCTdAdGdGTTdGdGdGdTdA-s-dGdGdGdTdGdGdTdGdGdGdCdAdGT | 230 |
| 366 | ARC2661 | dAdCTdGdCdCTdAdGdGTTdGdGdGdTdAdG-s-dGdGdTdGdGdTdGdGdGdCdAdGT | 246 |
| 367 | ARC2662 | dAdCTdGdCdCTdAdGdGTTdGdGdGdTdAdGdG-s-dGdTdGdGdTdGdGdGdCdAdGT | 165 |
| 368 | ARC2663 | dAdCTdGdCdCTdAdGdGTTdGdGdGdTdAdGdGdG-s-TdGdGdTdGdGdGdCdAdGT | 180 |
| 369 | ARC2664 | dAdCTdGdCdCTdAdGdGTTdGdGdGdTdAdGdGdGdT-s-dGdGdTdGdGdGdCdAdGT | 211 |
| 370 | ARC2665 | dAdCTdGdCdCTdAdGdGTTdGdGdGdTdAdGdGdGdTdG-s-dGdTdGdGdGdCdAdGT | 121 |
| 371 | ARC2666 | dAdCTdGdCdCTdAdGdGTTdGdGdGdTdAdGdGdGdTdGdG-s-TdGdGdGdCdAdGT | 992 |
| 372 | ARC2667 | dAdCTdGdCdCTdAdGdGTTdGdGdGdTdAdGdGdGdTdGdGdGT-s-dGdGdGdCdAdGT | 459 |
| 373 | ARC2668 | dAdCTdGdCdCTdAdGdGTTdGdGdGdTdAdGdGdGdTdGdGdTdG-s-dGdGdCdAdGT | 159 |
| 374 | ARC2669 | dAdCTdGdCdCTdAdGdGTTdGdGdGdTdAdGdGdGdTdGdGdTdGdGdG-s-dCdAdGT | 129 |
| 375 | ARC2670 | dAdCTdGdCdCTdAdGdGTTdGdGdGdTdAdGdGdGdTdGdGdTdGdGdGdC-s-dAdGT | 160 |
| 376 | ARC2671 | dAdCTdGdCdCTdAdGdGTTdGdGdGdTdAdGdGdGdTdGdGdTdGdGdGdCdA-s-dGT | 158 |
| 377 | ARC2672 | dAdCTdGdCdCTdAdGdGTTdGdGdGdTdAdGdGdGdTdGdGdTdGdGdGdCdAdG-s-T | 141 |
| 378 | ARC2673 | dAdCTdIdCdCTdAdGdGTTdGdGdGdTdAdGdGdGdTdGdGdTdGdGdGdCdAdGT | 207 |
| 379 | ARC2674 | dAdCTdGdCdCTdAdIdGTTdGdGdGdTdAdGdGdGdTdGdGdTdGdGdGdCdAdGT | 452 |
| 380 | ARC2675 | dAdCTdGdCdCTdAdGdITTdGdGdGdTdAdGdGdGdTdGdGdTdGdGdGdCdAdGT | 2030 |
| 381 | ARC2676 | dAdCTdGdCdCTdAdGdGTTdIdGdGdTdAdGdGdGdTdGdGdTdGdGdGdCdAdGT | 698 |
| 382 | ARC2677 | dAdCTdGdCdCTdAdGdGTTdGdGdIdTdAdGdGdGdTdGdGdTdGdGdGdCdAdGT | 199 |
| 383 | ARC2678 | dAdCTdGdCdCTdAdGdGTTdGdGdGdIdAdGdGdGdTdGdGdTdGdGdGdCdAdGT | 1430 |
| 384 | ARC2679 | dAdCTdGdCdCTdAdGdGTTdGdGdGdTdAdIdGdGdTdGdGdTdGdGdGdCdAdGT | 355 |
| 385 | ARC2680 | dAdCTdGdCdCTdAdGdGTTdGdGdGdTdAdGdIdGdTdGdGdTdGdGdGdCdAdGT | 240 |
| 386 | ARC2681 | dAdCTdGdCdCTdAdGdGTTdGdGdGdTdAdGdGdITdGdGdTdGdGdGdCdAdGT | 334 |
| 387 | ARC2682 | dAdCTdGdCdCTdAdGdGTTdGdGdGdTdAdGdGdGdTdIdGdTdGdGdGdCdAdGT | 1298 |
| 388 | ARC2683 | dAdCTdGdCdCTdAdGdGTTdGdGdGdTdAdGdGdGdTdGdIdTdGdGdGdCdAdGT | 151 |
| 389 | ARC2684 | dAdCTdGdCdCTdAdGdGTTdGdGdGdTdAdGdGdGdTdGdGdTdIdGdGdCdAdGT | 188 |
| 390 | ARC2685 | dAdCTdGdCdCTdAdGdGTTdGdGdGdTdAdGdGdGdTdGdGdTdGdIdCdAdGT | 226 |
| 391 | ARC2686 | dAdCTdGdCdCTdAdGdGTTdGdGdGdTdAdGdGdGdTdGdGdTdGdGdGdCdAdIT | 189 |
| 392 | ARC2687 | dAdCTmIdCdCTdAdGdGTTdGdGdGdTdAdGdGdGdTdGdGdTdGdGdGdCdAdGT | 220 |
| 393 | ARC2688 | dAdCTdGdCdCTdAdmIdGTTdGdGdGdTdAdGdGdGdTdGdGdTdGdGdGdCdAdGT | NB |
| 394 | ARC2689 | dAdCTdGdCdCTdAdGdmITTdGdGdGdTdAdGdGdGdTdGdGdTdGdGdGdCdAdGT | NB |
| 395 | ARC2690 | dAdCTdGdCdCTdAdGdGTTmIdGdGdTdAdGdGdGdTdGdGdTdGdGdGdCdAdGT | NB |
| 396 | ARC2691 | dAdCTdGdCdCTdAdGdGTTdGdmIdGdTdAdGdGdGdTdGdGdTdGdGdGdCdAdGT | 2279 |
| 397 | ARC2692 | dAdCTdGdCdCTdAdGdGTTdGdGdmITdAdGdGdGdTdGdGdTdGdGdGdCdAdGT | 1840 |
| 398 | ARC2693 | dAdCTdGdCdCTdAdGdGTTdGdGdGdTdAmIdGdGdTdGdGdTdGdGdGdCdAdGT | NB |
| 399 | ARC2694 | dAdCTdGdCdCTdAdGdGTTdGdGdGdTdAdGmIdGdTdGdGdTdGdGdGdCdAdGT | NB |
| 400 | ARC2695 | dAdCTdGdCdCTdAdGdGTTdGdGdGdTdAdGdGdmITdGdGdTdGdGdGdCdAdGT | 2084 |

TABLE 15-continued

Sequences of Aptamers Generated During Further Optimization of ARC2169 (SEQ ID NO 283)

| SEQ ID NO | Clone Name | Sequence | $K_D$ (pM) |
|---|---|---|---|
| 401 | ARC2696 | dAdCTdGdCdCTdAdGdGTTdGdGdGTd AdGdGdGTmIdGTdGdGdCdAdGT | NB |
| 402 | ARC2697 | dAdCTdGdCdCTdAdGdGTTdGdGdGTd AdGdGdGTdGmITdGdGdCdAdGT | 1558 |
| 403 | ARC2698 | dAdCTdGdCdCTdAdGdGTTdGdGdGTd AdGdGdGTdGdGTmIdGdCdAdGT | 165 |
| 404 | ARC2699 | dAdCTdGdCdCTdAdGdGTTdGdGdGTd AdGdGdGTdGdGTdGmIdCdAdGT | 128 |
| 405 | ARC2700 | dAdCTdGdCdCTdAdGdGTTdGdGdGTd AdGdGdGTdGdGTdGdGdCdAmIT | 46 |

*NB = Non binder

Example 2D

Phase 2 of ARC2169, ARC2170, ARC2171 and ARC2172

An additional phase of optimization was performed primarily to modulate the duration of the activity of the lead aptamers in vivo (since a rapid on/rapid off profile is desired for this compound). Toward that end, a series of constructs were designed with tolerated 2'-OMe bases in the stem regions. Stems were also altered to turn some G-C base pairs into A-T base pairs to weaken the base pairing and possibly reduce the stability of the molecule and allow quicker degradation. Mutations in the form of 2'-OMe substitutions and G-C to A-T base pairs are outlined below using ARC2169 (SEQ ID NO 283), ARC2170 (SEQ ID NO 292), ARC2171 (SEQ ID NO 293), and ARC2172 (SEQ ID NO 294) as parent molecules. Each aptamer was synthesized at 1 µmole synthesis scale and PAGE purified before being assayed for binding to Thrombin by the dot blot assay previously described in Example 1.

The sequences and binding characterization for this series of optimized constructs are listed below in Table 16. For the aptamers described in Table 16 below, "d" denotes a deoxynucleotide, and "m" denotes 2'-OMe nucleotide. Unless noted otherwise, the individual sequences are represented in the 5' to 3' orientation.

TABLE 16

Sequences and Binding Characterization of Optimized ARC2169, ARC2170, ARC2171, ARC2172

| SEQ ID NO | Clone Name | Sequence | $K_D$ (nM) |
|---|---|---|---|
| 406 | ARC2823 | mAmCmUmGmCmCmUdAdGdGTTdGdGdGT dAdGdGdGTdGdGmUmGdGmCmAmGmU | 9.10 |
| 407 | ARC2824 | mAmCmUmGmCmCTdAdGdGTTdGdGdGTd AdGdGdGTdGdGTmGdGmCmAmGmU | 0.73 |
| 408 | ARC2825 | mAmCmUmGmCdCTdAdGdGTTdGdGdGTd AdGdGdGTdGdGTdGdGmCmAmGmU | 1.03 |
| 409 | ARC2826 | dAdATdGdATTdAdGdGTTdGdGdGTdAd GdGdGTdGdGTdATdCdATT | 0.77 |
| 410 | ARC2827 | mAmAmUmGmAmUmUdAdGdGTTdGdGdGT dAdGdGdGTdGdGmUmAmUmCmAmUmU | 4.06 |
| 411 | ARC2828 | mAmAmUmGmAmUTdAdGdGTTdGdGdGTd AdGdGdGTdGdGTmAmUmCmAmUmU | 0.33 |
| 412 | ARC2829 | mAmAmUmGmATTdAdGdGTTdGdGdGTdA dGdGdGTdGdGTdAmUmCmAmUmU | 0.93 |
| 413 | ARC2830 | mCmUmGmCmCmUdAdGdGTTdGdGdGTdA dGdGdGTdGdGmUmGdGmCmAmG | 15.35 |
| 414 | ARC2831 | mCmUmGmCmCTdAdGdGTTdGdGdGTdAd GdGdGTdGdGTmGdGmCmAmG | 5.12 |
| 415 | ARC2832 | mCmUmGmCdCTdAdGdGTTdGdGdGTdAd GdGdGTdGdGTdGdGmCmAmG | 1.88 |
| 416 | ARC2833 | dATdGdATTdAdGdGTTdGdGdGTdAdGd GdGTdGdGTdATdCdAT | 2.16 |
| 417 | ARC2834 | mAmUmGmAmUmUdAdGdGTTdGdGdGTdA dGdGdGTdGdGmUmAmUmCmAmU | 10.31 |
| 418 | ARC2835 | mAmUmGmAmUTdAdGdGTTdGdGdGTdAd GdGdGTdGdGTmAmUmCmAmU | 1.27 |
| 419 | ARC2836 | mAmUmGmATTdAdGdGTTdGdGdGTdAdG dGdGTdGdGTdAmUmCmAmU | 0.96 |
| 420 | ARC2837 | mUmGmCmCmUdAdGdGTTdGdGdGTdAdG dGdGTdGdGmUmGdGmCmA | 2.61 |
| 421 | ARC2838 | mUmGmCmCTdAdGdGTTdGdGdGTdAdGd GdGTdGdGTmGdGmCmA | 0.77 |
| 422 | ARC2839 | mUmGmCdCTdAdGdGTTdGdGdGTdAdGd GdGTdGdGTdGdGmCmA | 0.58 |
| 423 | ARC2840 | TdGdATTdAdGdGTTdGdGdGTdAdGdGd GTdGdGTdATdCdA | 0.25 |
| 424 | ARC2841 | mUmGmAmUmUdAdGdGTTdGdGdGTdAdG dGdGTdGdGmUmAmUmCmA | 3.55 |
| 425 | ARC2842 | mUmGmAmUTdAdGdGTTdGdGdGTdAdGd GdGTdGdGTmAmUmCmA | 1.06 |
| 426 | ARC2843 | mUmGmATTdAdGdGTTdGdGdGTdAdGdG dGTdGdGTdAmUmCmA | 0.62 |
| 427 | ARC2844 | mGmCmCmUdAdGdGTTdGdGdGTdAdGdG dGTdGdGmUmGdGmC | 2.65 |
| 428 | ARC2845 | mGmCmCTdAdGdGTTdGdGdGTdAdGdGd GTdGdGTmGdGmC | 0.86 |
| 429 | ARC2846 | mGmCdCTdAdGdGTTdGdGdGTdAdGdGd GTdGdGTdGdGmC | 0.27 |
| 430 | ARC2847 | dGdATTdAdGdGTTdGdGdGTdAdGdGdG TdGdGTdATdC | 0.21 |
| 431 | ARC2848 | mGmAmUmUdAdGdGTTdGdGdGTdAdGdG dGTdGdGmUmAmUmC | 2.09 |
| 432 | ARC2849 | mGmAmUTdAdGdGTTdGdGdGTdAdGdGd GTdGdGTmAmUmC | 0.20 |
| 433 | ARC2850 | mGmATTdAdGdGTTdGdGdGTdAdGdGdG TdGdGTdAmUmC | 0.33 |

TABLE 16-continued

Sequences and Binding Characterization of
Optimized ARC2169, ARC2170, ARC2171, ARC2172

| SEQ ID NO | Clone Name | Sequence | $K_D$ (nM) |
|---|---|---|---|
| 434 | ARC2949 | mCmGdCTdAdGdGTTdGdGdGTdAdGdGd GTdGdGTdGmCmG | NB |

*Nd = Not determined

Example 2E

Synthesis of Aptamer-5'-PEG Conjugates

Based upon the preliminary results from the first optimization efforts described above using stem lengthening, small 5'-PEG conjugates of the anti-thrombin aptamers ARC2169 (SEQ ID NO 283) and ARC2172 (SEQ ID NO 294) were prepared. The concept was that small PEGs might improve aptamer potency without significantly extending the duration of functional activity in vivo (since a rapid on/rapid off profile is desired for this compound). Aptamers were prepared by first synthesizing 5'-amine modified versions of the aptamers to facilitate chemical coupling 5'NH2-dAdCTdGdCd-CTdAdGdGTrdGdGdGTdAdGdGdGTdOdGTdGdGdCd-AdGT3' (ARC2321, SEQ ID NO 435) and 5'NH2-dCdGd-CdCTdAdGdGTTdGdGdGTdAdGdGdGTdGdGTdGdGd-CdG 3'(ARC2324, SEQ ID NO 436) were synthesized on an AKTA OligoPilot 100 synthesizer (GE Healthcare, Uppsala, Sweden) according to the recommended manufacturer's procedures using standard commercially available DNA phosphoramidites (ChemGenes Corp. Wilmington, Mass.) and a support as indicated as follows: for ARC2327 (SEQ ID NO 439) and 2338 (SEQ ID NO 438) Primer Support 200 dG (CAT# 17-5262-02, GE Healthcare, Uppsala, Sweden); for ARC2329 (SEQ ID NO 440) a iBu DMT Deoxyguanosine CPG support (CAT# CPG60N11DGVN, Prime Synthesis, Aston, Pa.) and for ARC2323 (SEQ ID NO 437) a DMT Deoxythymidine CPG support (CAT# CPG60N11DTN, Prime Synthesis, Aston, Pa.)

Terminal amine functions were attached with a 5'-aminomodifier TFA Amino C-6 CED Phosporamidite (ChemGenes Corp. Wilmington, Mass.). After deprotection, the oligonucleotide was purified by ion exchange chromatography on Super Q 5PW (30) resin (Tosoh Biosciences, Montgomeryville, Pa.) and ethanol precipitated.

Aliquots of the 5'-amine-modified aptamers were conjugated to PEG moieties post-synthetically (e.g., 2, 5 and 10 kDa PEG moieties). Aptamers were dissolved in a water/DMSO (1:1) solution to a concentration between 1.5 and 3 mM. Sodium carbonate buffer, pH 8.5, was added to a final concentration of 100 mM and the oligo was reacted overnight with a 1.7-3 fold molar excess of the desired PEG reagent (10 kDa Sunbright GL2400NP p-nitrophenyl carbonate ester (NOF Corp, Japan]) dissolved in an equal volume of acetonitrile. The resulting PEGylated products were purified by ion exchange chromatography on Super Q 5PW (30) resin (Tosoh Biosciences, Montgomeryville, Pa.), and desalted using reverse phase chromatography performed on Amberchrom CG300-S resin (Rohm and Haas, Philadelphia, Pa.), and lyophilized.

The resulting PEGylated aptamer sequences are listed below. These aptamers, along with their 5' amine counterparts were tested in the ACT assay at varying concentrations of aptamer in human whole blood (see Example 3B).

For each sequence listed below, lower case letter "d" denotes a deoxy nucleotide (note, all nucleotides in the sequences listed below are deoxy including "T" which is represented as "T" not as "dT"), and "NH" denotes a hexyl amine to facilitate chemical coupling.

ARC2323 (SEQ ID NO 437) (ARC2169 + 5'-amine + 10 kDa PEG)

PEG10K-nh-dAdCTdGdCdCTdAdGdGTTdGdGdGTdAdGdGdGTdGdG
TdGdGdCdAdGT

Which comprises the following structure:

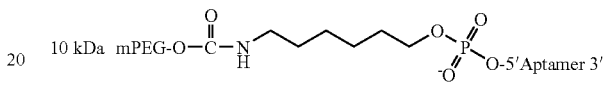

Where aptamer = dAdCTdGdCdCTdAdGdGTTdGdGdGTdAdGdGd
GTdGdGTdGdGdCdAdGT

ARC2338 (SEQ ID NO 438) (ARC2172 + 5'-amine + 2 kDa PEG)

PEG2K-nh-dCdGdCdCTdAdGdGTTdGdGdGTdAdGdGdGTdGdGTdGd
GdCdG

Which comprises the following structure:

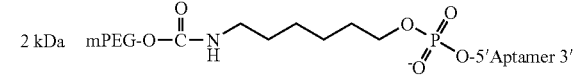

Where aptamer = dCdGdCdCTdAdGdGTTdGdGdGTdAdGdGdGTd
GdGTdGdGdCdG

ARC2327 (SEQ ID NO 439) (ARC2172 + 5'-amine + 5 kDa PEG)

PEG5K-nh-dCdGdCdCTdAdGdGTTdGdGdGTdAdGdGdGTdGdGTdGd
GdCdG

Which comprises the following structure:

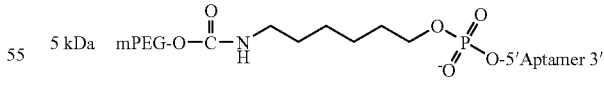

Where aptamer = dCdGdCdCTdAdGdGTTdGdGdGTdAdGdGdGTd
GdGTdGdGdCdG

ARC2329 (SEQ ID NO 440) (ARC2172 + 5'-amine + 10 kDa PEG)

PEG10K-nh-dCdGdCdCTdAdGdGTTdGdGdGTdAdGdGdGTdGdGTdG
dGdCdG

Which comprises the following structure

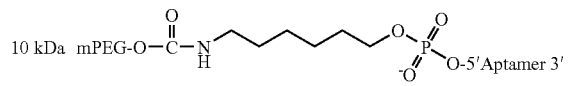

Where aptamer = dCdGdCdCTdAdGdGTTdGdGdGTdAdGdGdGTd
GdGTdGdGdCdG

Example 3

In Vitro Functional Assays

Example 3A

Prothrombin Assay

Tissue factor is a strong inducer of the "extrinsic" pathway of coagulation that is released at the site of injury. Prothrombin time ("PT") measures the time to clot upon the addition of excess tissue factor to plasma, and is most sensitive to the levels of extrinsic pathway factor VII and "common" pathway factors I (fibrinogen), II (prothrombin), V and X. The PT reagent, termed thromboplastin, consists of tissue factor mixed with phospholipids and calcium, which are necessary cofactors for the activation of several coagulation factors. Aside from diagnosis of factor deficiencies, clinical PT is most commonly used to monitor the oral anticoagulant warfarin, a vitamin K antagonist. The PT is not used for clinical monitoring of heparin, but it is sensitive to the high heparin concentrations used for CABG, which range up to 5 U/mL (e.g., the PT time at 1 U/mL heparin is 142% of the normal control; data not shown).

The PT assay utilizes a Coag-a-mate coagulation analyzer (Biomerieux, Durham, N.C.), lyophilized thromboplastin (Fisher Scientific), citrated human plasma (Innovative Research, Southfield, Mich.), and a known concentration of aptamer. The known concentration of aptamer was pre-incubated at 37° C. for 3 minutes with citrated plasma in a test tray (Biomerieux, Durham, N.C.). Clotting was then initiated with 200 µl of the thromboplastin-D Pacific Hemostasis, Fisher Diagnostics, Middletown, Va.) (resuspended from lyophilized form in 10 mLs of ddH$_2$O) and clot time was determined analyzing the test sample on the Coag-a-mate. Samples were taken in duplicate and averaged for a single PT time. A clot time of ~13 seconds was measured in the absence of any inhibitor/aptamer, which is within the clinical "normal" control range of 12-14 seconds. A value of 300 seconds is the maximum value measured by the instrument.

Aptamers identified from Round 9 of thrombin DNA Selection #1 (see Example 1A) were screened for the ability to decrease or inhibit thrombin activity using the PT assay described. PT values were measured in the presence of 3 or 10 micromolar aptamer by the addition of rabbit thromboplastin (Pacific Hemostasis, Pisher Diagnostics, Middletown, Va.) to citrated human plasma, using the Coag-A-Mate (Biomerieux, Durham, N.C.) for the optical detection of formation of fibrin polymers. The PT values for 10 uM of thrombin binding aptamers identified from Round 9 of DNA Selection #1 are listed in Table 17 below. Note that background values were not subtracted from the PT values listed in Table 17.

TABLE 17

PT values for Thrombin Aptamers-Round 9 DNA selection #1

| SEQ ID NO | Clone Name | PT (sec) at 10 uM aptamer |
|---|---|---|
| 9 | AMX(453)_A6 | 12.8 |
| 10 | AMX(453)_A9 | 29.3 |
| 11 | AMX(453)_B6 | 300.0 |
| 12 | AMX(453)_B8 | 11.9 |
| 13 | AMX(453)_B10 | 24.8 |
| 14 | AMX(453)_B12 | 12.8 |
| 15 | AMX(453)_C10 | 104.3 |
| 16 | AMX(453)_D12 | 12.7 |
| 17 | AMX(453)_E4 | 15.9 |
| 18 | AMX(453)_38 | 13.1 |
| 19 | AMX(453)_E10 | 11.8 |
| 20 | AMX(453)_E12 | 12.2 |
| 21 | AMX(453)_F6 | 300.0 |
| 22 | AMX(453)_F7 | 28.6 |
| 23 | AMX(453)_F11 | 65.8 |
| 24 | AMX(453)_G5 | 29.3 |
| 25 | AMX(453)_G11 | 12.2 |
| 26 | AMX(453)_H11 | 15.6 |
| 27 | AMX(454)_B7 | 12.2 |
| 28 | AMX(454)_B9 | 32.0 |
| 29 | AMX(454)_B12 | 21.9 |
| 30 | AMX(454)_D5 | 13.0 |
| 31 | AMX(454)_D6 | 11.4 |
| 32 | AMX(454)_D11 | 43.4 |
| 33 | AMX(454)_D12 | 12.0 |
| 34 | AMX(454)_F2 | 300.0 |
| 35 | AMX(454)_F7 | 12.7 |
| 36 | AMX(454)_F9 | 25.0 |
| 37 | AMX(454)_G2 | 15.6 |
| 38 | AMX(454)_G6 | 12.5 |
| 39 | AMX(454)_H3 | 35.4 |
| 40 | AMX(454)_H6 | 11.5 |
| 41 | AMX(454)_H7 | 12.1 |

Minimized constructs of thrombin binding aptamers identified during Round 7 of DNA Selections #2 and #3 (see Example 2A) were also screened for their ability to decrease or inhibit thrombin activity using 10 µM aptamer in the PT assay described above. The PT values (including background) for the minimized construct ARC1985 is shown below in Table 18.

TABLE 18

PT values for Minimized thrombin aptamer from Round 7, DNA Selection #2

| SEQ ID NO | Clone Name | PT (sec) at 10 uM aptamer |
|---|---|---|
| 191 | ARC1985 | 78 |

Selected thrombin binding aptamers identified during Round 9 of DNA Selections #2 and #3 (see Example 2A) that displayed high binding affinity for thrombin were also screened for their ability to decrease or inhibit thrombin activity using 10 μM aptamer in the PT assay described above. The results are shown in Table 19 below. Note that "N/A" in Table 19 below indicates PT values were not measured.

TABLE 19

PT values (including background) for thrombin aptamers from Round 9, DNA selection #2 and #3

| SEQ ID NO | Clone Name | PT (sec) at 10 uM aptamer |
|---|---|---|
| 63 | AMX(398)_A1 | N/A |
| 64 | AMX(398)_A2 | N/A |
| 65 | AMX(398)_A4 | 11.0 |
| 66 | AMX(398)_A6 | N/A |
| 67 | AMX(398)_A7 | N/A |
| 68 | AMX(398)_A8 | 11.2 |
| 69 | AMX(398)_A9 | N/A |
| 70 | AMX(398)_A12 | 12.0 |
| 71 | AMX(398)_B1 | N/A |
| 72 | AMX(398)_B2 | 11.0 |
| 73 | AMX(398)_B3 | N/A |
| 74 | AMX(398)_B5 | N/A |
| 75 | AMX(398)_B9 | N/A |
| 76 | AMX(398)_B10 | N/A |
| 77 | AMX(398)_B11 | N/A |
| 78 | AMX(398)_B12 | N/A |
| 79 | AMX(398)_C1 | 11.4 |
| 80 | AMX(398)_C2 | N/A |
| 81 | AMX(398)_C3 | N/A |
| 82 | AMX(398)_C5 | 64.7 |
| 83 | AMX(398)_C6 | N/A |
| 84 | AMX(398)_C8 | 300.0 |
| 85 | AMX(398)_C9 | N/A |
| 86 | AMX(398)_C10 | 58.8 |
| 87 | AMX(398)_C11 | 11.3 |
| 88 | AMX(398)_C12 | N/A |
| 89 | AMX(398)_D1 | N/A |
| 90 | AMX(398)_D3 | N/A |
| 91 | AMX(398)_D5 | N/A |
| 92 | AMX(398)_D6 | 300.0 |
| 93 | AMX(398)_D7 | 11.4 |
| 94 | AMX(398)_D9 | 80.8 |
| 95 | AMX(398)_E1 | N/A |
| 96 | AMX(398)_E2 | N/A |
| 97 | AMX(398)_E3 | 11.1 |
| 98 | AMX(398)_E5 | N/A |
| 99 | AMX(398)_E6 | N/A |
| 100 | AMX(398)_E7 | N/A |
| 101 | AMX(398)_E8 | N/A |
| 102 | AMX(398)_E11 | N/A |
| 103 | AMX(398)_E12 | 10.7 |
| 104 | AMX(398)_F2 | N/A |
| 105 | AMX(398)_F5 | N/A |
| 106 | AMX(398)_F6 | N/A |
| 107 | AMX(398)_F8 | N/A |
| 108 | AMX(398)_F9 | N/A |
| 109 | AMX(398)_F12 | 10.8 |
| 110 | AMX(398)_G2 | N/A |
| 111 | AMX(398)_G6 | 10.7 |
| 112 | AMX(398)_G7 | N/A |
| 113 | AMX(398)_G8 | N/A |
| 114 | AMX(398)_G11 | N/A |
| 115 | AMX(398)_H1 | N/A |
| 116 | AMX(398)_H5 | 71.0 |
| 117 | AMX(398)_H6 | 11.0 |
| 118 | AMX(398)_H7 | N/A |
| 119 | AMX(398)_H8 | N/A |
| 120 | AMX(398)_H10 | N/A |
| 121 | AMX(399)_A2 | 11.3 |
| 122 | AMX(399)_A3 | N/A |
| 123 | AMX(399)_A5 | N/A |

TABLE 19-continued

PT values (including background) for thrombin aptamers from Round 9, DNA selection #2 and #3

| SEQ ID NO | Clone Name | PT (sec) at 10 uM aptamer |
|---|---|---|
| 124 | AMX(399)_A6 | N/A |
| 125 | AMX(399)_A7 | N/A |
| 126 | AMX(399)_A10 | N/A |
| 127 | AMX(399)_A11 | N/A |
| 128 | AMX(399)_A12 | N/A |
| 129 | AMX(399)_B2 | N/A |
| 130 | AMX(399)_B3 | 10.9 |
| 131 | AMX(399)_B6 | N/A |
| 132 | AMX(399)_B8 | N/A |
| 133 | AMX(399)_B9 | N/A |
| 134 | AMX(399)_B10 | N/A |
| 135 | AMX(399)_B11 | N/A |
| 136 | AMX(399)_B12 | N/A |
| 137 | AMX(399)_C7 | N/A |
| 138 | AMX(399)_C9 | 10.7 |
| 139 | AMX(399)_C9 | N/A |
| 140 | AMX(399)_C10 | 10.9 |
| 141 | AMX(399)_C11 | 52.6 |
| 142 | AMX(399)_C12 | N/A |
| 143 | AMX(399)_D2 | 12.5 |
| 144 | AMX(399)_D3 | N/A |
| 145 | AMX(399)_D4 | N/A |
| 146 | AMX(399)_D5 | 10.5 |
| 147 | AMX(399)_D6 | N/A |
| 148 | AMX(399)_D7 | N/A |
| 149 | AMX(399)_D8 | N/A |
| 150 | AMX(399)_D9 | N/A |
| 151 | AMX(399)_D10 | 10.7 |
| 152 | AMX(399)_D11 | 13.2 |
| 153 | AMX(399)_D12 | N/A |
| 154 | AMX(399)_E1 | 10.8 |
| 155 | AMX(399)_E3 | N/A |
| 156 | AMX(399)_E4 | N/A |
| 157 | AMX(399)_E5 | N/A |
| 158 | AMX(399)_E8 | N/A |
| 159 | AMX(399)_E9 | N/A |
| 160 | AMX(399)_E10 | N/A |
| 161 | AMX(399)_E12 | N/A |
| 162 | AMX(399)_F1 | N/A |
| 163 | AMX(399)_F2 | N/A |
| 164 | AMX(399)_F3 | N/A |
| 165 | AMX(399)_F4 | N/A |
| 166 | AMX(399)_F5 | 11.0 |
| 167 | AMX(399)_F6 | N/A |
| 168 | AMX(399)_F7 | N/A |
| 169 | AMX(399)_F9 | N/A |
| 170 | AMX(399)_F10 | N/A |
| 171 | AMX(399)_F11 | 11.2 |
| 172 | AMX(399)_F12 | 74.9 |
| 173 | AMX(399)_G1 | N/A |
| 174 | AMX(399)_G2 | N/A |
| 175 | AMX(399)_G3 | N/A |
| 176 | AMX(399)_G5 | N/A |
| 177 | AMX(399)_G6 | 11.1 |
| 178 | AMX(399)_G8 | N/A |
| 179 | AMX(399)_G9 | N/A |
| 180 | AMX(399)_G10 | 18.8 |
| 181 | AMX(399)_G11 | N/A |
| 182 | AMX(399)_G12 | 13.4 |
| 183 | AMX(399)_H1 | N/A |
| 184 | AMX(399)_H2 | N/A |
| 185 | AMX(399)_H3 | 10.9 |
| 186 | AMX(399)_H4 | N/A |
| 187 | AMX(399)_H6 | N/A |
| 188 | AMX(399)_H7 | 10.9 |
| 189 | AMX(399)_H8 | N/A |
| 190 | AMX(399)_H9 | N/A |

Minimized constructs of highly thrombin specific aptamers identified during Round 9 of DNA Selections #2 and #3 (see Example 2A) were also screened for their ability to decrease or inhibit thrombin using 10 μM aptamer in the PT assay described above. A comparison of the PT values (including background) for these minimized aptamers relative to the parent aptamer from which the minimized constructs were derived are listed below in Table 20.

TABLE 20

Round 9 DNA SELEX #2 and #3: PT Values of Minimized aptamers compared to respective parent aptamers in PT assay

| SEQ ID NO of Minimized Aptamer | Minimized Aptamer Name | Parent Aptamer (SEQ ID NO) | PT (sec) at 10 uM Minimized aptamer | PT (sec) at 10 uM Parent aptamer |
|---|---|---|---|---|
| 193 | Minimer 1 | AMX(399)_B3 (SEQ ID NO 130) | 11.5 | 10.9 |
| 194 | Minimer 2 | AMX(398)_A4 (SEQ ID NO 65) | 12.2 | 11.0 |
| 195 | Minimer 3 | AMX(398)_D6 (ARC2026) SEQ ID NO 92 | 25.8 | 300.0 |
| 196 | Minimer 4 | AMX(398)_D6 (ARC2026) SEQ ID NO 92 | 11.4 | 300.0 |
| 197 | Minimer | AMX(398)_D6 (ARC2026) SEQ ID NO 92 | 300.0 | 300.0 |
| 198 | Minimer 6 | AMX(398)_D6 (ARC2026) SEQ ID NO 92 | 12.2 | 300.0 |
| 199 | Minimer 12 | AMX(398)_D6 (ARC2026) SEQ ID NO 92 | 10.3 | 300.0 |
| 200 | Minimer 7 | AMX(398)_C8 (SEQ ID NO 84) | 83.3 | 300.0 |
| 201 | Minimer 8 | AMX(398)_C8 (ARC2027) (ARC2027) | 10.1 | 300.0 |
| 202 | Minimer 9 | AMX(398)_C8 (ARC2027) SEQ ID NO 84 | 10.6 | 300.0 |
| 203 | Minimer 10 | AMX(398)_C8 (ARC2027) SEQ ID NO 84 | 11.0 | 300.0 |
| 204 | Minimer 11 | AMX(398)_C8 (ARC2027) SEQ ID NO 84 | 27.9 | 300.0 |

Minimized constructs designed based on the Doped Re-selection described in Example 2B were also screened for their ability to decrease or inhibit thrombin activity in the PT assay described above. The results are shown below in Table 21.

TABLE 21

PT values (including background) for Minimized thrombin aptamers from ARC2091 (SEQ ID NO 197) Doped Re-selection

| SEQ ID NO | Clone Name | PT (sec) at 10 uM aptamer |
|---|---|---|
| 283 | ARC2169 | 300 |
| 284 | ARC2169.1 | 300 |
| 285 | ARC2169.2 | 300 |
| 286 | ARC2169.3 | 11 |
| 287 | ARC2169.4 | 53.8 |
| 288 | ARC2169.5 | 12.8 |
| 289 | ARC2169.6 | 300 |
| 290 | ARC2169.7 | 300 |
| 291 | ARC2169.8 | 28.7 |
| 292 | ARC2170 | 300 |

TABLE 21-continued

PT values (including background) for Minimized
thrombin aptamers from ARC2091 (SEQ ID NO 197)
Doped Re-selection

| SEQ ID NO | Clone Name | PT (sec) at 10 uM aptamer |
|---|---|---|
| 293 | ARC2171 | 300 |
| 294 | ARC2172 | 300 |

Figure 8:
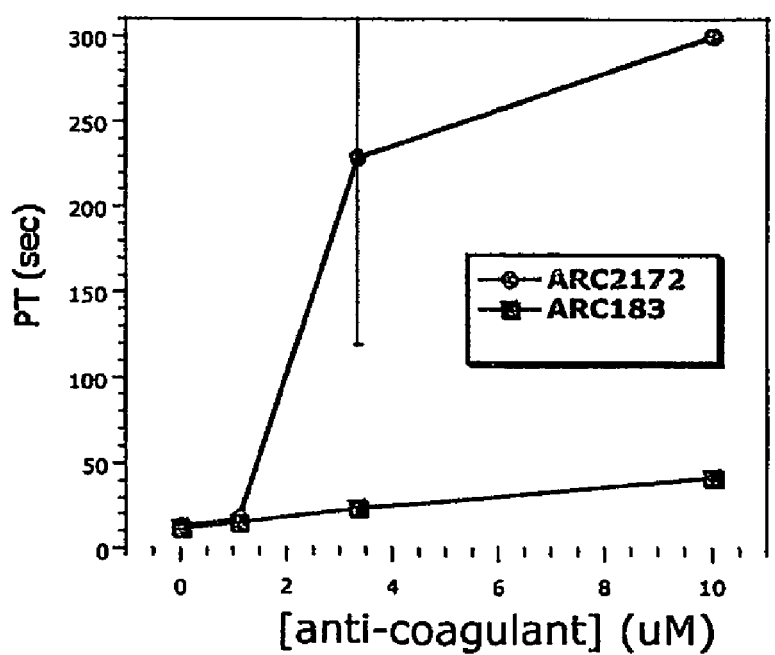
FIG. 8 is a graph depicting a comparison of the effects of ARC2172 (SEQ ID NO 294) and ARC 183 on the effects of prothrombin time (PT) as assayed in vitro using citrated human plasma.

ARC2172 (SEQ ID NO 294) was also screened for its ability to decrease or inhibit thrombin activity as compared to ARC183 using the PT assay described above. As shown in FIG. 8, ARC2172 (SEQ ID NO 294) is more potent than either ARC183 at the same molar concentrations.

Example 3B

Activated Clotting Time Assay

ACT measures the clotting time in non-citrated whole blood upon the addition of an intrinsic pathway activator. Less sensitive to heparin than the aPTT (e.g., the ACT time at 1 U/mL heparin is 181% of the normal control; data not shown), the ACT is commonly used as a bedside test to monitor high heparin doses during CABG. Unlike other coagulation tests, the ACT is not standardized; hence, ACT results vary depending upon the type of activator and detection method used. The published target clotting time for this instrument is >420 seconds for heparin anticoagulation in bypass surgery, corresponding to a concentration of 3-5 U/mL.

The following measurements were performed on a coagulation analyzer that utilizes optical detection (Hemochron Jr., ITC Med, Edison N.J.) using ACT+ cuvettes (ITC Med, Edison N.J.). Select aptamers described in Examples 1 and 2 which displayed high binding affinity for thrombin or excellent PT values in the PT assay described above were screened for their ability to decrease or inhibit thrombin activity using the ACT assay. Briefly, 70 µl of fresh whole blood was pre-incubated with a known concentration range (0-10 µM) of select aptamers, added to the blood in a 7 µl volume for 30 seconds at room temperature. Immediately afterwards, 30 µl of 25 mM $CaCl_2$ was added to the blood/aptamer mixture, then samples were loaded onto ACT+ cuvettes (Hemochron Jr., ITC Med, Edison N.J.) pre-warmed to 37° C. for analysis in the Hemochron Jr. coagulation analyzer (Hemochron Jr., ITC Med, Edison N.J.). A measured time of 125-150 seconds is considered background for the ACT assay. The results of select aptamers in the ACT assay are shown below in Table 22. Note that the background value has not been subtracted from the ACT values listed in Table 22 below.

TABLE 22

ACT values for ARC1985, ARC2026, ARC2027, ARC2091 ARC2169 and ARC2171

| Aptamer Concentration | ACT Value (sec) ARC 1985 (SEQ ID NO 191) | ACT Value (sec) ARC 2026 (SEQ ID NO 92) | ACT Value (sec) ARC 2027 (SEQ ID NO 84) | ACT Value (sec) ARC 2091 (SEQ ID NO 197) | ACT Value (sec) ARC 2169 (SEQ ID NO 283) | ACT Value (sec) ARC 2171 (SEQ ID NO 293) |
|---|---|---|---|---|---|---|
| 0 uM | 128 | 133 | 140 | 140 | 141 | 128 |
| .1 uM | N/A | 152 | 160 | 140 | N/A | N/A |
| .25 uM | N/A | 183 | 151 | 155 | 186 | N/A |
| .5 uM | 169 | 224 | 221 | 184 | 201 | 140 |
| 1 uM | 196 | 414 | 429 | 388 | 399 | 198 |
| 2.5 uM | 322 | 441 | 426 | 472 | 410 | 379 |
| 5 uM | 406 | 515 | 458 | 463 | 454 | 392 |
| 10 uM | 401 | 574 | 500 | 515 | 479 | 426 |

Figure 9:
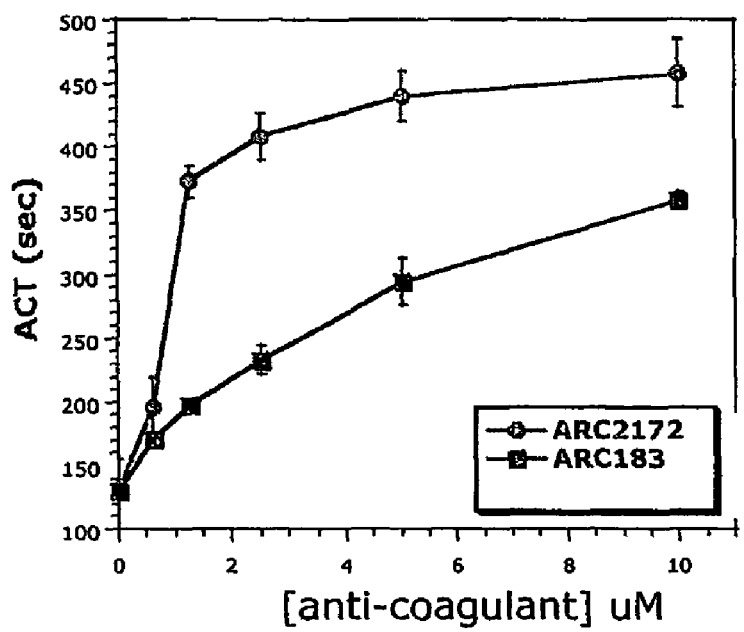
FIG. 9 is a graph depicting a comparison of the effects of ARC2172 (SEQ ID NO 294) and ARC183 on activated clot time (ACT) as assayed in vitro using human whole blood.

The ability of ARC 2172 (SEQ ID NO 294) to decrease or inhibit thrombin activity as compared to thrombin DNA aptamer ARC183 was also measured using the ACT assay as described above. As shown in FIG. 9, ARC2172 (SEQ ID NO 294) produced concentration-related prolongation of ACT with ≧2 µM aptamer required to reach a target clot time of >400 seconds. Over the concentration range from 2-10 µM, ARC2172 (SEQ ID NO 294) showed significantly greater potency than ARC183.

Optimized aptamers described above in Example 2C were also screened for their ability to decrease or inhibit thrombin activity at 10 µM aptamer concentration using the ACT assay described above. These results are shown in Table 23 below.

The loop regions of ARC2169 and ARC1985 were mutated to correspond to the sequence of ARC183, resulting in ARC2183 and ARC2184, respectively. These molecules were no more potent than ARC183 as can be seen in Table 23 below.

TABLE 23

ACT Values (including background) for Aptamers identified during Phase 1 Optimization Efforts

| SEQ ID NO | Clone name | ACT (sec) at 10 uM |
|---|---|---|
| 4 | ARC183 | 349 |
| 295 | ARC2173 | 415 |
| 296 | ARC2174 | 416 |
| 297 | ARC2175 | 392 |

TABLE 23-continued

ACT Values (including background) for Aptamers identified during Phase 1 Optimization Efforts

| SEQ ID NO | Clone name | ACT (sec) at 10 uM |
|---|---|---|
| 298 | ARC2176 | 394 |
| 299 | ARC2177 | 401 |
| 300 | ARC2178 | 429 |
| 301 | ARC2179 | 462 |
| 302 | ARC2180 | 516 |
| 303 | ARC2181 | 478 |
| 304 | ARC2182 | 518 |
| 305 | ARC2183 | 354 |
| 306 | ARC2184 | 368 |
| 307 | ARC2185 | 384 |
| 308 | ARC2186 | 408 |
| 309 | ARC2187 | 435 |
| 310 | ARC2188 | 426 |
| 311 | ARC2189 | 410 |
| 312 | ARC2190 | 389 |
| 313 | ARC2191 | 453 |
| 314 | ARC2192 | 423 |
| 315 | ARC2193 | 545 |
| 316 | ARC2194 | 462 |
| 317 | ARC2195 | 438 |
| 318 | ARC2196 | 441 |

The ACT values of the PEGylated aptamers and their 5'-amine conjugated intermediates described above in Example 2E were also measured using a concentration range of aptamers (0-10 uM) in the ACT assay described above. The results are shown in Table 24 below.

TABLE 24

ACT Values (including background) for a subset of PEGylated aptamers and respective 5'-amine intermediates

| Aptamer (uM) | ACT Value (sec) ARC2321 (SEQ ID NO 435) | ACT Value (sec) ARC2324 (SEQ ID NO 436) | ACT Value (sec) ARC2323 (SEQ ID NO 437) | ACT Value (sec) ARC2329 (SEQ ID NO 440) |
|---|---|---|---|---|
| 10 | 440.5 | 424.5 | 514.5 | 664 |
| 5 | 418 | 400 | 536 | 558.5 |
| 2.5 | 402.5 | 376.5 | 477.5 | 507.5 |
| 1 | 348 | 234 | 250.5 | 260 |
| 0.5 | 162 | 138.5 | 144.5 | 136 |
| 0 | 139 | 139 | 139 | 139 |

Example 3C

Activated Partial Thromboplastin Time (aPTT)

Contact with negatively charged surfaces (e.g., glass, silica, collagen) activates the "intrinsic" coagulation pathway. The aPTT measures the time to clot upon the addition of a negatively charged activator to plasma, and is sensitive to factors VIII, IX, XII, prekallikrein, high molecular weight kininogen and common pathway components. The aPTT reagent, which contains phospholipids (partial thromboplastin) in addition to activator, is pre-incubated with citrated plasma (the activation step) prior to the initiation of coagulation by the addition of CaCl2. Because heparin (in complex with antithrombin) targets several factors in both the intrinsic pathway and common pathways, the aPTT is considerably more sensitive to heparin than the PT (e.g., the aPTT time at 1 U/mL heparin is >1000% of the normal control; data not shown), and can be used to monitor therapeutic heparin at low doses.

The effects of ARC2172 (SEQ ID NO 294) as compared to ARC183 on aPTT was measured in human plasma using a Coag-a-Mate instrument (Biomerieux, Durham, N.C.), essentially as described for the PT assay, except that the plasma/inhibitor mixture was activated for 3 minutes with 100 µl aPTT-LS reagent (Pacific Hemostasis, Fisher Diagnostics, Middletown, Va.) prior to the addition of 100 µL 20 mM CaCl2 to initiate coagulation. The clotting time of ~20 seconds, measured in the absence of aptamer, is within the clinically normal range (20-40 seconds).

Figure 10:
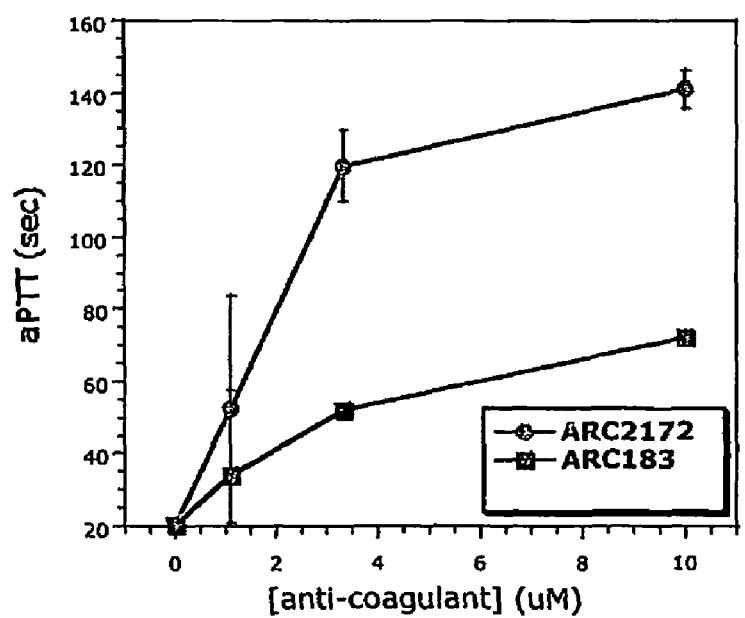
FIG. 10 is a graph depicting a comparison of the effects of ARC2172 (SEQ ID NO 294) and ARC183 on activated partial thromboplastin time (aPTT) as assayed in vitro using human plasma.

As shown in FIG. 10, the sensitivity of aPTT to ARC2172 (SEQ ID NO 294) was somewhat reduced relative to PT; nevertheless, clotting time in the aPTT assay was significantly prolonged by the anti-coagulant activity of ARC2172 (SEQ ID NO 294). Furthermore, ARC2172 (SEQ ID NO 294) was again shown to be significantly more potent in the aPTT assay than ARC183.

Example 3D

Clotting of Stagnant Blood

The ability of ARC2172 (SEQ ID NO 294) to maintain an anticoagulation effect over a sufficient amount of time to prevent clotting in stagnant blood, as compared to ARC183, was measured as follows.

Equimolar concentrations (5 µM) of ARC2172 (SEQ ID NO 294) or ARC183 were incubated in human whole blood at 37° C. for up to 1.5 hours, and the samples were monitored over time for activation of the coagulation cascade. Tissue plasminogen activator (5 kU/mL) was added to facilitate the breakdown of polymerized fibrin and maintain sample fluidity so that time points could be taken. Thrombin generation, assayed at each time point by ELISA of prothrombin proteolytic fragment 1.2 was used as a marker of coagulation cascade activation. Briefly, samples were added directly to pre-coated wells of an Enzygnost® TAT micro ELISA (Dade Behring; Deerfield, Ill.; cat. # OWMG15). The ELISA was subsequently completed according to the manufacturer's protocol. In order to obtain an indication of anticoagulant potency under these conditions, ACTs were measured as previously described in Example 3B, at the start of the incubation, and clot times of 388 and 266 seconds were observed for each of the compounds, respectively.

Figure 11:
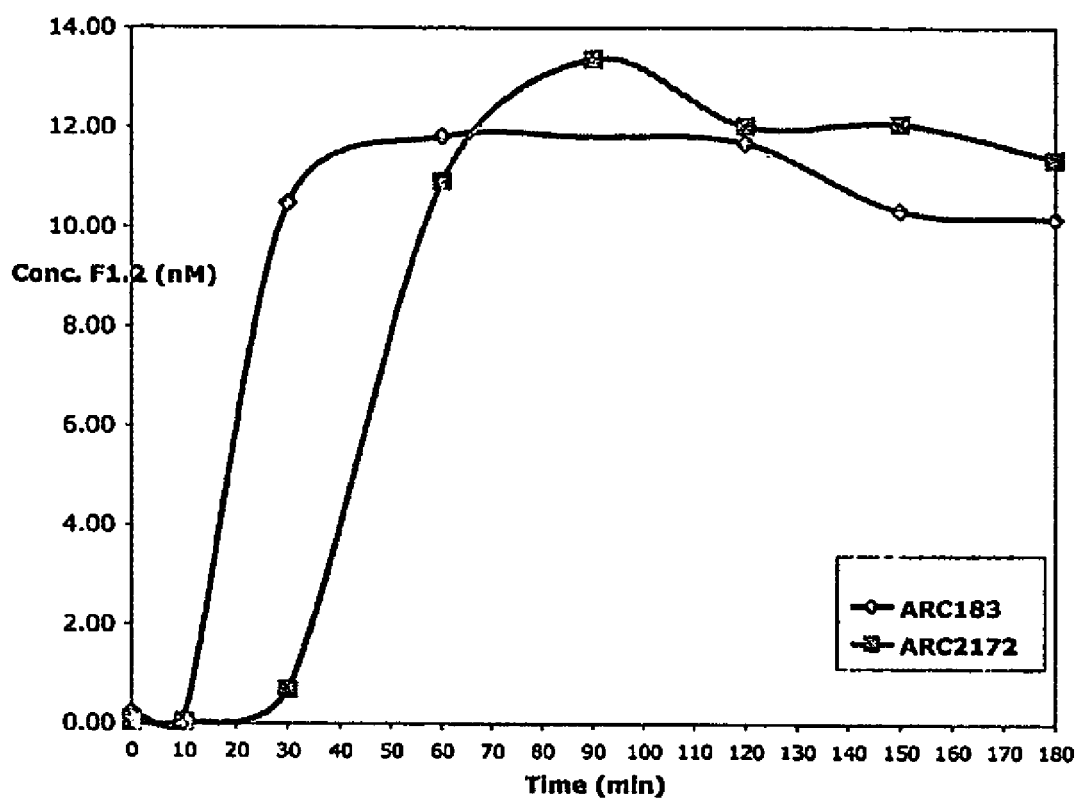
FIG. 11 is a graph depicting a comparison of the effects of ARC2172 and ARC183 on the clotting of stagnant blood, in an assay using human whole blood.

As shown in FIG. 11 ARC2172 (SEQ ID NO 294) at 5 µM prevented activation of the coagulation cascade in stagnant blood for 30 minutes. This effect represents a significant improvement over ARC183, for which the duration of anticoagulant effect is only about 10 minutes under similar conditions, and roughly parallels the improved potency of ARC2172 (SEQ ID NO 294) as measured prolongation of ACT values.

Example 4

Pharmacodynamic and Pharmacokinetic Studies

In Examples 4 and 5, all mass based concentration aptamer data refers only to the molecular weight of the oligonucleotide portion of the aptamer, irrespective of the mass conferred by PEG-conjugation.

Example 4A

Rat IV Bolus Study of Anti-Thrombin Aptamers

Ten of the thrombin binding aptamers (ARC2949 (SEQ ID NO 434), ARC2172 (SEQ ID NO 294), ARC2324 (SEQ ID NO 436), ARC2327 (SEQ ID NO 439), ARC2338 (SEQ ID NO 438), ARC2329 (SEQ ID NO 440), ARC2840 (SEQ ID NO 423), ARC2321 (SEQ ID NO 435), ARC2323 (SEQ ID NO 437); ARC2828 (SEQ ID NO 411) described in Examples 1 and 2 above) having desirable in vitro properties were ranked as to their anticoagulation pharmacodynamic characteristics and compared with ARC183 after being administered to Sprague-Dawley rats as an IV bolus. Aptamer dosing solutions were prepared previously by dissolving lyophilized aptamer into normal saline, adjusting the concentration of the dosing solution with normal saline until the correct concentration as determined by spectrophotometric analysis was achieved, and sterile filtering the resultant solutions through a 0.22 μm filter into sterile sample vials which was then frozen at −20° C. until used. Defrosted vials were kept on wet ice during dosing and used vials were stored at 4° C. when not being used for dosing.

All aptamers, except ARC183, were dosed at 1.5 μmole/kg, a dose which yielded maximum ACTs in the range of 300-700 seconds. ARC183 was dosed at 6.35 μmole/kg. Conscious male naïve Sprague-Dawley rats, cannulated in the femoral and jugular veins, were administered aptamer intravenously via the indwelling jugular vein cannula. At predetermined time points (pre-dose; 0.83, 1.83, 2.83, 5, 10, 15, 20, 30, 40, 50 and 60 minutes post-dose; if baseline ACT was not achieved by 60 minutes post dose additional time points of 90 and 120 minutes post dose were also used) 300 μl samples of blood were taken from the femoral vein cannula. ACTs were determined in real time using the ACT assay described in Example 3B above.

The study design and results are summarized in FIG. 12. ARC2949 (SEQ ID NO 434), ARC2172 (SEQ ID NO 294) and ARC2321 (SEQ ID NO 435), all unpegylated versions of ARC2169 (SEQ ID NO 283) composed of 24, 26 or 30 oligonucleotides respectively, were more potent than ARC183 at a significantly lower dose (38-48% of the mg/kg and 24% of the mole/kg ARC183 dose). When comparing these three aptamers on the basis of size, a strong trend toward increasing potency as measured by maximum ACT was noted. Also noted was the correlation of increased size with a prolongation of the aptamer activity as indicated by the time to an ACT of 170 seconds. ARC2172 (SEQ ID NO 294) exhibited increased potency in comparison with ARC2949 (SEQ ID NO 434), as indicated by maximum ACT.

ARC2840 (SEQ ID NO 423), a 26-mer like ARC2172 (SEQ ID NO 294), prepared with a weakened AU-rich 2'-OMe stem was found to be the least potent of any of the new aptamers. ARC2828 (SEQ ID NO 411), a 30-mer version of ARC2321 (SEQ ID NO 435), prepared with a weakened AT-rich 2'-OMe stem was found to be indistinguishable from ARC2321 (SEQ ID NO 435). The remaining aptamers tested were modifications of ARC2172 (SEQ ID NO 294) and ARC2321 (SEQ ID NO 435) above with either addition of a 5' amine linker±2-10K PEG groups. These modifications produced a moderate increase in potency but also increased in the prolongation of the pharmacodynamic effect (see FIG. 13).

Thus the ten aptamers tested displayed a range of pharmacodynamic properties with a correlation between increased size and a prolongation of the PD effect (as measured by ACT) balanced by a trend toward increased potency. ARC2172 (SEQ ID NO 294) exhibited a higher potency in comparison with ARC183.

Example 4B

Intravenous Bolus Administration in Sprague-Dawley Rats

Figures 13, 14:
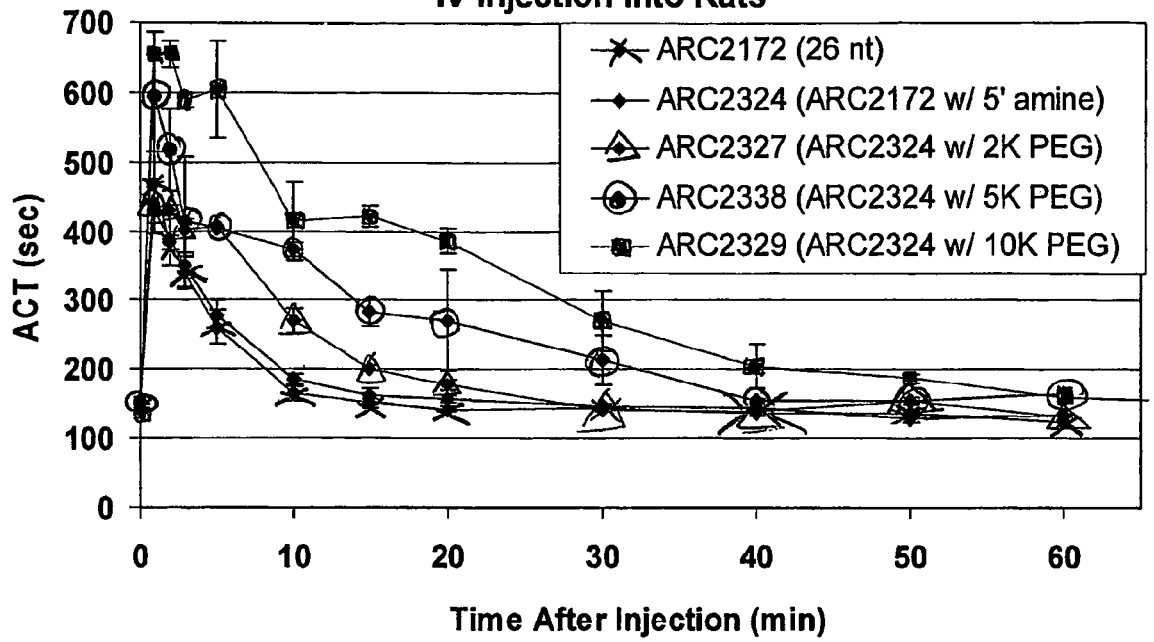
FIG. 13 is graph depicting a comparison of the effects of different size PEG groups attached to ARC2172 (SEQ ID NO 294) on activated clot time (ACT) in rats that received aptamer via IV bolus injection at 1.5 μmole/kg.
FIG. 14 is a table showing the experimental study design for a rat IV bolus study of anti-thrombin aptamers, described in Example 4B.

ARC2172 (SEQ ID NO 294) and ARC183 were administered intravenously (IV) via an indwelling jugular vein cannula as delineated in the study design presented in FIG. 14. In addition to Iv bolus injection, these rats were subjected to a sham renal ligation as part of a study to determine the renal elimination of these compounds; a description of the sham operation and the PK/PD results as related to the effects of renal ligation is described in Example 4C below. Blood was collected via an indwelling femoral vein catheter for ACT determination at defined time points up to two hours after injection. ACT values were measured using a Hemochron® Jr Signature+instrument with ACT(+) cuvettes as previously described in Example 3B.

Figures 15, 16, 17:
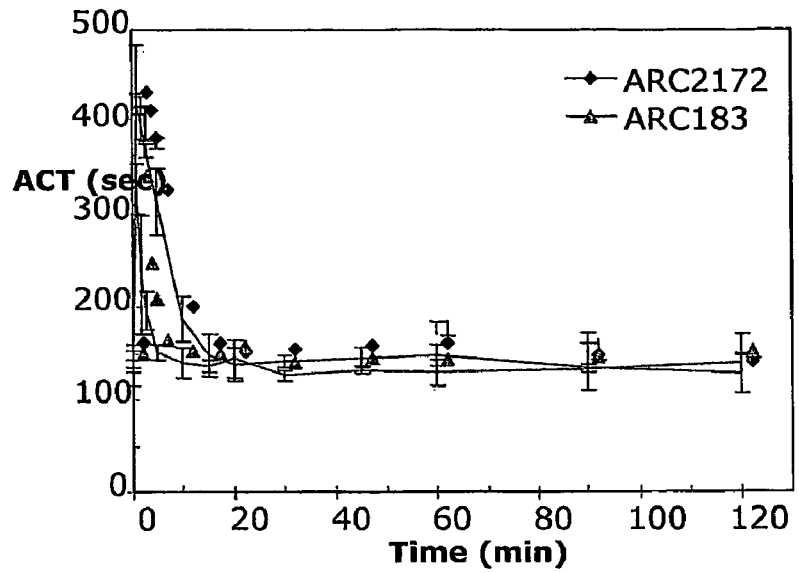
FIG. 15 is graph depicting a comparison of the effects ARC2172 (SEQ ID NO 294) and ARC186 on activated clot time (ACT) in rats that received aptamer via IV bolus injection at 12.2 mg/kg (ARC2172 (SEQ ID NO 294)) or 30 mg/kg (ARC183).
FIG. 16 is a table summarizing the effects of ARC2172 (SEQ ID NO 294) and ARC186 on activated clot time (ACT) in rats that received aptamer via IV bolus injection at 12.2 mg/kg (ARC2172 (SEQ ID NO 294)) and 30 mg/kg (ARC183)
FIG. 17 is a table showing the experimental study design of anti-thrombin aptamers in a rat renal ligation model, described in Example 4C.

The effects on ACT of administration of ARC2172 (SEQ ID NO 294) and ARC183 is shown in FIG. 15 with relevant parameters summarized in FIG. 16. Administration by IV bolus of ARC2172 (SEQ ID NO 294) produced an average maximum ACT value of 418. Dosing of ARC183 at 2.5-fold mg/kg (4.2-fold mole/kg) dose of ARC2172 (SEQ ID NO 294) resulted in a lower mean maximum ACT of 328 seconds. The off-rate for ARC183 was rapid, with an average time to an ACT of 200 or 170 seconds of 2.7 and 4.1 minutes, respectively. ARC2172 (SEQ ID NO 294) exhibited an average time to an ACT of 200 or 170 seconds of 9.5 and 12.2 minutes, respectively. In conclusion, following bolus IV administration in sham operated rats, ARC2172 (SEQ ID NO 294) was found to be more potent than ARC183.

Example 4C

ARC2172 and ARC183 in Renally Ligated and Sham-Operated Sprague-Dawley Rats

The objective of this study was to determine and compare the renal elimination and its effect on the pharmacodynamic activity of ARC2172 (SEQ ID NO 294) and ARC183 in renal ligated and sham-operated male Sprague-Dawley rats. Male Sprague-Dawley rats that underwent either a complete renal ligation surgery or a sham operation were administered ARC183 and ARC2172 (SEQ ID NO 294) by IV bolus. The study design is shown in FIG. 17.

Blood was collected at pre-dose and specified time points for ACT measurement and ARC2172 (SEQ ID NO 294) or ARC183 concentration analysis. ACT was measured as described in Example 3B. Plasma concentrations of ARC2172 (SEQ ID NO 294) and ARC183 were determined by HPLC assays with a lower limits of quantitation (LLOQ) of 0.05 μg/mL and 0.16 μg/mL, respectively. PK and PK/PD analysis were done using individual plasma concentration-time profiles by the noncompartmental and Emax models E=E0+(Emax−E0)*(Cγ/(Cγ+EC50γ)), respectively using WinNonlin™, version 5.1 (Pharsight Corporation, Mountainview, Calif.). A one-way analysis of variance (ANOVA, α=0.05) statistical analysis were used for $C_{max}$, $AUC_{last}$ and $MRT_{last}$ of the renal-ligated and sham-operated rats.

Figure 18:
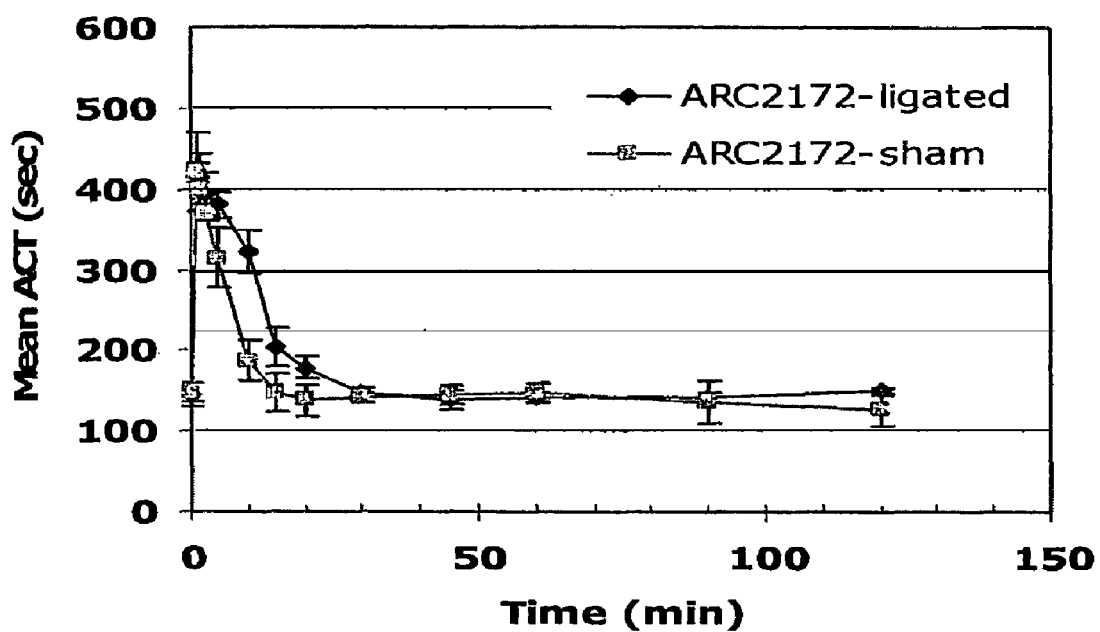
FIG. 18 is a graph showing a comparison of the effect of ARC2172 (SEQ ID NO 294) on activated clot time (ACT) in both renally ligated and sham operated rats when administered via IV bolus injection at 12.2 mg/kg (ARC2172 (SEQ ID NO 294)).
Figure 19:
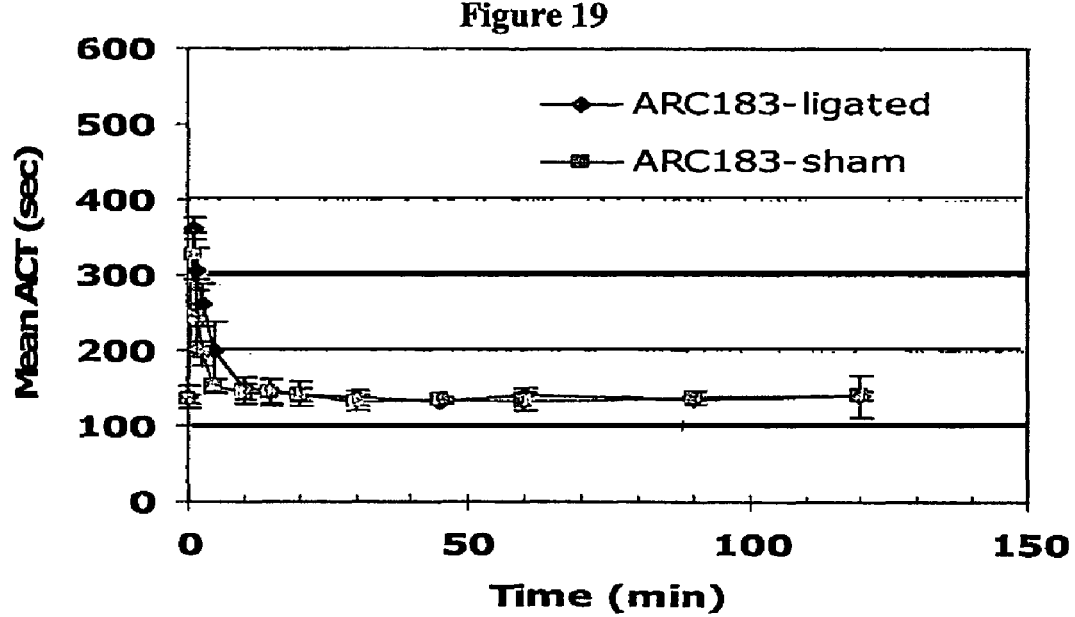
FIG. 19 is a graph showing a comparison of the effect of ARC183 on activated clot time (ACT) in both a renally ligated and sham operated rats when administered via IV bolus injection at 30 mg/kg (ARC183).

The pharmacodynamic profiles (ACT) for ARC2172 (SEQ ID NO 294) and ARC183 for renally-ligated and sham-operated groups are shown in FIG. 18 and FIG. 19, respectively. The mean maximum ACTs reached by ARC2172 (SEQ ID NO 294) in sham and renally-ligated rats were 422 seconds and 419 seconds, respectively, while for ARC183 the mean maximum ACTs were 325 seconds and 363 seconds, respectively. The mean ACT of ARC2172 (SEQ ID NO 294) dropped from its maximal value to 170 seconds within 15 minutes, while for ARC183 the mean ACT declined to 170 seconds within 5 to 10 minutes. The overall PD profiles of ARC2172 (SEQ ID NO 294) and ARC183 were not significantly affected by renal ligation in the rat when compared to sham-operated rats (P>0.05, using Mann-Whitney test). However, at early time-points (t=5-20 and t=0.83-5 min for ARC2172 (SEQ ID NO 294) and ARC183, respectively) there was a small, but statistically significant effect of renal ligation in the rat when compared to sham-operated rats (P<0.05, using Mann-Whitney test).

Following IV administration in both renal-ligated and sham-operated rats, the plasma concentration-time profiles for both ARC2172 (SEQ ID NO 294) and ARC183 were biphasic. The renal-ligated groups for both compounds showed increases in plasma concentrations at most sampling times, as compared to the sham-operated groups. The increased in $C_{max}$ and $AUC_{0-last}$ in ARC2172 (SEQ ID NO 294) and ARC183 were found to be statistically significant at P<0.05.

In summary, the overall PD profiles of ARC2172 (SEQ ID NO 294) and ARC183 were not significantly affected by renal ligation in the rat when compared to sham-operated rats (P>0.05, using Mann-Whitney test). However, at early time-points (t—5-20 and t—0.83-5 min for ARC2172 (SEQ ID NO 294) and ARC183, respectively) there was a small, but statistically significant effect of renal ligation in the rat when compared to sham-operated rats (P<0.05, using Mann-Whitney test). There was a small, but statistically significant effect on the overall exposure of both ARC2172 (SEQ ID NO 294) and ARC183 following a single IV bolus in renal-ligated rats as compared to sham-operated rats. The mean $C_{max}$ and $AUC_{0-last}$ values in renal-ligated rats were ~1.5-fold and 2-fold greater than sham-operated rats for ARC2172 (SEQ ID NO 294). For ARC183, the mean $C_{max}$ and $AUC_{0-last}$ values in renal-ligated rats were ~2.4-fold and 2.9-fold greater than sham-operated rats. Statistical analysis showed no significant difference for the $MT_{0-last}$ for renal-ligated rats as compared to sham-operated rats for both ARC183 and ARC2172 (SEQ ID NO 294). This data shows that in the renal ligation rat model of the most severe form of renal impairment that the pharmacodynamic affect of ARC2172 is minimally impacted. While not wishing to be bound by any theory, as ARC2172 showed minimal change in its pharmacodynamic reversibility (time to return to a mean ACT value of 200 seconds) and only moderate change in its pharmacokinetics in this rat model representing severe renal impairment (bilateral ligation), renal elimination does not appear to be a primary mechanism of clearance for ARC2172. Further, while not wishing to be bound by any theory taken together these data suggest that no dose adjustment will be necessary for ARC2172 (SEQ ID NO 294) in patients with renal impairment.

Example 4D

Example 4F

Monkey IV Bolus Studies to Rank Anti-Thrombin Aptamers

Four of the thrombin binding aptamers compared in the rat study described in Example 4A (ARC2172 (SEQ ID NO 294), ARC2949 (SEQ ID NO 434), ARC2169 (SEQ ID NO 283) and ARC2840 (SEQ ID NO 423)) were evaluated in an IV bolus study in monkeys. (ARC2169 (SEQ ID NO 283) is the version of the 30 oligonucleotide ARC2321 (SEQ ID NO 435) without the 5' amine). Aptamer dosing solutions were prepared by dissolving lyophilized aptamer or peptide into normal saline, adjusting the concentration of the dosing solution with normal saline until the correct concentration as determined by spectophotometric analysis was achieved, and sterile filtering the resultant solutions through a 0.22 μm filter into sterile sample vials which was then frozen at −20° C. until used. Defrosted vials were kept on wet ice during dosing and used vials were stored at 4° C. when not being used for dosing.

In the following IV bolus study in Cynomolgus monkeys all aptamers were dosed at 0.46 μmole/kg. An IV catheter was placed in the cephalic vein of an anesthetized cynomolgus monkey and used to administer aptamer via bolus. Lactated Ringer's solution was provided via this cephalic venous catheter at a rate of approximately 5-10 mL/kg/hr to provide fluid maintenance and catheter patency. Blood was drawn from a vascular access port as previously described at defined time points for one hour after the bolus injection (total volume=~3 mL). For all aptamers the time points were pre-dose and 0.83, 1.83, 2.83, 5, 10, 15, 20, 30, 45, 60 minutes post-dose; in the case of ARC2169 (SEQ ID NO 283) additional time points of 90 and 120 minutes post dose were also used. Activated ACTs were determined in real time with a Hemachron Jr Signature+ instrument (ITC Med, Edison N.J.) using the ACT+(ITC Med, Edison N.J.) cartridges as previously described in Example 3B.

Figures 20, 21:
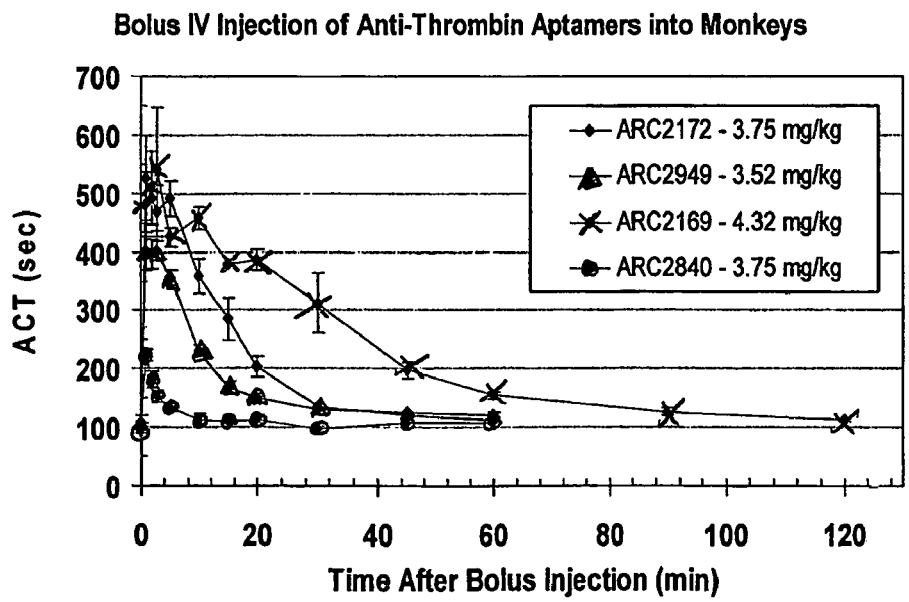
FIG. 20 is a table summarizing the effects of anti-thrombin aptamers ARC2172 (SEQ ID NO 294), ARC2949 (SEQ ID NO 434), ARC2169 (SEQ ID NO 283) and ARC2840 (SEQ ID NO 423) on activated clot time (ACT) in cynomolgus monkeys that received the aptamer via IV bolus injection at 0.46 μmole/kg.
FIG. 21 is a graph showing a comparison of the effects of anti-thrombin aptamers ARC2172 (SEQ ID NO 294), ARC2949 (SEQ ID NO 434), ARC2169 (SEQ ID NO 283) and ARC2840 (SEQ BD NO 423) on activated clot time (ACT) in cynomolgus monkeys that received the aptamer via IV bolus injection at 0.46 μmole/kg.

FIG. 20 and FIG. 21 summarize the results. All of the aptamers showed increased potency in the monkeys in comparison with the results obtained with them in the IV bolus model in the rats (Example 4A), as evidenced by the maximum ACTs achieved using a mole/kg dose in the monkeys that was 31% of that used in the rats. ARC2840 (SEQ ID NO 423), the 26-mer with the AU-rich 2'-Ome stem, showed the least potency, with a maximum ACT of only 223.3 seconds and a time to an ACT of 170 seconds of 2.2 minutes. ARC2949 (SEQ ID NO 434) achieved a maximum ACT of 402.7 seconds and a time to an ACT of 170 seconds of 14.9 minutes. ARC2172 (SEQ ID NO 294) and ARC2169 (SEQ ID NO 283) were quite similar in their maximum ACTs (526.8 and 541.7 seconds, respectively), but the time to an ACT of 170 seconds for ARC2169 (SEQ ID NO 283) was almost twice as long as for ARC2172 (SEQ ID NO 294) (54.6 minutes versus 24.9 minutes).

Example 4E

Intravenous Bolus+Infusion Administration of ARC2172 and ARC183 in Cynomolgus Monkeys ARC2172 (SEQ ID NO 294) and ARC183 were evaluated in the following single IV bolus+continuous 1 hour IV infusion study in the cynomolgus macaque. Cynomolgus monkeys were administered ARC2172 (SEQ ID NO 294) or ARC183 in an IV bolus followed immediately by initiation of a continuous infusion for 1 hour as shown by the study design in FIG. 22.

Blood was drawn from a vascular access port as described above, and ACT values, were measured with a Hemachron Jr Signature+instrument (ITC Med, Edison N.J.) using the ACT+(ITC Med, Edison N.J.) cartridges as previously described in Example 3B.

The effect as measured by ACT following IV bolus+1 hour infusion administration of ARC2172 (SEQ ID NO 294) or ARC183 is shown in FIG. 23, with the relevant parameters summarized in FIG. 24. Administration of ARC2172 (SEQ ID NO 294) by IV bolus plus a one hour infusion targeting a plasma concentration of 5 µM produced an average maximum ACT value of 397 seconds and an average time to an ACT of 200 or 170 seconds of 22.2 and 26.5 minutes, respectively. Increasing the dose of ARC2172 (SEQ ID NO 294) to achieve a target plasma concentration of 7.5 µM increased the average maximum ACT to 414 seconds, while the average time to an ACT of 200 or 170 seconds was 13.9 and 18.0 minutes, respectively (differences in these later times between the two ARC2172 (SEQ ID NO 294) dosing regimens are within experimental error). ARC183, when given as an IV bolus+ one hour infusion to achieve a plasma concentration of 15 µM resulted in an average maximum ACT of 343 seconds, and an average time to an ACT of 200 or 170 seconds of 4.9 and 7.3 minutes, respectively. Thus, in comparing the results with ARC183 to those observed with the lower dose regimen of ARC2172 (SEQ ID NO 294), in which the total dose given was 7% of the mg/kg dose administered with ARC183, treatment with ARC2172 (SEQ ID NO 294) was able to produce a stable ACT of approximately 400 seconds during the infusion. The off-rate was approximately 4 times slower for ARC2172 (SEQ ID NO 294) in comparison with ARC183.

Example 4F

Pharmacodynamic Drug Interactions

Effect of ARC2172 on Platelet Aggregation

Aside from the generation of fibrin, thrombin further stimulates clot formation by activating platelets. In vitro, platelets are activated by a variety of agonists including thrombin, collagen, and ADP. Once activated, platelets undergo profound changes in morphology, receptor expression, and factors released. These changes, under certain conditions, induce platelets to aggregate and this aggregation is not dependent on the presence of other cells. Platelet rich plasma (PRP) is generated by low speed centrifugation of whole blood. Adding platelet agonists to PRP can induce platelet activation and aggregation. Platelet aggregation in PRP can be monitored by the degree of light absorbance as the normally turbid PRP clears as platelets aggregate and drop out of solution. The objective of this study was to assess the effect of ARC2172 (SEQ ID NO 294) on platelet aggregation in human PRP.

Figure 25:
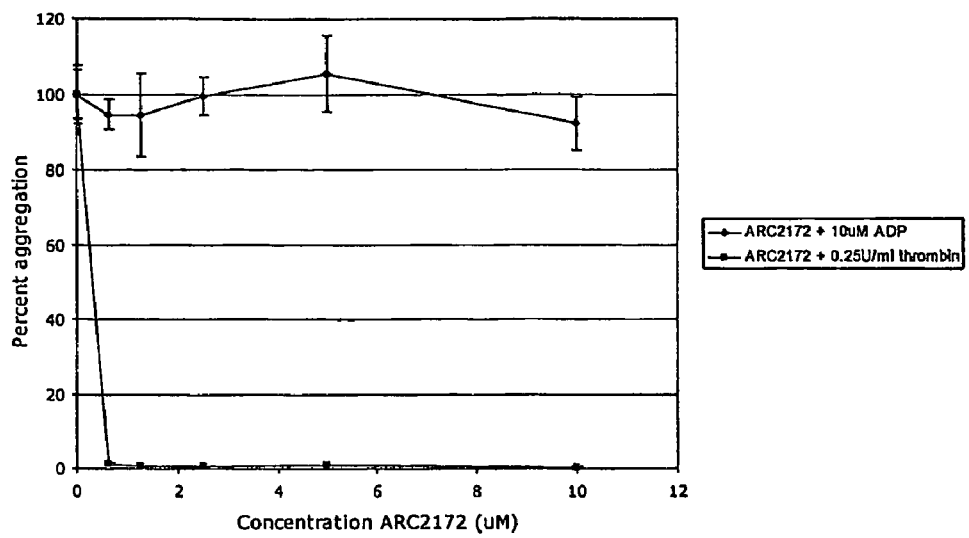
FIG. 25 is a graph comparing the effect of ARC2172 (SEQ ID NO 294) 3 on thrombin-induced platelet aggregation, and ADP-induced platelet aggregation.

PRP was mixed with α-thrombin (0.25 units/mL) or ADP (10 µM) in the presence and absence of ARC2172 (SEQ ID NO 294) at various concentrations. Platelet aggregation was assessed with an optical aggregometer. ARC2172 (SEQ ID NO 294) inhibited platelet aggregation (i.e., activation of receptor GPIIb/IIIa) induced by thrombin, but not by ADP (FIG. 25). These data demonstrate that ARC2172 (SEQ ID NO 294) is a thrombin antagonist that binds to thrombin with high affinity.

Effect in vitro of ARC2172 on Activities Aspirin and Integrilin

In vitro, platelets are activated by a variety of agonists including thrombin, collagen, and ADP, or inhibited by antagonists such as aspirin or platelet IIb/IIIa inhibitors. The objective of this study was to assess the effect of ARC2172 (SEQ ID NO 294) on activity of aspirin or the disulfide-linked heptapeptide GPIIb/IIIa inhibitor, Integrilin, on platelet aggregation in human PRP.

Figure 26:
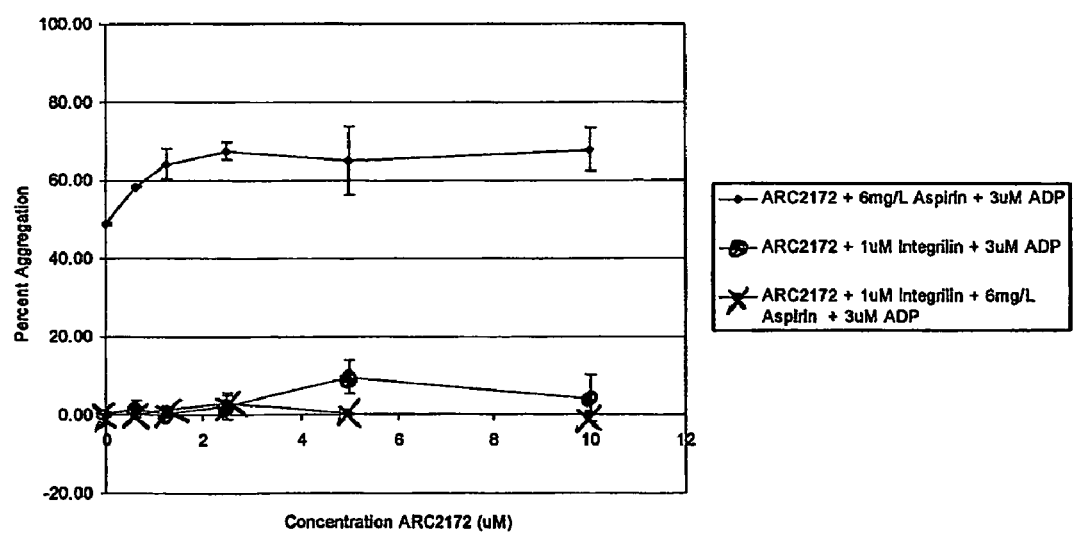
FIG. 26 is a graph comparing the effect of ARC2172 (SEQ ID NO 294) on aspirin, and Integrilin-dependent inhibition of platelet aggregation.

PRP was preincubated for 20 minutes at room temperature with Integrilin (1 µM) in the presence of absence of aspirin (6 mg/L) and in the presence and absence of ARC2172 (SEQ ID NO 294) at various concentrations. The platelet mixture was preheated to 37° C. for 3 minutes before assessment for platelet aggregation by ADP (3 M) using an optical aggregometer. Aspirin reduced ADP-induced platelet aggregation in human PRP, while Integrilin completely blocked ADP-induced platelet aggregation in human PRP with and without aspirin. ARC2172 (SEQ ID NO 294) did not decrease or inhibit the activity of either aspirin or Integrilin (FIG. 26).

Example 5

Functional Animal Studies

Example 5A

ARC2172 in Open, Non-Heparin Bonded Bypass Circuits

ARC2172 (SEQ ID NO 294) was evaluated in a porcine cardiopulmonary bypass model using an open, non-heparin-bonded bypass circuit. Animals were treated with saline (n=2), heparin (n=5), and ARC2172 (SEQ ID NO 294) (n=5, animals 38 and 39 were not included in the statistical analysis) by bolus or bolus+infusion to achieve a target ACT of 400 seconds prior to initiation of bypass. A third group of animals (n=2) did not receive anticoagulant treatment and was not subjected to cardioplegia and aortic cross-clamp. The study design is depicted FIG. 27.

ARC2172 (SEQ ID NO 294) was synthesized on Primer-Support 200 with a loading of 202 mmol/g. The standard synthesis cycle employed 1.8 equivalents of amidite and 3 equivalents of oxidizer. A post synthetic base wash was conducted with 20% diethylamine in acetonitrile and deprotected with ammonia overnight followed by preparative SAX-HPLC. The aptamer was subsequently lyophilized and then resuspended in sterile saline at a concentration of 20.0 mg/ml. Sodium heparin prepared from pig pancreas was used in the study Pig Bypass Model Male and female pigs were randomized into various treatment groups as depicted in FIG. 27. Animals 38 and 39 were not included in the statistical analysis.

The animals were pre-anesthetized with atropine SO4/Telazol®/Xylazine (0.04 mg/kg 4-6 mg/kg/2 mg/kg intramuscularly [IM], respectively) prior to surgical preparation. Animals were then intubated and maintained on isoflurane inhalant anesthetic to effect delivered through a volume-regulated respirator.

Following onset of anesthesia, femoral arteries and vein were cannulated to monitor blood pressure and obtain blood samples, respectively. Patency of the femoral vein cannula was maintained either with a slow saline drip or via infusion of ARC2172 (SEQ ID NO 294).

A skin incision was made over the length of the sternum. The sternum was subsequently incised and the thoracic cavity opened. Hemostasis was achieved with a Bovi electrocautery probe. The pericardium was opened to provide access to the heart. The aorta was dissected free from the surrounding tissue and a purse string suture was placed in the ascending aorta 4 cm distal to the heart using 5.0 polyester sutures. Similarly, a purse string suture was placed in the right atrial appendage using 5.0 polyester sutures. Following placement of the sutures, the animals were treated with either heparin, or ARC2172 (SEQ ID NO 294). Heparin (40,000 to 60,000 units) was administered as multiple I.V. boluses to achieve an ACT above 400 as measured by the ACT Plus system Medtronic, Minneapolis Minn.) and about 1000 on the Hemochron Junior Signature+microcoagulation instrument (ITC Med, Edison, N.J.) with ACT+test cuvettes (ITC Med, Edison, N.J.) as described in Example 3b. It generally took between 1020 minutes to adjust the heparin dose and insure that the ACT was in the correct range. ARC2172 (SEQ ID NO 294) was administered via bolus+continuous intravenous infusion (0.139) to achieve an ACT of approximately 400 seconds on the Hemochron Junior Signature+microcoagulation instrument (ITC Med, Edison, N.J.) with ACT+test cuvettes (ITC Med, Edison, N.J.) as described in Example 3b (see FIG. 27). It generally took between 10 to 20 minutes to administer the drug and insure that the ACT was in the correct range.

Following administration of the appropriate dosage of anticoagulant, the arterial and venous cannulas were placed. The aortic cannula was rapidly attached to the pre-primed arterial line of the heart/lung machine, taking care to fill both the aortic cannula and arterial line with saline to eliminate bubbles prior to the connection. The arterial line was quickly clamped. A similar technique was used to place and secure the venous cannula (29/37 two stage venous cannula, Medtronic, Minneapolis, Minn.) in the right atrial appendage and to then attach the cannula to the venous line of the heart/lung machine. The entire bypass circuit was composed of non-heparin-bonded components (Affinity CVR Cardiotomy/Venous reservoir and Membrane Oxygenator with Plasma Resistant Fiber, Medtronic, Minneapolis, Minn.). Subsequently, the animal was placed on cardiopulmonary bypass for a period of 3 hours. The arterial and venous lines of the heart/lung machine had Doppler ultrasound probes attached midway between the animal and the machine to monitor for the presence of clot emboli. Direct blood pressure was monitored during the procedure and blood pressure was maintained during bypass by a) adjusting the bypass blood flow rate, b) administration of intravenous fluids and c) administration of various drugs via intravenous injection, including neosynephrine, dopamine, epinephrine and calcium to effect. The animal was maintained in a surgical plane of anesthesia by adjusting the isoflurane vaporizer flow rate and the occasional administration of an IV pentobarbital bolus as needed.

Figure 28:
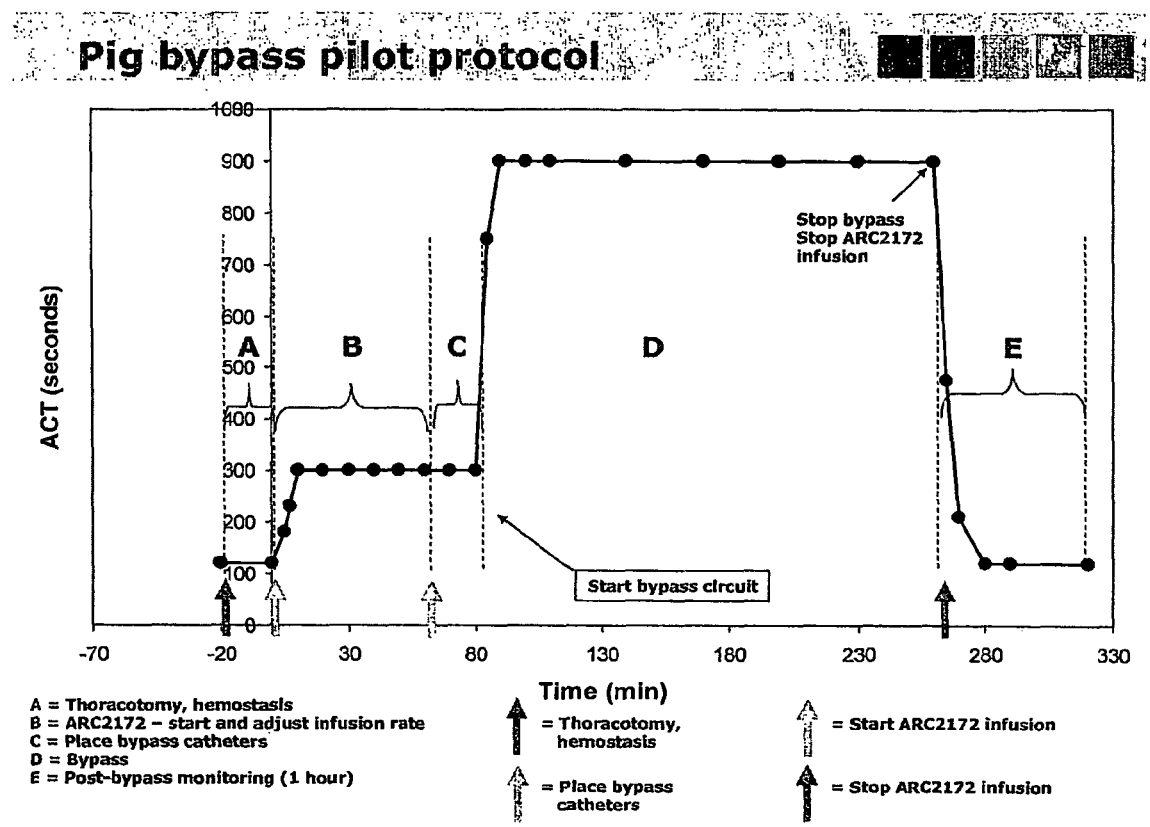
FIG. 28 is an outline of the porcine cardiopulmonary bypass study protocol.

After the three hours of bypass was completed, animals were taken off of bypass, the cannulas were removed when blood pressure was stabilized and then the anticoagulant activity was stopped either by treatment with protamine (heparin treatment group) or by stopping aptamer infusion (ARC2172 treatment group). The animals were maintained for one additional hour after cessation of drug infusion. Blood pressure was maintained post-bypass using a combination of I.V. neosynephrine and/or I.V. fluid administration to effect. An outline of the CPB study protocol is shown in FIG. 28.

ACT Assay and Examination of Cardiopulmonary Bypass Circuit for Evidence of Gross Blood Clot or Fibrin Deposition:

Samples of fresh, whole blood were obtained at scheduled sample collection time points and measured immediately using both the Hemochron Junior Signature+microcoagulation instrument (ITC Med, Edison, N.J.) with ACT+test cuvettes (ITC Med, Edison, N.J.) and the ACT Plus system (Medtronic, Minneapolis, Minn.), as described in Example 3B. Following completion of each experiment, the cardiopulmonary bypass circuit was flushed with saline and the reservoir, oxygenator membrane and arterial filter were inspected for evidence of gross clot formation and photographed.

Figure 29:
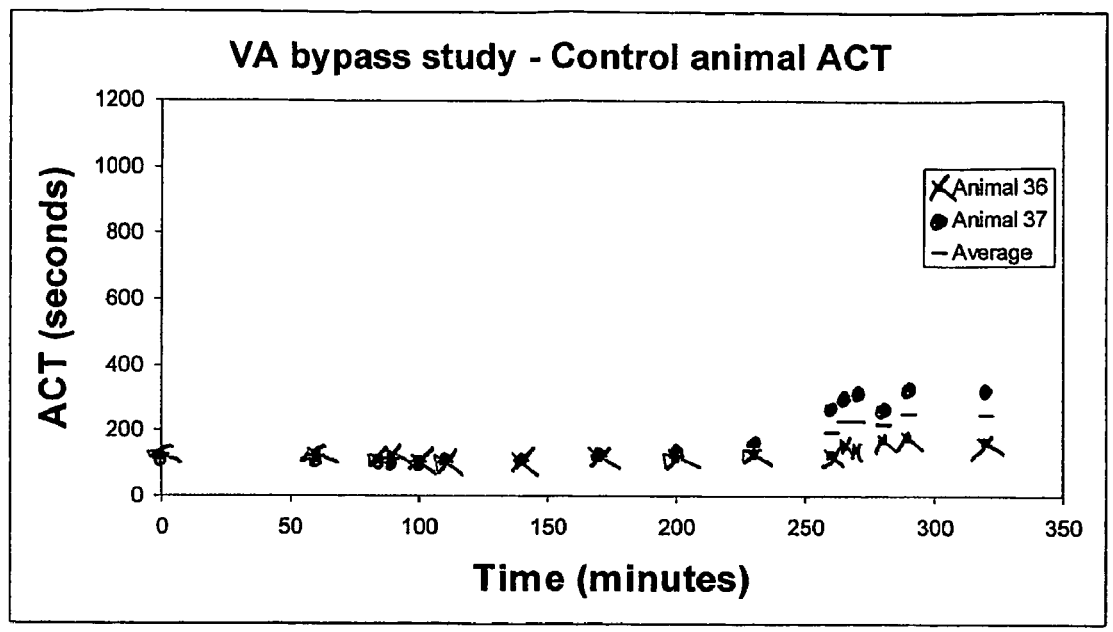
FIG. 29 is a graph showing the activated clot time (ACT) in the control animals (no anticoagulant treatment) used in the open, non-heparin bonded porcine cardiopulmonary bypass study described in Example 5A.

Control animal ACT values remained relatively constant during the procedure, but drifted up following bypass (FIG. 29). Large gross blood clots were visible in the bypass circuit within 15 minutes of starting bypass and became so large that flow through the bypass circuit was almost stopped after 3 hours of bypass.

Figure 30:
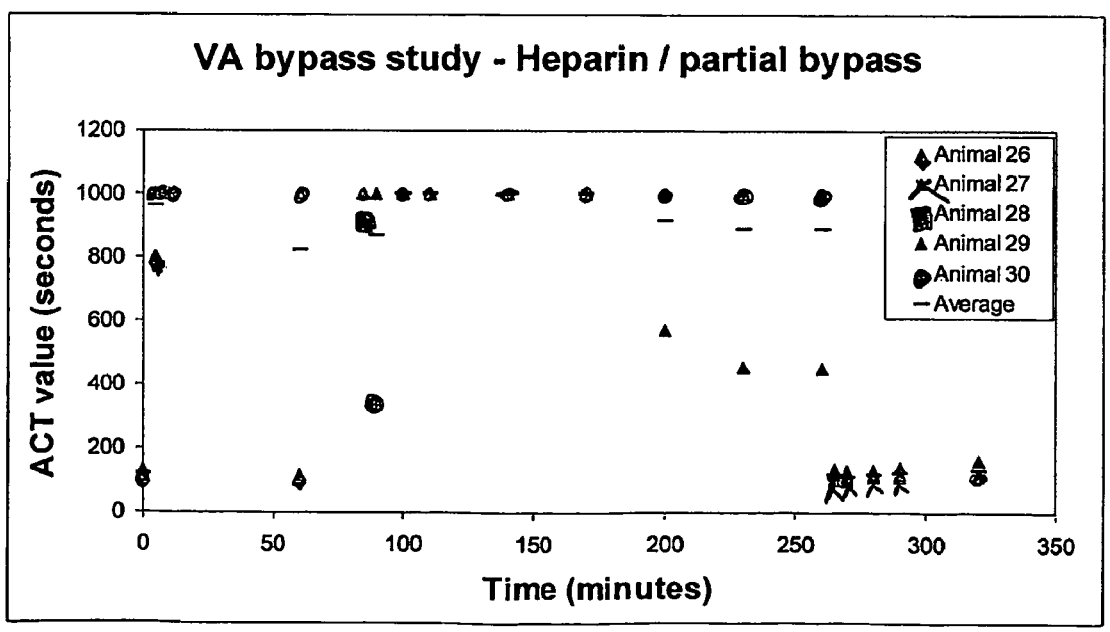
FIG. 30 is a graph showing the activated clot time (ACT) in pigs that received heparin via IV bolus injection to maintain ACT >400 seconds in the open, non-heparin bonded cardiopulmonary bypass study, described in example 5A.

Following heparin administration, animals in this treatment group had exceptionally high ACT values that were usually off scale (over 1000 sec) (see FIG. 30). The animals were given repeated boluses to maintain the ACT at this elevated level. Administration of protamine at the end of the experiment caused ACT values to return to baseline. Gross clots were not visible in the bypass circuit.

Figure 31:
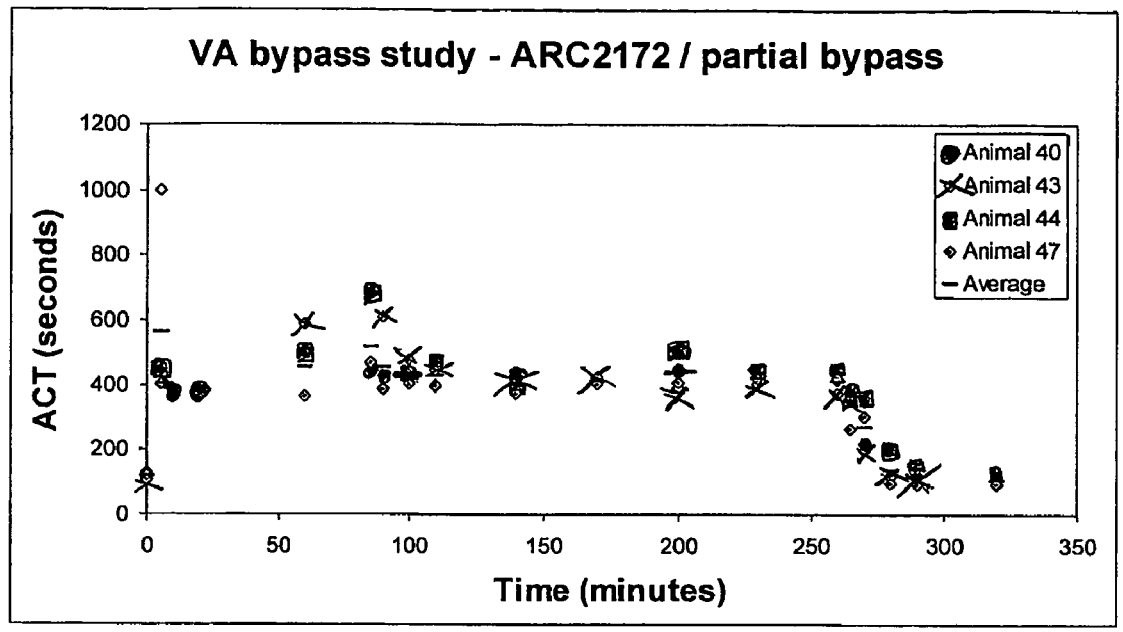
FIG. 31 is a graph showing the activated clot time (ACT) in pigs that received ARC2172 (SEQ ID NO 294) via IV bolus plus infusion to maintain ACT >400 seconds in the open, non-heparin bonded cardiopulmonary bypass study, described in example 5A.
Figure 32:
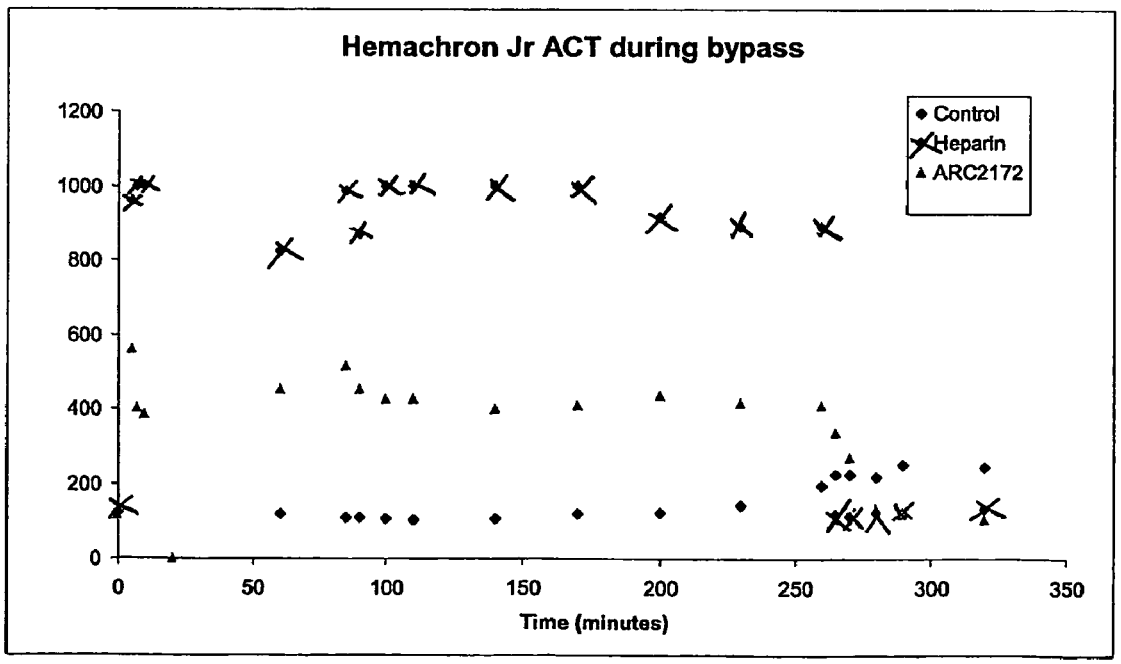
FIG. 32 is a graph showing a comparison of the effect of heparin and ARC2172 (SEQ ID NO 294), on activated clot time (ACT) (plotted in seconds on the vertical axis) in the cardiopulmonary bypass model using open, non-heparin bonded bypass circuits, as described in Example 5A.

In animals treated with ARC2172 (SEQ ID NO 294) by bolus+infusion, the ACT was maintained within a relatively narrow range during bypass and the ACT returned to baseline within 20 minutes of stopping ARC2172 (SEQ ID NO 294) administration (FIG. 31). Gross clots were not visible in the bypass circuit. A comparison of ACT values during bypass with each of the anticoagulants used is shown in FIG. 32.

Figure 33:
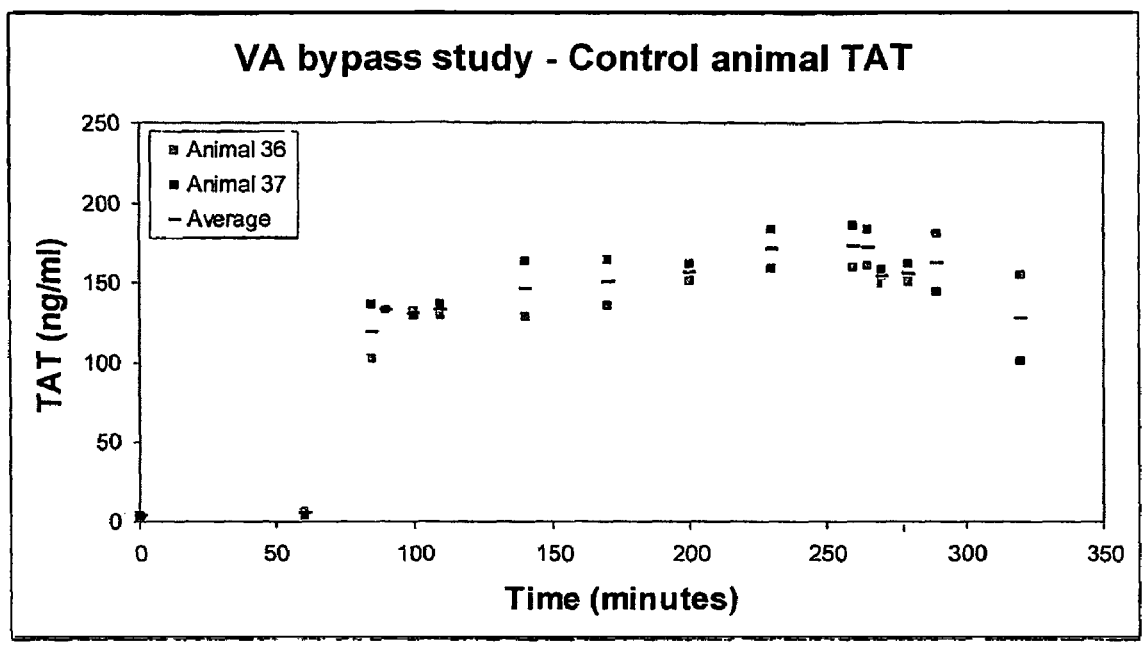
FIG. 33 is a graph showing the concentration of plasma TAT complexes in the control animals (no anticoagulant treatment) used in the open, non-heparin bonded porcine cardiopulmonary bypass study described in Example 5A.
Figure 34:
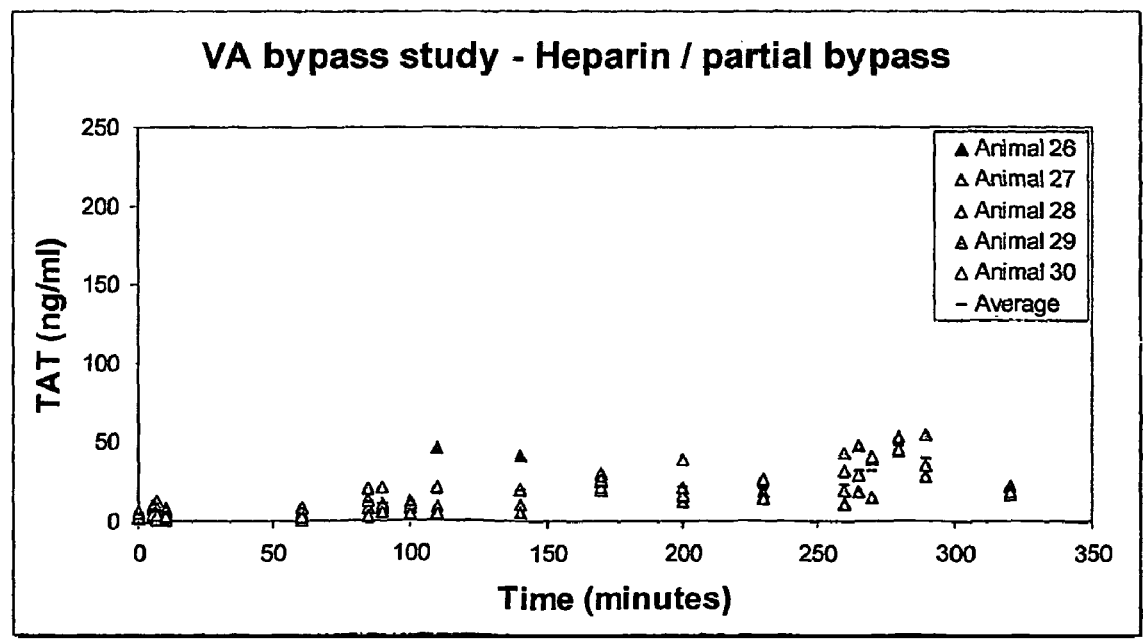
FIG. 34 is a graph showing the concentration of plasma TAT complexes in pigs that received heparin via IV bolus injection to maintain ACT >400 seconds in the open, non-heparin bonded cardiopulmonary bypass study, described in example 5A.
Figure 35:
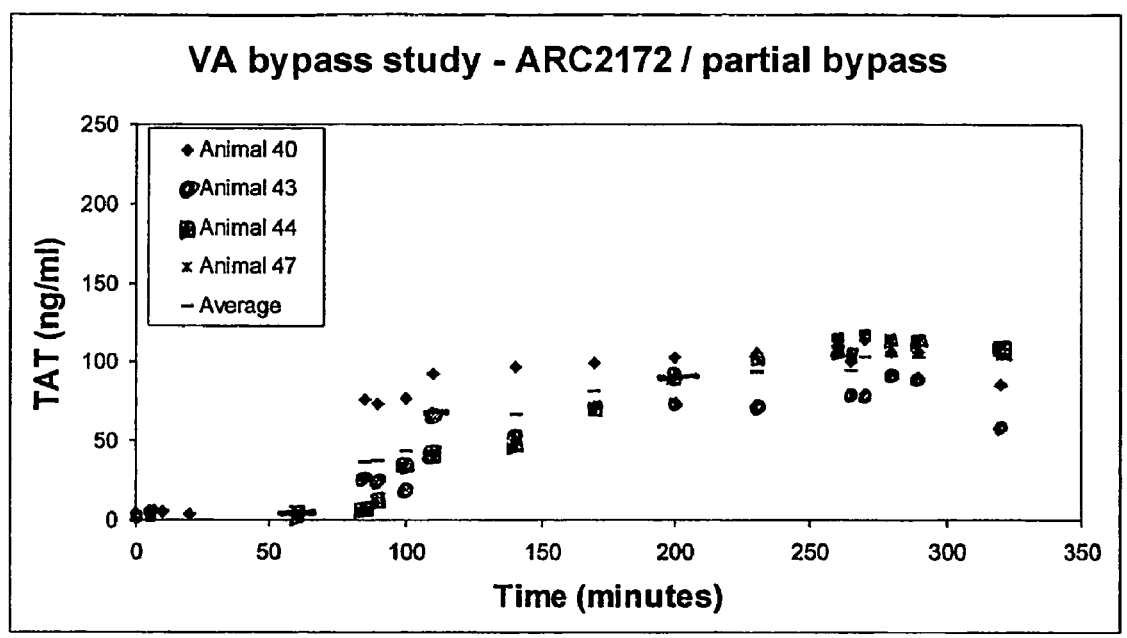
FIG. 35 is a graph showing the concentration of plasma TAT complexes in pigs that received ARC2172 (SEQ ID NO 294) via IV bolus plus infusion to maintain ACT >400 seconds in the open, non-heparin bonded cardiopulmonary bypass study, described in example 5A.

Correlation Between Whole Blood Act and T/ATIII Complex Formation:

During bypass, samples of citrated plasma were collected to monitor the presence of thrombin/anti-thrombin III (TAT) complexes as an indirect measurement of clotting cascade activation. Briefly, undiluted plasma samples were added directly to pre-coated wells of an Enzygnost® TAT micro ELISA (Dade Behring; Deerfield, Ill.; cat. # OWMG15). The ELISA was subsequently completed according to the manufacturer's protocol. All wash steps were completed using an automated plate washer (Bio-Tek; Winooski, Vt.; cat. # ELx405 Magna MVR). Absorbance values were detected with a Versamax Tunable microplate reader (Molecular Devices; Sunnyvale, Calif.). In all animals the concentration of plasma TAT complexes was measured at less than 10 ng/ml at baseline. In control animals that were not treated with anticoagulant, TAT complexes began to accumulate in the plasma within minutes of being placed on bypass to a maximum of 150+/−87 ng/ml immediately before bypass was stopped. The concentration of plasma TAT complexes decreased in these animals during the post-bypass observation period, but never returned to baseline (see FIG. 33). In contrast, heparin treatment suppressed activation of the clotting cascade during bypass as indicated by the relatively low plasma TAT complex concentration (<50 ng/ml) (See FIG. 34). Heparin inhibits the activity of multiple clotting factors higher up on the intrinsic clotting cascade, in addition to inhibiting the activity of thrombin Although ARC2172 (SEQ ID NO 294) prevented the formation of gross blood clots in the bypass circuit, it did not inhibit activation of the clotting cascade as indicated by the rapid increase in plasma TAT complex concentrations following the initiation of bypass (see FIG. 35). However, the TAT complex concentrations were not as high as those seen in control animals. While not wishing to be bound by any theory, this result is expected as ARC2172 (SEQ ID NO 294) only decreases the activity of thrombin, not other activated clotting factors higher up in the intrinsic clotting cascade.

In summary, ARC2172 (SEQ ID NO 294) was evaluated in a porcine cardiopulmonary bypass model using an open, non-heparin-bonded bypass circuit. Animals were treated with saline (n=2), heparin (n=75), and ARC2172 (SEQ ID NO 294) (n=5) by bolus or bolus+infusion to achieve a target ACT of 400 seconds (as measured by the Hemachron Jr. instrument) prior to initiation of bypass. The average ACT values during bypass for each of these groups was 123+/−39 sec (control), 950+/−158 seconds (heparin), and 433+/−61 seconds (ARC2172 (SEQ ID NO 294)). Heparin and ARC2172 (SEQ ID NO 294) decreased gross clot formation during bypass. Furthermore, only heparin inhibited accumulation of TAT complexes during bypass. While not wishing to be bound by any theory, it is believed that this indicates the other treatments did not inhibit activation of the intrinsic clotting cascade.

The invention having now been described by way of written description and example, those of skill in the art will recognize that the invention can be practiced in a variety of embodiments and that the description and examples above are for purposes of illustration and not limitation of the following claims.

What is claimed is:

1. An aptamer that binds to thrombin comprising the following nucleic acid sequence: CCTAGGTTGGGTAGGGTGGTGG (SEQ ID NO 441).

2. The aptamer of claim 1, wherein the aptamer does not comprise a 5-bromodeoxyuridine modification at the majority of its thymidine residues.

3. The aptamer of claim 1, wherein the aptamer comprises a nucleic acid sequence selected from the group consisting of:
ACTGCCTAGGTTGGGTAGGGTGGTGGCAGT (ARC2169 (SEQ ID NO 283)),
GCTGCCTAGGTTGGGTAGGGTGGTGGCAGC (ARC2170 (SEQ ID NO 292)),
CTGCCTAGGTTGGGTAGGGTGGTGGCAG, (ARC2171 (SEQ ID NO 293)), and,
CGCCTAGGTTGGGTAGGGTGGTGGCG (ARC2172 (SEQ ID NO 294)).

4. An aptamer according to claim 1, wherein the aptamer binds to human thrombin with a $K_D$ of less than 1 nM as determined by dot blot titration.

5. An aptamer according to claim 1, wherein the aptamer has at least substantially the same ability as ARC2172 (SEQ ID NO 294) to decrease or inhibit thrombin mediated coagulation.

6. An aptamer according to claim 1, wherein the thrombin target is human thrombin.

7. An aptamer according to claim 1, wherein the aptamer is a single stranded deoxyribonucleic acid.

8. An aptamer according to claim 1, wherein the aptamer comprises at least one chemical modification.

9. The aptamer of claim 8, wherein the modification is selected from the group consisting of: a chemical substitution at a sugar position, a chemical substitution at a phosphate position, and a chemical substitution at a base position.

10. The aptamer of claim 8, wherein the modification is selected from the group consisting of: incorporation of a modified nucleotide; 3' capping; conjugation to a high molecular weight of at least 10 kDa, non-immunogenic polymer; and conjugation to a lipophilic compound.

11. The aptamer of claim 8, wherein the modification is conjugation to a non-immunogenic, high molecular weight polymer of at least 10 kDa and wherein the polymer is polyalkylene glycol.

12. The aptamer of claim 11 wherein the polyalkylene glycol is polyethylene glycol.

13. An aptamer of claim 1, wherein the aptamer decreases or inhibits thrombin mediated coagulation in vitro.

14. A method comprising administering an aptamer according to claim 1 to a subject or an extracorporeal circuit in an amount effective to decrease or inhibit thrombin mediated coagulation in the subject.

15. The method of claim 14, wherein the subject is human.

16. A composition comprising an aptamer of claim 1 or a salt thereof in an amount effective to decrease or inhibit thrombin mediated coagulation in a subject and a pharmaceutically acceptable carrier or diluent.

17. A method comprising administering the composition of claim 16 to a subject.

18. The method of claim 17, wherein the subject is human.

19. A method according to claim 14, wherein the subject is renally impaired and wherein the aptamer for use in the method is not conjugated to a polyethylene glycol (PEG).

20. A method according to claim 14, wherein the subject has heparin induced thrombocytopenia.

21. A method according to claim 14, wherein the subject is heparin resistant.

22. A method according to claim 14, wherein the subject has impaired hepatic function.

23. A method according to claim 14, wherein the aptamer is administered to the subject before, during, after or any combination thereof, a surgical procedure on the subject.

24. The method of claim 23, wherein the surgical procedure is selected from the group consisting of: cardiopulmonary by-pass surgery, coronary artery bypass graft surgery, percutaneous coronary intervention, angioplasty, cardiovascular and peripheral vascular open and endovascular surgery, stent placement surgery, heart valve replacement surgery, surgery to treat coronary disease and/or vascular disease in veins or arteries, and surgery to treat peripheral arterial occlusive disease.

25. The method of claim 14, wherein the aptamer is ARC2172 (SEQ ID NO 294).

26. The method of claim 24, wherein the aptamer is ARC2172 (SEQ ID NO 294) and the surgical procedure is coronary artery bypass graft surgery.

27. The method of claim 24, wherein the aptamer is ARC2172 (SEQ ID NO 294) and the surgical procedure is percutaneous coronary intervention.

28. The method of claim 24, wherein the surgical procedure is cardiopulmonary by-pass surgery and an open, and non-heparin bonded circuit is used during the surgery.

29. The aptamer of claim 1, wherein the aptamer comprises SEQ ID NO 294.

30. The aptamer of claim 1, wherein the aptamer is ARC2172 (SEQ ID NO 294).

\* \* \* \* \*